(12) United States Patent
Corti

(10) Patent No.: US 11,912,757 B2
(45) Date of Patent: Feb. 27, 2024

(54) ANTIBODIES SPECIFICALLY BINDING TO ZIKA VIRUS EPITOPES AND USES THEREOF

(71) Applicant: HUMABS BIOMED SA, Bellinzona (CH)

(72) Inventor: Davide Corti, Bellinzona (CH)

(73) Assignee: HUMABS BIOMED SA, Bellinzona (CH)

( * ) Notice: Subject to any disclaimer, the term of this patent is extended or adjusted under 35 U.S.C. 154(b) by 361 days.

(21) Appl. No.: 17/335,792

(22) Filed: Jun. 1, 2021

(65) Prior Publication Data

US 2021/0355198 A1 Nov. 18, 2021

Related U.S. Application Data

(62) Division of application No. 16/317,533, filed as application No. PCT/EP2017/067581 on Jul. 12, 2017, now Pat. No. 11,117,954.

(30) Foreign Application Priority Data

Jul. 13, 2016 (WO) ................. PCT/EP2016/066684

(51) Int. Cl.
| | |
|---|---|
| C07K 16/10 | (2006.01) |
| A61K 9/00 | (2006.01) |
| A61P 31/14 | (2006.01) |
| A61P 31/20 | (2006.01) |
| G01N 33/569 | (2006.01) |
| A61K 39/00 | (2006.01) |

(52) U.S. Cl.
CPC ........ *C07K 16/1081* (2013.01); *A61K 9/0019* (2013.01); *A61P 31/20* (2018.01); *G01N 33/56983* (2013.01); *A61K 2039/505* (2013.01); *C07K 2317/21* (2013.01); *C07K 2317/33* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| | | |
|---|---|---|
| 3,766,162 A | 10/1973 | Spector |
| 3,791,932 A | 2/1974 | Schuurs et al. |
| 3,817,837 A | 6/1974 | Rubenstein et al. |
| 4,179,337 A | 12/1979 | Davis et al. |
| 4,233,402 A | 11/1980 | Maggio et al. |
| 4,495,285 A | 1/1985 | Shimizu et al. |
| 4,609,546 A | 9/1986 | Hiratani |
| 4,676,980 A | 6/1987 | Segal et al. |
| 4,766,106 A | 8/1988 | Katre et al. |
| 4,831,175 A | 5/1989 | Gansow et al. |
| 5,595,721 A | 1/1997 | Kaminski et al. |
| 7,785,799 B2 | 8/2010 | Barrett et al. |
| 10,421,804 B2 | 9/2019 | Kyratsous et al. |
| 11,046,698 B2 | 6/2021 | Masse et al. |
| 2005/0163783 A1 | 7/2005 | Braslawsky et al. |
| 2019/0194260 A1 | 6/2019 | Whitehead et al. |

FOREIGN PATENT DOCUMENTS

| | | |
|---|---|---|
| WO | 00/52031 A2 | 9/2000 |
| WO | 00/52473 A2 | 9/2000 |
| WO | 2004/076677 A2 | 9/2004 |
| WO | 2008/143954 A2 | 11/2008 |
| WO | 2010/046775 A2 | 4/2010 |

OTHER PUBLICATIONS

Amsbio, "MAb to Zika Virus NS1 Monoclonal Antibody to Zika Virus Nonstructural Protein (NS1)," Certificate of Analysis, Catalog No. C01864M, May 3, 2016, 1 page.
Amsbio, "MAb to Zika Virus NS1 Monoclonal Antibody to Zika Virus Nonstructural Protein (NS1)," Certificate of Analysis, Catalog No. C01865M, Jun. 23, 2016, 1 page.
Amsbio, "MAb to Zika Virus NS1 Monoclonal Antibody to Zika Virus Nonstructural Protein (NS1)," Certificate of Analysis, Catalog No. C01866M, Apr. 26, 2016, 1 page.
Amsbio, "Zika Virus Antibodies & Antigens," product datasheet, Jul. 2016, 2 pages.
Arigo Biolaboratories, ARG65781: anti-Zika virus NS1 antibody [SQab1609], https://www.biomol.com/products/antibodies/primary-antibodies/general/anti-zika-virus-ns1-clone-sqab1609-arg65781.100?Fs=1295927266, 2015. (4 pages).
Arigo Biolaboratories, "Choose the Best ZIKA Virus Antibodies," downloaded on Dec. 4, 2018 from https://www.arigobio.com/news/view/Zika_Virus, 2014, 4 pages.
Armour et al., "Recombinant human IgG molecules lacking Fcγ receptor I binding and monocyte triggering activities," *Eur. J. Immunol.* 29:2613-2624, 1999.
Balmaseda et al., "Antibody-based assay discriminates Zika virus infection from other flaviviruses," *PNAS* 114(31):8384-8389, 2017.
Barba-Spaeth et al., "Structural basis of potent Zika-dengue virus antibody cross-neutralization," *Nature* 536:48-53, 2016. (20 pages).
Bardelli et al., "Epitope mapping by solution NMR spectroscopy," *Journal of Molecular Recognition* 28(6):393-400, 2015.
Beatty et al., "Dengue virus NS1 triggers endothelial permeability and vascular leak that is prevented by NS1 vaccination," *Science Translational Medicine* 7(304):304ra141, 2015. (13 pages).

(Continued)

*Primary Examiner* — Stacy B Chen
(74) *Attorney, Agent, or Firm* — Seed IP Law Group LLP

(57) ABSTRACT

The invention relates to antibodies, and antigen binding fragments thereof, that potently neutralize infection of ZIKV. The invention also relates to antigenic sites to which the antibodies and antigen binding fragments bind, as well as to nucleic acids that encode and immortalized B cells that produce such antibodies and antibody fragments. In addition, the invention relates to the use of the antibodies and antibody fragments of the invention in screening methods as well as in the diagnosis, prophylaxis and treatment of ZIKV infection.

32 Claims, 23 Drawing Sheets

Specification includes a Sequence Listing.

(56) References Cited

OTHER PUBLICATIONS

Beltramello et al., "The Human Immune Response to Dengue Virus Is Dominated by Highly Cross-Reactive Antibodies Endowed with Neutralizing and Enhancing Activity," *Cell Host & Microbe* 8:271-283, 2010.
Blackman et al., "Challenges of Vaccine Development for Zika Virus," *Viral Immunology*, vol. 31:2, 2018, pp. 117-123.
Boerner et al., "Production of Antigen-Specific Human Monoclonal Antibodies from In Vitro-Primed Human Splenocytes," *The Journal of Immunology* 147(1): 86-95, 1991. (11 pages).
Bressanelli et al., "Structure of a flavivirus envelope glycoprotein in its low-pH-induced membrane fusion conformation," *The EMBO Journal* 23:728-738, 2004.
Calvet et al., "Detection and sequencing of Zika virus from amniotic fluid of fetuses with microcephaly in Brazil: a case study," *The Lancet Infectious Diseases* 16(6):653-660, 2016.
Cao-Lormeau et al., "Emerging arboviruses in the Pacific," *The Lancet* 384:1571-1572, 2014.
Cao-Lormeau et al., "Guillain-Barré Syndrome outbreak associated with Zika virus infection in French Polynesia: a case-control study," *The Lancet* 387:1531-1539, 2016.
Capel et al., "Heterogeneity of Human IgG Fc Receptors," *Immunomethods* 4:25-34, 1994.
Chu et al., "Inhibition of B cell receptor-mediated activation of primary human B cells by coengagement of CD19 and FcγRIIb with Fc-engineered antibodies," *Molecular Immunology* 45:3926-3933, 2008.
Corti et al., "Cross-neutralization of four paramyxoviruses by a human monoclonal antibody," *Nature* 501:439-445, 2013.
Dai et al., "Structures of the Zika Virus Envelope Protein and Its Complex with a Flavivirus Broadly Protective Antibody," *Cell Host & Microbe* 19:696-704, 2016. (10 pages).
De Haas et al., "Fcγ receptors of phagocytes," *J. Lab. Clin. Med.* 126(4):330-341, 1995.
Dejnirattisai et al., "Dengue virus sero-cross-reactivity drives antibody-dependent enhancement of infection with zika virus," *Nat Immunol.* 17(9):1102-1108, 2016. (18 pages).
Dejnirattisai et al., "Enhancing cross-reactive anti-prM dominates the human antibody response in dengue infection," *Science* 328(5979):745-748, 2010. (12 pages).
Dick et al., "Zika Virus (I). Isolations and Serological Specificity," *Transactions of the Royal Society of Tropical Medicine and Hygiene* 46(5):509-520, 1952.
Dowall et al., "A Susceptible Mouse Model for Zika Virus Infection," *PLoS Neglected Tropical Diseases* 10(5):e0004658, 2016. (13 pages).
Duffy et al., "Zika Virus Outbreak on Yap Island, Federated States of Micronesia," *New England Journal of Medicine* 360(24):2536-2543, 2009.
Duncan et al., "The binding site for Clq on IgG," *Nature* 332:738-740, 1988.
Ganesan et al., "FcγRIIb on Liver Sinusoidal Endothelium Clears Small Immune Complexes," *The Journal of Immunology* 189(10):4981-4988, 2012. (9 pages).
Gessner et al., "The IgG Fc receptor family," *Ann. Hematol.* 76:231-248, 1998.
Goldsby et al. (Ed.), Kuby Immunology, fourth edition, W H Freeman & Co, Macmillan, London, UK, 2000, chapter 4, "Antibodies: Structure and Function," pp. 76-104. (30 pages).
Grevys et al., "Fc Engineering of Human IgG1 for Altered Binding to the Neonatal Fc Receptor Affects Fc Effector Functions," *The Journal of Immunology* 194(11):5497-5508, 2015.
Halstead et al., "Dengue Hemorrhagic Fever in Infants: Research Opportunities Ignored," *Emerging Infectious Diseases* 8(12):1474-1479, 2002.
Halstead, "Dengue Antibody-Dependent Enhancement: Knowns and Unknowns," *Microbiol. Spectrum* 2(6), 2014, 18 pages.
Halstead, "Neutralization and Antibody-Dependent Enhancement of Dengue Viruses," *Advances in Virus Research* 60:421-467, 2003.
Hessell et al., "Fc receptor but not complement binding is important in antibody protection against HIV," *Nature* 449:101-105, 2007.
Heymann et al., "Zika virus and microcephaly: why is this situation a PHEIC?" *The Lancet* 387:719-721, 2016.
Holliger et al., "Engineered antibody fragments and the rise of single domains," *Nature Biotechnology* 23(9):1126-1136, 2005.
Hoogenboom et al., "By-passing Immunisation: Human Antibodies from Synthetic Repertoires of Germline $V_H$ Gene Segments Rearranged in Vitro," *J. Mol. Biol.* 227:381-388, 1992.
Hung et al., "Dengue Hemorrhagic Fever in Infants: A Study of Clinical and Cytokine Profiles," *The Journal of Infectious Diseases* 189:221-232, 2004.
Huzly et al., "High specificity of a novel Zika virus ELISA in European patients after exposure to different flaviviruses," *Euro Surveillance* 21(16), 2016. (4 pages).
Jakobovits et al., "Analysis of homozygous mutant chimeric mice: Deletion of the immunoglobulin heavy-chain joining region blocks B-cell development and antibody production," *Proc. Nat. Acad. Sci. USA* 90:2551-2555, 1993.
Jakobovits et al., "Germ-line transmission and expression of a human-derived yeast artificial chromosome," *Nature* 362:255-258, 1993.
Kostyuchenko et al., "Structure of the thermally stable Zika virus," *Nature* 533:425-429, 2016. (12 pages).
Lefranc et al., "IMGT®, the international ImMunoGene Tics information system®," *Nucleic Acids Research* 37:D1006-1012, 2009.
Li et al., "Enzyme-Linked Immunosorbent Assay-Format Tissue Culture Infectious Dose-50 Test for Titrating Dengue Virus," *PLoS One* 6(7):e22553, 2011. (4 pages).
MacNamara, "Zika Virus: A Report on Three Cases of Human Infection During an Epidemic of Jaundice in Nigeria," *Transactions of the Royal Society of Tropical Medicine and Hygiene* 48(2):139-145, 1954.
Marchetto et al., "A Model for Neural Development and Treatment of Rett Syndrome Using Human Induced Pluripotent Stem Cells," *Cell* 143:527-539, 2010.
Marks et al., "By-passing Immunization: Human Antibodies from V-gene Libraries Displayed on Phage," *J. Mol. Biol.* 222:581-597, 1991.
Mlakar et al., "Zika Virus Associated with Microcephaly," *The New England Journal of Medicine* 374(10):951-958, 2016.
Modis et al., "Structure of the dengue virus envelope protein after membrane fusion," *Nature* 427:313-319, 2004.
Moore et al., "Accelerated Clearance Of Ige In Chimpanzees Is Mediated By Xmab7195, An Fc-Engineered Antibody With Enhanced Affinity For Inhibitory Receptor Fcγriib," C33. Cytokines and Asthma Mediators, *American Thoracic Society 2014 International Conference*, San Diego, California, May 16-21, 2014. (1 page).
Muller et al., "The flavivirus NS1 protein: Molecular and structural biology, immunology, role in pathogenesis and application as a diagnostic biomarker," *Antiviral Research* 98(2):192-208, 2013.
Musso et al., "Potential Sexual Transmission of Zika Virus," *Emerging Infectious Diseases* 21(2):359-361, 2015.
Musso et al., "Zika virus: following the path of dengue and chikungunya?" *The Lancet* 386:243-244, 2015.
Native Antigen Company, "Mouse anti-Zika virus NS1," Antibody Datasheet / Certificate of Analysis, downloaded on Dec. 4, 2018 from https://thenativeantigencompany.com/product/mouse-anti-zika-virus-nsl-antibody-b4/, 4 pages.
Nigro et al., "Passive Immunization during Pregnancy for Congenital Cytomegalovirus Infection," *The New England Journal of Medicine* 353(13):1350-1362, 2005.
Perez et al., "Utilization of Immunoglobulin G Fc Receptors by Human Immunodeficiency Virus Type 1: a Specific Role for Antibodies against the Membrane-Proximal External Region of gp41," *Journal of Virology* 83(15):7397-7410, 2009.
Piccoli et al., "Neutralization and clearance of GM-CSF by autoantibodies in pulmonary alveolar proteinosis," *Nature Communications* 6:7375, 2015. (9 pages).

(56) References Cited

OTHER PUBLICATIONS

Priyamvada et al., "Human antibody responses after dengue virus infection are highly cross-reactive to Zika virus," *PNAS* 113(28):7852-7857, 2016.

Quick et al., "Multiplex PCR method for MinION and Illumina Sequencing of Zika and other virus genomes directly from clinical samples," *Nature Protoc.* 12(6):1261-1276, 2017. (28 pages).

Ravetch et al., "Fc Receptors," *Annu. Rev. Immunol.* 9:457-492, 1991.

Rothman, "Dengue: defining protective versus pathologic immunity," *The Journal of Clinical Investigation* 113(7):946-951, 2004.

Rubin et al., "Zika Virus and Microcephaly," *The New England Journal of Medicine* 374(10):984-985, 2016.

Rudikoff et al., "Single amino acid substitution altering antigen-binding specificity," *Proc. Natl. Acad. Sci. USA* 79:1979-1983, 1982.

Screaton et al., "New insights into the immunopathology and control of dengue virus infection," *Nature Reviews Immunology* 15:745-759, 2015.

Shields et al., "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry* 276(9):6591-6604, 2001. (15 pages).

Simonelli et al., "Rapid Structural Characterization of Human Antibody-Antigen Complexes through Experimentally Validated Computational Docking," *J. Mol. Biol.* 396:1491-1507, 2010.

Simonelli et al., "Rational Engineering of a Human Anti-Dengue Antibody through Experimentally Validated Computational Docking," *PLoS One* 8(2):e55561, 2013. (11 pages).

Sirohi et al., "The 3.8 Å resolution cryo-EM structure of Zika virus," *Science* 352(6284):467-470, 2016. (8 pages).

Song et al., "Zika virus NS1 structure reveals diversity of electrostatic surfaces among flaviviruses," *Nature Structural & Molecular Biology* 23(5):456-459, 2016.

Stettler et al., "Specificity, cross-reactivity, and function of antibodies elicited by Zika virus infection," *Science* 353(6301):823-826, 2016. (5 pages).

Stettler et al., "Supplementary Material for Specificity, cross-reactivity and function of antibodies elicited by Zika virus infection," *Science* 353(6301), 2016. (39 pages).

Tang et al., "Zika Virus Infects Human Cortical Neural Progenitors and Attenuates Their Growth," *Cell Stem Cell* 18(5):587-590, 2016. (9 pages).

Tiller et al., "Efficient generation of monoclonal antibodies from single human B cells by single cell RT-PCR and expression vector cloning," *J Immunol Methods* 329(1-2):112-124, 2008. (19 pages).

Traggiai et al., "An efficient method to make human monoclonal antibodies from memory B cells: potent neutralization of SARS coronavirus," *Nature Medicine* 10(8):871-875, 2004.

Van de Winkel et al., "Biology of Human Immunoglobulin G Fc Receptors," *Journal of Leukocyte Biology* 49:511-524, 1991.

Wang et al., "A human bi-specific antibody against Zika virus with high therapeutic potential," *Cell* 171(1):229-241, 2017. (41 pages).

Wang et al., "Supplemental Figures for A human bi-specific antibody against Zika virus with high therapeutic potential," *Cell* 171(1), 2017. (6 pages).

Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," *The Journal of Immunology* 164:5313-5318, 2000. (7 pages).

Wisdom, "Conjugation of Antibodies to Horseradish Peroxidase," Chapter 9, in Burns (Ed.), *Methods in Molecular Biology* vol. 295: Immunochemical Protocols, Third Edition, Humana Press Inc., Totowa, New Jersey, 2005, pp. 127-130. (9 pages).

Xu et al., "Isolation of a Bluetongue virus group-specific monoclonal antibody and application to a diagnostic competitive ELISA," *Appl. Microbiol. Biotechnol.* 99:729-739, 2015.

Zhao et al., "Structural Basis of Zika Virus-Specific Antibody Protection," *Cell* 166:1016-1027, 2016. (13 pages).

|  | Binding (EC50, ng/ml) | | | | | | | | | | Neut. (IC50, ng/ml) | | |
|---|---|---|---|---|---|---|---|---|---|---|---|---|---|
|  | ZIKV E | DENV1 E | DENV2 E | DENV3 E | DENV4 E | DENV1 VLP | DENV2 VLP | DENV3 VLP | DENV4 VLP | DIII ZKA | ZIKV neut | DENV1 neut | |
| ZKA3 | 172 | 510 | 108 | 17 | 134 | 12 | 28 | 10 | 7 | - | 411 | 346 | |
| ZKA4 | 172 | 135 | 23 | 9 | 22 | 9 | 11 | 10 | 8 | - | 961 | 592 | |
| ZKA5 | 243 | 877 | 133 | 22 | 123 | 37 | 32 | 25 | 31 | - | 1978 | - | |
| ZKA6 | 79 | 355 | 28 | 13 | 58 | 13 | 14 | 9 | 10 | - | 1661 | - | |
| ZKA7 | 112 | 329 | 74 | 11 | 95 | 9 | 18 | 8 | 7 | - | 646 | 513 | |
| ZKA8 | 70 | 136 | 31 | 8 | 28 | 8 | 11 | 7 | 11 | - | 1336 | 102 | |
| ZKA76 | 408 | - | - | - | - | - | - | - | - | 3756 | 62 | nd | |
| ZKA78 | 2759 | 1407 | 982 | 33 | 365 | 158 | 83 | 131 | 136 | - | 2863 | 266 | |
| ZKA117 | 376 | 1780 | 341 | 49 | 391 | 142 | 86 | 36 | 158 | - | 1945 | 83 | |
| ZKB27 | 225 | - | - | - | - | nd | nd | nd | nd | - | 257 | nd | |
| ZKB29 | 285 | - | - | - | - | nd | nd | nd | nd | - | - | nd | |
| ZKB30 | 1560 | 2011 | 2320 | 344 | 459 | nd | nd | nd | nd | - | - | nd | |
| ZKB32 | 1668 | - | - | - | - | nd | nd | nd | nd | - | 545 | nd | |
| ZKB34 | 122 | - | - | - | - | nd | nd | nd | nd | - | - | nd | |
| ZKB39 | 136 | - | - | - | - | nd | nd | nd | nd | - | 667 | nd | |
| ZKB41 | 241 | - | - | - | - | nd | nd | nd | nd | - | - | nd | |
| ZKB45 | 125 | - | - | - | - | nd | nd | nd | nd | - | 1461 | nd | |
| ZKB46 | 3238 | - | - | - | - | nd | nd | nd | nd | - | - | nd | |
| ZKB51 | 645 | 220 | 115 | 66 | 62 | nd | nd | nd | nd | - | - | nd | EDI/II |
| ZKB52 | 3398 | - | - | - | - | nd | nd | nd | nd | - | - | nd | |
| ZKB53 | 59 | - | - | - | - | nd | nd | nd | nd | - | - | nd | |
| ZKB84 | 4373 | - | - | - | - | nd | nd | nd | nd | - | - | nd | |
| ZKC21 | 2069 | 4201 | 3659 | 877 | 1252 | nd | nd | nd | nd | - | - | nd | |
| ZKC22 | 181 | 347 | 133 | 330 | 75 | nd | nd | nd | nd | - | - | nd | |
| ZKC23 | 87 | 2152 | 97 | 37 | 21 | nd | nd | nd | nd | - | - | nd | |
| ZKC24 | 92 | 177 | 71 | 240 | 55 | nd | nd | nd | nd | - | - | nd | |
| ZKC26 | 52 | 150 | 61 | 21 | 28 | nd | nd | nd | nd | - | 420 | nd | |
| ZKD4 | 20 | 80 | 24 | 8 | 11 | nd | nd | nd | nd | - | - | nd | |
| ZKD5 | 42 | 254 | 103 | 17 | 41 | nd | nd | nd | nd | - | - | nd | |
| ZKD6 | 115 | 585 | 600 | 31 | 96 | nd | nd | nd | nd | - | - | nd | |
| ZKD7 | 33 | 474 | 147 | 12 | 44 | nd | nd | nd | nd | - | - | nd | |
| ZKD8 | 24 | 169 | 52 | 12 | 25 | nd | nd | nd | nd | - | - | nd | |
| ZKD15 | 581 | - | - | - | - | nd | nd | nd | nd | - | - | nd | |
| ZKD16 | 62 | 692 | 475 | 10 | 27 | nd | nd | nd | nd | - | - | nd | |
| ZKD17 | 14 | 93 | 32 | 7 | 12 | nd | nd | nd | nd | - | - | nd | |
| ZKD20 | 565 | - | - | 50 | - | nd | nd | nd | nd | - | - | nd | |
| ZKD21 | 53 | 63 | 189 | 13 | 17 | nd | nd | nd | nd | - | - | nd | |
| ZKA64 | 65 | - | - | - | - | - | - | - | - | 161 | 155 | - | |
| ZKA134 | 168 | - | - | - | - | - | - | - | - | 826 | 432 | nd | |
| ZKA190 | 113 | - | - | - | - | - | - | - | - | 444 | 12 | nd | |
| ZKA246 | 473 | - | - | - | - | - | - | - | - | 5974 | 243 | nd | |
| ZKA256 | 115 | - | - | - | - | - | - | - | - | 214 | 224 | nd | |
| ZKB31 | 73 | - | - | - | - | nd | nd | nd | nd | 18 | - | nd | |
| ZKB42 | 5561 | 7073 | 6485 | 12065 | 6884 | nd | nd | nd | nd | 5158 | - | nd | EDIII |
| ZKB50 | 653 | 10000 | - | - | - | nd | nd | nd | nd | - | - | nd | |
| ZKB85 | 953 | - | - | - | - | nd | nd | nd | nd | 2400 | 2387 | nd | |
| ZKB47 | 13 | - | - | - | - | nd | nd | nd | nd | 574 | - | nd | |
| ZKC6 | 8575 | - | - | - | - | nd | nd | nd | nd | 5533 | 32 | nd | |
| ZKC25 | 162 | 144 | 147 | 150 | 158 | nd | nd | nd | nd | 200 | - | nd | |
| ZKD18 | 17 | - | - | - | - | nd | nd | nd | nd | 12 | - | nd | |
| ZKA81 | - | - | - | - | - | nd | nd | nd | nd | - | 243 | nd | |
| ZKA144 | - | - | - | - | - | nd | nd | nd | nd | - | 48 | nd | |
| ZKA146 | - | - | - | - | - | nd | nd | nd | nd | - | 45 | nd | |
| ZKA155 | - | - | - | - | - | nd | nd | nd | nd | - | 99 | nd | |
| ZKA160 | - | - | - | - | - | nd | nd | nd | nd | - | 38 | 26 | |
| ZKA167 | - | - | - | - | - | nd | nd | nd | nd | - | 121 | nd | |
| ZKA169 | - | - | - | - | - | nd | nd | nd | nd | - | 321 | nd | |
| ZKA171 | - | - | - | - | - | nd | nd | nd | nd | - | 47 | nd | |
| ZKA172 | - | - | - | - | - | nd | nd | nd | nd | - | 9 | nd | |
| ZKA174 | - | - | - | - | - | nd | nd | nd | nd | - | 55 | - | |
| ZKA183 | - | - | - | - | - | nd | nd | nd | nd | - | 34 | nd | |
| ZKA185 | - | - | - | - | - | nd | nd | nd | nd | - | 13 | - | |
| ZKA189 | - | - | - | - | - | nd | nd | nd | nd | - | 273 | nd | |
| ZKA191 | - | - | - | - | - | nd | nd | nd | nd | - | 52 | nd | NNB |
| ZKA195 | - | - | - | - | - | nd | nd | nd | nd | - | 33 | - | |
| ZKA207 | - | - | - | - | - | nd | nd | nd | nd | - | 43 | nd | |
| ZKA215 | - | - | - | - | - | nd | nd | nd | nd | - | 26 | nd | |
| ZKA218 | - | - | - | - | - | nd | nd | nd | nd | - | 14 | nd | |
| ZKA228 | - | - | - | - | - | nd | nd | nd | nd | - | 36 | nd | |
| ZKA230 | - | - | - | - | - | nd | nd | nd | nd | - | 10 | nd | |
| ZKB75 | - | - | - | - | - | nd | nd | nd | nd | - | 190 | nd | |
| ZKB79 | - | - | - | - | - | nd | nd | nd | nd | - | 391 | nd | |
| ZKB83 | - | - | - | - | - | nd | nd | nd | nd | - | 59 | nd | |
| ZKC3 | - | - | - | - | - | nd | nd | nd | nd | - | 170 | nd | |
| ZKC8 | - | - | - | - | - | nd | nd | nd | nd | - | 762 | nd | |
| ZKC15 | - | - | - | - | - | nd | nd | nd | nd | - | 15 | nd | |
| ZKC18 | - | - | - | - | - | nd | nd | nd | nd | - | 662 | nd | |
| ZKD1 | - | - | - | - | - | nd | nd | nd | nd | - | 1141 | nd | |

Figure 1

| mAbs | Binding (EC50, ng/ml) | | | | | | | | |
|---|---|---|---|---|---|---|---|---|---|
| | ZIKV NS1 | DENV1 NS1 | DENV2 NS1 | DENV3 NS1 | DENV4 NS1 | YFV NS1 | WNV NS1 | JEV NS1 | TBEV NS1 |
| ZKA10 | 4 | - | - | - | - | - | - | - | - |
| ZKA15 | 3 | - | - | - | - | 2784 | 3217 | 5499 | 4613 |
| ZKA16 | 3 | - | - | - | - | - | - | - | - |
| ZKA18 | 56 | - | - | - | 489 | 255 | - | 200 | - |
| ZKA19 | 7 | - | - | - | - | - | - | - | - |
| ZKA24 | 3 | - | - | - | - | - | - | - | - |
| ZKA25 | 2 | - | - | - | - | - | - | - | - |
| ZKA28 | 3 | - | - | - | - | - | - | 5570 | - |
| ZKA29 | 6 | 81 | 15 | 30 | - | - | 2178 | 2890 | 9941 |
| ZKA30 | 2 | - | - | - | - | 4280 | 5619 | 4813 | 4050 |
| ZKA32 | 3 | - | - | - | - | - | - | - | - |
| ZKA33 | 5 | - | - | - | - | nd | nd | nd | nd |
| ZKA34 | 4 | - | - | - | - | - | - | 2466 | 2806 |
| ZKA35 | 2 | - | - | - | - | - | - | - | - |
| ZKA37 | 2 | - | - | - | - | - | - | - | - |
| ZKA39 | 22 | 1316 | 330 | 236 | 1254 | 757 | - | - | - |
| ZKA40 | 15 | - | - | - | - | - | - | - | - |
| ZKA42 | 2 | - | - | - | - | - | - | - | - |
| ZKA43 | 2 | - | - | - | - | - | - | - | 6867 |
| ZKA44 | 3 | - | - | - | - | - | - | - | - |
| ZKA45 | 3 | - | - | - | - | - | - | - | - |
| ZKA46 | 2 | - | - | - | - | - | - | - | - |
| ZKA48 | 2 | - | - | - | - | 5673 | 9444 | - | - |
| ZKA50 | 4 | - | - | - | - | 6601 | 4940 | - | - |
| ZKA51 | 4 | - | - | - | - | 5891 | 4168 | 6886 | 8867 |
| ZKA52 | 6 | - | - | - | - | 3419 | 1821 | 2705 | - |
| ZKA53 | 22 | 1733 | - | - | 465 | 97 | - | - | - |
| ZKA54 | 56 | - | 3887 | - | 489 | 255 | - | 200 | - |
| ZKB17 | 7 | - | - | - | - | nd | nd | nd | nd |
| ZKB18 | 27 | - | - | - | - | nd | nd | nd | nd |
| ZKB19 | 416 | 119 | 123 | 127 | - | nd | nd | nd | nd |
| ZKB20 | 2124 | - | - | - | - | nd | nd | nd | nd |
| ZKB21 | 14 | 5913 | 8057 | 3014 | 0,2 | nd | nd | nd | nd |
| ZKB23 | 4 | 11 | 64 | 69 | 306 | nd | nd | nd | nd |
| ZKC29 | 557 | 397 | 536 | 609 | 10 | nd | nd | nd | nd |
| ZKC31 | 11 | - | - | - | - | nd | nd | nd | nd |
| ZKC32 | 5 | - | - | - | - | nd | nd | nd | nd |
| ZKC33 | 4 | 2 | 2 | 2 | 2 | nd | nd | nd | nd |
| ZKC34 | 3 | 5 | 6 | 6 | 4 | nd | nd | nd | nd |
| ZKD25 | 906 | - | - | - | - | nd | nd | nd | nd |
| ZKD26 | 2 | 184 | 303 | 314 | - | nd | nd | nd | nd |

| ZIKV strain | IC50 (ng/ml) | |
|---|---|---|
| | ZKA190 | C8 |
| H/PF/2013 | 4,09 | 115,80 |
| MR766 | 8,37 | 1,67 |
| MRS-OPY | 0,65 | 23,48 |
| PV10552 | 1,09 | 34,60 |

C

| | ZKA190 | C8 |
|---|---|---|
| Number of values | 4 | 4 |
| | | |
| Minimum | 0,6484 | 1,665 |
| 25% Percentile | 0,7581 | 7,119 |
| Median | 2,586 | 29,04 |
| 75% Percentile | 7,302 | 95,5 |
| Maximum | 8,374 | 115,8 |
| | | |
| Mean | 3,549 | 43,89 |
| Std. Deviation | 3,561 | 49,86 |
| Std. Error of Mean | 1,781 | 24,93 |
| | | |
| Lower 95% CI of mean | -2,118 | -35,45 |
| Upper 95% CI of mean | 9,215 | 123,2 |
| | | |
| Coefficient of variation | 100,35% | 113,60% |
| | | |
| Geometric mean | 2,216 | 19,89 |
| Geometric SD factor | 3,246 | 5,977 |
| | | |
| Sum | 14,19 | 175,5 |

Figure 17

SEQUENCE LISTING

<160> NUMBER OF SEQ ID NOS: 414

<210> SEQ ID NO 1
<211> LENGTH: 8
<212> TYPE: PRT
<213> ORGANISM: Artificial Sequence
<220> FEATURE:
<223> OTHER INFORMATION: ZKA190 CDRH1

<400> SEQUENCE: 1

Gly Phe Thr Phe Ser Lys Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: ZKA190 CDRH2

<400> SEQUENCE: 2

Ile Ser Tyr Glu Gly Ser Asn Lys
1               5

<210> SEQ ID NO 3
<211> LENGTH: 23
<212> TYPE: PRT
<213> ORGANISM: Artificial Sequence
<220> FEATURE:
<223> OTHER INFORMATION: ZKA190 CDRH3

<400> SEQUENCE: 3

Ala Lys Ser Gly Thr Gln Tyr Tyr Asp Thr Thr Gly Tyr Glu Tyr Arg
1               5                   10                  15

Gly Leu Glu Tyr Phe Gly Tyr
            20

<210> SEQ ID NO 4
<211> LENGTH: 7
<212> TYPE: PRT
<213> ORGANISM: Artificial Sequence
<220> FEATURE:
<223> OTHER INFORMATION: ZKA190 CDRL1

<400> SEQUENCE: 4

Gln Ser Val Ser Ser Tyr
1               5

<210> SEQ ID NO 5

<400> SEQUENCE: 5

000

<210> SEQ ID NO 6
<211> LENGTH: 9
<212> TYPE: PRT
<213> ORGANISM: Artificial Sequence
<220> FEATURE:
<223> OTHER INFORMATION: ZKA190 CDRL2 long

<400> SEQUENCE: 6

Leu Ile Tyr Asp Ala Ser Ser Arg Ala
1               5

<210> SEQ ID NO 7

```
<211> LENGTH: 9
<212> TYPE: PRT
<213> ORGANISM: Artificial Sequence
<220> FEATURE:
<223> OTHER INFORMATION: ZKA190 CDRL3

<400> SEQUENCE: 7

Gln Gln Tyr Gly Arg Ser Arg Trp Thr
1               5

<210> SEQ ID NO 8
<211> LENGTH: 130
<212> TYPE: PRT
<213> ORGANISM: Artificial Sequence
<220> FEATURE:
<223> OTHER INFORMATION: ZKA190 VH

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Lys Tyr
                20                  25                  30

Gly Met His Trp Val Arg Gln Ala Pro Gly Lys Gly Leu Glu Trp Val
            35                  40                  45

Ala Val Ile Ser Tyr Glu Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Thr Gln Tyr Tyr Asp Thr Thr Gly Tyr Glu Tyr Arg
            100                 105                 110

Gly Leu Glu Tyr Phe Gly Tyr Trp Gly Gln Gly Thr Leu Val Thr Val
        115                 120                 125

Ser Ser
    130

<210> SEQ ID NO 9
<211> LENGTH: 108
<212> TYPE: PRT
<213> ORGANISM: Artificial Sequence
<220> FEATURE:
<223> OTHER INFORMATION: ZKA190 VL

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Arg Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Arg
                85                  90                  95

Trp Thr Phe Gly Gln Gly Thr Lys Val Glu Ile Lys
            100                 105
```

```
<210> SEQ ID NO 10
<211> LENGTH: 24
<212> TYPE: DNA
<213> ORGANISM: Artificial Sequence
<220> FEATURE:
<223> OTHER INFORMATION: ZKA190 CDRH1

<400> SEQUENCE: 10
ggattcacct tcagtaaata tggc                                          24

<210> SEQ ID NO 11
<211> LENGTH: 24
<212> TYPE: DNA
<213> ORGANISM: Artificial Sequence
<220> FEATURE:
<223> OTHER INFORMATION: ZKA190 CDRH2

<400> SEQUENCE: 11
atatcatatg agggaagtaa taaa                                          24

<210> SEQ ID NO 12
<211> LENGTH: 69
<212> TYPE: DNA
<213> ORGANISM: Artificial Sequence
<220> FEATURE:
<223> OTHER INFORMATION: ZKA190 CDRH3

<400> SEQUENCE: 12
gcgaaatcgg ggacccaata ctatgatact actggttatg agtatagggg tttggaatac   60
tttggctac                                                           69

<210> SEQ ID NO 13
<211> LENGTH: 21
<212> TYPE: DNA
<213> ORGANISM: Artificial Sequence
<220> FEATURE:
<223> OTHER INFORMATION: ZKA190 CDRL1

<400> SEQUENCE: 13
cagagtgtta gtagcagtta c                                             21

<210> SEQ ID NO 14

<400> SEQUENCE: 14

000

<210> SEQ ID NO 15
<211> LENGTH: 27
<212> TYPE: DNA
<213> ORGANISM: Artificial Sequence
<220> FEATURE:
<223> OTHER INFORMATION: ZKA190 CDRL2 long

<400> SEQUENCE: 15
ctcatctatg atgcatccag cagggcc                                       27

<210> SEQ ID NO 16
<211> LENGTH: 27
<212> TYPE: DNA
<213> ORGANISM: Artificial Sequence
<220> FEATURE:
<223> OTHER INFORMATION: ZKA190 CDRL3

<400> SEQUENCE: 16
```

```
cagcagtatg gtaggtcaag gtggaca                                          27

<210> SEQ ID NO 17
<211> LENGTH: 391
<212> TYPE: DNA
<213> ORGANISM: Artificial Sequence
<220> FEATURE:
<223> OTHER INFORMATION: ZKA190 VH

<400> SEQUENCE: 17
caggtgcagc tggtggagtc tgggggaggc gtggtccagc ctggagggtc cctgagactc        60
tcctgtgcag cctctggatt caccttcagt aaatatggca tgcactgggt ccgccaggct       120
ccaggcaagg ggctggagtg ggtggcagtt atatcatatg agggaagtaa taaatattat       180
gcagactccg tgaagggccg attcaccatc tccagagaca attccaagaa cacgctgtat       240
ctgcaaatga acagcctgag agctgaggac acggcagtgt attactgtgc gaaatcgggg       300
acccaatact atgatactac tggttatgag tataggggtt tggaatactt tggctactgg       360
ggccagggaa ccctggtcac cgtctcctca g                                     391

<210> SEQ ID NO 18
<211> LENGTH: 325
<212> TYPE: DNA
<213> ORGANISM: Artificial Sequence
<220> FEATURE:
<223> OTHER INFORMATION: ZKA190 VL

<400> SEQUENCE: 18
gaaattgtgt tgacgcagtc tccaggcacc ctgtctttgt ctccagggga aagagccacc        60
ctctcctgca gggccagtca gagtgttagt agcagttact tagcctggta ccagcagaaa       120
cgtggccagg ctcccaggct cctcatctat gatgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta ggtcaaggtg gacattcggc       300
caagggacca aggtggaaat caaac                                            325

<210> SEQ ID NO 19
<211> LENGTH: 8
<212> TYPE: PRT
<213> ORGANISM: Artificial Sequence
<220> FEATURE:
<223> OTHER INFORMATION: ZKA185 CDRH1

<400> SEQUENCE: 19

Gly Tyr Ser Phe Thr Ser Tyr Trp
1               5

<210> SEQ ID NO 20
<211> LENGTH: 8
<212> TYPE: PRT
<213> ORGANISM: Artificial Sequence
<220> FEATURE:
<223> OTHER INFORMATION: ZKA185 CDRH2

<400> SEQUENCE: 20

Phe Asp Pro Ser Asp Ser Gln Thr
1               5

<210> SEQ ID NO 21
<211> LENGTH: 14
<212> TYPE: PRT
<213> ORGANISM: Artificial Sequence
```

<220> FEATURE:
<223> OTHER INFORMATION: ZKA185 CDRH3

<400> SEQUENCE: 21

Ala Arg Arg Tyr Cys Ser Ser Ser Cys Tyr Val Asp Asn
1               5                   10

<210> SEQ ID NO 22
<211> LENGTH: 6
<212> TYPE: PRT
<213> ORGANISM: Artificial Sequence
<220> FEATURE:
<223> OTHER INFORMATION: ZKA185 CDRL1

<400> SEQUENCE: 22

Ala Leu Pro Asn Lys Phe
1               5

<210> SEQ ID NO 23

<400> SEQUENCE: 23

000

<210> SEQ ID NO 24
<211> LENGTH: 9
<212> TYPE: PRT
<213> ORGANISM: Artificial Sequence
<220> FEATURE:
<223> OTHER INFORMATION: ZKA185 CDRL2 long

<400> SEQUENCE: 24

Val Ile Tyr Glu Asp Asn Lys Arg Pro
1               5

<210> SEQ ID NO 25
<211> LENGTH: 12
<212> TYPE: PRT
<213> ORGANISM: Artificial Sequence
<220> FEATURE:
<223> OTHER INFORMATION: ZKA185 CDRL3

<400> SEQUENCE: 25

Tyr Ser Thr Asp Ser Ser Ser Asn Pro Leu Gly Val
1               5                   10

<210> SEQ ID NO 26
<211> LENGTH: 121
<212> TYPE: PRT
<213> ORGANISM: Artificial Sequence
<220> FEATURE:
<223> OTHER INFORMATION: ZKA185 VH

<400> SEQUENCE: 26

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Thr Trp Val Arg Gln Met Pro Gly Lys Gly Leu Glu Trp Met
            35                  40                  45

Ala Lys Phe Asp Pro Ser Asp Ser Gln Thr Asn Tyr Ser Pro Ser Phe
        50                  55                  60

Gln Gly His Val Thr Ile Ser Val Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Arg Tyr Cys Ser Ser Ser Cys Tyr Val Asp Asn Trp Gly
            100                 105                 110

Gln Gly Thr Leu Val Thr Ile Phe Ser
        115                 120

<210> SEQ ID NO 27
<211> LENGTH: 109
<212> TYPE: PRT
<213> ORGANISM: Artificial Sequence
<220> FEATURE:
<223> OTHER INFORMATION: ZKA185 VL

<400> SEQUENCE: 27

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Asn Lys Phe Ala
            20                  25                  30

Tyr Trp Tyr Arg Gln Lys Ser Gly Gln Ala Pro Val Leu Val Ile Tyr
        35                  40                  45

Glu Asp Asn Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr His Cys Tyr Ser Thr Asp Ser Ser Ser Asn Pro
                85                  90                  95

Leu Gly Val Phe Gly Gly Gly Thr Lys Leu Thr Val Leu
            100                 105

<210> SEQ ID NO 28
<211> LENGTH: 24
<212> TYPE: DNA
<213> ORGANISM: Artificial Sequence
<220> FEATURE:
<223> OTHER INFORMATION: ZKA185 CDRH1

<400> SEQUENCE: 28
ggatatagtt ttaccagtta ctgg                                    24

<210> SEQ ID NO 29
<211> LENGTH: 24
<212> TYPE: DNA
<213> ORGANISM: Artificial Sequence
<220> FEATURE:
<223> OTHER INFORMATION: ZKA185 CDRH2

<400> SEQUENCE: 29
tttgatccta gtgactctca aacc                                    24

<210> SEQ ID NO 30
<211> LENGTH: 42
<212> TYPE: DNA
<213> ORGANISM: Artificial Sequence
<220> FEATURE:
<223> OTHER INFORMATION: ZKA185 CDRH3

<400> SEQUENCE: 30
gcgagaagat attgtagtag tagtagttgt tatgtggaca at                42

<210> SEQ ID NO 31
<211> LENGTH: 18
```

<212> TYPE: DNA
<213> ORGANISM: Artificial Sequence
<220> FEATURE:
<223> OTHER INFORMATION: ZKA185 CDRL1

<400> SEQUENCE: 31
gcattgccaa ataaattt                                                    18

<210> SEQ ID NO 32

<400> SEQUENCE: 32

000

<210> SEQ ID NO 33
<211> LENGTH: 27
<212> TYPE: DNA
<213> ORGANISM: Artificial Sequence
<220> FEATURE:
<223> OTHER INFORMATION: ZKA185 CDRL2 long

<400> SEQUENCE: 33
gtcatctatg aggacaacaa acgaccc                                          27

<210> SEQ ID NO 34
<211> LENGTH: 36
<212> TYPE: DNA
<213> ORGANISM: Artificial Sequence
<220> FEATURE:
<223> OTHER INFORMATION: ZKA185 CDRL3

<400> SEQUENCE: 34
tactcaacag acagcagttc taatcccctg ggagta                                36

<210> SEQ ID NO 35
<211> LENGTH: 364
<212> TYPE: DNA
<213> ORGANISM: Artificial Sequence
<220> FEATURE:
<223> OTHER INFORMATION: ZKA185 VH

<400> SEQUENCE: 35
gaagtgcagc tggtgcagtc cggagcagag gtgaaaaagc ccggggagtc tctgaggatc      60
tcctgtaagg gttctggata tagttttacc agttactgga tcacctgggt gcgccagatg     120
cccgggaaag gcctggagtg gatggcgaag tttgatccta gtgactctca aaccaactac     180
agcccgtcct ccaaggcca cgtcaccatc tcagttgaca gtccatcag cactgcctac      240 ttgcagtgga gcagcctgaa ggcctcggac accgccatgt attactgtgc gagaagatat    300
tgtagtagta gtagttgtta tgtggacaat tggggccagg gaaccctggt caccatcttc    360
tcag                                                                 364

<210> SEQ ID NO 36
<211> LENGTH: 328
<212> TYPE: DNA
<213> ORGANISM: Artificial Sequence
<220> FEATURE:
<223> OTHER INFORMATION: ZKA185 VL

<400> SEQUENCE: 36
tcctatgagc tgacacagcc accctcggtg tcagtgtccc caggacaaac ggccaggatc      60
acctgctctg gagatgcatt gccaaataaa tttgcttatt ggtaccggca gaagtcaggc    120
caggcccctg ttctggtcat ctatgaggac aacaaacgac cctccgggat ccctgagaga    180

```
ttctctggct ccagctcagg gacaatggcc accttgacta tcagtggggc ccaggtggag    240
gatgaagctg actaccactg ttactcaaca gacagcagtt ctaatcccct gggagtattc    300
ggcggaggga ccaagctgac cgtcctag                                       328
```

<210> SEQ ID NO 37
<211> LENGTH: 8
<212> TYPE: PRT
<213> ORGANISM: Artificial Sequence
<220> FEATURE:
<223> OTHER INFORMATION: ZKA230 CDRH1

<400> SEQUENCE: 37

Gly Gly Ser Ile Ser Ser Asp Tyr
1               5

<210> SEQ ID NO 38
<211> LENGTH: 7
<212> TYPE: PRT
<213> ORGANISM: Artificial Sequence
<220> FEATURE:
<223> OTHER INFORMATION: ZKA230 CDRH2

<400> SEQUENCE: 38

Ile Tyr Tyr Ser Gly Ser Thr
1               5

<210> SEQ ID NO 39
<211> LENGTH: 17
<212> TYPE: PRT
<213> ORGANISM: Artificial Sequence
<220> FEATURE:
<223> OTHER INFORMATION: ZKA230 CDRH3

<400> SEQUENCE: 39

Ala Arg Arg Arg Lys Tyr Asp Ser Leu Trp Gly Ser Phe Ala Phe Asp
1               5                   10                  15

Ile

<210> SEQ ID NO 40
<211> LENGTH: 8
<212> TYPE: PRT
<213> ORGANISM: Artificial Sequence
<220> FEATURE:
<223> OTHER INFORMATION: ZKA230 CDRL1

<400> SEQUENCE: 40

Ser Ser Asn Ile Gly Gly Asn Tyr
1               5

<210> SEQ ID NO 41

<400> SEQUENCE: 41

000

<210> SEQ ID NO 42
<211> LENGTH: 9
<212> TYPE: PRT
<213> ORGANISM: Artificial Sequence
<220> FEATURE:
<223> OTHER INFORMATION: ZKA230 CDRL2 long

<400> SEQUENCE: 42

Leu Ile Cys Ile Asn Asp His Arg Pro

<210> SEQ ID NO 43
<211> LENGTH: 11
<212> TYPE: PRT
<213> ORGANISM: Artificial Sequence
<220> FEATURE:
<223> OTHER INFORMATION: ZKA230 CDRL3

<400> SEQUENCE: 43

```
Ala Thr Trp Asp Asp Ser Leu Gly Gly Leu Val
1               5                   10
```

<210> SEQ ID NO 44
<211> LENGTH: 123
<212> TYPE: PRT
<213> ORGANISM: Artificial Sequence
<220> FEATURE:
<223> OTHER INFORMATION: ZKA230 VH

<400> SEQUENCE: 44

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Asp
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Asn Ser Val Thr Ala Ala Asp Thr Ala Val Tyr Tyr Cys Ala
                85                  90                  95

Arg Arg Arg Lys Tyr Asp Ser Leu Trp Gly Ser Phe Ala Phe Asp Ile
            100                 105                 110

Trp Gly Gln Gly Thr Met Val Thr Val Ser Ser
        115                 120
```

<210> SEQ ID NO 45
<211> LENGTH: 110
<212> TYPE: PRT
<213> ORGANISM: Artificial Sequence
<220> FEATURE:
<223> OTHER INFORMATION: ZKA230 VL

<400> SEQUENCE: 45

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Tyr Val Tyr Trp Tyr Gln Gln Leu Pro Gly Thr Ala Pro Lys Leu Leu
        35                  40                  45

Ile Cys Ile Asn Asp His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Gly Gly Leu Val Phe Gly Gly Gly Thr Lys Leu Thr Val Leu
            100                 105                 110
```

<210> SEQ ID NO 46
<211> LENGTH: 24
<212> TYPE: DNA
<213> ORGANISM: Artificial Sequence
<220> FEATURE:
<223> OTHER INFORMATION: ZKA230 CDRH1

<400> SEQUENCE: 46
ggtggctcca tcagtagtga ctac                                         24

<210> SEQ ID NO 47
<211> LENGTH: 21
<212> TYPE: DNA
<213> ORGANISM: Artificial Sequence
<220> FEATURE:
<223> OTHER INFORMATION: ZKA230 CDRH2

<400> SEQUENCE: 47
atctattaca gtgggagcac c                                            21

<210> SEQ ID NO 48
<211> LENGTH: 51
<212> TYPE: DNA
<213> ORGANISM: Artificial Sequence
<220> FEATURE:
<223> OTHER INFORMATION: ZKA230 CDRH3

<400> SEQUENCE: 48
gcgaggagga ggaagtatga ttcccttcgg gggagttttg cttttgatat c            51

<210> SEQ ID NO 49
<211> LENGTH: 24
<212> TYPE: DNA
<213> ORGANISM: Artificial Sequence
<220> FEATURE:
<223> OTHER INFORMATION: ZKA230 CDRL1

<400> SEQUENCE: 49
agctccaaca tcggaggtaa ttat                                         24

<210> SEQ ID NO 50

<400> SEQUENCE: 50

000

<210> SEQ ID NO 51
<211> LENGTH: 27
<212> TYPE: DNA
<213> ORGANISM: Artificial Sequence
<220> FEATURE:
<223> OTHER INFORMATION: ZKA230 CDRL2 long

<400> SEQUENCE: 51
ctcatctgta ttaatgatca ccggccc                                      27

<210> SEQ ID NO 52
<211> LENGTH: 33
<212> TYPE: DNA
<213> ORGANISM: Artificial Sequence
<220> FEATURE:
<223> OTHER INFORMATION: ZKA230 CDRL3

<400> SEQUENCE: 52
gcaacatggg atgacagcct gggtggcctt gta                               33

<210> SEQ ID NO 53
<211> LENGTH: 370
<212> TYPE: DNA
<213> ORGANISM: Artificial Sequence
<220> FEATURE:
<223> OTHER INFORMATION: ZKA230 VH

<400> SEQUENCE: 53

```
caggtgcagc tgcaggagtc gggcccaggc ctggtgaagc cttcggagac cctgtccctc      60
acctgcgcag tctctggtgg ctccatcagt agtgactact ggagctggat ccggcagccc     120
ccagggaagg gactggagtg gattgggtat atctattaca gtgggagcac caactacaac     180
ccctccctca agagtcgagt caccatatca gtagacacgt ccaagaacca cttctccctg     240
aagctgaact ctgtgaccgc tgcggacacg gccgtgtatt actgtgcgag gaggaggaag     300
tatgattccc tttggggggag ttttgctttt gatatctggg gccaagggac aatggtcacc     360
gtctcttcag                                                            370
```

<210> SEQ ID NO 54
<211> LENGTH: 331
<212> TYPE: DNA
<213> ORGANISM: Artificial Sequence
<220> FEATURE:
<223> OTHER INFORMATION: ZKA230 VL

<400> SEQUENCE: 54

```
cagtctgtgc tgactcagcc accctcagcg tctgggaccc ccgggcagag ggtcaccatc      60
tcttgttctg gaagcagctc caacatcgga ggtaattatg tatactggta ccagcagctc     120
ccaggaacgg cccccaaact cctcatctgt attaatgatc accggccctc aggggtccct     180
gaccgattct ctggctccaa gtctggcacc tcagcctccc tggccatcag tgggctccag     240
tccgaggatg aggctgatta ttactgtgca acatgggatg acagcctggg tggccttgta     300
ttcggcggag ggaccaagct gaccgtccta g                                    331
```

<210> SEQ ID NO 55
<211> LENGTH: 8
<212> TYPE: PRT
<213> ORGANISM: Artificial Sequence
<220> FEATURE:
<223> OTHER INFORMATION: ZKA78 CDRH1

<400> SEQUENCE: 55

Gly Phe Thr Phe Ser Asn Tyr Ala
1               5

<210> SEQ ID NO 56
<211> LENGTH: 8
<212> TYPE: PRT
<213> ORGANISM: Artificial Sequence
<220> FEATURE:
<223> OTHER INFORMATION: ZKA78 CDRH2

<400> SEQUENCE: 56

Ile Gly Arg Asn Gly Asp Ser Ile
1               5

<210> SEQ ID NO 57
<211> LENGTH: 16
<212> TYPE: PRT
<213> ORGANISM: Artificial Sequence
<220> FEATURE:

```
<223> OTHER INFORMATION: ZKA78 CDRH3

<400> SEQUENCE: 57

Val Lys Asp Leu Ala Ile Pro Glu Ser Tyr Arg Ile Glu Ala Asp Tyr
1               5                   10                  15

<210> SEQ ID NO 58
<211> LENGTH: 12
<212> TYPE: PRT
<213> ORGANISM: Artificial Sequence
<220> FEATURE:
<223> OTHER INFORMATION: ZKA78 CDRL1

<400> SEQUENCE: 58

Gln Ser Val Leu Tyr Arg Ser Asn Asn Lys Asn Tyr
1               5                   10

<210> SEQ ID NO 59

<400> SEQUENCE: 59

000

<210> SEQ ID NO 60
<211> LENGTH: 9
<212> TYPE: PRT
<213> ORGANISM: Artificial Sequence
<220> FEATURE:
<223> OTHER INFORMATION: ZKA78 CDRL2 long

<400> SEQUENCE: 60

Leu Ile Tyr Trp Ala Ser Thr Arg Glu
1               5

<210> SEQ ID NO 61
<211> LENGTH: 9
<212> TYPE: PRT
<213> ORGANISM: Artificial Sequence
<220> FEATURE:
<223> OTHER INFORMATION: ZKA78 CDRL3

<400> SEQUENCE: 61

Gln Gln Tyr Tyr Ser Ser Pro Arg Thr
1               5

<210> SEQ ID NO 62
<211> LENGTH: 123
<212> TYPE: PRT
<213> ORGANISM: Artificial Sequence
<220> FEATURE:
<223> OTHER INFORMATION: ZKA78 VH

<400> SEQUENCE: 62

Glu Val Gln Leu Ala Glu Ser Gly Gly Gly Leu Val Gln Pro Gly Gly
1               5                   10                  15

Ser Leu Thr Leu Ser Cys Ser Gly Ser Gly Phe Thr Phe Ser Asn Tyr
            20                  25                  30

Ala Met Val Trp Ala Arg Gln Ala Pro Gly Lys Gly Leu Glu Tyr Val
        35                  40                  45

Ser Gly Ile Gly Arg Asn Gly Asp Ser Ile Tyr Tyr Thr Asp Ser Val
    50                  55                  60

Lys Gly Arg Phe Thr Ile Ser Arg Asp Asn Ser Lys Ser Met Val Tyr
65                  70                  75                  80

Leu Gln Met Ser Ser Leu Arg Thr Glu Asp Thr Ala Val Tyr Tyr Cys
```

```
                85                  90                  95
Val Lys Asp Leu Ala Ile Pro Glu Ser Tyr Arg Ile Glu Ala Asp Tyr
            100                 105                 110

Trp Gly Gln Gly Thr Leu Val Ile Val Ser Ala
            115                 120
```

<210> SEQ ID NO 63
<211> LENGTH: 113
<212> TYPE: PRT
<213> ORGANISM: Artificial Sequence
<220> FEATURE:
<223> OTHER INFORMATION: ZKA78 VL

<400> SEQUENCE: 63

```
Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Arg
            20                  25                  30

Ser Asn Asn Lys Asn Tyr Leu Ser Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Pro Leu Gln Ala Glu Asp Val Ala Val Tyr Tyr Cys Gln Gln
                85                  90                  95

Tyr Tyr Ser Ser Pro Arg Thr Phe Gly Gln Gly Thr Lys Val Glu Ile
            100                 105                 110

Lys
```

<210> SEQ ID NO 64
<211> LENGTH: 24
<212> TYPE: DNA
<213> ORGANISM: Artificial Sequence
<220> FEATURE:
<223> OTHER INFORMATION: ZKA78 CDRH1

<400> SEQUENCE: 64
ggcttcactt ttagtaacta tgca                                          24

<210> SEQ ID NO 65
<211> LENGTH: 24
<212> TYPE: DNA
<213> ORGANISM: Artificial Sequence
<220> FEATURE:
<223> OTHER INFORMATION: ZKA78 CDRH2

<400> SEQUENCE: 65
atcgggcgca acggggactc tatc                                          24

<210> SEQ ID NO 66
<211> LENGTH: 48
<212> TYPE: DNA
<213> ORGANISM: Artificial Sequence
<220> FEATURE:
<223> OTHER INFORMATION: ZKA78 CDRH3

<400> SEQUENCE: 66
gtgaaagatc tggccatccc cgagtcctac agaattgaag ctgattat                48

<210> SEQ ID NO 67

```
<211> LENGTH: 36
<212> TYPE: DNA
<213> ORGANISM: Artificial Sequence
<220> FEATURE:
<223> OTHER INFORMATION: ZKA78 CDRL1

<400> SEQUENCE: 67
cagtccgtgc tgtaccgctc taacaacaag aattac                          36

<210> SEQ ID NO 68

<400> SEQUENCE: 68

000

<210> SEQ ID NO 69
<211> LENGTH: 27
<212> TYPE: DNA
<213> ORGANISM: Artificial Sequence
<220> FEATURE:
<223> OTHER INFORMATION: ZKA78 CDRL2 long

<400> SEQUENCE: 69
ctgatctatt gggcttcaac ccgggaa                                    27

<210> SEQ ID NO 70
<211> LENGTH: 27
<212> TYPE: DNA
<213> ORGANISM: Artificial Sequence
<220> FEATURE:
<223> OTHER INFORMATION: ZKA78 CDRL3

<400> SEQUENCE: 70
cagcagtact attctagtcc tcgaact                                    27

<210> SEQ ID NO 71
<211> LENGTH: 370
<212> TYPE: DNA
<213> ORGANISM: Artificial Sequence
<220> FEATURE:
<223> OTHER INFORMATION: ZKA78 VH

<400> SEQUENCE: 71
gaggtgcagc tggcagaatc aggcggggga ctggtccagc ctggcggcag cctgacactg    60
tcttgcagtg gatcaggctt cacttttagt aactatgcaa tggtgtgggc aaggcaggct   120
cctgggaagg gactggagta tgtctctggc atcgggcgca acggggactc tatctactat   180
actgatagtg tgaagggccg gttcaccatc agcagagaca atagcaaatc catggtgtac   240
ctgcagatga gctccctgcg aaccgaagac acagcagtgt actattgcgt gaaagatctg   300
gccatccccg agtcctacag aattgaagct gattattggg gacagggcac cctggtcatc   360
gtgagcgccg                                                          370

<210> SEQ ID NO 72
<211> LENGTH: 340
<212> TYPE: DNA
<213> ORGANISM: Artificial Sequence
<220> FEATURE:
<223> OTHER INFORMATION: ZKA78 VL

<400> SEQUENCE: 72
gacatcgtga tgacacagtc tccagatagt ctggcagtca gtctggggga gagggccact    60
attaactgca agagctccca gtccgtgctg taccgctcta acaacaagaa ttacctgtct   120
```

```
tggtatcagc agaagcccgg acagccccct aaactgctga tctattgggc ttcaacccgg      180
gaaagcggcg tcccagacag attctcaggc agcgggtccg gaacagactt caccctgaca      240
attagccccc tgcaggcaga ggacgtggct gtctactatt gtcagcagta ctattctagt      300
cctcgaactt tcggccaggg gaccaaggtg gaaatcaaac                            340
```

<210> SEQ ID NO 73
<211> LENGTH: 8
<212> TYPE: PRT
<213> ORGANISM: Artificial Sequence
<220> FEATURE:
<223> OTHER INFORMATION: ZKA64 CDRH1

<400> SEQUENCE: 73

Gly Tyr Thr Phe Thr Gly Tyr His
1               5

<210> SEQ ID NO 74
<211> LENGTH: 8
<212> TYPE: PRT
<213> ORGANISM: Artificial Sequence
<220> FEATURE:
<223> OTHER INFORMATION: ZKA64 CDRH2

<400> SEQUENCE: 74

Ile Asn Pro Asn Ser Gly Gly Thr
1               5

<210> SEQ ID NO 75
<211> LENGTH: 12
<212> TYPE: PRT
<213> ORGANISM: Artificial Sequence
<220> FEATURE:
<223> OTHER INFORMATION: ZKA64 CDRH3

<400> SEQUENCE: 75

Ala Arg Met Ser Ser Ser Ile Trp Gly Phe Asp His
1               5                   10

<210> SEQ ID NO 76
<211> LENGTH: 6
<212> TYPE: PRT
<213> ORGANISM: Artificial Sequence
<220> FEATURE:
<223> OTHER INFORMATION: ZKA64 CDRL1

<400> SEQUENCE: 76

Gln Ser Val Leu Ile Asn
1               5

<210> SEQ ID NO 77

<400> SEQUENCE: 77

000

<210> SEQ ID NO 78
<211> LENGTH: 9
<212> TYPE: PRT
<213> ORGANISM: Artificial Sequence
<220> FEATURE:
<223> OTHER INFORMATION: ZKA64 CDRL2 long

<400> SEQUENCE: 78

Leu Ile Tyr Gly Ala Ser Ser Arg Ala
1               5

-continued

<210> SEQ ID NO 79
<211> LENGTH: 10
<212> TYPE: PRT
<213> ORGANISM: Artificial Sequence
<220> FEATURE:
<223> OTHER INFORMATION: ZKA64 CDRL3

<400> SEQUENCE: 79

Gln Gln Tyr Asn Asp Trp Pro Pro Ile Thr
1               5                   10

<210> SEQ ID NO 80
<211> LENGTH: 119
<212> TYPE: PRT
<213> ORGANISM: Artificial Sequence
<220> FEATURE:
<223> OTHER INFORMATION: ZKA64 VH

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Ile Asp Trp Val Arg Gln Ala Arg Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Ser Asp Asp Ser Ala Val Tyr Tyr Cys
                85                  90                  95

Ala Arg Met Ser Ser Ser Ile Trp Gly Phe Asp His Trp Gly Gln Gly
            100                 105                 110

Thr Leu Val Thr Val Ser Ser
        115

<210> SEQ ID NO 81
<211> LENGTH: 108
<212> TYPE: PRT
<213> ORGANISM: Artificial Sequence
<220> FEATURE:
<223> OTHER INFORMATION: ZKA64 VL

<400> SEQUENCE: 81

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Leu Ile Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Pro
                85                  90                  95

Ile Thr Phe Gly Gln Gly Thr Arg Leu Glu Ile Lys
            100                 105

```
<210> SEQ ID NO 82
<211> LENGTH: 24
<212> TYPE: DNA
<213> ORGANISM: Artificial Sequence
<220> FEATURE:
<223> OTHER INFORMATION: ZKA64 CDRH1

<400> SEQUENCE: 82
ggctacacct tcacagggta tcac                                          24

<210> SEQ ID NO 83
<211> LENGTH: 24
<212> TYPE: DNA
<213> ORGANISM: Artificial Sequence
<220> FEATURE:
<223> OTHER INFORMATION: ZKA64 CDRH2

<400> SEQUENCE: 83 attaaccta attctggcgg gacc                                           24

<210> SEQ ID NO 84
<211> LENGTH: 36
<212> TYPE: DNA
<213> ORGANISM: Artificial Sequence
<220> FEATURE:
<223> OTHER INFORMATION: ZKA64 CDRH3

<400> SEQUENCE: 84
gctcggatga gctcctctat ttggggcttc gatcat                             36

<210> SEQ ID NO 85
<211> LENGTH: 18
<212> TYPE: DNA
<213> ORGANISM: Artificial Sequence
<220> FEATURE:
<223> OTHER INFORMATION: ZKA64 CDRL1

<400> SEQUENCE: 85
cagtctgtgc tgattaac                                                 18

<210> SEQ ID NO 86

<400> SEQUENCE: 86

000

<210> SEQ ID NO 87
<211> LENGTH: 27
<212> TYPE: DNA
<213> ORGANISM: Artificial Sequence
<220> FEATURE:
<223> OTHER INFORMATION: ZKA64 CDRL2 long

<400> SEQUENCE: 87
ctgatctatg gagcatcctc cagggct                                       27

<210> SEQ ID NO 88
<211> LENGTH: 30
<212> TYPE: DNA
<213> ORGANISM: Artificial Sequence
<220> FEATURE:
<223> OTHER INFORMATION: ZKA64 CDRL3

<400> SEQUENCE: 88
cagcagtaca atgattggcc ccctatcaca                                    30
```

-continued

<210> SEQ ID NO 89
<211> LENGTH: 358
<212> TYPE: DNA
<213> ORGANISM: Artificial Sequence
<220> FEATURE:
<223> OTHER INFORMATION: ZKA64 VH

<400> SEQUENCE: 89

```
caggtgcagc tggtccagag cggagcagag gtgaagaaac ccggcgcctc agtgaaggtc    60
agctgcaaag cttccggcta caccttcaca gggtatcaca tcgactgggt gaggcaggca   120
agaggacagg gactgaatg gatgggacgg attaaccta attctggcgg gaccaactac    180
gcccagaagt ttcagggccg agtgactatg accagagaca ccagcatctc acagcttat    240 atgcagctgt cccggctgag atctgacgat agtgccgtct actattgtgc tcggatgagc   300
tcctctattt ggggcttcga tcattgggg cagggaacac tggtgactgt cagttcag    358
```

<210> SEQ ID NO 90
<211> LENGTH: 325
<212> TYPE: DNA
<213> ORGANISM: Artificial Sequence
<220> FEATURE:
<223> OTHER INFORMATION: ZKA64 VL

<400> SEQUENCE: 90

```
gagatcgtga tgactcagtc tccagccacc ctgtcagtca gcccaggaga acgggcaacc    60
ctgtcttgca gagcctccca gtctgtgctg attaacctgg cttggtacca gcagaagcca   120
ggccaggcac cccgactgct gatctatgga gcatcctcca gggctaccgg cattcctgca   180
cgcttcagtg gatcaggaag cggaacagag tttaccctga caatctctag tctgcagtcc   240
gaagacttcg ctgtctacta ttgtcagcag tacaatgatt ggccccctat cacatttggc   300
caggggacta gactggagat caagc                                         325
```

<210> SEQ ID NO 91
<211> LENGTH: 8
<212> TYPE: PRT
<213> ORGANISM: Artificial Sequence
<220> FEATURE:
<223> OTHER INFORMATION: ZKA15 CDRH1

<400> SEQUENCE: 91

Gly Gly Phe Ile Asn Ser Tyr Tyr
1               5

<210> SEQ ID NO 92
<211> LENGTH: 7
<212> TYPE: PRT
<213> ORGANISM: Artificial Sequence
<220> FEATURE:
<223> OTHER INFORMATION: ZKA15 CDRH2

<400> SEQUENCE: 92

Ile Tyr Lys Ser Gly Ser Thr
1               5

<210> SEQ ID NO 93
<211> LENGTH: 14
<212> TYPE: PRT
<213> ORGANISM: Artificial Sequence
<220> FEATURE:
<223> OTHER INFORMATION: ZKA15 CDRH3

<400> SEQUENCE: 93

Ala Arg Asp Pro Tyr Gly Asp Tyr Val Lys Ala Phe Asp Ile
1               5                   10

<210> SEQ ID NO 94
<211> LENGTH: 11
<212> TYPE: PRT
<213> ORGANISM: Artificial Sequence
<220> FEATURE:
<223> OTHER INFORMATION: ZKA15 CDRL1

<400> SEQUENCE: 94

Gln Ser Leu Leu His Ser Asn Gly Tyr Asn Tyr
1               5                   10

<210> SEQ ID NO 95

<400> SEQUENCE: 95

000

<210> SEQ ID NO 96
<211> LENGTH: 9
<212> TYPE: PRT
<213> ORGANISM: Artificial Sequence
<220> FEATURE:
<223> OTHER INFORMATION: ZKA15 CDRL2 long

<400> SEQUENCE: 96

Leu Ile Tyr Leu Gly Ser Asn Arg Ala
1               5

<210> SEQ ID NO 97
<211> LENGTH: 8
<212> TYPE: PRT
<213> ORGANISM: Artificial Sequence
<220> FEATURE:
<223> OTHER INFORMATION: ZKA15 CDRL3

<400> SEQUENCE: 97

Met Gln Ala Leu Gln Thr Val Thr
1               5

<210> SEQ ID NO 98
<211> LENGTH: 120
<212> TYPE: PRT
<213> ORGANISM: Artificial Sequence
<220> FEATURE:
<223> OTHER INFORMATION: ZKA15 VH

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Phe Ile Asn Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Lys Ser Gly Ser Thr Asn Tyr Asn Pro Ser Leu Lys
        50                  55                  60

Ser Arg Val Thr Met Ser Leu Asp Thr Ser Lys Tyr Gln Phe Ser Leu
65                  70                  75                  80

Lys Leu Arg Ser Val Thr Ala Ala Asp Thr Ala Val Tyr Tyr Cys Ala
                85                  90                  95

Arg Asp Pro Tyr Gly Asp Tyr Val Lys Ala Phe Asp Ile Trp Gly Gln

```
                    100                 105                 110
Gly Thr Met Val Thr Val Ser Ser
        115                 120

<210> SEQ ID NO 99
<211> LENGTH: 111
<212> TYPE: PRT
<213> ORGANISM: Artificial Sequence
<220> FEATURE:
<223> OTHER INFORMATION: ZKA15 VL

<400> SEQUENCE: 99

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Val Thr Phe Gly Pro Gly Thr Lys Val Asp Ile Lys
            100                 105                 110

<210> SEQ ID NO 100
<211> LENGTH: 24
<212> TYPE: DNA
<213> ORGANISM: Artificial Sequence
<220> FEATURE:
<223> OTHER INFORMATION: ZKA15 CDRH1

<400> SEQUENCE: 100
ggtggcttca tcaatagtta ctac                                              24

<210> SEQ ID NO 101
<211> LENGTH: 21
<212> TYPE: DNA
<213> ORGANISM: Artificial Sequence
<220> FEATURE:
<223> OTHER INFORMATION: ZKA15 CDRH2

<400> SEQUENCE: 101
atctataaaa gtgggagcac c                                                 21

<210> SEQ ID NO 102
<211> LENGTH: 42
<212> TYPE: DNA
<213> ORGANISM: Artificial Sequence
<220> FEATURE:
<223> OTHER INFORMATION: ZKA15 CDRH3

<400> SEQUENCE: 102
gcgagagatc cctacggtga ctacgttaag gcttttgata tt                          42

<210> SEQ ID NO 103
<211> LENGTH: 33
<212> TYPE: DNA
<213> ORGANISM: Artificial Sequence
<220> FEATURE:
<223> OTHER INFORMATION: ZKA15 CDRL1
```

```
<400> SEQUENCE: 103
cagagcctcc tgcatagtaa tggatacaac tat                         33

<210> SEQ ID NO 104

<400> SEQUENCE: 104

000

<210> SEQ ID NO 105
<211> LENGTH: 27
<212> TYPE: DNA
<213> ORGANISM: Artificial Sequence
<220> FEATURE:
<223> OTHER INFORMATION: ZKA15 CDRL2 long

<400> SEQUENCE: 105
ctgatctatt tgggttctaa tcgggcc                                27

<210> SEQ ID NO 106
<211> LENGTH: 24
<212> TYPE: DNA
<213> ORGANISM: Artificial Sequence
<220> FEATURE:
<223> OTHER INFORMATION: ZKA15 CDRL3

<400> SEQUENCE: 106
atgcaagctc tacaaactgt cact                                   24

<210> SEQ ID NO 107
<211> LENGTH: 361
<212> TYPE: DNA
<213> ORGANISM: Artificial Sequence
<220> FEATURE:
<223> OTHER INFORMATION: ZKA15 VH

<400> SEQUENCE: 107
caggtgcagc tgcaggagtc ggggccagga ctggtgaagc cttcggagac cctgtccctc    60
acctgcactg tctccggtgg cttcatcaat agttactact ggagctggat ccggcagccc   120
gccgggaagg gactggagtg gattgggcgt atctataaaa gtgggagcac caactacaac   180
ccctccctca gagtcgagt caccatgtca ctagacacgt ccaagtacca gttctccctg   240
aagctgaggt ctgtgaccgc cgctgacacg gccgtgtatt actgtgcgag agatccctac   300
ggtgactacg ttaaggcttt tgatatttgg ggccaaggga caatggtcac cgtctcttca   360
g                                                                  361

<210> SEQ ID NO 108
<211> LENGTH: 334
<212> TYPE: DNA
<213> ORGANISM: Artificial Sequence
<220> FEATURE:
<223> OTHER INFORMATION: ZKA15 VL

<400> SEQUENCE: 108
gatattgtga tgactcagtc tccactctcc ctgcccgtca cccctggaga gccggcctcc    60
atctcctgca ggtctagtca gagcctcctg catagtaatg gatacaacta tttgaattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttgggggtt tattactgca tgcaagctct acaaactgtc   300
```

```
actttcggcc ctgggaccaa agtggatatc aaac                                334
```

<210> SEQ ID NO 109
<211> LENGTH: 8
<212> TYPE: PRT
<213> ORGANISM: Artificial Sequence
<220> FEATURE:
<223> OTHER INFORMATION: ZKA25 CDRH1

<400> SEQUENCE: 109

Gly Phe Thr Phe Arg Ser His Trp
1               5

<210> SEQ ID NO 110
<211> LENGTH: 8
<212> TYPE: PRT
<213> ORGANISM: Artificial Sequence
<220> FEATURE:
<223> OTHER INFORMATION: ZKA25 CDRH2

<400> SEQUENCE: 110

Ile Lys Glu Asp Gly Tyr Glu Lys
1               5

<210> SEQ ID NO 111
<211> LENGTH: 14
<212> TYPE: PRT
<213> ORGANISM: Artificial Sequence
<220> FEATURE:
<223> OTHER INFORMATION: ZKA25 CDRH3

<400> SEQUENCE: 111

Ala Arg Asp Leu Arg Val Tyr Ser Gly Arg Gly Phe Asp Pro
1               5                   10

<210> SEQ ID NO 112
<211> LENGTH: 6
<212> TYPE: PRT
<213> ORGANISM: Artificial Sequence
<220> FEATURE:
<223> OTHER INFORMATION: ZKA25 CDRL1

<400> SEQUENCE: 112

Lys Leu Gly Asp Lys Tyr
1               5

<210> SEQ ID NO 113

<400> SEQUENCE: 113

000

<210> SEQ ID NO 114
<211> LENGTH: 9
<213> ORGANISM: Artificial Sequence
<220> FEATURE:
<223> OTHER INFORMATION: ZKA25 CDRL2 long

<400> SEQUENCE: 114

Val Ile Tyr Gln Asp Ser Lys Arg Pro
1               5

<210> SEQ ID NO 115
<211> LENGTH: 9
<212> TYPE: PRT

```
<213> ORGANISM: Artificial Sequence
<220> FEATURE:
<223> OTHER INFORMATION: ZKA25 CDRL3

<400> SEQUENCE: 115

Gln Ala Trp Asp Ser Ser Thr Val Val
1               5

<210> SEQ ID NO 116
<211> LENGTH: 121
<212> TYPE: PRT
<213> ORGANISM: Artificial Sequence
<220> FEATURE:
<223> OTHER INFORMATION: ZKA25 VH

<400> SEQUENCE: 116

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Arg Ser His
            20                  25                  30

Trp Met Ser Trp Val Arg Gln Ala Pro Gly Lys Gly Leu Glu Trp Val
        35                  40                  45

Ala Asn Ile Lys Glu Asp Gly Tyr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Lys Ser Leu Arg Ala Glu Asp Thr Ala Val Tyr Tyr Cys
                85                  90                  95

Ala Arg Asp Leu Arg Val Tyr Ser Gly Arg Gly Phe Asp Pro Trp Gly
            100                 105                 110

Gln Gly Thr Leu Val Thr Val Ser Ser
        115                 120

<210> SEQ ID NO 117
<211> LENGTH: 106
<212> TYPE: PRT
<213> ORGANISM: Artificial Sequence
<220> FEATURE:
<223> OTHER INFORMATION: ZKA25 VL

<400> SEQUENCE: 117

Ser Tyr Glu Leu Thr Gln Pro Pro Ser Leu Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Ala Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 118
<211> LENGTH: 24
<212> TYPE: DNA
<213> ORGANISM: Artificial Sequence
```

```
<220> FEATURE:
<223> OTHER INFORMATION: ZKA25 CDRH1

<400> SEQUENCE: 118
ggattcacct ttagaagtca ttgg                                          24

<210> SEQ ID NO 119
<211> LENGTH: 24
<212> TYPE: DNA
<213> ORGANISM: Artificial Sequence
<220> FEATURE:
<223> OTHER INFORMATION: ZKA25 CDRH2

<400> SEQUENCE: 119
ataaaggaag atggatatga gaaa                                          24

<210> SEQ ID NO 120
<211> LENGTH: 42
<212> TYPE: DNA
<213> ORGANISM: Artificial Sequence
<220> FEATURE:
<223> OTHER INFORMATION: ZKA25 CDRH3

<400> SEQUENCE: 120
gcgagagatt tgagggtata tagtgggaga ggtttcgacc cc                      42

<210> SEQ ID NO 121
<211> LENGTH: 18
<212> TYPE: DNA
<213> ORGANISM: Artificial Sequence
<220> FEATURE:
<223> OTHER INFORMATION: ZKA25 CDRL1

<400> SEQUENCE: 121
aaattggggg ataaatat                                                 18

<210> SEQ ID NO 122

<400> SEQUENCE: 122

000

<210> SEQ ID NO 123
<211> LENGTH: 27
<212> TYPE: DNA
<213> ORGANISM: Artificial Sequence
<220> FEATURE:
<223> OTHER INFORMATION: ZKA25 CDRL2 long

<400> SEQUENCE: 123
gtcatctatc aagatagcaa gcggccc                                       27

<210> SEQ ID NO 124
<211> LENGTH: 27
<212> TYPE: DNA
<213> ORGANISM: Artificial Sequence
<220> FEATURE:
<223> OTHER INFORMATION: ZKA25 CDRL3

<400> SEQUENCE: 124
caggcgtggg acagcagcac tgtggta                                       27

<210> SEQ ID NO 125
<211> LENGTH: 364
<212> TYPE: DNA
<213> ORGANISM: Artificial Sequence
```

<220> FEATURE:
<223> OTHER INFORMATION: ZKA25 VH

<400> SEQUENCE: 125
gaggtgcagt tggtggagtc tgggggaggc ttggtccggc ctgggggtc cctgagactc    60 tcctgtgcag cctctggatt cacctttaga agtcattgga tgagttgggt ccgccaggct   120
ccagggaagg gctggagtg gtggccaac ataaaggaag atggatatga aaatactat    180 gtggactctg tgaagggccg attcaccatc tccagagaca cgccaagaa ctcactgtat    240 ctgcaaatga gagcctgag agccgaggac acggccgtgt attactgtgc gagagatttg    300
agggtatata gtgggagagg tttcgacccc tggggccagg gaaccctggt caccgtctcc    360
tcag    364

<210> SEQ ID NO 126
<211> LENGTH: 319
<212> TYPE: DNA
<213> ORGANISM: Artificial Sequence
<220> FEATURE:
<223> OTHER INFORMATION: ZKA25 VL

<400> SEQUENCE: 126
tcctatgagc tgactcagcc accctcactg tccgtgtccc caggacagac agccagcatc    60
acctgctctg gagataaaatt gggggataaa tatgcttgct ggtatcagca aaagccaggc   120 cagtccctg tgttggtcat ctatcaagat agcaagcggc cctcagggat ccctgcgcga    180
ttctctggct ccaactctgg gaacacagcc actctgacca tcagcgggac ccaggctatg    240
gatgaggctg actattactg tcaggcgtgg gacagcagca ctgtggtatt cggtggaggg    300
accaagctga ccgtcctag    319

<210> SEQ ID NO 127
<211> LENGTH: 10
<212> TYPE: PRT
<213> ORGANISM: Artificial Sequence
<220> FEATURE:
<223> OTHER INFORMATION: ZKA35 CDRH1

<400> SEQUENCE: 127

Gly Gly Ser Ile Ser Thr Gly Gly Tyr Tyr
1               5                   10

<210> SEQ ID NO 128
<211> LENGTH: 7
<212> TYPE: PRT
<213> ORGANISM: Artificial Sequence
<220> FEATURE:
<223> OTHER INFORMATION: ZKA35 CDRH2

<400> SEQUENCE: 128

Ile Tyr Tyr Ser Gly Asn Thr
1               5

<210> SEQ ID NO 129
<211> LENGTH: 12
<212> TYPE: PRT
<213> ORGANISM: Artificial Sequence
<220> FEATURE:
<223> OTHER INFORMATION: ZKA35 CDRH3

<400> SEQUENCE: 129

Ala Lys Gly Gly Gly Arg Glu Arg Pro Phe Asp Tyr
1               5                   10

<210> SEQ ID NO 130
<211> LENGTH: 8
<212> TYPE: PRT
<213> ORGANISM: Artificial Sequence
<220> FEATURE:
<223> OTHER INFORMATION: ZKA35 CDRL1

<400> SEQUENCE: 130

Ser Ser Asn Ile Gly Arg Asn Tyr
1               5

<210> SEQ ID NO 131

<400> SEQUENCE: 131

000

<210> SEQ ID NO 132
<211> LENGTH: 9
<212> TYPE: PRT
<213> ORGANISM: Artificial Sequence
<220> FEATURE:
<223> OTHER INFORMATION: ZKA35 CDRL2 long

<400> SEQUENCE: 132

Leu Ile Tyr Arg Asn Asn Gln Arg Pro
1               5

<210> SEQ ID NO 133
<211> LENGTH: 12
<212> TYPE: PRT
<213> ORGANISM: Artificial Sequence
<220> FEATURE:
<223> OTHER INFORMATION: ZKA35 CDRL3

<400> SEQUENCE: 133

Val Ala Trp Asp Asp Ser Arg Ser Gly Phe Val Val
1               5                   10

<210> SEQ ID NO 134
<211> LENGTH: 120
<212> TYPE: PRT
<213> ORGANISM: Artificial Sequence
<220> FEATURE:
<223> OTHER INFORMATION: ZKA35 VH

<400> SEQUENCE: 134

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Lys Leu Ser Ser Val Thr Ala Ala Asp Thr Ala Val Tyr Tyr
                85                  90                  95

Cys Ala Lys Gly Gly Gly Arg Glu Arg Pro Phe Asp Tyr Trp Gly Gln
                100                 105                 110

Gly Thr Leu Val Thr Val Ser Ser

<210> SEQ ID NO 135
<211> LENGTH: 111
<212> TYPE: PRT
<213> ORGANISM: Artificial Sequence
<220> FEATURE:
<223> OTHER INFORMATION: ZKA35 VL

<400> SEQUENCE: 135

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Arg Asn
            20                  25                  30
Tyr Val Asp Trp Tyr Gln Gln Leu Pro Gly Thr Ala Pro Lys Leu Leu
        35                  40                  45
Ile Tyr Arg Asn Asn Gln Arg Pro Ser Gly Val Pro Glu Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Val Ala Trp Asp Asp Ser Arg
                85                  90                  95
Ser Gly Phe Val Val Phe Gly Gly Gly Thr Lys Val Thr Val Leu
            100                 105                 110
```

<210> SEQ ID NO 136
<211> LENGTH: 30
<212> TYPE: DNA
<213> ORGANISM: Artificial Sequence
<220> FEATURE:
<223> OTHER INFORMATION: ZKA35 CDRH1

<400> SEQUENCE: 136
ggtggctcca tcagcactgg tggttactac                                    30

<210> SEQ ID NO 137
<211> LENGTH: 21
<212> TYPE: DNA
<213> ORGANISM: Artificial Sequence
<220> FEATURE:
<223> OTHER INFORMATION: ZKA35 CDRH2

<400> SEQUENCE: 137
atctattaca gtgggaacac c                                             21

<210> SEQ ID NO 138
<211> LENGTH: 36
<212> TYPE: DNA
<213> ORGANISM: Artificial Sequence
<220> FEATURE:
<223> OTHER INFORMATION: ZKA35 CDRH3

<400> SEQUENCE: 138
gcgaaaggag gagggaggga gcgacccttt gactac                             36

<210> SEQ ID NO 139
<211> LENGTH: 24
<212> TYPE: DNA
<213> ORGANISM: Artificial Sequence
<220> FEATURE:
<223> OTHER INFORMATION: ZKA35 CDRL1

<400> SEQUENCE: 139
agctccaaca tcggaagaaa ttat                                         24

<210> SEQ ID NO 140

<400> SEQUENCE: 140

000

<210> SEQ ID NO 141
<211> LENGTH: 27
<212> TYPE: DNA
<213> ORGANISM: Artificial Sequence
<220> FEATURE:
<223> OTHER INFORMATION: ZKA35 CDRL2 long

<400> SEQUENCE: 141
ctcatctata ggaataatca gcggccc                                      27

<210> SEQ ID NO 142
<211> LENGTH: 36
<212> TYPE: DNA
<213> ORGANISM: Artificial Sequence
<220> FEATURE:
<223> OTHER INFORMATION: ZKA35 CDRL3

<400> SEQUENCE: 142
gtagcatggg atgacagccg gagtggtttt gtggta                            36

<210> SEQ ID NO 143
<211> LENGTH: 361
<212> TYPE: DNA
<213> ORGANISM: Artificial Sequence
<220> FEATURE:
<223> OTHER INFORMATION: ZKA35 VH

<400> SEQUENCE: 143
caggtgcagc tgcaggagtc gggcccagga ctggtgaagc cttcacagac cctgtccctc    60
acctgcactg tctctggtgg ctccatcagc actggtggtt actactggag ctggatccgc   120
cagcacccag ggaagggcct ggagtggatt ggttacatct attacagtgg gaacacctac   180
tacaacccgt ccctcaagag tcgagttacc atatcagttg acacctctaa gaagcagttc   240
tccctgaagc tgagctctgt gactgccgcg gacacggccg tgtattactg tgcgaaagga   300
ggagggaggg agcgaccctt tgactactgg ggccagggaa ccctggtcac cgtctcctca   360
g                                                                 361

<210> SEQ ID NO 144
<211> LENGTH: 334
<212> TYPE: DNA
<213> ORGANISM: Artificial Sequence
<220> FEATURE:
<223> OTHER INFORMATION: ZKA35 VL

<400> SEQUENCE: 144
cagtctgtgc tgactcagcc accctcagcg tctgggaccc ccgggcagag ggtcaccatc    60
tcttgttctg gaagcagctc caacatcgga agaaattatg tagactggta ccagcaactc   120
ccaggaacgg cccccaaact cctcatctat aggaataatc agcggccctc agggtccct   180 gagcgattct ctggctccaa gtctggcacc tcagcctccc tggccatcag tgggctccgg   240
tccgaggatg aggctgatta ttactgtgta gcatgggatg acagccgag tggttttgtg   300 gtattcggcg gagggaccaa ggtgaccgtc ctag                              334

<210> SEQ ID NO 145
<211> LENGTH: 330
<212> TYPE: PRT
<213> ORGANISM: Artificial Sequence
<220> FEATURE:
<223> OTHER INFORMATION: IgG1 CH1-CH2-CH3 aa

<400> SEQUENCE: 145

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 146
<211> LENGTH: 330
<212> TYPE: PRT
<213> ORGANISM: Artificial Sequence
<220> FEATURE:

<223> OTHER INFORMATION: IgG1 CH1-CH2-CH3 LALA aa

<400> SEQUENCE: 146

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 147
<211> LENGTH: 107
<212> TYPE: PRT
<213> ORGANISM: Artificial Sequence
<220> FEATURE:
<223> OTHER INFORMATION: IgG CK aa

<400> SEQUENCE: 147

```
Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 148
<211> LENGTH: 106
<212> TYPE: PRT
<213> ORGANISM: Artificial Sequence
<220> FEATURE:
<223> OTHER INFORMATION: IgG CL aa

<400> SEQUENCE: 148

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 149
<211> LENGTH: 990
<212> TYPE: DNA
<213> ORGANISM: Artificial Sequence
<220> FEATURE:
<223> OTHER INFORMATION: IgG1 CH1-CH2-CH3 nucl

<400> SEQUENCE: 149

```
gcgtcgacca agggcccatc ggtcttcccc ctggcaccct cctccaagag cacctctggg      60
ggcacagcgg ccctgggctg cctggtcaag gactacttcc ccgaacctgt gacggtctcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
```

```
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggtaaa                                    990

<210> SEQ ID NO 150
<211> LENGTH: 990
<212> TYPE: DNA
<213> ORGANISM: Artificial Sequence
<220> FEATURE:
<223> OTHER INFORMATION: IgG1 CH1-CH2-CH3 LALA nucl

<400> SEQUENCE: 150
gcgtcgacca agggcccatc ggtcttcccc ctggcaccct cctccaagag cacctctggg     60
ggcacagcgg ccctgggctg cctggtcaag gactacttcc ccgaacctgt gacggtctcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaagc cgcggggggga    360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggtaaa                                    990

<210> SEQ ID NO 151
<211> LENGTH: 321
<212> TYPE: DNA
<213> ORGANISM: Artificial Sequence
<220> FEATURE:
<223> OTHER INFORMATION: IgG CK nucl

<400> SEQUENCE: 151
cgtacggtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
```

```
agcttcaaca ggggagagtg t                                               321
```

<210> SEQ ID NO 152
<211> LENGTH: 318
<212> TYPE: DNA
<213> ORGANISM: Artificial Sequence
<220> FEATURE:
<223> OTHER INFORMATION: IgG CL nucl

<400> SEQUENCE: 152

```
ggtcagccca aggctgcccc ctcggtcact ctgttcccgc cctcctctga ggagcttcaa       60
gccaacaagg ccacactggt gtgtctcata agtgacttct acccgggagc cgtgacagtg      120
gcttggaaag cagatagcag ccccgtcaag gcgggagtgg agaccaccac accctccaaa      180
caaagcaaca caagtacgc ggccagcagc tatctgagcc tgacgcctga gcagtggaag       240
tcccacagaa gctacagctg ccaggtcacg catgaaggga gcaccgtgga aagacagtg       300 gcccctacag aatgttca                                                    318
```

<210> SEQ ID NO 153
<211> LENGTH: 8
<212> TYPE: PRT
<213> ORGANISM: Artificial Sequence
<220> FEATURE:
<223> OTHER INFORMATION: ZKA10 CDRH1

<400> SEQUENCE: 153

Gly Phe Thr Phe Ser Asp Ser Tyr
1               5

<210> SEQ ID NO 154
<211> LENGTH: 8
<212> TYPE: PRT
<213> ORGANISM: Artificial Sequence
<220> FEATURE:
<223> OTHER INFORMATION: ZKA10 CDRH2

<400> SEQUENCE: 154

Ile Ser Ser Ser Ser Pro Phe Thr
1               5

<210> SEQ ID NO 155
<211> LENGTH: 17
<212> TYPE: PRT
<213> ORGANISM: Artificial Sequence
<220> FEATURE:
<223> OTHER INFORMATION: ZKA10 CDRH3

<400> SEQUENCE: 155

Ala Arg Gly Leu Val Arg Asp Gly Tyr Lys Trp Leu Tyr Phe Phe Asp
1               5                   10                  15

Tyr

<210> SEQ ID NO 156
<211> LENGTH: 124
<212> TYPE: PRT
<213> ORGANISM: Artificial Sequence
<220> FEATURE:
<223> OTHER INFORMATION: ZKA10 VH

<400> SEQUENCE: 156

Gln Val Gln Leu Val Glu Ser Gly Gly Gly Leu Val Glu Pro Arg Gly
1               5                   10                  15

Ser Leu Arg Leu Ser Cys Ala Ala Ser Gly Phe Thr Phe Ser Asp Ser

```
                    20                  25                  30
Tyr Met Ser Trp Ile Arg Gln Ala Pro Gly Lys Gly Leu Glu Trp Ile
            35                  40                  45

Ser Tyr Ile Ser Ser Ser Pro Phe Thr Asn Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Val Arg Asp Gly Tyr Lys Trp Leu Tyr Phe Phe Asp
            100                 105                 110

Tyr Trp Gly Gln Gly Thr Leu Val Thr Val Ser Ser
        115                 120

<210> SEQ ID NO 157
<211> LENGTH: 8
<212> TYPE: PRT
<213> ORGANISM: Artificial Sequence
<220> FEATURE:
<223> OTHER INFORMATION: ZKA18 CDRH1

<400> SEQUENCE: 157

Gly Phe Thr Phe Ser Ser Tyr Gly
1               5

<210> SEQ ID NO 158
<211> LENGTH: 8
<212> TYPE: PRT
<213> ORGANISM: Artificial Sequence
<220> FEATURE:
<223> OTHER INFORMATION: ZKA18 CDRH2

<400> SEQUENCE: 158

Ile Trp Tyr Asp Gly Ser Asn Lys
1               5

<210> SEQ ID NO 159
<211> LENGTH: 13
<212> TYPE: PRT
<213> ORGANISM: Artificial Sequence
<220> FEATURE:
<223> OTHER INFORMATION: ZKA18 CDRH3

<400> SEQUENCE: 159

Ala Arg Asp Asp Ser Gly Tyr Ser Glu Pro Phe Asp Tyr
1               5                   10

<210> SEQ ID NO 160
<211> LENGTH: 120
<212> TYPE: PRT
<213> ORGANISM: Artificial Sequence
<220> FEATURE:
<223> OTHER INFORMATION: ZKA18 VH

<400> SEQUENCE: 160

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
```

```
                    50                  55                  60
Lys Gly Arg Phe Thr Ile Thr Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                     85                  90                  95

Ala Arg Asp Asp Ser Gly Tyr Ser Glu Pro Phe Asp Tyr Trp Gly Gln
                100                 105                 110

Gly Thr Leu Val Thr Val Ser Ser
            115                 120

<210> SEQ ID NO 161
<211> LENGTH: 8
<212> TYPE: PRT
<213> ORGANISM: Artificial Sequence
<220> FEATURE:
<223> OTHER INFORMATION: ZKA28 CDRH1

<400> SEQUENCE: 161

Gly Phe Thr Val Ser Arg Asn Tyr
1               5

<210> SEQ ID NO 162
<211> LENGTH: 7
<212> TYPE: PRT
<213> ORGANISM: Artificial Sequence
<220> FEATURE:
<223> OTHER INFORMATION: ZKA28 CDRH2

<400> SEQUENCE: 162

Ile Tyr Ser Gly Gly Ser Thr
1               5

<210> SEQ ID NO 163
<211> LENGTH: 10
<212> TYPE: PRT
<213> ORGANISM: Artificial Sequence
<220> FEATURE:
<223> OTHER INFORMATION: ZKA28 CDRH3

<400> SEQUENCE: 163

Ala Arg Trp Ile Asn Asp Ala Phe Asp Ile
1               5                   10

<210> SEQ ID NO 164
<211> LENGTH: 116
<212> TYPE: PRT
<213> ORGANISM: Artificial Sequence
<220> FEATURE:
<223> OTHER INFORMATION: ZKA28 VH

<400> SEQUENCE: 164

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
```

```
                85                  90                  95

Arg Trp Ile Asn Asp Ala Phe Asp Ile Trp Gly Gln Gly Thr Met Val
            100                 105                 110

Thr Val Ser Ser
        115

<210> SEQ ID NO 165
<211> LENGTH: 8
<212> TYPE: PRT
<213> ORGANISM: Artificial Sequence
<220> FEATURE:
<223> OTHER INFORMATION: ZKA29 CDRH1

<400> SEQUENCE: 165

Gly Phe Thr Phe Ser Arg Tyr Ser
1               5

<210> SEQ ID NO 166
<211> LENGTH: 8
<212> TYPE: PRT
<213> ORGANISM: Artificial Sequence
<220> FEATURE:
<223> OTHER INFORMATION: ZKA29 CDRH2

<400> SEQUENCE: 166

Ile Ser Pro Arg Ser Thr Thr Ile
1               5

<210> SEQ ID NO 167
<211> LENGTH: 15
<212> TYPE: PRT
<213> ORGANISM: Artificial Sequence
<220> FEATURE:
<223> OTHER INFORMATION: ZKA29 CDRH3

<400> SEQUENCE: 167

Ala Arg Glu Asp Cys Thr Asn Gly Val Cys Tyr Arg Val Asp Tyr
1               5                   10                  15

<210> SEQ ID NO 168
<211> LENGTH: 122
<212> TYPE: PRT
<213> ORGANISM: Artificial Sequence
<220> FEATURE:
<223> OTHER INFORMATION: ZKA29 VH

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Arg Tyr
            20                  25                  30

Ser Met Asn Trp Val Arg Gln Ala Pro Gly Lys Gly Leu Glu Trp Val
        35                  40                  45

Ser Tyr Ile Ser Pro Arg Ser Thr Thr Ile Tyr Tyr Ala Asp Ser Val
    50                  55                  60

Glu Gly Arg Phe Thr Val Ser Arg Asp Asn Ala Lys Asn Ser Leu Tyr
65                  70                  75                  80

Leu Gln Leu Asn Ser Leu Arg Ala Glu Asp Thr Ala Val Tyr Tyr Cys
                85                  90                  95

Ala Arg Glu Asp Cys Thr Asn Gly Val Cys Tyr Arg Val Asp Tyr Trp
            100                 105                 110

Gly Gln Gly Thr Leu Val Thr Val Ser Ser
```

-continued

<210> SEQ ID NO 169
<211> LENGTH: 8
<212> TYPE: PRT
<213> ORGANISM: Artificial Sequence
<220> FEATURE:
<223> OTHER INFORMATION: ZKA33 CDRH1

<400> SEQUENCE: 169

Gly Phe Thr Phe Ser Arg Asn Trp
1               5

<210> SEQ ID NO 170
<211> LENGTH: 8
<212> TYPE: PRT
<213> ORGANISM: Artificial Sequence
<220> FEATURE:
<223> OTHER INFORMATION: ZKA33 CDRH2

<400> SEQUENCE: 170

Ile Lys Glu Asp Gly Asn Glu Lys
1               5

<210> SEQ ID NO 171
<211> LENGTH: 15
<212> TYPE: PRT
<213> ORGANISM: Artificial Sequence
<220> FEATURE:
<223> OTHER INFORMATION: ZKA33 CDRH3

<400> SEQUENCE: 171

Ala Arg Pro Phe His Gln Gly Gly Tyr Ala Tyr Gly Leu Ala Tyr
1               5                   10                  15

<210> SEQ ID NO 172
<211> LENGTH: 122
<212> TYPE: PRT
<213> ORGANISM: Artificial Sequence
<220> FEATURE:
<223> OTHER INFORMATION: ZKA33 VH

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Trp Met Thr Trp Val Arg Gln Ala Pro Gly Lys Gly Leu Glu Trp Val
        35                  40                  45

Ala Asn Ile Lys Glu Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Phe His Gln Gly Gly Tyr Ala Tyr Gly Leu Ala Tyr Trp
            100                 105                 110

Gly Gln Gly Thr Leu Val Thr Val Ser Ser
        115                 120

<210> SEQ ID NO 173
<211> LENGTH: 8
<212> TYPE: PRT

<210> SEQ ID NO 173
<211> LENGTH: 8
<212> TYPE: PRT
<213> ORGANISM: Artificial Sequence
<220> FEATURE:
<223> OTHER INFORMATION: ZKA39 CDRH1

<400> SEQUENCE: 173

Gly Phe Thr Phe Ser Thr Tyr Ser
1               5

<210> SEQ ID NO 174
<211> LENGTH: 8
<212> TYPE: PRT
<213> ORGANISM: Artificial Sequence
<220> FEATURE:
<223> OTHER INFORMATION: ZKA39 CDRH2

<400> SEQUENCE: 174

Ile Ser Pro Ser Ser Ser Thr Ile
1               5

<210> SEQ ID NO 175
<211> LENGTH: 15
<212> TYPE: PRT
<213> ORGANISM: Artificial Sequence
<220> FEATURE:
<223> OTHER INFORMATION: ZKA39 CDRH3

<400> SEQUENCE: 175

Ala Arg Glu Tyr Cys Ser Gly Gly Ser Cys Tyr Leu Leu Asp Tyr
1               5                   10                  15

<210> SEQ ID NO 176
<211> LENGTH: 122
<212> TYPE: PRT
<213> ORGANISM: Artificial Sequence
<220> FEATURE:
<223> OTHER INFORMATION: ZKA39 VH

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Pro Ser Ser Ser Thr Ile Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Gln Tyr Tyr Cys
                85                  90                  95

Ala Arg Glu Tyr Cys Ser Gly Gly Ser Cys Tyr Leu Leu Asp Tyr Trp
            100                 105                 110

Gly Gln Gly Thr Leu Val Thr Val Ser Ser
        115                 120

<210> SEQ ID NO 177
<211> LENGTH: 8
<212> TYPE: PRT
<213> ORGANISM: Artificial Sequence
<220> FEATURE:
<223> OTHER INFORMATION: ZKA43 CDRH1

<400> SEQUENCE: 177

```
Gly Gly Ser Ile Thr Ser Tyr Tyr
1               5
```

<210> SEQ ID NO 178
<211> LENGTH: 7
<212> TYPE: PRT
<213> ORGANISM: Artificial Sequence
<220> FEATURE:
<223> OTHER INFORMATION: ZKA43 CDRH2

<400> SEQUENCE: 178

```
Ser His Tyr Ser Gly Ser Thr
1               5
```

<210> SEQ ID NO 179
<211> LENGTH: 13
<212> TYPE: PRT
<213> ORGANISM: Artificial Sequence
<220> FEATURE:
<223> OTHER INFORMATION: ZKA43 CDRH3

<400> SEQUENCE: 179

```
Ala Arg Gly Ile Tyr Ser Gly Lys Asn Trp Phe Asp Pro
1               5                   10
```

<210> SEQ ID NO 180
<211> LENGTH: 119
<212> TYPE: PRT
<213> ORGANISM: Artificial Sequence
<220> FEATURE:
<223> OTHER INFORMATION: ZKA43 VH

<400> SEQUENCE: 180

```
Gln Val Gln Leu Gln Glu Ser Gly Pro Gly Leu Val Lys Pro Ser Glu
1               5                   10                  15

Thr Leu Ser Leu Thr Cys Thr Val Tyr Gly Ser Ile Thr Ser Tyr
            20                  25                  30

Tyr Trp Thr Trp Ile Arg Gln Pro Pro Gly Lys Gly Leu Glu Trp Ile
        35                  40                  45

Gly Tyr Ser His Tyr Ser Gly Ser Thr Asn Tyr Asn Pro Ser Leu Lys
    50                  55                  60

Ser Arg Val Thr Ile Ser Ile Asp Thr Ser Lys Ser Gln Phe Ser Leu
65                  70                  75                  80

Asn Leu Asn Ser Val Thr Ala Ala Asp Thr Ala Val Tyr Tyr Cys Ala
                85                  90                  95

Arg Gly Ile Tyr Ser Gly Lys Asn Trp Phe Asp Pro Trp Gly Gln Gly
            100                 105                 110

Thr Leu Val Thr Val Ser Ser
        115
```

<210> SEQ ID NO 181
<211> LENGTH: 8
<212> TYPE: PRT
<213> ORGANISM: Artificial Sequence
<220> FEATURE:
<223> OTHER INFORMATION: ZKA44 CDRH1

<400> SEQUENCE: 181

```
Gly Phe Thr Val Ser Thr Ser Tyr
1               5
```

<210> SEQ ID NO 182
<211> LENGTH: 7

```
<212> TYPE: PRT
<213> ORGANISM: Artificial Sequence
<220> FEATURE:
<223> OTHER INFORMATION: ZKA44 CDRH2

<400> SEQUENCE: 182

Ile Tyr Ser Ser Gly Ser Thr
1               5

<210> SEQ ID NO 183
<211> LENGTH: 10
<212> TYPE: PRT
<213> ORGANISM: Artificial Sequence
<220> FEATURE:
<223> OTHER INFORMATION: ZKA44 CDRH3

<400> SEQUENCE: 183

Ala Arg Val Ser Leu Gly Gly Leu Asp Pro
1               5                   10

<210> SEQ ID NO 184
<211> LENGTH: 116
<212> TYPE: PRT
<213> ORGANISM: Artificial Sequence
<220> FEATURE:
<223> OTHER INFORMATION: ZKA44 VH

<400> SEQUENCE: 184

Glu Val Gln Leu Val Glu Ser Gly Gly Gly Leu Ile Gln Pro Gly Gly
1               5                   10                  15

Ser Leu Arg Leu Ser Cys Val Ala Ser Gly Phe Thr Val Ser Thr Ser
            20                  25                  30

Tyr Met Asn Trp Val Arg Gln Ala Pro Gly Lys Gly Leu Glu Trp Val
        35                  40                  45

Ser Val Ile Tyr Ser Ser Gly Ser Thr Tyr Tyr Ala Asp Ser Val Lys
    50                  55                  60

Gly Arg Phe Thr Ile Ser Arg Asn Thr Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Ser Leu Gly Gly Leu Asp Pro Trp Gly Gln Gly Thr Pro Val
            100                 105                 110

Thr Val Ser Ser
        115

<210> SEQ ID NO 185
<211> LENGTH: 10
<212> TYPE: PRT
<213> ORGANISM: Artificial Sequence
<220> FEATURE:
<223> OTHER INFORMATION: ZKA46 CDRH1

<400> SEQUENCE: 185

Gly Phe Ser Leu Ser Asn Gly Arg Met Gly
1               5                   10

<210> SEQ ID NO 186
<211> LENGTH: 7
<212> TYPE: PRT
<213> ORGANISM: Artificial Sequence
<220> FEATURE:
<223> OTHER INFORMATION: ZKA46 CDRH2

<400> SEQUENCE: 186
```

Ile Phe Ser Asn Asp Glu Lys
1               5

<210> SEQ ID NO 187
<211> LENGTH: 13
<212> TYPE: PRT
<213> ORGANISM: Artificial Sequence
<220> FEATURE:
<223> OTHER INFORMATION: ZKA46 CDRH3

<400> SEQUENCE: 187

Ala Arg Val Glu Phe Arg Ala Gly Asn Tyr Leu Asp Ser
1               5                   10

<210> SEQ ID NO 188
<211> LENGTH: 121
<212> TYPE: PRT
<213> ORGANISM: Artificial Sequence
<220> FEATURE:
<223> OTHER INFORMATION: ZKA46 VH

<400> SEQUENCE: 188

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Gly
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Tyr Tyr Ser Thr Ser
    50                  55                  60

Leu Lys Asn Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Val Glu Phe Arg Ala Gly Asn Tyr Leu Asp Ser Trp Gly
            100                 105                 110

Gln Gly Thr Leu Val Thr Val Ser Ser
        115                 120

<210> SEQ ID NO 189
<211> LENGTH: 8
<212> TYPE: PRT
<213> ORGANISM: Artificial Sequence
<220> FEATURE:
<223> OTHER INFORMATION: ZKA50 CDRH1

<400> SEQUENCE: 189

Gly Tyr Thr Phe Thr Asn Ser Trp
1               5

<210> SEQ ID NO 190
<211> LENGTH: 8
<212> TYPE: PRT
<213> ORGANISM: Artificial Sequence
<220> FEATURE:
<223> OTHER INFORMATION: ZKA50 CDRH2

<400> SEQUENCE: 190

Ile Tyr Pro Gly Asp Ser Asp Thr
1               5

<210> SEQ ID NO 191

```
<211> LENGTH: 8
<212> TYPE: PRT
<213> ORGANISM: Artificial Sequence
<220> FEATURE:
<223> OTHER INFORMATION: ZKA50 CDRH3

<400> SEQUENCE: 191

Ala Arg Gln Pro Phe Phe Asp Tyr
1               5

<210> SEQ ID NO 192
<211> LENGTH: 115
<212> TYPE: PRT
<213> ORGANISM: Artificial Sequence
<220> FEATURE:
<223> OTHER INFORMATION: ZKA50 VH

<400> SEQUENCE: 192

Glu Val Gln Leu Val Gln Ser Gly Ala Gln Val Lys Lys Pro Gly Glu
1               5                   10                  15

Ser Leu Lys Ile Ser Cys Lys Ala Ser Gly Tyr Thr Phe Thr Asn Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Pro Phe Phe Asp Tyr Trp Gly Gln Gly Thr Leu Val Thr
            100                 105                 110

Val Ser Ser
        115

<210> SEQ ID NO 193
<211> LENGTH: 8
<212> TYPE: PRT
<213> ORGANISM: Artificial Sequence
<220> FEATURE:
<223> OTHER INFORMATION: ZKA54 CDRH1

<400> SEQUENCE: 193

Gly Tyr Thr Phe Thr Gly Tyr Tyr
1               5

<210> SEQ ID NO 194
<211> LENGTH: 8
<212> TYPE: PRT
<213> ORGANISM: Artificial Sequence
<220> FEATURE:
<223> OTHER INFORMATION: ZKA54 CDRH2

<400> SEQUENCE: 194

Ile Asn Ala Asn Ser Gly Gly Thr
1               5

<210> SEQ ID NO 195
<211> LENGTH: 18
<212> TYPE: PRT
<213> ORGANISM: Artificial Sequence
<220> FEATURE:
<223> OTHER INFORMATION: ZKA54 CDRH3
```

```
<400> SEQUENCE: 195

Ala His Ser Asp Ile Val Val Val Pro Ser Asp Asp Tyr Tyr Ala Leu
1               5                   10                  15

Asp Val

<210> SEQ ID NO 196
<211> LENGTH: 125
<212> TYPE: PRT
<213> ORGANISM: Artificial Sequence
<220> FEATURE:
<223> OTHER INFORMATION: ZKA54 VH

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Ala Asn Ser Gly Gly Thr Asn Phe Ala Gln Arg Phe
    50                  55                  60

Gln Gly Arg Val Thr Met Thr Trp Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala His Ser Asp Ile Val Val Val Pro Ser Asp Asp Tyr Tyr Ala Leu
            100                 105                 110

Asp Val Trp Gly Gln Gly Thr Thr Val Thr Val Ser Ser
        115                 120                 125

<210> SEQ ID NO 197
<211> LENGTH: 8
<212> TYPE: PRT
<213> ORGANISM: Artificial Sequence
<220> FEATURE:
<223> OTHER INFORMATION: ZKB18 CDRH1

<400> SEQUENCE: 197

Gly Tyr Ser Phe Thr Ser Tyr Trp
1               5

<210> SEQ ID NO 198
<211> LENGTH: 8
<212> TYPE: PRT
<213> ORGANISM: Artificial Sequence
<220> FEATURE:
<223> OTHER INFORMATION: ZKB18 CDRH2

<400> SEQUENCE: 198

Ile Tyr Pro Gly Asp Ser Asp Thr
1               5

<210> SEQ ID NO 199
<211> LENGTH: 8
<212> TYPE: PRT
<213> ORGANISM: Artificial Sequence
<220> FEATURE:
<223> OTHER INFORMATION: ZKB18 CDRH3

<400> SEQUENCE: 199

Ala Arg Gln Thr Pro Gly Asp Tyr
1               5
```

```
<210> SEQ ID NO 200
<211> LENGTH: 115
<212> TYPE: PRT
<213> ORGANISM: Artificial Sequence
<220> FEATURE:
<223> OTHER INFORMATION: ZKB18 VH

<400> SEQUENCE: 200

Glu Val Gln Leu Val Gln Ser Gly Ala Glu Val Lys Lys Pro Gly Glu
1               5                   10                  15

Ser Leu Lys Ile Ser Cys Lys Thr Phe Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Met Ile Tyr Pro Gly Asp Ser Asp Thr Arg Tyr Ser Pro Ser Phe
    50                  55                  60

Gln Gly Gln Val Thr Ile Ser Ala Asp Met Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Thr Pro Gly Asp Tyr Trp Gly Gln Gly Thr Leu Val Thr
            100                 105                 110

Val Ser Ser
        115

<210> SEQ ID NO 201
<211> LENGTH: 8
<212> TYPE: PRT
<213> ORGANISM: Artificial Sequence
<220> FEATURE:
<223> OTHER INFORMATION: ZKB20 CDRH1

<400> SEQUENCE: 201

Gly Tyr Phe Phe Thr Arg Tyr Val
1               5

<210> SEQ ID NO 202
<211> LENGTH: 8
<212> TYPE: PRT
<213> ORGANISM: Artificial Sequence
<220> FEATURE:
<223> OTHER INFORMATION: ZKB20 CDRH2

<400> SEQUENCE: 202

Ile Asn Thr Asp Asn Gly Ser Thr
1               5

<210> SEQ ID NO 203
<211> LENGTH: 15
<212> TYPE: PRT
<213> ORGANISM: Artificial Sequence
<220> FEATURE:
<223> OTHER INFORMATION: ZKB20 CDRH3

<400> SEQUENCE: 203

Ala Arg Gly Thr Gly Arg Asp Gly Tyr Asn Ser Phe Phe Ala Asn
1               5                   10                  15

<210> SEQ ID NO 204
<211> LENGTH: 122
<212> TYPE: PRT
<213> ORGANISM: Artificial Sequence
```

```
<220> FEATURE:
<223> OTHER INFORMATION: ZKB20 VH

<400> SEQUENCE: 204

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Phe Phe Thr Arg Tyr
            20                  25                  30

Val Ile Leu Trp Val Arg Gln Ala Pro Gly Gln Arg Pro Glu Trp Met
        35                  40                  45

Gly Trp Ile Asn Thr Asp Asn Gly Ser Thr Arg Tyr Ser Gln Lys Phe
    50                  55                  60

Gln Gly Arg Val Thr Ile Thr Lys Asp Thr Ser Ala Thr Ala Tyr
65                  70                  75                  80

Met Asp Leu Ser Ser Leu Lys Ser Asp Asp Thr Ala Val Tyr Tyr Cys
                85                  90                  95

Ala Arg Gly Thr Gly Arg Asp Gly Tyr Asn Ser Phe Phe Ala Asn Trp
            100                 105                 110

Gly Gln Gly Thr Leu Val Thr Val Ser Pro
        115                 120

<210> SEQ ID NO 205
<211> LENGTH: 8
<212> TYPE: PRT
<213> ORGANISM: Artificial Sequence
<220> FEATURE:
<223> OTHER INFORMATION: ZKB21 CDRH1

<400> SEQUENCE: 205

Gly Tyr Thr Phe Thr Gly Tyr Ser
1               5

<210> SEQ ID NO 206
<211> LENGTH: 8
<212> TYPE: PRT
<213> ORGANISM: Artificial Sequence
<220> FEATURE:
<223> OTHER INFORMATION: ZKB21 CDRH2

<400> SEQUENCE: 206

Ile Asp Thr Asn Ser Gly Asp Thr
1               5

<210> SEQ ID NO 207
<211> LENGTH: 11
<212> TYPE: PRT
<213> ORGANISM: Artificial Sequence
<220> FEATURE:
<223> OTHER INFORMATION: ZKB21 CDRH3

<400> SEQUENCE: 207

Ala Arg Asp Arg Glu Arg His Pro Phe Ser Tyr
1               5                   10

<210> SEQ ID NO 208
<211> LENGTH: 118
<212> TYPE: PRT
<213> ORGANISM: Artificial Sequence
<220> FEATURE:
<223> OTHER INFORMATION: ZKB21 VH

<400> SEQUENCE: 208

Gln Val Gln Leu Val Gln Ser Gly Ala Glu Val Lys Lys Pro Gly Ala
```

```
                1               5                  10                 15
            Ser Val Lys Val Ser Cys Lys Ala Ser Gly Tyr Thr Phe Thr Gly Tyr
                           20                  25                 30

Ser Ile His Trp Val Arg Gln Ala Pro Gly Gln Gly Leu Ala Trp Met
                       35                  40                 45

Gly Arg Ile Asp Thr Asn Ser Gly Asp Thr Asn Tyr Ala Glu Arg Phe
                   50                  55                 60

Gln Gly Arg Val Thr Met Thr Arg Asp Thr Ser Ile Ser Thr Ala Tyr
             65                 70                  75                 80

Met Glu Val Arg Arg Leu Arg Ser Asp Asp Thr Ala Val Tyr Tyr Cys
                           85                  90                 95

Ala Arg Asp Arg Glu Arg His Pro Phe Ser Tyr Trp Gly Gln Gly Thr
                       100                 105                110

Leu Val Thr Val Ser Ser
                    115

<210> SEQ ID NO 209
<211> LENGTH: 10
<212> TYPE: PRT
<213> ORGANISM: Artificial Sequence
<220> FEATURE:
<223> OTHER INFORMATION: ZKB23 CDRH1

<400> SEQUENCE: 209

Gly Gly Ser Ile Ser Ser Gly Asp Tyr Ser
1               5                  10

<210> SEQ ID NO 210
<211> LENGTH: 7
<212> TYPE: PRT
<213> ORGANISM: Artificial Sequence
<220> FEATURE:
<223> OTHER INFORMATION: ZKB23 CDRH2

<400> SEQUENCE: 210

Ile Thr His Ser Gly Thr Thr
1               5

<210> SEQ ID NO 211
<211> LENGTH: 9
<212> TYPE: PRT
<213> ORGANISM: Artificial Sequence
<220> FEATURE:
<223> OTHER INFORMATION: ZKB23 CDRH3

<400> SEQUENCE: 211

Ala Arg His Phe Gly Trp Phe Asp Pro
1               5

<210> SEQ ID NO 212
<211> LENGTH: 117
<212> TYPE: PRT
<213> ORGANISM: Artificial Sequence
<220> FEATURE:
<223> OTHER INFORMATION: ZKB23 VH

<400> SEQUENCE: 212

Gln Leu Gln Leu Gln Glu Ser Gly Ser Gly Leu Val Lys Pro Ser Gln
1               5                  10                 15

Thr Leu Ser Leu Thr Cys Ala Val Ser Gly Gly Ser Ile Ser Ser Gly
            20                  25                 30

Asp Tyr Ser Trp Ser Trp Ile Arg Gln Pro Pro Gly Lys Gly Leu Glu
```

```
                35                  40                  45
Trp Ile Gly Tyr Ile Thr His Ser Gly Thr Thr Tyr Phe Asn Pro Ser
         50                  55                  60

Leu Lys Ser Arg Val Thr Ile Ser Val Asp Arg Ser Arg Asn Gln Phe
 65                  70                  75                  80

Ser Leu Lys Val Thr Ser Val Thr Ala Ala Asp Thr Ala Val Tyr Tyr
                 85                  90                  95

Cys Ala Arg His Phe Gly Trp Phe Asp Pro Trp Gly Gln Gly Thr Leu
            100                 105                 110

Val Thr Val Ser Ser
        115
```

<210> SEQ ID NO 213
<211> LENGTH: 10
<212> TYPE: PRT
<213> ORGANISM: Artificial Sequence
<220> FEATURE:
<223> OTHER INFORMATION: ZKC29 CDRH1

<400> SEQUENCE: 213

```
Gly Gly Ser Ile Ser Ser Gly Glu Tyr Phe
 1               5                  10
```

<210> SEQ ID NO 214
<211> LENGTH: 7
<212> TYPE: PRT
<213> ORGANISM: Artificial Sequence
<220> FEATURE:
<223> OTHER INFORMATION: ZKC29 CDRH2

<400> SEQUENCE: 214

```
Ile His Asn Arg Gly Asn Thr
 1               5
```

<210> SEQ ID NO 215
<211> LENGTH: 22
<212> TYPE: PRT
<213> ORGANISM: Artificial Sequence
<220> FEATURE:
<223> OTHER INFORMATION: ZKC29 CDRH3

<400> SEQUENCE: 215

```
Ala Arg Gly Gly Gly Asp Leu Val Val Val Pro Asp Ser Ile Trp Asp
 1               5                  10                  15

Tyr Tyr Gly Met Asp Val
            20
```

<210> SEQ ID NO 216
<211> LENGTH: 130
<212> TYPE: PRT
<213> ORGANISM: Artificial Sequence
<220> FEATURE:
<223> OTHER INFORMATION: ZKC29 VH

<400> SEQUENCE: 216

```
Gln Val Gln Leu Gln Glu Ser Gly Pro Gly Leu Val Arg Pro Ser Gln
 1               5                  10                  15

Thr Leu Ser Leu Thr Cys Thr Val Ser Gly Gly Ser Ile Ser Ser Gly
                20                  25                  30

Glu Tyr Phe Trp Thr Trp Ile Arg Gln His Pro Lys Lys Gly Leu Glu
            35                  40                  45

Trp Ile Gly Tyr Ile His Asn Arg Gly Asn Thr Tyr Tyr Asn Pro Ser
```

```
                    50                  55                  60

Leu Lys Ser Arg Leu Ser Ile Ser Leu Asp Thr Ser Lys Asn His Leu
65                  70                  75                  80

Ser Leu Arg Leu Ser Ser Val Thr Ala Ala Asp Thr Ala Val Tyr Tyr
                    85                  90                  95

Cys Ala Arg Gly Gly Asp Leu Val Val Pro Asp Ser Ile Trp
                100                 105                 110

Asp Tyr Tyr Gly Met Asp Val Trp Gly Gln Gly Thr Thr Val Thr Val
                115                 120                 125

Ser Ser
    130

<210> SEQ ID NO 217
<211> LENGTH: 10
<212> TYPE: PRT
<213> ORGANISM: Artificial Sequence
<220> FEATURE:
<223> OTHER INFORMATION: ZKC31 CDRH1

<400> SEQUENCE: 217

Gly Gly Ser Ile Ser Ser Gly Gly Tyr His
1               5                   10

<210> SEQ ID NO 218
<211> LENGTH: 7
<212> TYPE: PRT
<213> ORGANISM: Artificial Sequence
<220> FEATURE:
<223> OTHER INFORMATION: ZKC31 CDRH2

<400> SEQUENCE: 218

Ile Tyr Tyr Ser Gly Ser Thr
1               5

<210> SEQ ID NO 219
<211> LENGTH: 19
<212> TYPE: PRT
<213> ORGANISM: Artificial Sequence
<220> FEATURE:
<223> OTHER INFORMATION: ZKC31 CDRH3

<400> SEQUENCE: 219

Ala Arg Asp Arg Ser Glu Pro Gly Glu Tyr His Tyr Tyr Tyr Ala
1               5                   10                  15

Met Asp Val

<210> SEQ ID NO 220
<211> LENGTH: 127
<212> TYPE: PRT
<213> ORGANISM: Artificial Sequence
<220> FEATURE:
<223> OTHER INFORMATION: ZKC31 VH

<400> SEQUENCE: 220

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gly Tyr His Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60
```

Leu Lys Arg Arg Val Thr Ile Ser Val Asp Thr Ser Lys Asn Gln Phe
65                  70                  75                  80

Ser Leu Lys Leu Ser Ser Val Ser Ala Ala Asp Thr Ala Val Tyr Tyr
                85                  90                  95

Cys Ala Arg Asp Arg Ser Glu Pro Gly Glu Tyr His Tyr Tyr Tyr Tyr
            100                 105                 110

Ala Met Asp Val Trp Gly Gln Gly Thr Thr Val Thr Val Ser Ser
        115                 120                 125

<210> SEQ ID NO 221
<211> LENGTH: 8
<212> TYPE: PRT
<213> ORGANISM: Artificial Sequence
<220> FEATURE:
<223> OTHER INFORMATION: ZKC32 CDRH1

<400> SEQUENCE: 221

Gly Phe Thr Val Ser Ser Asn Tyr
1               5

<210> SEQ ID NO 222
<211> LENGTH: 7
<212> TYPE: PRT
<213> ORGANISM: Artificial Sequence
<220> FEATURE:
<223> OTHER INFORMATION: ZKC32 CDRH2

<400> SEQUENCE: 222

Ile Tyr Ser Ser Gly Ser Thr
1               5

<210> SEQ ID NO 223
<211> LENGTH: 11
<212> TYPE: PRT
<213> ORGANISM: Artificial Sequence
<220> FEATURE:
<223> OTHER INFORMATION: ZKC32 CDRH3

<400> SEQUENCE: 223

Ala Arg Gly Lys Lys Gly Asn Ala Phe Asp Ile
1               5                   10

<210> SEQ ID NO 224
<211> LENGTH: 117
<212> TYPE: PRT
<213> ORGANISM: Artificial Sequence
<220> FEATURE:
<223> OTHER INFORMATION: ZKC32 VH

<400> SEQUENCE: 224

Glu Val Gln Leu Val Glu Ser Gly Gly Asp Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Ser Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Gly Asp Thr Ala Val Tyr Tyr Cys Ala
                85                  90                  95

```
Arg Gly Lys Lys Gly Asn Ala Phe Asp Ile Trp Gly Gln Gly Thr Val
            100                 105                 110

Val Thr Val Ser Ser
        115

<210> SEQ ID NO 225
<211> LENGTH: 10
<212> TYPE: PRT
<213> ORGANISM: Artificial Sequence
<220> FEATURE:
<223> OTHER INFORMATION: ZKC33, CDRH1

<400> SEQUENCE: 225

Gly Asp Ser Ile Ser Ser Arg Thr Phe Ser
1               5                   10

<210> SEQ ID NO 226
<211> LENGTH: 7
<212> TYPE: PRT
<213> ORGANISM: Artificial Sequence
<220> FEATURE:
<223> OTHER INFORMATION: ZKC33 CDRH2

<400> SEQUENCE: 226

Ile Tyr Tyr Ser Gly Ser Thr
1               5

<210> SEQ ID NO 227
<211> LENGTH: 18
<212> TYPE: PRT
<213> ORGANISM: Artificial Sequence
<220> FEATURE:
<223> OTHER INFORMATION: ZKC33 CDRH3

<400> SEQUENCE: 227

Ala Arg Arg Asn Ala Glu Phe Phe Ser Phe Trp Ser Tyr Tyr Gly Met
1               5                   10                  15

Asp Val

<210> SEQ ID NO 228
<211> LENGTH: 126
<212> TYPE: PRT
<213> ORGANISM: Artificial Sequence
<220> FEATURE:
<223> OTHER INFORMATION: ZKC33 VH

<400> SEQUENCE: 228

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Ser Ser Arg
            20                  25                  30

Thr Phe Ser Trp Ser Trp Ile Arg Gln Pro Pro Gly Lys Gly Leu Glu
        35                  40                  45

Trp Val Gly His Ile Tyr Tyr Ser Gly Ser Thr Asp Tyr Asn Pro Ser
    50                  55                  60

Leu Lys Ser Arg Ile Ser Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Asn Ala Glu Phe Phe Ser Phe Trp Ser Tyr Tyr Gly
            100                 105                 110
```

```
Met Asp Val Trp Gly His Gly Thr Ala Val Ile Val Ser Ser
            115                 120                 125
```

<210> SEQ ID NO 229
<211> LENGTH: 10
<212> TYPE: PRT
<213> ORGANISM: Artificial Sequence
<220> FEATURE:
<223> OTHER INFORMATION: ZKC34 CDRH1

<400> SEQUENCE: 229

```
Gly Gly Ser Ile Asn Ser Gly Gly Tyr Tyr
1               5                   10
```

<210> SEQ ID NO 230
<211> LENGTH: 7
<212> TYPE: PRT
<213> ORGANISM: Artificial Sequence
<220> FEATURE:
<223> OTHER INFORMATION: ZKC34 CDRH2

<400> SEQUENCE: 230

```
Ile Leu His Ser Gly Asn Thr
1               5
```

<210> SEQ ID NO 231
<211> LENGTH: 15
<212> TYPE: PRT
<213> ORGANISM: Artificial Sequence
<220> FEATURE:
<223> OTHER INFORMATION: ZKC34 CDRH3

<400> SEQUENCE: 231

```
Ala Arg Ala Gly Asp Tyr Tyr Ser Gly Tyr Val Pro Pro Glu Tyr
1               5                   10                  15
```

<210> SEQ ID NO 232
<211> LENGTH: 123
<212> TYPE: PRT
<213> ORGANISM: Artificial Sequence
<220> FEATURE:
<223> OTHER INFORMATION: ZKC34 VH

<400> SEQUENCE: 232

```
Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Asn Ser Gly
            20                  25                  30

Gly Tyr Tyr Trp Ser Trp Val Arg Gln His Pro Gly Lys Gly Leu Glu
        35                  40                  45

Trp Ile Gly Tyr Ile Leu His Ser Gly Asn Thr Asn Tyr Asn Pro Ser
    50                  55                  60

Leu Lys Ser Arg Val Asn Ile Phe Val Asp Thr Ser Glu Asn Gln Phe
65                  70                  75                  80

Ser Leu Lys Leu Arg Ser Val Thr Ala Ala Asp Thr Ala Ile Tyr Phe
                85                  90                  95

Cys Ala Arg Ala Gly Asp Tyr Tyr Ser Gly Tyr Val Pro Pro Glu Tyr
            100                 105                 110

Trp Gly Pro Gly Thr Leu Val Thr Val Ser Ser
            115                 120
```

<210> SEQ ID NO 233
<211> LENGTH: 8

```
<212> TYPE: PRT
<213> ORGANISM: Artificial Sequence
<220> FEATURE:
<223> OTHER INFORMATION: ZKD25 CDRH1

<400> SEQUENCE: 233

Gly Phe Thr Val Ser Ser Asn Tyr
1               5

<210> SEQ ID NO 234
<211> LENGTH: 7
<212> TYPE: PRT
<213> ORGANISM: Artificial Sequence
<220> FEATURE:
<223> OTHER INFORMATION: ZKD25 CDRH2

<400> SEQUENCE: 234

Ile Tyr Ser Gly Gly Ser Thr
1               5

<210> SEQ ID NO 235
<211> LENGTH: 11
<212> TYPE: PRT
<213> ORGANISM: Artificial Sequence
<220> FEATURE:
<223> OTHER INFORMATION: ZKD25 CDRH3

<400> SEQUENCE: 235

Ala Arg Phe Gly Gly Asn Pro Ser Phe Asp Tyr
1               5                   10

<210> SEQ ID NO 236
<211> LENGTH: 117
<212> TYPE: PRT
<213> ORGANISM: Artificial Sequence
<220> FEATURE:
<223> OTHER INFORMATION: ZKD25 VH

<400> SEQUENCE: 236

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asn Ser Val Lys
    50                  55                  60

Gly Arg Phe Thr Ile Ser Arg Asp Lys Ser Lys Asn Thr Leu Tyr Leu
65                  70                  75                  80

Gln Met Asn Asn Leu Arg Ala Glu Asp Thr Ala Val Tyr Phe Cys Ala
                85                  90                  95

Arg Phe Gly Gly Asn Pro Ser Phe Asp Tyr Trp Gly Gln Gly Thr Leu
            100                 105                 110

Val Thr Val Ser Ser
        115

<210> SEQ ID NO 237
<211> LENGTH: 8
<212> TYPE: PRT
<213> ORGANISM: Artificial Sequence
<220> FEATURE:
<223> OTHER INFORMATION: ZKA3 CDRH1

<400> SEQUENCE: 237
```

Gly Phe Ile Phe Ser Asn Tyr Ala
1               5

<210> SEQ ID NO 238
<211> LENGTH: 8
<212> TYPE: PRT
<213> ORGANISM: Artificial Sequence
<220> FEATURE:
<223> OTHER INFORMATION: ZKA3 CDRH2

<400> SEQUENCE: 238

Ile Gly Gly Lys Gly Asp Ser Ile
1               5

<210> SEQ ID NO 239
<211> LENGTH: 16
<212> TYPE: PRT
<213> ORGANISM: Artificial Sequence
<220> FEATURE:
<223> OTHER INFORMATION: ZKA3 CDRH3

<400> SEQUENCE: 239

Val Lys Asp Leu Ala Val Leu Glu Ser Asp Arg Leu Glu Val Asp Gln
1               5                   10                  15

<210> SEQ ID NO 240
<211> LENGTH: 123
<212> TYPE: PRT
<213> ORGANISM: Artificial Sequence
<220> FEATURE:
<223> OTHER INFORMATION: ZKA3 VH

<400> SEQUENCE: 240

Glu Val Gln Leu Ala Glu Ser Gly Gly Gly Leu Val Gln Pro Gly Gly
1               5                   10                  15

Ser Leu Arg Leu Ser Cys Ser Gly Ser Gly Phe Ile Phe Ser Asn Tyr
            20                  25                  30

Ala Met Val Trp Ala Arg Gln Ala Pro Gly Lys Gly Leu Glu Tyr Val
        35                  40                  45

Ser Gly Ile Gly Gly Lys Gly Asp Ser Ile Tyr His Ile Asp Ser Val
    50                  55                  60

Lys Gly Arg Phe Thr Ile Ser Arg Asp Asn Ser Lys Arg Thr Val Tyr
65                  70                  75                  80

Leu Gln Met Ser Arg Leu Arg Thr Glu Asp Thr Ala Val Tyr Tyr Cys
                85                  90                  95

Val Lys Asp Leu Ala Val Leu Glu Ser Asp Arg Leu Glu Val Asp Gln
            100                 105                 110

Trp Gly Gln Gly Thr Leu Val Ile Val Ser Ala
        115                 120

<210> SEQ ID NO 241
<211> LENGTH: 8
<212> TYPE: PRT
<213> ORGANISM: Artificial Sequence
<220> FEATURE:
<223> OTHER INFORMATION: ZKA4 CDRH1

<400> SEQUENCE: 241

Gly Phe Thr Phe Ser Ser Tyr Val
1               5

<210> SEQ ID NO 242

```
<211> LENGTH: 8
<212> TYPE: PRT
<213> ORGANISM: Artificial Sequence
<220> FEATURE:
<223> OTHER INFORMATION: ZKA4 CDRH2

<400> SEQUENCE: 242

Thr Ser Tyr Asp Gly Ser Asn Lys
1               5

<210> SEQ ID NO 243
<211> LENGTH: 20
<212> TYPE: PRT
<213> ORGANISM: Artificial Sequence
<220> FEATURE:
<223> OTHER INFORMATION: ZKA4 CDRH3

<400> SEQUENCE: 243

Ala Arg Gly Pro Val Pro Tyr Trp Ser Gly Glu Ser Tyr Ser Gly Ala
1               5                   10                  15

Tyr Phe Asp Phe
            20

<210> SEQ ID NO 244
<211> LENGTH: 127
<212> TYPE: PRT
<213> ORGANISM: Artificial Sequence
<220> FEATURE:
<223> OTHER INFORMATION: ZKA4 VH

<400> SEQUENCE: 244

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Thr Val Thr Ser Tyr Asp Gly Ser Asn Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Gly Glu Asp Thr Ala Ile Tyr Tyr Cys
                85                  90                  95

Ala Arg Gly Pro Val Pro Tyr Trp Ser Gly Glu Ser Tyr Ser Gly Ala
            100                 105                 110

Tyr Phe Asp Phe Trp Gly Gln Gly Ile Leu Val Thr Val Ser Ser
        115                 120                 125

<210> SEQ ID NO 245
<211> LENGTH: 8
<212> TYPE: PRT
<213> ORGANISM: Artificial Sequence
<220> FEATURE:
<223> OTHER INFORMATION: ZKA5 CDRH1

<400> SEQUENCE: 245

Gly Phe Thr Phe Ser Asn Tyr Tyr
1               5

<210> SEQ ID NO 246
<211> LENGTH: 8
<212> TYPE: PRT
<213> ORGANISM: Artificial Sequence
```

<220> FEATURE:
<223> OTHER INFORMATION: ZKA5 CDRH2

<400> SEQUENCE: 246

Met Ser Ser Ser Glu Thr Ile Lys
1               5

<210> SEQ ID NO 247
<211> LENGTH: 19
<212> TYPE: PRT
<213> ORGANISM: Artificial Sequence
<220> FEATURE:
<223> OTHER INFORMATION: ZKA5 CDRH3

<400> SEQUENCE: 247

Ala Arg Ser Gly Ile Glu Thr Val Ala Gly Ser Ile Asp Tyr Tyr Gly
1               5                   10                  15
Met Asp Val

<210> SEQ ID NO 248
<211> LENGTH: 126
<212> TYPE: PRT
<213> ORGANISM: Artificial Sequence
<220> FEATURE:
<223> OTHER INFORMATION: ZKA5 VH

<400> SEQUENCE: 248

Gln Val Gln Leu Val Glu Ser Gly Gly Gly Leu Val Lys Pro Gly Gly
1               5                   10                  15

Ser Leu Arg Leu Ser Cys Ala Gly Ser Gly Phe Thr Phe Ser Asn Tyr
            20                  25                  30

Tyr Met Thr Trp Ile Arg Gln Ala Pro Gly Lys Gly Leu Glu Leu Val
        35                  40                  45

Ser Tyr Met Ser Ser Ser Glu Thr Ile Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Arg Tyr Tyr Cys
                85                  90                  95

Ala Arg Ser Gly Ile Glu Thr Val Ala Gly Ser Ile Asp Tyr Tyr Gly
            100                 105                 110

Met Asp Val Trp Gly His Gly Thr Pro Val Thr Val Ser Ser
        115                 120                 125

<210> SEQ ID NO 249
<211> LENGTH: 8
<212> TYPE: PRT
<213> ORGANISM: Artificial Sequence
<220> FEATURE:
<223> OTHER INFORMATION: ZKA6 CDRH1

<400> SEQUENCE: 249

Asp Phe Thr Val Ser Asn Tyr Ala
1               5

<210> SEQ ID NO 250
<211> LENGTH: 8
<212> TYPE: PRT
<213> ORGANISM: Artificial Sequence
<220> FEATURE:
<223> OTHER INFORMATION: ZKA6 CDRH2

<400> SEQUENCE: 250

Val Ser Tyr Asp Gly Ser Asn Lys
1               5

<210> SEQ ID NO 251
<211> LENGTH: 19
<212> TYPE: PRT
<213> ORGANISM: Artificial Sequence
<220> FEATURE:
<223> OTHER INFORMATION: ZKA6 CDRH3

<400> SEQUENCE: 251

Ala Thr Gly Val Thr Met Phe Gln Gly Ala Gln Thr Asn Ala Glu Tyr
1               5                   10                  15

Leu His Tyr

<210> SEQ ID NO 252
<211> LENGTH: 126
<212> TYPE: PRT
<213> ORGANISM: Artificial Sequence
<220> FEATURE:
<223> OTHER INFORMATION: ZKA6 VH

<400> SEQUENCE: 252

Gln Val His Leu Val Glu Ser Gly Gly Gly Val Val Gln Pro Gly Arg
1               5                   10                  15

Ser Leu Arg Leu Ser Cys Glu Ala Ser Asp Phe Thr Val Ser Asn Tyr
            20                  25                  30

Ala Met His Trp Val Arg Gln Ala Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Thr Gly Val Thr Met Phe Gln Gly Ala Gln Thr Asn Ala Glu Tyr
            100                 105                 110

Leu His Tyr Trp Gly Gln Gly Ser Leu Val Thr Ile Ser Ser
        115                 120                 125

<210> SEQ ID NO 253
<211> LENGTH: 8
<212> TYPE: PRT
<213> ORGANISM: Artificial Sequence
<220> FEATURE:
<223> OTHER INFORMATION: ZKA7 CDRH1

<400> SEQUENCE: 253

Gly Phe Thr Phe Ser Arg Tyr Gly
1               5

<210> SEQ ID NO 254
<211> LENGTH: 8
<212> TYPE: PRT
<213> ORGANISM: Artificial Sequence
<220> FEATURE:
<223> OTHER INFORMATION: ZKA7 CDRH2

<400> SEQUENCE: 254

Val Ser Gly Asp Gly Ser Ser Thr
1               5

```
<210> SEQ ID NO 255
<211> LENGTH: 15
<212> TYPE: PRT
<213> ORGANISM: Artificial Sequence
<220> FEATURE:
<223> OTHER INFORMATION: ZKA7 CDRH3

<400> SEQUENCE: 255

Val Lys Asp Phe Trp Ser Gly Asp Gln Ser Leu Glu Ser Asp Phe
1               5                   10                  15

<210> SEQ ID NO 256
<211> LENGTH: 122
<212> TYPE: PRT
<213> ORGANISM: Artificial Sequence
<220> FEATURE:
<223> OTHER INFORMATION: ZKA7 VH

<400> SEQUENCE: 256

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Arg Tyr
            20                  25                  30

Gly Met Val Trp Ala Arg Gln Ala Pro Gly Lys Gly Leu Glu Tyr Leu
        35                  40                  45

Ser Gly Val Ser Gly Asp Gly Ser Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu His Met Ser Arg Leu Arg Asp Glu Asp Thr Ala Met Tyr Tyr Cys
                85                  90                  95

Val Lys Asp Phe Trp Ser Gly Asp Gln Ser Leu Glu Ser Asp Phe Trp
            100                 105                 110

Gly Gln Gly Ala Leu Val Thr Val Ser Ser
        115                 120

<210> SEQ ID NO 257
<211> LENGTH: 8
<212> TYPE: PRT
<213> ORGANISM: Artificial Sequence
<220> FEATURE:
<223> OTHER INFORMATION: ZKA8 CDRH1

<400> SEQUENCE: 257

Gly Phe Thr Phe Ser Ala His Ala
1               5

<210> SEQ ID NO 258
<211> LENGTH: 8
<212> TYPE: PRT
<213> ORGANISM: Artificial Sequence
<220> FEATURE:
<223> OTHER INFORMATION: ZKA8 CDRH2

<400> SEQUENCE: 258

Ile Ser Arg Asn Glu Asp Tyr Thr
1               5

<210> SEQ ID NO 259
<211> LENGTH: 12
<212> TYPE: PRT
<213> ORGANISM: Artificial Sequence
<220> FEATURE:
```

<223> OTHER INFORMATION: ZKA8 CDRH3

<400> SEQUENCE: 259

Val Lys Asp Phe Gly Thr Ser Pro Gln Thr Asp Phe
1               5                   10

<210> SEQ ID NO 260
<211> LENGTH: 119
<212> TYPE: PRT
<213> ORGANISM: Artificial Sequence
<220> FEATURE:
<223> OTHER INFORMATION: ZKA8 VH

<400> SEQUENCE: 260

Asp Glu Arg Leu Val Glu Ser Gly Gly Gly Leu Val Gln Pro Gly Gly
1               5                   10                  15

Ser Leu Arg Leu Val Cys Ser Ala Ser Gly Phe Thr Phe Ser Ala His
            20                  25                  30

Ala Met His Trp Val Arg Gln Pro Pro Gly Lys Gly Leu Glu Tyr Val
        35                  40                  45

Ser Thr Ile Ser Arg Asn Glu Asp Tyr Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Arg Arg Leu Arg Pro Glu Asp Thr Ala Ile Tyr Tyr Cys
                85                  90                  95

Val Lys Asp Phe Gly Thr Ser Pro Gln Thr Asp Phe Trp Gly Gln Gly
            100                 105                 110

Thr Leu Val Ala Val Ser Ser
        115

<210> SEQ ID NO 261
<211> LENGTH: 8
<212> TYPE: PRT
<213> ORGANISM: Artificial Sequence
<220> FEATURE:
<223> OTHER INFORMATION: ZKA76 CDRH1

<400> SEQUENCE: 261

Gly Phe Thr Phe Ser Thr Tyr Phe
1               5

<210> SEQ ID NO 262
<211> LENGTH: 8
<212> TYPE: PRT
<213> ORGANISM: Artificial Sequence
<220> FEATURE:
<223> OTHER INFORMATION: ZKA76 CDRH2

<400> SEQUENCE: 262

Ile Ser Ser Thr Gly Ser Tyr Lys
1               5

<210> SEQ ID NO 263
<211> LENGTH: 17
<212> TYPE: PRT
<213> ORGANISM: Artificial Sequence
<220> FEATURE:
<223> OTHER INFORMATION: ZKA76 CDRH3

<400> SEQUENCE: 263

Ala Arg Pro Phe His Ser Glu Tyr Thr Tyr Gly Leu Asp Ala Phe Asp
1               5                   10                  15

Ile

<210> SEQ ID NO 264
<211> LENGTH: 124
<212> TYPE: PRT
<213> ORGANISM: Artificial Sequence
<220> FEATURE:
<223> OTHER INFORMATION: ZKA76 VH

<400> SEQUENCE: 264

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Phe Met His Trp Val Arg Gln Ala Pro Gly Lys Gly Leu Glu Trp Val
        35                  40                  45

Ala Ser Ile Ser Ser Thr Gly Ser Tyr Lys Phe Tyr Ala Asp Ser Val
    50                  55                  60

Lys Gly Arg Phe Thr Ile Ser Arg Asp Asn Thr Lys Asn Ser Leu Phe
65                  70                  75                  80

Leu Gln Met Asn Ser Leu Arg Ala Glu Asp Thr Ala Val Phe Tyr Cys
                85                  90                  95

Ala Arg Pro Phe His Ser Glu Tyr Thr Tyr Gly Leu Asp Ala Phe Asp
            100                 105                 110

Ile Trp Gly Gln Gly Thr Met Leu Thr Val Ser Ser
        115                 120

<210> SEQ ID NO 265
<211> LENGTH: 10
<212> TYPE: PRT
<213> ORGANISM: Artificial Sequence
<220> FEATURE:
<223> OTHER INFORMATION: ZKA117 CDRH1

<400> SEQUENCE: 265

Gly Gly Ser Ile Arg Arg Thr Asn Ser Tyr
1               5                   10

<210> SEQ ID NO 266
<211> LENGTH: 7
<212> TYPE: PRT
<213> ORGANISM: Artificial Sequence
<220> FEATURE:
<223> OTHER INFORMATION: ZKA117 CDRH2

<400> SEQUENCE: 266

Ile Ser Tyr Ser Gly Ser Thr
1               5

<210> SEQ ID NO 267
<211> LENGTH: 17
<212> TYPE: PRT
<213> ORGANISM: Artificial Sequence
<220> FEATURE:
<223> OTHER INFORMATION: ZKA117 CDRH3

<400> SEQUENCE: 267

Ala Arg Leu Asn Asp Gly Ser Thr Val Thr Thr Ser Ser Tyr Phe Asp
1               5                   10                  15

Tyr

<210> SEQ ID NO 268
<211> LENGTH: 125
<212> TYPE: PRT
<213> ORGANISM: Artificial Sequence
<220> FEATURE:
<223> OTHER INFORMATION: ZKA117 VH

<400> SEQUENCE: 268

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Arg Thr
            20                  25                  30

Asn Ser Tyr Trp Gly Trp Ile Arg Gln Thr Thr Gly Lys Gly Leu Gln
        35                  40                  45

Trp Ile Gly Ser Ile Ser Tyr Ser Gly Ser Thr Phe Tyr Asn Pro Ser
    50                  55                  60

Leu Lys Ser Arg Val Thr Ile Ser Leu Asp Thr Ser Lys Asp His Phe
65                  70                  75                  80

Ser Leu Glu Leu Ser Ser Val Thr Ala Ala Asp Thr Ala Ile Tyr Tyr
                85                  90                  95

Cys Ala Arg Leu Asn Asp Gly Ser Thr Val Thr Thr Ser Ser Tyr Phe
            100                 105                 110

Asp Tyr Trp Gly Gln Gly Thr Leu Val Thr Val Ser Ser
        115                 120                 125

<210> SEQ ID NO 269
<211> LENGTH: 8
<212> TYPE: PRT
<213> ORGANISM: Artificial Sequence
<220> FEATURE:
<223> OTHER INFORMATION: ZKB27 CDRH1

<400> SEQUENCE: 269

Gly Tyr Ser Phe Thr Ser Ser Trp
1               5

<210> SEQ ID NO 270
<211> LENGTH: 8
<212> TYPE: PRT
<213> ORGANISM: Artificial Sequence
<220> FEATURE:
<223> OTHER INFORMATION: ZKB27 CDRH2

<400> SEQUENCE: 270

Ile Asp Pro Ser Asp Ser Tyr Thr
1               5

<210> SEQ ID NO 271
<211> LENGTH: 14
<212> TYPE: PRT
<213> ORGANISM: Artificial Sequence
<220> FEATURE:
<223> OTHER INFORMATION: ZKB27 CDRH3

<400> SEQUENCE: 271

Ala Arg His Asp Tyr Ser Val Ser Glu Asn Gly Met Asp Val
1               5                   10

<210> SEQ ID NO 272
<211> LENGTH: 121
<212> TYPE: PRT
<213> ORGANISM: Artificial Sequence
<220> FEATURE:
<223> OTHER INFORMATION: ZKB27 VH

<400> SEQUENCE: 272

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Ser
            20                  25                  30

Trp Ile Asn Trp Val Arg Gln Met Pro Gly Lys Gly Leu Glu Trp Met
        35                  40                  45

Gly Arg Ile Asp Pro Ser Asp Ser Tyr Thr Thr Tyr Asn Pro Ser Phe
50                  55                  60

Gln Gly His Val Thr Ile Ser Val Asp Lys Ser Ile Gly Thr Ala Tyr
65                  70                  75                  80

Leu Gln Trp Asn Ser Leu Arg Ala Ser Asp Thr Ala Met Tyr Tyr Cys
                85                  90                  95

Ala Arg His Asp Tyr Ser Val Ser Glu Asn Gly Met Asp Val Trp Gly
            100                 105                 110

Gln Gly Thr Thr Val Thr Val Ser Ser
        115                 120

<210> SEQ ID NO 273
<211> LENGTH: 8
<212> TYPE: PRT
<213> ORGANISM: Artificial Sequence
<220> FEATURE:
<223> OTHER INFORMATION: ZKB29 CDRH1

<400> SEQUENCE: 273

Gly Phe Thr Phe Ser Ser Tyr Thr
1               5

<210> SEQ ID NO 274
<211> LENGTH: 8
<212> TYPE: PRT
<213> ORGANISM: Artificial Sequence
<220> FEATURE:
<223> OTHER INFORMATION: ZKB29 CDRH2

<400> SEQUENCE: 274

Ile Ser Tyr Asp Gly Ser His Lys
1               5

<210> SEQ ID NO 275
<211> LENGTH: 12
<212> TYPE: PRT
<213> ORGANISM: Artificial Sequence
<220> FEATURE:
<223> OTHER INFORMATION: ZKB29 CDRH3

<400> SEQUENCE: 275

Ala Arg Arg Ser Tyr Ser Ile Ser Cys Phe Asp Tyr
1               5                   10

<210> SEQ ID NO 276
<211> LENGTH: 119
<212> TYPE: PRT
<213> ORGANISM: Artificial Sequence
<220> FEATURE:
<223> OTHER INFORMATION: ZKB29 VH

<400> SEQUENCE: 276

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Ala Val Ile Ser Tyr Asp Gly Ser His Lys Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Tyr Tyr Cys
                85                  90                  95

Ala Arg Arg Ser Tyr Ser Ile Ser Cys Phe Asp Tyr Trp Gly Gln Gly
                100                 105                 110

Thr Leu Val Thr Ile Ser Ser
            115
```

<210> SEQ ID NO 277
<211> LENGTH: 8
<212> TYPE: PRT
<213> ORGANISM: Artificial Sequence
<220> FEATURE:
<223> OTHER INFORMATION: ZKB34 CDRH1

<400> SEQUENCE: 277

```
Gly Phe Thr Phe Ser Arg Ser Gly
1               5
```

<210> SEQ ID NO 278
<211> LENGTH: 8
<212> TYPE: PRT
<213> ORGANISM: Artificial Sequence
<220> FEATURE:
<223> OTHER INFORMATION: ZKB34 CDRH2

<400> SEQUENCE: 278

```
Val Ser Tyr Asp Gly Ser Asn Lys
1               5
```

<210> SEQ ID NO 279
<211> LENGTH: 19
<212> TYPE: PRT
<213> ORGANISM: Artificial Sequence
<220> FEATURE:
<223> OTHER INFORMATION: ZKB34 CDRH3

<400> SEQUENCE: 279

```
Ala Lys Asp Leu Thr Met Val Arg Gly Val His Tyr Tyr Tyr Tyr Val
1               5                   10                  15

Met Asp Val
```

<210> SEQ ID NO 280
<211> LENGTH: 126
<212> TYPE: PRT
<213> ORGANISM: Artificial Sequence
<220> FEATURE:
<223> OTHER INFORMATION: ZKB34 VH

<400> SEQUENCE: 280

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Ser
            20                  25                  30

Gly Met His Trp Val Arg Gln Ala Pro Gly Lys Gly Leu Glu Trp Val
```

```
                35                  40                  45
Ala Val Val Ser Tyr Asp Gly Ser Asn Lys Tyr Tyr Ser Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Lys Asp Leu Thr Met Val Arg Gly Val His Tyr Tyr Tyr Tyr Val
             100                 105                 110

Met Asp Val Trp Gly Gln Gly Thr Thr Val Thr Val Ser Ser
         115                 120                 125

<210> SEQ ID NO 281
<211> LENGTH: 8
<212> TYPE: PRT
<213> ORGANISM: Artificial Sequence
<220> FEATURE:
<223> OTHER INFORMATION: ZKB39 CDRH1

<400> SEQUENCE: 281

Gly Tyr Thr Phe Asp Asp Tyr Tyr
1               5

<210> SEQ ID NO 282
<211> LENGTH: 8
<212> TYPE: PRT
<213> ORGANISM: Artificial Sequence
<220> FEATURE:
<223> OTHER INFORMATION: ZKB39 CDRH2

<400> SEQUENCE: 282

Ile Asn Pro His Arg Gly Gly Thr
1               5

<210> SEQ ID NO 283
<211> LENGTH: 23
<212> TYPE: PRT
<213> ORGANISM: Artificial Sequence
<220> FEATURE:
<223> OTHER INFORMATION: ZKB39 CDRH3

<400> SEQUENCE: 283

Val Arg Asp Gln Tyr Cys Asp Gly Gly Asn Cys Tyr Gly Ile His Gln
1               5                  10                  15

Pro His Tyr Gly Met Asp Val
            20

<210> SEQ ID NO 284
<211> LENGTH: 130
<212> TYPE: PRT
<213> ORGANISM: Artificial Sequence
<220> FEATURE:
<223> OTHER INFORMATION: ZKB39 VH

<400> SEQUENCE: 284

Gln Val Gln Leu Val Gln Ser Gly Ala Glu Val Lys Lys Pro Gly Ala
1               5                  10                  15

Ser Leu Lys Val Ser Cys Lys Ala Ser Gly Tyr Thr Phe Asp Asp Tyr
                20                  25                  30

Tyr Ile His Trp Val Arg Gln Ala Pro Gly Gln Gly Leu Glu Trp Leu
            35                  40                  45

Gly Arg Ile Asn Pro His Arg Gly Gly Thr Asn Tyr Ala Gln Lys Phe
```

```
            50                  55                  60
Gln Gly Arg Val Ile Met Thr Leu Asp Met Ser Ile Ser Thr Thr Tyr
 65                  70                  75                  80

Met Glu Leu Arg Arg Ile Thr Ser Asp Ala Ala Val Tyr Tyr Cys
                 85                  90                  95

Val Arg Asp Gln Tyr Cys Asp Gly Gly Asn Cys Tyr Gly Ile His Gln
             100                 105                 110

Pro His Tyr Gly Met Asp Val Trp Gly Gln Gly Thr Thr Val Thr Val
         115                 120                 125

Ser Ser
    130

<210> SEQ ID NO 285
<211> LENGTH: 8
<212> TYPE: PRT
<213> ORGANISM: Artificial Sequence
<220> FEATURE:
<223> OTHER INFORMATION: ZKB46 CDRH1

<400> SEQUENCE: 285

Gly Tyr Ser Phe Thr Ser Tyr Trp
1               5

<210> SEQ ID NO 286
<211> LENGTH: 8
<212> TYPE: PRT
<213> ORGANISM: Artificial Sequence
<220> FEATURE:
<223> OTHER INFORMATION: ZKB46 CDRH2

<400> SEQUENCE: 286

Ile Asp Pro Ser Asp Ser Tyr Thr
1               5

<210> SEQ ID NO 287
<211> LENGTH: 17
<212> TYPE: PRT
<213> ORGANISM: Artificial Sequence
<220> FEATURE:
<223> OTHER INFORMATION: ZKB46 CDRH3

<400> SEQUENCE: 287

Ala Arg Arg Glu Tyr Ser Ser Ser Gly Gln Glu Asp Trp Phe Asp
1               5                   10                  15

Pro

<210> SEQ ID NO 288
<211> LENGTH: 124
<212> TYPE: PRT
<213> ORGANISM: Artificial Sequence
<220> FEATURE:
<223> OTHER INFORMATION: ZKB46 VH

<400> SEQUENCE: 288

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60
```

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Glu Tyr Ser Ser Ser Gly Gln Glu Asp Trp Phe Asp
            100                 105                 110

Pro Trp Gly Gln Gly Thr Leu Val Thr Val Ser Ser
        115                 120

<210> SEQ ID NO 289
<211> LENGTH: 8
<212> TYPE: PRT
<213> ORGANISM: Artificial Sequence
<220> FEATURE:
<223> OTHER INFORMATION: ZKB53 CDRH1

<400> SEQUENCE: 289

Gly Phe Thr Phe Ser Ser Tyr Ala
1               5

<210> SEQ ID NO 290
<211> LENGTH: 8
<212> TYPE: PRT
<213> ORGANISM: Artificial Sequence
<220> FEATURE:
<223> OTHER INFORMATION: ZKB53 CDRH2

<400> SEQUENCE: 290

Ile Ser Tyr Asp Gly Ser Asn Arg
1               5

<210> SEQ ID NO 291
<211> LENGTH: 15
<212> TYPE: PRT
<213> ORGANISM: Artificial Sequence
<220> FEATURE:
<223> OTHER INFORMATION: ZKB53 CDRH3

<400> SEQUENCE: 291

Ala Arg His Val Glu Gln Leu Pro Ser Ser Gly Tyr Phe Gln His
1               5                   10                  15

<210> SEQ ID NO 292
<211> LENGTH: 122
<212> TYPE: PRT
<213> ORGANISM: Artificial Sequence
<220> FEATURE:
<223> OTHER INFORMATION: ZKB53 VH

<400> SEQUENCE: 292

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Thr Pro Gly Lys Gly Leu Glu Trp Val
        35                  40                  45

Thr Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg His Val Glu Gln Leu Pro Ser Ser Gly Tyr Phe Gln His Trp
            100                 105                 110

Gly Gln Gly Thr Leu Val Thr Val Ser Ser
        115                 120

<210> SEQ ID NO 293
<211> LENGTH: 8
<212> TYPE: PRT
<213> ORGANISM: Artificial Sequence
<220> FEATURE:
<223> OTHER INFORMATION: ZKC26 CDRH1

<400> SEQUENCE: 293

Gly Phe Ile Phe Ser Asp Phe Tyr
1               5

<210> SEQ ID NO 294
<211> LENGTH: 8
<212> TYPE: PRT
<213> ORGANISM: Artificial Sequence
<220> FEATURE:
<223> OTHER INFORMATION: ZKC26 CDRH2

<400> SEQUENCE: 294

Ile Gly His Asp Gly Ser Tyr Ile
1               5

<210> SEQ ID NO 295
<211> LENGTH: 9
<212> TYPE: PRT
<213> ORGANISM: Artificial Sequence
<220> FEATURE:
<223> OTHER INFORMATION: ZKC26 CDRH3

<400> SEQUENCE: 295

Ala Arg Ala His Gly Gly Phe Arg His
1               5

<210> SEQ ID NO 296
<211> LENGTH: 116
<212> TYPE: PRT
<213> ORGANISM: Artificial Sequence
<220> FEATURE:
<223> OTHER INFORMATION: ZKC26 VH

<400> SEQUENCE: 296

Gln Val Gln Val Glu Ser Gly Gly Leu Val Lys Pro Gly Gly
1               5                   10                  15

Ser Leu Arg Leu Ser Cys Ala Ala Ser Gly Phe Ile Phe Ser Asp Phe
            20                  25                  30

Tyr Met Ser Trp Met Arg Gln Ala Pro Gly Lys Gly Leu Glu Trp Val
        35                  40                  45

Ala Tyr Ile Gly His Asp Gly Ser Tyr Ile Leu Tyr Ala Asp Ser Val
    50                  55                  60

Lys Gly Arg Phe Thr Ile Ser Arg Asp Asn Ala Lys Asn Ser Leu Phe
65                  70                  75                  80

Leu Arg Met Asn Ser Leu Arg Val Glu Asp Thr Ala Val Tyr Tyr Cys
                85                  90                  95

Ala Arg Ala His Gly Gly Phe Arg His Trp Gly Gln Gly Thr Val Val
            100                 105                 110

Ala Val Ser Pro
        115

<210> SEQ ID NO 297
<211> LENGTH: 8
<212> TYPE: PRT
<213> ORGANISM: Artificial Sequence
<220> FEATURE:
<223> OTHER INFORMATION: ZKD5 CDRH1

<400> SEQUENCE: 297

Gly Phe Thr Phe Thr Ser Tyr Gly
1               5

<210> SEQ ID NO 298
<211> LENGTH: 8
<212> TYPE: PRT
<213> ORGANISM: Artificial Sequence
<220> FEATURE:
<223> OTHER INFORMATION: ZKD5 CDRH2

<400> SEQUENCE: 298

Ile Ser Tyr Asp Gly Ser Asn Lys
1               5

<210> SEQ ID NO 299
<211> LENGTH: 17
<212> TYPE: PRT
<213> ORGANISM: Artificial Sequence
<220> FEATURE:
<223> OTHER INFORMATION: ZKD5 CDRH3

<400> SEQUENCE: 299

Ala Arg Asp Arg Asp His Tyr Asp Leu Trp Asn Ala Tyr Thr Phe Asp
1               5                   10                  15

Tyr

<210> SEQ ID NO 300
<211> LENGTH: 124
<212> TYPE: PRT
<213> ORGANISM: Artificial Sequence
<220> FEATURE:
<223> OTHER INFORMATION: ZKD5 VH

<400> SEQUENCE: 300

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met His Trp Val Arg Gln Thr Pro Gly Lys Gly Leu Asp Trp Val
        35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Ala Asp Thr Ala Leu Tyr Tyr Cys
                85                  90                  95

Ala Arg Asp Arg Asp His Tyr Asp Leu Trp Asn Ala Tyr Thr Phe Asp
            100                 105                 110

Tyr Trp Gly Gln Gly Thr Leu Val Thr Val Ser Ser
        115                 120

<210> SEQ ID NO 301
<211> LENGTH: 8

-continued

```
<212> TYPE: PRT
<213> ORGANISM: Artificial Sequence
<220> FEATURE:
<223> OTHER INFORMATION: ZKD7 CDRH1

<400> SEQUENCE: 301

Gly Phe Thr Phe Ser Asn Tyr Ala
1               5

<210> SEQ ID NO 302
<211> LENGTH: 8
<212> TYPE: PRT
<213> ORGANISM: Artificial Sequence
<220> FEATURE:
<223> OTHER INFORMATION: ZKD7 CDRH2

<400> SEQUENCE: 302

Ile Ser Tyr Asp Val Ser Asp Lys
1               5

<210> SEQ ID NO 303
<211> LENGTH: 20
<212> TYPE: PRT
<213> ORGANISM: Artificial Sequence
<220> FEATURE:
<223> OTHER INFORMATION: ZKD7 CDRH3

<400> SEQUENCE: 303

Ala Gly Gly Pro Leu Gly Val Val Val Ile Lys Pro Ser Asn Ala Glu
1               5                   10                  15

His Phe His His
            20

<210> SEQ ID NO 304
<211> LENGTH: 127
<212> TYPE: PRT
<213> ORGANISM: Artificial Sequence
<220> FEATURE:
<223> OTHER INFORMATION: ZKD7 VH

<400> SEQUENCE: 304

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Val Ser Asp Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Ala Tyr Tyr Cys
                85                  90                  95

Ala Gly Gly Pro Leu Gly Val Val Val Ile Lys Pro Ser Asn Ala Glu
            100                 105                 110

His Phe His His Trp Gly Gln Gly Thr Leu Val Thr Val Ser Ser
        115                 120                 125

<210> SEQ ID NO 305
<211> LENGTH: 8
<212> TYPE: PRT
<213> ORGANISM: Artificial Sequence
<220> FEATURE:
```

<223> OTHER INFORMATION: ZKD8 CDRH1

<400> SEQUENCE: 305

Gly Phe Thr Phe Ile Asn Tyr Ala
1               5

<210> SEQ ID NO 306
<211> LENGTH: 8
<212> TYPE: PRT
<213> ORGANISM: Artificial Sequence
<220> FEATURE:
<223> OTHER INFORMATION: ZKD8 CDRH2

<400> SEQUENCE: 306

Ile Ser Tyr Asp Gly Ser Asn Lys
1               5

<210> SEQ ID NO 307
<211> LENGTH: 16
<212> TYPE: PRT
<213> ORGANISM: Artificial Sequence
<220> FEATURE:
<223> OTHER INFORMATION: ZKD8 CDRH3

<400> SEQUENCE: 307

Ala Thr Asp Ala Asp Ala Tyr Gly Asp Ser Gly Ala Asn Phe His Tyr
1               5                   10                  15

<210> SEQ ID NO 308
<211> LENGTH: 123
<212> TYPE: PRT
<213> ORGANISM: Artificial Sequence
<220> FEATURE:
<223> OTHER INFORMATION: ZKD8 VH

<400> SEQUENCE: 308

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ile Asn Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Ser Asn Lys Phe Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Thr Ala Val Tyr Tyr Cys
                85                  90                  95

Ala Thr Asp Ala Asp Ala Tyr Gly Asp Ser Gly Ala Asn Phe His Tyr
            100                 105                 110

Trp Gly Gln Gly Thr Leu Val Thr Val Ser Ser
        115                 120

<210> SEQ ID NO 309
<211> LENGTH: 10
<212> TYPE: PRT
<213> ORGANISM: Artificial Sequence
<220> FEATURE:
<223> OTHER INFORMATION: ZKD15 CDRH1

<400> SEQUENCE: 309

Asp Ala Ser Ile Ser Ser Gly Gly Phe Ser
1               5                   10

<210> SEQ ID NO 310
<211> LENGTH: 7
<212> TYPE: PRT
<213> ORGANISM: Artificial Sequence
<220> FEATURE:
<223> OTHER INFORMATION: ZKD15 CDRH2

<400> SEQUENCE: 310

Ile Tyr Ser Ser Gly Asp Thr
1               5

<210> SEQ ID NO 311
<211> LENGTH: 18
<212> TYPE: PRT
<213> ORGANISM: Artificial Sequence
<220> FEATURE:
<223> OTHER INFORMATION: ZKD15 CDRH3

<400> SEQUENCE: 311

Ala Arg Ala His Thr Pro Thr Ser Lys Phe Tyr Tyr Tyr Ala Met
1               5                   10                  15

Asp Val

<210> SEQ ID NO 312
<211> LENGTH: 126
<212> TYPE: PRT
<213> ORGANISM: Artificial Sequence
<220> FEATURE:
<223> OTHER INFORMATION: ZKD15 VH

<400> SEQUENCE: 312

Gln Leu Gln Leu Gln Glu Ser Gly Ser Gly Leu Val Lys Pro Ser Gln
1               5                   10                  15

Thr Leu Ser Leu Thr Cys Thr Val Ser Asp Ala Ser Ile Ser Ser Gly
                20                  25                  30

Gly Phe Ser Trp Ser Trp Ile Arg Gln Pro Leu Gly Lys Gly Leu Glu
            35                  40                  45

Trp Leu Gly Tyr Ile Tyr Ser Ser Gly Asp Thr Phe Tyr Asn Pro Ser
50                  55                  60

Leu Gln Gly Arg Val Thr Met Ser Val Asp Ile Phe Arg Ser Gln Phe
65                  70                  75                  80

Ser Leu Lys Leu Thr Ser Val Thr Ala Ala Asp Thr Ala Met Tyr Tyr
                85                  90                  95

Cys Ala Arg Ala His Thr Pro Thr Ser Lys Phe Tyr Tyr Tyr Ala
            100                 105                 110

Met Asp Val Trp Gly Gln Gly Thr Thr Val Thr Val Ser Ser
        115                 120                 125

<210> SEQ ID NO 313
<211> LENGTH: 8
<212> TYPE: PRT
<213> ORGANISM: Artificial Sequence
<220> FEATURE:
<223> OTHER INFORMATION: ZKD16 CDRH1

<400> SEQUENCE: 313

Gly Phe Thr Phe Ser Asp His Phe
1               5

<210> SEQ ID NO 314
<211> LENGTH: 10

```
<212> TYPE: PRT
<213> ORGANISM: Artificial Sequence
<220> FEATURE:
<223> OTHER INFORMATION: ZKD16 CDRH2

<400> SEQUENCE: 314

Ser Arg Asn Lys Pro Asn Ser Tyr Thr Thr
1               5                   10

<210> SEQ ID NO 315
<211> LENGTH: 17
<212> TYPE: PRT
<213> ORGANISM: Artificial Sequence
<220> FEATURE:
<223> OTHER INFORMATION: ZKD16 CDRH3

<400> SEQUENCE: 315

Ala Lys Val Gly Gly Cys Tyr Gly Gly Asp Cys His Val Glu Asn Asp
1               5                   10                  15

Tyr

<210> SEQ ID NO 316
<211> LENGTH: 126
<212> TYPE: PRT
<213> ORGANISM: Artificial Sequence
<220> FEATURE:
<223> OTHER INFORMATION: ZKD16 VH

<400> SEQUENCE: 316

Glu Val Gln Leu Val Glu Ser Gly Gly Asp Leu Val Gln Pro Gly Gly
1               5                   10                  15

Ser Leu Arg Leu Ser Cys Val Ala Ser Gly Phe Thr Phe Ser Asp His
                20                  25                  30

Phe Met Asp Trp Val Arg Gln Ala Pro Gly Lys Gly Leu Glu Trp Val
            35                  40                  45

Gly Arg Ser Arg Asn Lys Pro Asn Ser Tyr Thr Thr Glu Tyr Ala Ala
        50                  55                  60

Ser Val Lys Gly Arg Phe Ser Ile Ser Arg Asp Asp Ser Lys Lys Ala
65                  70                  75                  80

Leu Tyr Leu Gln Met Asn Ser Leu Gln Thr Glu Asp Thr Ala Val Tyr
                85                  90                  95

Tyr Cys Ala Lys Val Gly Gly Cys Tyr Gly Gly Asp Cys His Val Glu
            100                 105                 110

Asn Asp Tyr Trp Gly Gln Gly Thr Leu Val Thr Val Ser Ser
        115                 120                 125

<210> SEQ ID NO 317
<211> LENGTH: 8
<212> TYPE: PRT
<213> ORGANISM: Artificial Sequence
<220> FEATURE:
<223> OTHER INFORMATION: ZKD17 CDRH1

<400> SEQUENCE: 317

Gly Phe Ile Phe Ser Asp Tyr Ala
1               5

<210> SEQ ID NO 318
<211> LENGTH: 8
<212> TYPE: PRT
<213> ORGANISM: Artificial Sequence
<220> FEATURE:
<223> OTHER INFORMATION: ZKD17 CDRH2
```

-continued

<400> SEQUENCE: 318

Ile Ser Tyr Asp Gly Ser Ser Arg
1               5

<210> SEQ ID NO 319
<211> LENGTH: 20
<212> TYPE: PRT
<213> ORGANISM: Artificial Sequence
<220> FEATURE:
<223> OTHER INFORMATION: ZKD17 CDRH3

<400> SEQUENCE: 319

Ala Arg Gly Tyr Cys Ser Ser Gly Thr Cys Phe Ser Thr Asn Ala Glu
1               5                   10                  15

Tyr Phe His Pro
            20

<210> SEQ ID NO 320
<211> LENGTH: 127
<212> TYPE: PRT
<213> ORGANISM: Artificial Sequence
<220> FEATURE:
<223> OTHER INFORMATION: ZKD17 VH

<400> SEQUENCE: 320

Gln Val Gln Met Val Glu Ser Gly Gly Val Val Gln Pro Gly Thr
1               5                   10                  15

Ser Leu Arg Leu Ser Cys Ala Thr Ser Gly Phe Ile Phe Ser Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ser Arg Leu Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met His Ser Leu Arg Ala Gly Asp Thr Ala Val Tyr Tyr Cys
                85                  90                  95

Ala Arg Gly Tyr Cys Ser Ser Gly Thr Cys Phe Ser Thr Asn Ala Glu
            100                 105                 110

Tyr Phe His Pro Trp Gly Gln Gly Thr Leu Ala Thr Ile Ser Ser
        115                 120                 125

<210> SEQ ID NO 321
<211> LENGTH: 8
<212> TYPE: PRT
<213> ORGANISM: Artificial Sequence
<220> FEATURE:
<223> OTHER INFORMATION: ZKD20 CDRH1

<400> SEQUENCE: 321

Gly Phe Thr Phe Ser Asp His Phe
1               5

<210> SEQ ID NO 322
<211> LENGTH: 10
<212> TYPE: PRT
<213> ORGANISM: Artificial Sequence
<220> FEATURE:
<223> OTHER INFORMATION: ZKD20 CDRH2

<400> SEQUENCE: 322

```
Ser Arg Asn Lys Pro Asn Ser Tyr Thr Thr
1               5                   10
```

<210> SEQ ID NO 323
<211> LENGTH: 17
<212> TYPE: PRT
<213> ORGANISM: Artificial Sequence
<220> FEATURE:
<223> OTHER INFORMATION: ZKD20 CDRH3

<400> SEQUENCE: 323

```
Ala Arg Val Gly Gly Cys Asn Gly Gly Asp Cys His Val Glu Asn Asp
1               5                   10                  15
Tyr
```

<210> SEQ ID NO 324
<211> LENGTH: 126
<212> TYPE: PRT
<213> ORGANISM: Artificial Sequence
<220> FEATURE:
<223> OTHER INFORMATION: ZKD20 VH

<400> SEQUENCE: 324

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp His
            20                  25                  30

Phe Met Asp Trp Val Arg Gln Ala Pro Gly Lys Gly Leu Glu Trp Val
        35                  40                  45

Gly Arg Ser Arg Asn Lys Pro Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Gln Thr Glu Asp Thr Ala Val Tyr
                85                  90                  95

Tyr Cys Ala Arg Val Gly Gly Cys Asn Gly Gly Asp Cys His Val Glu
            100                 105                 110

Asn Asp Tyr Trp Gly Gln Gly Thr Leu Val Thr Val Ser Ser
        115                 120                 125
```

<210> SEQ ID NO 325
<211> LENGTH: 8
<212> TYPE: PRT
<213> ORGANISM: Artificial Sequence
<220> FEATURE:
<223> OTHER INFORMATION: ZKA134 CDRH1

<400> SEQUENCE: 325

```
Gly Gly Thr Phe Ser Ala Tyr Ala
1               5
```

<210> SEQ ID NO 326
<211> LENGTH: 8
<212> TYPE: PRT
<213> ORGANISM: Artificial Sequence
<220> FEATURE:
<223> OTHER INFORMATION: ZKA134 CDRH2

<400> SEQUENCE: 326

```
Ile Ile Pro Phe Phe Gly Thr Ala
1               5
```

```
<210> SEQ ID NO 327
<211> LENGTH: 19
<212> TYPE: PRT
<213> ORGANISM: Artificial Sequence
<220> FEATURE:
<223> OTHER INFORMATION: ZKA134 CDRH3

<400> SEQUENCE: 327

Ala Arg Ser Asp Ile Val Ser Thr Thr Arg Gly Tyr His His Tyr Gly
1               5                   10                  15

Met Asp Val

<210> SEQ ID NO 328
<211> LENGTH: 126
<212> TYPE: PRT
<213> ORGANISM: Artificial Sequence
<220> FEATURE:
<223> OTHER INFORMATION: ZKA134 VH

<400> SEQUENCE: 328

Gln Val His Leu Val Gln Ser Gly Ala Glu Val Lys Lys Pro Gly Ser
1               5                   10                  15

Ser Val Asn Val Ser Cys Lys Ala Ser Gly Gly Thr Phe Ser Ala Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Thr Ala Tyr Tyr Ala Gln Lys Phe
    50                  55                  60

Lys Gly Arg Val Thr Val Thr Ala Asp Lys Ser Thr Ser Thr Val Tyr
65                  70                  75                  80

Met Glu Met Thr Ser Leu Arg Ser Glu Asp Thr Ala Val Tyr Tyr Cys
                85                  90                  95

Ala Arg Ser Asp Ile Val Ser Thr Thr Arg Gly Tyr His His Tyr Gly
            100                 105                 110

Met Asp Val Trp Gly Gln Gly Thr Thr Val Thr Val Ser Ser
        115                 120                 125

<210> SEQ ID NO 329
<211> LENGTH: 8
<212> TYPE: PRT
<213> ORGANISM: Artificial Sequence
<220> FEATURE:
<223> OTHER INFORMATION: ZKA246 CDRH1

<400> SEQUENCE: 329

Gly Tyr Thr Phe Ser Asp Tyr Tyr
1               5

<210> SEQ ID NO 330
<211> LENGTH: 8
<212> TYPE: PRT
<213> ORGANISM: Artificial Sequence
<220> FEATURE:
<223> OTHER INFORMATION: ZKA246 CDRH2

<400> SEQUENCE: 330

Ile Asn Pro Tyr Ser Gly Gly Thr
1               5

<210> SEQ ID NO 331
<211> LENGTH: 14
<212> TYPE: PRT
<213> ORGANISM: Artificial Sequence
```

<220> FEATURE:
<223> OTHER INFORMATION: ZKA246 CDRH3

<400> SEQUENCE: 331

Ala Arg Gly Phe Thr Met Ile Ser Asp Arg Glu Phe Asp Pro
1               5                   10

<210> SEQ ID NO 332
<211> LENGTH: 121
<212> TYPE: PRT
<213> ORGANISM: Artificial Sequence
<220> FEATURE:
<223> OTHER INFORMATION: ZKA246 VH

<400> SEQUENCE: 332

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Ser Asp Tyr
                20                  25                  30

Tyr Met His Trp Val Arg Gln Ala Pro Gly Gln Gly Leu Glu Trp Met
            35                  40                  45

Gly Arg Ile Asn Pro Tyr Ser Gly Gly Thr Asn Tyr Ala Gln Lys Phe
        50                  55                  60

His Gly Arg Val Thr Val Thr Arg Asp Thr Ser Ile Ser Thr Val Tyr
65                  70                  75                  80

Met Glu Leu Arg Gly Leu Arg Ser Asp Asp Thr Ala Val Tyr Tyr Cys
                85                  90                  95

Ala Arg Gly Phe Thr Met Ile Ser Asp Arg Glu Phe Asp Pro Trp Gly
            100                 105                 110

Gln Gly Thr Leu Val Thr Val Ser Ser
        115                 120

<210> SEQ ID NO 333
<211> LENGTH: 8
<212> TYPE: PRT
<213> ORGANISM: Artificial Sequence
<220> FEATURE:
<223> OTHER INFORMATION: ZKA256 CDRH1

<400> SEQUENCE: 333

Gly Phe Thr Phe Ser Thr Tyr Trp
1               5

<210> SEQ ID NO 334
<211> LENGTH: 8
<212> TYPE: PRT
<213> ORGANISM: Artificial Sequence
<220> FEATURE:
<223> OTHER INFORMATION: ZKA256 CDRH2

<400> SEQUENCE: 334

Ile Lys Gln Asp Gly Ser Glu Lys
1               5

<210> SEQ ID NO 335
<211> LENGTH: 20
<212> TYPE: PRT
<213> ORGANISM: Artificial Sequence
<220> FEATURE:
<223> OTHER INFORMATION: ZKA256 CDRH3

<400> SEQUENCE: 335

Ala Arg Asp Pro Gly Tyr Asp Asp Phe Trp Ser Gly Ser Tyr Ser Gly

```
1               5                   10                  15

Ser Phe Asp Ile
            20

<210> SEQ ID NO 336
<211> LENGTH: 127
<212> TYPE: PRT
<213> ORGANISM: Artificial Sequence
<220> FEATURE:
<223> OTHER INFORMATION: ZKA256 VH

<400> SEQUENCE: 336

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Thr Lys Asn Ser Leu Tyr
65                  70                  75                  80

Leu Gln Val Asn Ser Leu Arg Ala Glu Asp Thr Ala Ile Tyr Tyr Cys
                85                  90                  95

Ala Arg Asp Pro Gly Tyr Asp Asp Phe Trp Ser Gly Ser Tyr Ser Gly
            100                 105                 110

Ser Phe Asp Ile Trp Gly Gln Gly Thr Met Val Thr Val Ser Ser
        115                 120                 125

<210> SEQ ID NO 337
<211> LENGTH: 8
<212> TYPE: PRT
<213> ORGANISM: Artificial Sequence
<220> FEATURE:
<223> OTHER INFORMATION: ZKB42 CDRH1

<400> SEQUENCE: 337

Gly Phe Thr Phe Asn Asn Tyr Gly
1               5

<210> SEQ ID NO 338
<211> LENGTH: 8
<212> TYPE: PRT
<213> ORGANISM: Artificial Sequence
<220> FEATURE:
<223> OTHER INFORMATION: ZKB42 CDRH2

<400> SEQUENCE: 338

Ile Ser Tyr Asp Gly Asn Lys Lys
1               5

<210> SEQ ID NO 339
<211> LENGTH: 16
<212> TYPE: PRT
<213> ORGANISM: Artificial Sequence
<220> FEATURE:
<223> OTHER INFORMATION: ZKB42 CDRH3

<400> SEQUENCE: 339

Val Lys Tyr Gly Glu Arg Ile Asn Gly Tyr Ser Asp Pro Phe Asp His
1               5                   10                  15
```

```
<210> SEQ ID NO 340
<211> LENGTH: 123
<212> TYPE: PRT
<213> ORGANISM: Artificial Sequence
<220> FEATURE:
<223> OTHER INFORMATION: ZKB42 VH

<400> SEQUENCE: 340

Gln Val Gln Val Val Glu Ser Gly Gly Val Val Gln Pro Gly Arg
1               5                   10                  15

Ser Leu Arg Leu Phe Cys Ala Ala Ser Gly Phe Thr Phe Asn Asn Tyr
                20                  25                  30

Gly Met His Trp Val Arg Gln Ala Pro Gly Lys Gly Leu Glu Trp Val
            35                  40                  45

Ala Leu Ile Ser Tyr Asp Gly Asn Lys Lys Tyr Tyr Ala Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Arg Leu Arg Ser Gly Asp Thr Ala Val Tyr His Cys
                85                  90                  95

Val Lys Tyr Gly Glu Arg Ile Asn Gly Tyr Ser Asp Pro Phe Asp His
            100                 105                 110

Trp Gly Gln Gly Thr Leu Val Thr Val Ser Ser
        115                 120

<210> SEQ ID NO 341
<211> LENGTH: 8
<212> TYPE: PRT
<213> ORGANISM: Artificial Sequence
<220> FEATURE:
<223> OTHER INFORMATION: ZKB85 CDRH1

<400> SEQUENCE: 341

Gly Tyr Thr Phe Thr Thr Tyr Ala
1               5

<210> SEQ ID NO 342
<211> LENGTH: 8
<212> TYPE: PRT
<213> ORGANISM: Artificial Sequence
<220> FEATURE:
<223> OTHER INFORMATION: ZKB85 CDRH2

<400> SEQUENCE: 342

Ile Asn Thr Asn Thr Gly Asn Pro
1               5

<210> SEQ ID NO 343
<211> LENGTH: 11
<212> TYPE: PRT
<213> ORGANISM: Artificial Sequence
<220> FEATURE:
<223> OTHER INFORMATION: ZKB85 CDRH3

<400> SEQUENCE: 343

Ala Arg Val Ile Val Pro Tyr Ala Phe Asp Ile
1               5                   10

<210> SEQ ID NO 344
<211> LENGTH: 118
<212> TYPE: PRT
<213> ORGANISM: Artificial Sequence
<220> FEATURE:
<223> OTHER INFORMATION: ZKB85 VH
```

<400> SEQUENCE: 344

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ala Met Asn Trp Val Arg Gln Ala Pro Gly Gln Gly Pro Glu Trp Val
        35                  40                  45

Gly Trp Ile Asn Thr Asn Thr Gly Asn Pro Thr Tyr Ala Gln Gly Phe
    50                  55                  60

Thr Gly Arg Phe Val Leu Ser Leu Asp Thr Ser Val Ser Thr Ala Phe
65                  70                  75                  80

Leu Gln Ile Ser Ser Leu Lys Ala Glu Asp Thr Ala Val Tyr Tyr Cys
                85                  90                  95

Ala Arg Val Ile Val Pro Tyr Ala Phe Asp Ile Trp Gly Gln Gly Thr
            100                 105                 110

Met Val Thr Val Ser Ser
        115

<210> SEQ ID NO 345
<211> LENGTH: 8
<212> TYPE: PRT
<213> ORGANISM: Artificial Sequence
<220> FEATURE:
<223> OTHER INFORMATION: ZKB47 CDRH1

<400> SEQUENCE: 345

Gly Tyr Thr Phe Thr Asn Tyr Tyr
1               5

<210> SEQ ID NO 346
<211> LENGTH: 8
<212> TYPE: PRT
<213> ORGANISM: Artificial Sequence
<220> FEATURE:
<223> OTHER INFORMATION: ZKB47 CDRH2

<400> SEQUENCE: 346

Ile Asn Pro Ser Gly Gly Pro Thr
1               5

<210> SEQ ID NO 347
<211> LENGTH: 15
<212> TYPE: PRT
<213> ORGANISM: Artificial Sequence
<220> FEATURE:
<223> OTHER INFORMATION: ZKB47 CDRH3

<400> SEQUENCE: 347

Ala Arg Asp Gln Tyr Gly Gly Tyr Ala Arg Tyr Gly Met Asp Val
1               5                   10                  15

<210> SEQ ID NO 348
<211> LENGTH: 122
<212> TYPE: PRT
<213> ORGANISM: Artificial Sequence
<220> FEATURE:
<223> OTHER INFORMATION: ZKB47 VH

<400> SEQUENCE: 348

Gln Val Gln Leu Val Gln Ser Gly Ala Glu Val Lys Lys Pro Gly Ala
1               5                   10                  15

```
Ser Val Lys Val Ser Cys Gln Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Pro Thr Ser Tyr Ala Gln Lys Phe
    50                  55                  60

Gln Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Tyr Gly Gly Tyr Ala Arg Tyr Gly Met Asp Val Trp
            100                 105                 110

Gly Gln Gly Thr Thr Val Thr Val Ser Ser
        115                 120
```

<210> SEQ ID NO 349
<211> LENGTH: 8
<212> TYPE: PRT
<213> ORGANISM: Artificial Sequence
<220> FEATURE:
<223> OTHER INFORMATION: ZKC6 CDRH1

<400> SEQUENCE: 349

```
Gly Tyr Thr Phe Thr Gly Tyr Tyr
1               5
```

<210> SEQ ID NO 350
<211> LENGTH: 8
<212> TYPE: PRT
<213> ORGANISM: Artificial Sequence
<220> FEATURE:
<223> OTHER INFORMATION: ZKC6 CDRH2

<400> SEQUENCE: 350

```
Ile Asn Pro Asn Ser Gly Gly Thr
1               5
```

<210> SEQ ID NO 351
<211> LENGTH: 12
<212> TYPE: PRT
<213> ORGANISM: Artificial Sequence
<220> FEATURE:
<223> OTHER INFORMATION: ZKC6 CDRH3

<400> SEQUENCE: 351

```
Ala Arg Val Ser Asp Trp Gly Phe Ala Phe Asp Ile
1               5                   10
```

<210> SEQ ID NO 352
<211> LENGTH: 119
<212> TYPE: PRT
<213> ORGANISM: Artificial Sequence
<220> FEATURE:
<223> OTHER INFORMATION: ZKC6 VH

<400> SEQUENCE: 352

```
Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

```
Gly Arg Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Arg Val Ser Asp Trp Gly Phe Ala Phe Asp Ile Trp Gly Gln Gly
            100                 105                 110

Thr Met Val Thr Val Ser Gln
        115

<210> SEQ ID NO 353
<211> LENGTH: 8
<212> TYPE: PRT
<213> ORGANISM: Artificial Sequence
<220> FEATURE:
<223> OTHER INFORMATION: ZKA160 CDRH1

<400> SEQUENCE: 353

Gly Gly Ser Ile Thr Ser Tyr Ser
1               5

<210> SEQ ID NO 354
<211> LENGTH: 7
<212> TYPE: PRT
<213> ORGANISM: Artificial Sequence
<220> FEATURE:
<223> OTHER INFORMATION: ZKA160 CDRH2

<400> SEQUENCE: 354

Ile Phe Tyr Ser Gly Ser Thr
1               5

<210> SEQ ID NO 355
<211> LENGTH: 15
<212> TYPE: PRT
<213> ORGANISM: Artificial Sequence
<220> FEATURE:
<223> OTHER INFORMATION: ZKA160 CDRH3

<400> SEQUENCE: 355

Ala Arg Asp Gln Thr Met Pro Val Trp Val Gly Gly Met Asp Val
1               5                   10                  15

<210> SEQ ID NO 356
<211> LENGTH: 121
<212> TYPE: PRT
<213> ORGANISM: Artificial Sequence
<220> FEATURE:
<223> OTHER INFORMATION: ZKA160 VH

<400> SEQUENCE: 356

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Ser Trp Ser Trp Ile Arg Gln Pro Pro Gly Lys Gly Leu Glu Trp Ile
        35                  40                  45

Gly Tyr Ile Phe Tyr Ser Gly Ser Thr Asp Tyr Asn Pro Ser Leu Lys
    50                  55                  60

Ser Arg Val Thr Ile Ser Val Asp Thr Ser Lys Asp Gln Phe Ser Leu
65                  70                  75                  80
```

```
Arg Leu Arg Ser Val Thr Ala Ala Asp Thr Ala Val Tyr Tyr Cys Ala
                85                  90                  95

Arg Asp Gln Thr Met Pro Val Trp Val Gly Gly Met Asp Val Trp Gly
            100                 105                 110

Gln Gly Thr Thr Val Thr Val Ser Ser
        115                 120

<210> SEQ ID NO 357
<211> LENGTH: 8
<212> TYPE: PRT
<213> ORGANISM: Artificial Sequence
<220> FEATURE:
<223> OTHER INFORMATION: ZKA172 CDRH1

<400> SEQUENCE: 357

Gly Tyr Ile Phe Thr Arg Tyr Trp
1               5

<210> SEQ ID NO 358
<211> LENGTH: 8
<212> TYPE: PRT
<213> ORGANISM: Artificial Sequence
<220> FEATURE:
<223> OTHER INFORMATION: ZKA172 CDRH2

<400> SEQUENCE: 358

Ile Asp Pro Ser Asp Ser Tyr Thr
1               5

<210> SEQ ID NO 359
<211> LENGTH: 13
<212> TYPE: PRT
<213> ORGANISM: Artificial Sequence
<220> FEATURE:
<223> OTHER INFORMATION: ZKA172 CDRH3

<400> SEQUENCE: 359

Ala Arg Gln Glu Thr Ala Arg Glu Asp Gly Met Ala Val
1               5                   10

<210> SEQ ID NO 360
<211> LENGTH: 120
<212> TYPE: PRT
<213> ORGANISM: Artificial Sequence
<220> FEATURE:
<223> OTHER INFORMATION: ZKA172 VH

<400> SEQUENCE: 360

Glu Val Gln Leu Val Gln Ser Gly Ala Glu Val Lys Lys Pro Gly Lys
1               5                   10                  15

Ser Leu Arg Ile Ser Cys Lys Gly Ser Gly Tyr Ile Phe Thr Arg Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Glu Thr Ala Arg Glu Asp Gly Met Ala Val Trp Gly Gln
            100                 105                 110
```

```
Gly Thr Thr Val Thr Val Ser Ser
        115                 120
```

<210> SEQ ID NO 361
<211> LENGTH: 10
<212> TYPE: PRT
<213> ORGANISM: Artificial Sequence
<220> FEATURE:
<223> OTHER INFORMATION: ZKA174 CDRH1

<400> SEQUENCE: 361

```
Gly Gly Ser Met Ser Asn Ser Tyr Tyr His
1               5                   10
```

<210> SEQ ID NO 362
<211> LENGTH: 7
<212> TYPE: PRT
<213> ORGANISM: Artificial Sequence
<220> FEATURE:
<223> OTHER INFORMATION: ZKA174 CDRH2

<400> SEQUENCE: 362

```
Ile Tyr Tyr Ser Gly Ser Thr
1               5
```

<210> SEQ ID NO 363
<211> LENGTH: 18
<212> TYPE: PRT
<213> ORGANISM: Artificial Sequence
<220> FEATURE:
<223> OTHER INFORMATION: ZKA174 CDRH3

<400> SEQUENCE: 363

```
Ala Arg Asn Pro Val Phe Asn Pro Leu Thr Leu Thr His Asp Ala Phe
1               5                   10                  15

Asp Ile
```

<210> SEQ ID NO 364
<211> LENGTH: 126
<212> TYPE: PRT
<213> ORGANISM: Artificial Sequence
<220> FEATURE:
<223> OTHER INFORMATION: ZKA174 VH

<400> SEQUENCE: 364

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Ser Asn Ser
            20                  25                  30

Tyr Tyr His Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Asn Pro Val Phe Asn Pro Leu Thr Leu Thr His Asp Ala
            100                 105                 110

Phe Asp Ile Trp Gly Gln Gly Thr Met Val Thr Val Ser Ser
        115                 120                 125
```

```
<210> SEQ ID NO 365
<211> LENGTH: 8
<212> TYPE: PRT
<213> ORGANISM: Artificial Sequence
<220> FEATURE:
<223> OTHER INFORMATION: ZKA189 CDRH1

<400> SEQUENCE: 365

Gly Phe Thr Phe Ser Ser Tyr Ala
1               5

<210> SEQ ID NO 366
<211> LENGTH: 8
<212> TYPE: PRT
<213> ORGANISM: Artificial Sequence
<220> FEATURE:
<223> OTHER INFORMATION: ZKA189 CDRH2

<400> SEQUENCE: 366

Ile Ser Gly Ser Gly Asp Asn Thr
1               5

<210> SEQ ID NO 367
<211> LENGTH: 18
<212> TYPE: PRT
<213> ORGANISM: Artificial Sequence
<220> FEATURE:
<223> OTHER INFORMATION: ZKA189 CDRH3

<400> SEQUENCE: 367

Ala Lys Trp Pro Tyr Tyr Asp Phe Trp Ser Gly Ser Glu Ser Tyr Phe
1               5                   10                  15

Asp Pro

<210> SEQ ID NO 368
<211> LENGTH: 125
<212> TYPE: PRT
<213> ORGANISM: Artificial Sequence
<220> FEATURE:
<223> OTHER INFORMATION: ZKA189 VH

<400> SEQUENCE: 368

Gly Val Gln Leu Leu Glu Ser Gly Gly Ala Leu Val Gln Pro Gly Lys
1               5                   10                  15

Ser Leu Arg Leu Ser Cys Ala Ala Ser Gly Phe Thr Phe Ser Ser Tyr
            20                  25                  30

Ala Leu Thr Trp Val Arg Gln Ala Pro Gly Lys Gly Leu Gln Trp Val
        35                  40                  45

Ser Ala Ile Ser Gly Ser Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Pro Tyr Tyr Asp Phe Trp Ser Gly Ser Glu Ser Tyr Phe
                100                 105                 110

Asp Pro Trp Gly Gln Gly Thr Leu Val Thr Val Ser Ser
            115                 120                 125

<210> SEQ ID NO 369
<211> LENGTH: 8
<212> TYPE: PRT
<213> ORGANISM: Artificial Sequence
```

```
<220> FEATURE:
<223> OTHER INFORMATION: ZKA195 CDRH1

<400> SEQUENCE: 369

Gly Tyr Asn Phe Pro Ser Tyr Trp
1               5

<210> SEQ ID NO 370
<211> LENGTH: 8
<212> TYPE: PRT
<213> ORGANISM: Artificial Sequence
<220> FEATURE:
<223> OTHER INFORMATION: ZKA195 CDRH2

<400> SEQUENCE: 370

Ile Asp Pro Ser Asp Ser Tyr Thr
1               5

<210> SEQ ID NO 371
<211> LENGTH: 15
<212> TYPE: PRT
<213> ORGANISM: Artificial Sequence
<220> FEATURE:
<223> OTHER INFORMATION: ZKA195 CDRH3

<400> SEQUENCE: 371

Ala Arg Ala Asp Cys Arg Ser Thr Ser Cys Tyr Leu Val Phe Glu
1               5                   10                  15

<210> SEQ ID NO 372
<211> LENGTH: 121
<212> TYPE: PRT
<213> ORGANISM: Artificial Sequence
<220> FEATURE:
<223> OTHER INFORMATION: ZKA195 VH

<400> SEQUENCE: 372

Glu Val Gln Leu Val Gln Ser Gly Ala Glu Val Lys Lys Pro Gly Glu
1               5                   10                  15

Ser Leu Arg Ile Ser Cys Lys Asp Ser Gly Tyr Asn Phe Pro Ser Tyr
                20                  25                  30

Trp Ile His Trp Val Arg Gln Met Pro Gly Lys Gly Leu Glu Trp Met
            35                  40                  45

Gly Thr Ile Asp Pro Ser Asp Ser Tyr Thr Asn Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Asp Cys Arg Ser Thr Ser Cys Tyr Leu Val Phe Glu Gly
            100                 105                 110

Gln Gly Thr Leu Val Thr Val Ser Ser
        115                 120

<210> SEQ ID NO 373
<211> LENGTH: 8
<212> TYPE: PRT
<213> ORGANISM: Artificial Sequence
<220> FEATURE:
<223> OTHER INFORMATION: ZKA215 CDRH1

<400> SEQUENCE: 373

Gly Tyr Thr Phe Thr Ser Tyr Trp
1               5
```

```
<210> SEQ ID NO 374
<211> LENGTH: 8
<212> TYPE: PRT
<213> ORGANISM: Artificial Sequence
<220> FEATURE:
<223> OTHER INFORMATION: ZKA215 CDRH2

<400> SEQUENCE: 374

Ile Asp Pro Ser Asp Ser His Thr
1               5

<210> SEQ ID NO 375
<211> LENGTH: 11
<212> TYPE: PRT
<213> ORGANISM: Artificial Sequence
<220> FEATURE:
<223> OTHER INFORMATION: ZKA215 CDRH3

<400> SEQUENCE: 375

Ala Arg His Ala Leu Pro Asn Tyr Phe Asp Ser
1               5                   10

<210> SEQ ID NO 376
<211> LENGTH: 118
<212> TYPE: PRT
<213> ORGANISM: Artificial Sequence
<220> FEATURE:
<223> OTHER INFORMATION: ZKA215 VH

<400> SEQUENCE: 376

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser His Thr Asp Tyr Ser Pro Ser Phe
    50                  55                  60

Gln Gly His Val Thr Ile Ser Ala Asp Lys Ser Ile Ser Ala Ala Tyr
65                  70                  75                  80

Leu Gln Trp Ser Ser Leu Lys Ala Ser Asp Thr Ala Met Tyr Tyr Cys
                85                  90                  95

Ala Arg His Ala Leu Pro Asn Tyr Phe Asp Ser Trp Gly Gln Gly Thr
            100                 105                 110

Leu Val Thr Val Ser Ser
        115

<210> SEQ ID NO 377
<211> LENGTH: 8
<212> TYPE: PRT
<213> ORGANISM: Artificial Sequence
<220> FEATURE:
<223> OTHER INFORMATION: ZKA218 CDRH1

<400> SEQUENCE: 377

Gly Phe Pro Phe Ser Ser Tyr Trp
1               5

<210> SEQ ID NO 378
<211> LENGTH: 8
<212> TYPE: PRT
```

<213> ORGANISM: Artificial Sequence
<220> FEATURE:
<223> OTHER INFORMATION: ZKA218 CDRH2

<400> SEQUENCE: 378

Ile Asn Ser Asp Gly Arg Asn Thr
1               5

<210> SEQ ID NO 379
<211> LENGTH: 15
<212> TYPE: PRT
<213> ORGANISM: Artificial Sequence
<220> FEATURE:
<223> OTHER INFORMATION: ZKA218 CDRH3

<400> SEQUENCE: 379

Ala Arg Gly Gly Tyr Asp Tyr Asp Ser Ser Gly Cys Phe Asp Tyr
1               5                   10                  15

<210> SEQ ID NO 380
<211> LENGTH: 122
<212> TYPE: PRT
<213> ORGANISM: Artificial Sequence
<220> FEATURE:
<223> OTHER INFORMATION: ZKA218 VH

<400> SEQUENCE: 380

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Arg Asn Thr Asn Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Tyr Asp Ser Ser Gly Cys Phe Asp Tyr Trp
            100                 105                 110

Gly Gln Gly Thr Leu Val Thr Val Ser Ser
        115                 120

<210> SEQ ID NO 381
<211> LENGTH: 8
<212> TYPE: PRT
<213> ORGANISM: Artificial Sequence
<220> FEATURE:
<223> OTHER INFORMATION: ZKB75 CDRH1

<400> SEQUENCE: 381

Gly Phe Thr Phe Ser Asn Tyr Ala
1               5

<210> SEQ ID NO 382
<211> LENGTH: 8
<212> TYPE: PRT
<213> ORGANISM: Artificial Sequence
<220> FEATURE:
<223> OTHER INFORMATION: ZKB75 CDRH2

<400> SEQUENCE: 382

Ile Ser Gly Thr Gly Gly Ser Thr
1               5

<210> SEQ ID NO 383
<211> LENGTH: 25
<212> TYPE: PRT
<213> ORGANISM: Artificial Sequence
<220> FEATURE:
<223> OTHER INFORMATION: ZKB75 CDRH3

<400> SEQUENCE: 383

Ala Lys Asp Ser Ala Ser Arg Gly Gly Tyr Cys Ser Gly Val Cys
1               5                   10                  15

Tyr Leu Asn Pro Gly His His Asp Tyr
            20                  25

<210> SEQ ID NO 384
<211> LENGTH: 132
<212> TYPE: PRT
<213> ORGANISM: Artificial Sequence
<220> FEATURE:
<223> OTHER INFORMATION: ZKB75 VH

<400> SEQUENCE: 384

Glu Val Gln Val Leu Glu Ser Gly Gly Gly Leu Leu Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Ala Ser Arg Gly Gly Tyr Cys Ser Gly Gly Val Cys
            100                 105                 110

Tyr Leu Asn Pro Gly His His Asp Tyr Trp Gly Gln Gly Thr Leu Val
        115                 120                 125

Thr Val Ser Ser
    130

<210> SEQ ID NO 385
<211> LENGTH: 8
<212> TYPE: PRT
<213> ORGANISM: Artificial Sequence
<220> FEATURE:
<223> OTHER INFORMATION: ZKB83 CDRH1

<400> SEQUENCE: 385

Gly Tyr Ser Phe Thr Asn Tyr Trp
1               5

<210> SEQ ID NO 386
<211> LENGTH: 8
<212> TYPE: PRT
<213> ORGANISM: Artificial Sequence
<220> FEATURE:
<223> OTHER INFORMATION: ZKB83 CDRH2

<400> SEQUENCE: 386

Ile Asp Pro Ser Asp Ser Tyr Thr
1               5

<210> SEQ ID NO 387
<211> LENGTH: 27
<212> TYPE: PRT
<213> ORGANISM: Artificial Sequence
<220> FEATURE:
<223> OTHER INFORMATION: ZKB83 CDRH3

<400> SEQUENCE: 387

Ala Arg Leu Arg Gly Ser Leu Tyr Cys Ser Gly Gly Arg Cys Tyr Ser
1               5                   10                  15

Val Pro Gly Glu Thr Pro Asn Trp Phe Asp Pro
            20                  25

<210> SEQ ID NO 388
<211> LENGTH: 134
<212> TYPE: PRT
<213> ORGANISM: Artificial Sequence
<220> FEATURE:
<223> OTHER INFORMATION: ZKB83 VH

<400> SEQUENCE: 388

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asn Tyr
            20                  25                  30

Trp Ile Thr Trp Val Arg Gln Met Pro Gly Lys Gly Leu Glu Trp Met
        35                  40                  45

Gly Ser Ile Asp Pro Ser Asp Ser Tyr Thr Asn Tyr Ser Pro Ser Phe
    50                  55                  60

Gln Gly His Val Thr Ile Ser Ala Asp Trp Ser Ile Asn Thr Ala Tyr
65                  70                  75                  80

Leu Gln Trp Ser Ser Leu Lys Ala Ser Asp Thr Ala Lys Tyr Tyr Cys
                85                  90                  95

Ala Arg Leu Arg Gly Ser Leu Tyr Cys Ser Gly Gly Arg Cys Tyr Ser
            100                 105                 110

Val Pro Gly Glu Thr Pro Asn Trp Phe Asp Pro Trp Gly Gln Gly Thr
        115                 120                 125

Leu Val Thr Val Ser Ser
    130

<210> SEQ ID NO 389
<211> LENGTH: 8
<212> TYPE: PRT
<213> ORGANISM: Artificial Sequence
<220> FEATURE:
<223> OTHER INFORMATION: ZKC3 CDRH1

<400> SEQUENCE: 389

Gly Gly Ser Ile Thr Ser Tyr Tyr
1               5

<210> SEQ ID NO 390
<211> LENGTH: 7
<212> TYPE: PRT
<213> ORGANISM: Artificial Sequence
<220> FEATURE:
<223> OTHER INFORMATION: ZKC3 CDRH2

<400> SEQUENCE: 390

```
Ile Tyr Tyr Ser Gly Ser Thr
1               5

<210> SEQ ID NO 391
<211> LENGTH: 15
<212> TYPE: PRT
<213> ORGANISM: Artificial Sequence
<220> FEATURE:
<223> OTHER INFORMATION: ZKC3 CDRH3

<400> SEQUENCE: 391

Ala Arg Val Gly Gly Ala Pro Tyr Tyr Tyr Tyr Gly Met Asp Val
1               5                   10                  15

<210> SEQ ID NO 392
<211> LENGTH: 121
<212> TYPE: PRT
<213> ORGANISM: Artificial Sequence
<220> FEATURE:
<223> OTHER INFORMATION: ZKC3 VH

<400> SEQUENCE: 392

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Gly Ala Pro Tyr Tyr Tyr Tyr Gly Met Asp Val Trp Gly
            100                 105                 110

Gln Gly Thr Thr Val Thr Val Ser Ser
        115                 120

<210> SEQ ID NO 393
<211> LENGTH: 8
<212> TYPE: PRT
<213> ORGANISM: Artificial Sequence
<220> FEATURE:
<223> OTHER INFORMATION: ZKC18 CDRH1

<400> SEQUENCE: 393

Gly Phe Thr Phe Gly Asp Tyr Ala
1               5

<210> SEQ ID NO 394
<211> LENGTH: 10
<212> TYPE: PRT
<213> ORGANISM: Artificial Sequence
<220> FEATURE:
<223> OTHER INFORMATION: ZKC18 CDRH2

<400> SEQUENCE: 394

Ile Arg Ser Lys Ala Tyr Gly Gly Thr Thr
1               5                   10

<210> SEQ ID NO 395
<211> LENGTH: 13
```

```
<212> TYPE: PRT
<213> ORGANISM: Artificial Sequence
<220> FEATURE:
<223> OTHER INFORMATION: ZKC18 CDRH3

<400> SEQUENCE: 395

Ser Arg Asp His Thr Gly Thr Thr Tyr Ala Phe Asp Ile
1               5                   10

<210> SEQ ID NO 396
<211> LENGTH: 122
<212> TYPE: PRT
<213> ORGANISM: Artificial Sequence
<220> FEATURE:
<223> OTHER INFORMATION: ZKC18 VH

<400> SEQUENCE: 396

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ser Arg Asp His Thr Gly Thr Thr Tyr Ala Phe Asp Ile Trp
            100                 105                 110

Gly Gln Gly Thr Met Val Thr Val Ser Gln
        115                 120

<210> SEQ ID NO 397
<211> LENGTH: 8
<212> TYPE: PRT
<213> ORGANISM: Artificial Sequence
<220> FEATURE:
<223> OTHER INFORMATION: ZKD1 CDRH1

<400> SEQUENCE: 397

Gly Phe Thr Phe Ser Ser Tyr Gly
1               5

<210> SEQ ID NO 398
<211> LENGTH: 8
<212> TYPE: PRT
<213> ORGANISM: Artificial Sequence
<220> FEATURE:
<223> OTHER INFORMATION: ZKD1 CDRH2

<400> SEQUENCE: 398

Ile Trp Tyr Asp Gly Ser Asn Lys
1               5

<210> SEQ ID NO 399
<211> LENGTH: 19
<212> TYPE: PRT
<213> ORGANISM: Artificial Sequence
<220> FEATURE:
<223> OTHER INFORMATION: ZKD1 CDRH3

<400> SEQUENCE: 399
```

Ala Arg Asp Arg Arg Gly Tyr Gly Asp Tyr Val Gly Tyr Tyr Tyr Gly
1 5 10 15

Met Asp Val

<210> SEQ ID NO 400
<211> LENGTH: 126
<212> TYPE: PRT
<213> ORGANISM: Artificial Sequence
<220> FEATURE:
<223> OTHER INFORMATION: ZKD1 VH

<400> SEQUENCE: 400

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Arg Arg Gly Tyr Gly Asp Tyr Val Gly Tyr Tyr Tyr Gly
100 105 110

Met Asp Val Trp Gly Gln Gly Thr Thr Val Thr Val Ser Ser
115 120 125

<210> SEQ ID NO 401
<211> LENGTH: 95
<212> TYPE: PRT
<213> ORGANISM: Artificial Sequence
<220> FEATURE:
<223> OTHER INFORMATION: Zika Virus EDIII
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

```
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid

<400> SEQUENCE: 401

Thr Ala Ala Phe Thr Phe Thr Lys Xaa Pro Ala Glu Xaa Xaa His Gly
1               5                   10                  15

Thr Val Thr Val Glu Xaa Gln Tyr Xaa Gly Xaa Asp Gly Pro Cys Lys
                20                  25                  30

Xaa Pro Xaa Gln Met Ala Val Asp Xaa Gln Thr Leu Thr Pro Val Gly
        35                  40                  45

Arg Leu Ile Thr Ala Asn Pro Val Ile Thr Glu Xaa Thr Glu Asn Ser
    50                  55                  60

Lys Met Met Leu Glu Leu Asp Pro Pro Phe Gly Asp Ser Tyr Ile Val
65                  70                  75                  80

Ile Gly Xaa Gly Xaa Lys Lys Ile Thr His His Trp His Arg Ser
                85                  90                  95

<210> SEQ ID NO 402
<211> LENGTH: 95
<212> TYPE: PRT
<213> ORGANISM: Artificial Sequence
<220> FEATURE:
<223> OTHER INFORMATION: ZIKAV H PF 2013 EDIII

<400> SEQUENCE: 402

Thr Ala Ala Phe Thr Phe Thr Lys Ile Pro Ala Glu Thr Leu His Gly
1               5                   10                  15

Thr Val Thr Val Glu Val Gln Tyr Ala Gly Thr Asp Gly Pro Cys Lys
                20                  25                  30

Val Pro Ala Gln Met Ala Val Asp Met Gln Thr Leu Thr Pro Val Gly
        35                  40                  45

Arg Leu Ile Thr Ala Asn Pro Val Ile Thr Glu Ser Thr Glu Asn Ser
    50                  55                  60

Lys Met Met Leu Glu Leu Asp Pro Pro Phe Gly Asp Ser Tyr Ile Val
65                  70                  75                  80

Ile Gly Val Gly Glu Lys Lys Ile Thr His His Trp His Arg Ser
                85                  90                  95

<210> SEQ ID NO 403
<211> LENGTH: 20
<212> TYPE: DNA
<213> ORGANISM: Artificial Sequence
<220> FEATURE:
<223> OTHER INFORMATION: ZIKV-NS1 forward primer

<400> SEQUENCE: 403
tggagttcaa ctgacggtcg                                           20

<210> SEQ ID NO 404
<211> LENGTH: 20
<212> TYPE: DNA
<213> ORGANISM: Artificial Sequence
<220> FEATURE:
```

```
<223> OTHER INFORMATION: ZIKV-NS1-reverse primer

<400> SEQUENCE: 404
taccccgaac ccatgatcct                                                    20

<210> SEQ ID NO 405
<211> LENGTH: 21
<212> TYPE: DNA
<213> ORGANISM: Artificial Sequence
<220> FEATURE:
<223> OTHER INFORMATION: Gapdh- forward primer

<400> SEQUENCE: 405
ggcaagttca aaggcacagt c                                                  21

<210> SEQ ID NO 406
<211> LENGTH: 19
<212> TYPE: DNA
<213> ORGANISM: Artificial Sequence
<220> FEATURE:
<223> OTHER INFORMATION: Gapdh-reverse primer

<400> SEQUENCE: 406
caccagcatc accccattt                                                     19

<210> SEQ ID NO 407
<211> LENGTH: 104
<212> TYPE: PRT
<213> ORGANISM: Artificial Sequence
<220> FEATURE:
<223> OTHER INFORMATION: ZIKV EDIII generic
<220> FEATURE:
<221> NAME/KEY: misc_feature
<222> LOCATION: (1)..(1)
<223> OTHER INFORMATION: X may be any (naturally occurring) amino acid,
      preferably K, A, or E
<220> FEATURE:
<221> NAME/KEY: misc_feature
<222> LOCATION: (3)..(3)
<223> OTHER INFORMATION: X may be any (naturally occurring) amino acid,
      preferably V, F, or L
<220> FEATURE:
<221> NAME/KEY: misc_feature
<222> LOCATION: (4)..(4)
<223> OTHER INFORMATION: X may be any (naturally occurring) amino acid,
      preferably S or F
<220> FEATURE:
<221> NAME/KEY: misc_feature
<222> LOCATION: (17)..(17)
<223> OTHER INFORMATION: X may be any (naturally occurring) amino acid,
      preferably I or V
<220> FEATURE:
<221> NAME/KEY: misc_feature
<222> LOCATION: (21)..(21)
<223> OTHER INFORMATION: X may be any (naturally occurring) amino acid,
      preferably T or V
<220> FEATURE:
<221> NAME/KEY: misc_feature
<222> LOCATION: (22)..(22)
<223> OTHER INFORMATION: X may be any (naturally occurring) amino acid,
      preferably L or D
<220> FEATURE:
<221> NAME/KEY: misc_feature
<222> LOCATION: (30)..(30)
<223> OTHER INFORMATION: X may be any (naturally occurring) amino acid,
      preferably V or G
<220> FEATURE:
<221> NAME/KEY: misc_feature
<222> LOCATION: (33)..(33)
<223> OTHER INFORMATION: X may be any (naturally occurring) amino acid,
      preferably A or G
<220> FEATURE:
<221> NAME/KEY: misc_feature
```

```
<222> LOCATION: (35)..(35)
<223> OTHER INFORMATION: X may be any (naturally occurring) amino acid
      except R, preferably T or A
<220> FEATURE:
<221> NAME/KEY: misc_feature
<222> LOCATION: (41)..(41)
<223> OTHER INFORMATION: X may be any (naturally occurring) amino acid,
      preferably V or I
<220> FEATURE:
<221> NAME/KEY: misc_feature
<222> LOCATION: (43)..(43)
<223> OTHER INFORMATION: X may be any (naturally occurring) amino acid,
      preferably A or V
<220> FEATURE:
<221> NAME/KEY: misc_feature
<222> LOCATION: (49)..(49)
<223> OTHER INFORMATION: X may be any (naturally occurring) amino acid,
      preferably M or T
<220> FEATURE:
<221> NAME/KEY: misc_feature
<222> LOCATION: (68)..(68)
<223> OTHER INFORMATION: X may be any (naturally occurring) amino acid,
      preferably S or G
<220> FEATURE:
<221> NAME/KEY: misc_feature
<222> LOCATION: (70)..(70)
<223> OTHER INFORMATION: X may be any (naturally occurring) amino acid,
      preferably E or K
<220> FEATURE:
<221> NAME/KEY: misc_feature
<222> LOCATION: (91)..(91)
<223> OTHER INFORMATION: X may be any (naturally occurring) amino acid,
      preferably V or I
<220> FEATURE:
<221> NAME/KEY: misc_feature
<222> LOCATION: (93)..(93)
<223> OTHER INFORMATION: X may be any (naturally occurring) amino acid,
      preferably E, A, K, or D
<220> FEATURE:
<221> NAME/KEY: misc_feature
<222> LOCATION: (94)..(94)
<223> OTHER INFORMATION: X may be any (naturally occurring) amino acid,
      preferably E, A, or K, more preferably K or A

<400> SEQUENCE: 407

Xaa Gly Xaa Xaa Tyr Ser Leu Cys Thr Ala Ala Phe Thr Phe Thr Lys
1               5                   10                  15

Xaa Pro Ala Glu Xaa Xaa His Gly Thr Val Thr Val Glu Xaa Gln Tyr
            20                  25                  30

Xaa Gly Xaa Asp Gly Pro Cys Lys Xaa Pro Xaa Gln Met Ala Val Asp
        35                  40                  45

Xaa Gln Thr Leu Thr Pro Val Gly Arg Leu Ile Thr Ala Asn Pro Val
    50                  55                  60

Ile Thr Glu Xaa Thr Xaa Asn Ser Lys Met Met Leu Glu Leu Asp Pro
65                  70                  75                  80

Pro Phe Gly Asp Ser Tyr Ile Val Ile Gly Xaa Gly Xaa Xaa Lys Ile
                85                  90                  95

Thr His His Trp His Arg Ser Gly
            100

<210> SEQ ID NO 408
<211> LENGTH: 19
<212> TYPE: PRT
<213> ORGANISM: Artificial Sequence
<220> FEATURE:
<223> OTHER INFORMATION: chimeric hinge

<400> SEQUENCE: 408

Glu Ser Lys Tyr Gly Pro Pro Cys Pro Pro Cys Pro Ala Pro Pro Val
1               5                   10                  15
```

Ala Gly Pro

<210> SEQ ID NO 409
<211> LENGTH: 95
<212> TYPE: PRT
<213> ORGANISM: Artificial Sequence
<220> FEATURE:
<223> OTHER INFORMATION: ZIKV MR766 (AY632535) EDIII

<400> SEQUENCE: 409

```
Thr Ala Ala Phe Thr Phe Thr Lys Val Pro Ala Glu Thr Leu His Gly
1               5                   10                  15

Thr Val Thr Val Glu Val Gln Tyr Ala Gly Thr Asp Gly Pro Cys Lys
            20                  25                  30

Leu Pro Val Gln Met Ala Val Asp Met Gln Thr Leu Thr Pro Val Gly
        35                  40                  45

Arg Leu Ile Thr Ala Asn Pro Val Ile Thr Glu Ser Thr Glu Asn Ser
    50                  55                  60

Lys Met Met Leu Glu Leu Asp Pro Pro Phe Gly Asp Ser Tyr Ile Val
65                  70                  75                  80

Ile Gly Val Gly Asp Lys Lys Ile Thr His His Trp His Arg Ser
                85                  90                  95
```

<210> SEQ ID NO 410
<211> LENGTH: 95
<212> TYPE: PRT
<213> ORGANISM: Artificial Sequence
<220> FEATURE:
<223> OTHER INFORMATION: ZIKV KU870645 (USA) 02-Feb-2016 EDIII

<400> SEQUENCE: 410

```
Thr Ala Ala Phe Thr Phe Thr Lys Ile Pro Ala Glu Thr Leu His Gly
1               5                   10                  15

Thr Val Thr Val Glu Val Gln Tyr Ala Gly Thr Asp Gly Pro Cys Lys
            20                  25                  30

Val Pro Ala Gln Met Ala Val Asp Met Gln Thr Leu Thr Pro Val Gly
        35                  40                  45

Arg Leu Ile Thr Ala Asn Pro Val Ile Thr Glu Ser Thr Glu Asn Ser
    50                  55                  60

Lys Met Met Leu Glu Leu Asp Pro Pro Phe Gly Asp Ser Tyr Ile Val
65                  70                  75                  80

Ile Gly Leu Gly Glu Lys Lys Ile Thr His His Trp His Arg Ser
                85                  90                  95
```

<210> SEQ ID NO 411
<211> LENGTH: 95
<212> TYPE: PRT
<213> ORGANISM: Artificial Sequence
<220> FEATURE:
<223> OTHER INFORMATION: ZIKV KU729218 (Brazil) 2015 EDIII

<400> SEQUENCE: 411

```
Thr Ala Ala Phe Thr Phe Thr Lys Ile Pro Ala Glu Thr Leu His Gly
1               5                   10                  15

Thr Val Thr Val Glu Val Gln Tyr Ala Gly Thr Asp Gly Pro Cys Lys
            20                  25                  30

Val Pro Ala Gln Met Ala Val Asp Thr Gln Thr Leu Thr Pro Val Gly
        35                  40                  45

Arg Leu Ile Thr Ala Asn Pro Val Ile Thr Glu Ser Thr Glu Asn Ser
```

```
                    50                  55                  60

Lys Met Met Leu Glu Leu Asp Pro Pro Phe Gly Asp Ser Tyr Ile Val
 65                  70                  75                  80

Ile Gly Val Gly Glu Lys Lys Ile Thr His His Trp His Arg Ser
                 85                  90                  95

<210> SEQ ID NO 412
<211> LENGTH: 95
<212> TYPE: PRT
<213> ORGANISM: Artificial Sequence
<220> FEATURE:
<223> OTHER INFORMATION: ZIKV KU681081 (Thailand) 9-Jul-14 EDIII

<400> SEQUENCE: 412

Thr Ala Ala Phe Thr Phe Thr Lys Ile Pro Ala Glu Thr Leu His Gly
 1               5                  10                  15

Thr Val Thr Val Glu Val Gln Tyr Ala Gly Thr Asp Gly Pro Cys Lys
                 20                  25                  30

Val Pro Ala Gln Met Ala Val Asp Met Gln Thr Leu Thr Pro Val Gly
             35                  40                  45

Arg Leu Ile Thr Ala Asn Pro Val Ile Thr Glu Gly Thr Glu Asn Ser
     50                  55                  60

Lys Met Met Leu Glu Leu Asp Pro Pro Phe Gly Asp Ser Tyr Ile Val
 65                  70                  75                  80

Ile Gly Val Gly Glu Lys Lys Ile Thr His His Trp His Arg Ser
                 85                  90                  95

<210> SEQ ID NO 413
<211> LENGTH: 95
<212> TYPE: PRT
<213> ORGANISM: Artificial Sequence
<220> FEATURE:
<223> OTHER INFORMATION: ZIKV KU926310 (Brazil) 29-Jan-2016 EDIII

<400> SEQUENCE: 413

Thr Ala Ala Phe Thr Phe Thr Lys Ile Pro Ala Glu Thr Leu His Gly
 1               5                  10                  15

Thr Val Thr Val Glu Val Gln Tyr Ala Gly Ala Asp Gly Pro Cys Lys
                 20                  25                  30

Val Pro Ala Gln Met Ala Val Asp Met Gln Thr Leu Thr Pro Val Gly
             35                  40                  45

Arg Leu Ile Thr Ala Asn Pro Val Ile Thr Glu Ser Thr Glu Asn Ser
     50                  55                  60

Lys Met Met Leu Glu Leu Asp Pro Pro Phe Gly Asp Ser Tyr Ile Val
 65                  70                  75                  80

Ile Gly Val Gly Glu Lys Lys Ile Thr His His Trp His Arg Ser
                 85                  90                  95

<210> SEQ ID NO 414
<211> LENGTH: 95
<212> TYPE: PRT
<213> ORGANISM: Artificial Sequence
<220> FEATURE:
<223> OTHER INFORMATION: ZIKV KU744693 (China) 6-Feb-16 EDIII

<400> SEQUENCE: 414

Thr Ala Ala Phe Thr Phe Thr Lys Ile Pro Ala Glu Thr Val Asp Gly
 1               5                  10                  15

Thr Val Thr Val Glu Gly Gln Tyr Gly Gly Thr Asp Gly Pro Cys Lys
                 20                  25                  30
```

```
Val Pro Ala Gln Met Ala Val Asp Met Gln Thr Leu Thr Pro Val Gly
        35                  40                  45

Arg Leu Ile Thr Ala Asn Pro Val Ile Thr Glu Ser Thr Glu Asn Ser
        50                  55                  60

Lys Met Met Leu Glu Leu Asp Pro Pro Phe Gly Asp Ser Tyr Ile Val
65                  70                  75                  80

Ile Gly Val Gly Glu Lys Lys Ile Thr His His Trp His Arg Ser
                85                  90                  95
```

ANTIBODIES SPECIFICALLY BINDING TO ZIKA VIRUS EPITOPES AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 470082_407 D1_SEQUENCE-LISTING.txt. The text file is 175 kb, was created on May 26, 2021, and is being submitted electronically via EFS-Web.

The present invention relates to antibodies, and antigen binding fragments thereof, that bind specifically to Zika virus (ZIKV) epitopes. Such antibodies (i) potently neutralize infection of Zika virus (ZIKV) or (ii) are directed against NS1 ZIKV and can be used as diagnostics. The invention also relates to antigenic sites to which the antibodies and antigen binding fragments bind to, as well as to nucleic acids that encode the antibodies and immortalized B cells that produce such antibodies and antibody fragments. In addition, the invention relates to the use of the antibodies and antibody fragments of the invention in screening methods as well as in the diagnosis, prevention and treatment of ZIKV infection.

Zika virus (ZIKV), a mosquito-borne flavivirus, is a public health emergency. ZIKV was first isolated from macaques in 1947 in the Zika forest in Uganda (G. W. A. Dick, S. F. Kitchen, A. J. Haddow, Zika virus. I. Isolations and serological specificity. *Trans. R. Soc. Trop. Med. Hyg.* 46, 509-520 (1952)) and the first human infection was reported in Nigeria in 1954 F. N. Macnamara, Zika virus: a report on three cases of human infection during an epidemic of jaundice in Nigeria. *Trans. R. Soc. Trop. Med. Hyg.* 48, 139-145 (1954)). Since then, ZIKV infections were sporadically reported in Africa and southeast Asia (D. Musso, Van Mai Cao-Lormeau, D. J. Gubler, Zika virus: following the path of dengue and chikungunya? *The Lancet.* 386, 243-244 (2015)), but epidemics were reported in Micronesia in 2007 (M. R. Duffy et al., Zika virus outbreak on Yap Island, Federated States of Micronesia. *N Engl J Med.* 360, 2536-2543 (2009)) and in French Polynesia in 2013-14, with the virus subsequently spreading to other countries in the Oceanian continent (V.-M. Cao-Lormeau, D. Musso, Emerging arboviruses in the Pacific. *Lancet.* 384, 1571-1572 (2014); D. Musso, E. J. Nilles, V.-M. Cao-Lormeau, Rapid spread of emerging Zika virus in the Pacific area. *Clin. Microbiol. Infect.* 20, 0595-6 (2014)). After its introduction into Brazil in 2015, ZIKV has spread rapidly and in February 2016 the World Health Organization (WHO) declared it a Public Health Emergency of International Concern (L. R. Baden, L. R. Petersen, D. J. Jamieson, A. M. Powers, M. A. Honein, Zika Virus. *N. Engl. J. Med.* 374, 1552-1563 (2016); A. S. Fauci, D. M. Morens, Zika Virus in the Americas—Yet Another Arbovirus Threat. N Engl J Med, 160113142101009 (2016); D. L. Heymann et al., Zika virus and microcephaly: why is this situation a PHEIC? *Lancet.* 387, 719-721 (2016)). The main route of ZIKV infection is through bites by *Aedes* mosquitos, but the virus may also be sexually (D. Musso et al., Potential sexual transmission of Zika virus. *Emerg Infect Dis.* 21, 359-361 (2015)) and vertically transmitted (J. Mlakar et al., Zika Virus Associated with Microcephaly. *N Engl J Med.* 374, 951-958 (2016)). While most of the ZIKV infections are asymptomatic or cause only mild symptoms, there is evidence that ZIKV infection can lead to neurological complications, such as Guillain-Barre Syndrome in adults (V.-M. Cao-Lormeau et al., Guillain-Barré Syndrome outbreak associated with Zika virus infection in French Polynesia: a case-control study. *Lancet.* 0 (2016), doi:10.1016/S0140-6736(16)00562-6) and congenital birth defects including microcephaly in the developing fetus G. Calvet, R. S. Aguiar, A. Melo, S. A. Sampaio, Detection and sequencing of Zika virus from amniotic fluid of fetuses with microcephaly in Brazil: a case study. *Lancet Infect Dis* (2016), doi:10.1016/S1473-3099(16)00095-5; J. Mlakar et al., Zika Virus Associated with Microcephaly. *N Engl J Med.* 374, 951-958 (2016); E. J. Rubin, M. F. Greene, L. R. Baden, Zika Virus and Microcephaly. *N Engl J Med* (2016), doi:10.1056/NEJMe1601862), likely through its ability to infect human neural progenitor cells H. Tang et al., Zika Virus Infects Human Cortical Neural Progenitors and Attenuates Their Growth. *Stem Cell,* 1-5 (2016)).

ZIKV belongs to the genus flavivirus, which also includes the West Nile virus, dengue virus, tick-borne encephalitis virus, yellow fever virus, and several other viruses which may cause encephalitis. Flaviviruses are enveloped, with icosahedral and spherical geometries. The diameter is around 50 nm. Genomes are linear positive-sense RNA and non-segmented, around 10-11 kb in length. The genome of flaviviruses encodes 3 structural proteins (Capsid, prM, and Envelope) and 8 non-structural proteins (NS1, NS2A, NS2B, NS3, NS4A, NS4B, NS5 and NSSB).

While flavivirus envelope (E) proteins mediate fusion and are the main target of neutralizing antibodies, the non-structural protein 1 (NS1) is secreted by infected cells and is involved in immune evasion and pathogenesis (D. A. Muller, P. R. Young, The flavivirus NS1 protein: molecular and structural biology, immunology, role in pathogenesis and application as a diagnostic biomarker. *Antiviral Res.* 98, 192-208 (2013)). Two recent structural studies showed a high level of structural similarity between the E protein of ZIKV and that of other flaviviruses, such as dengue virus (DENV), yellow fever virus (YFV) and West Nile virus (WNV) but also revealed unique features that may be related to the ZIKV neurotropism (L. Dai et al., *Structures of the Zika Virus Envelope Protein and Its Complex with a Flavivirus Broadly Protective Antibody. Cell Host Microbe* (2016), doi:10.1016/j.chom.2016.04.013; D. Sirohi et al., The 3.8 Å resolution cryo-EM structure of Zika virus. *Science,* aaf5316 (2016)). Similarly, the structural analysis of ZIKV NS1 revealed conserved features with NS1 of other flaviviruses although with different electrostatic characteristics (J. Kim et al., Zika virus NS1 structure reveals diversity of electrostatic surfaces among flaviviruses, 1-6 (2016)).

A phenomenon that is characteristic of certain flaviviruses is the disease-enhancing activity of cross-reactive antibodies elicited by previous infection by heterologous viruses. In the case of Dengue virus (DENV), for which 4 serotypes are known, there is epidemiological evidence that a primary infection protects from reinfection with the same serotype, but represents a risk factor for the development of severe disease upon reinfection with a different serotype (S. B. Halstead, Dengue Antibody-Dependent Enhancement: Knowns and Unknowns. *Microbiol Spectr.* 2, 249-271 (2014)). The exacerbated disease is triggered by E and prM-specific antibodies that fail to neutralize the incoming virus but instead enhance its capture by Fc receptor-expressing ($FcR^+$) cells, leading to enhanced viral replication and activation of cross-reactive memory T cells. The resulting cytokine storm is thought to be the basis of the most severe form of disease known as dengue hemorragic fever/dengue shock syndrome (S. B. Halstead, Neutralization and antibody-dependent enhancement of dengue viruses. *Adv Virus Res.* 60, 421-467 (2003); G. Screaton, J. Mongkolsapaya, S. Yacoub, C. Roberts, New insights into the immunopathology and control of dengue virus infection. *Nat Rev Immunol.* 15, 745-759 (2015). The role of antibodies in severe dengue is supported by studies showing that waning levels of maternal antibodies in infants represent a higher risk for development of severe dengue disease (S. B. Halstead, Neutralization and antibody-dependent enhancement of dengue viruses. *Adv Virus Res.* 60, 421-467 (2003); S. B. Halstead et al., Dengue hemorrhagic fever in infants: research opportunities ignored. *Emerging Infect Dis.* 8, 1474-1479 (2002); T. H. Nguyen et al., Dengue hemorrhagic fever in infants: a study of clinical and cytokine profiles. *J Infect Dis.* 189, 221-232 (2004); A. L. Rothman, Dengue: defining protective versus pathologic immunity. *J Clin Invest.* 113, 946-951 (2004)).

Recently, it was shown that most antibodies that reacted to DENV envelope protein also bound to ZIKV, but those that recognize the major linear fusion-loop epitope (FLE) did not neutralize ZIKV and instead promoted antibody-dependent enhancement (ADE) of ZIKV infection (Dejnirattisai W, Supasa P, Wongwiwat W, Rouvinski A, Barba-Spaeth G, Duangchinda T, Sakuntabhai A, Cao-Lormeau V M, Malasit P, Rey F A, Mongkolsapaya J, Screaton G R: Dengue virus sero-cross-reactivity drives antibody-dependent enhancement of infection with zika virus. Nat Immunol. 2016 Jun. 23. doi: 10.1038/ni.3515. [Epub ahead of print]).

Moreover, according to the WHO, the recent increase in cases of microcephaly and other neurological disorders potentially associated with Zika virus infection has prompted an increase in demand for laboratory testing to detect Zika virus infection. In this context, high specificity of the antibodies is required in order to distinguish ZIKV infection from infection of other flaviviruses. However, known anti-Zika antibodies are typically cross-reactive for other flaviviruses and, thus, not useful to distinguish ZIKV infection from infection of other flaviviruses.

In view of the above, it is an object of the present invention to provide novel antibodies, which specifically bind to ZIKV epitopes. It is also an object of the present invention to provide potently neutralizing anti-ZIKV antibodies. Such antibodies do preferably not contribute to antibody-dependent enhancement (ADE) of Zika virus infection. It is also an object of the present invention to provide highly specific anti-ZIKV antibodies useful in diagnosis and testing of ZIKV infection and diagnosis methods using such antibodies.

The object underlying the present invention is solved by the claimed subject matter.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, the term "antibody" encompasses various forms of antibodies including, without being limited to, whole antibodies, antibody fragments, in particular antigen binding fragments, human antibodies, chimeric antibodies, humanized antibodies, recombinant antibodies and genetically engineered antibodies (variant or mutant antibodies) as long as the characteristic properties according to the invention are retained. Human antibodies and monoclonal antibodies are preferred and especially preferred are human monoclonal antibodies, in particular as recombinant human monoclonal antibodies.

Human antibodies are well-known in the state of the art (van Dijk, M. A., and van de Winkel, J. G., *Curr. Opin. Chem. Biol.* 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., *Proc. Natl. Acad. Sci. USA* 90 (1993) 2551-2555; Jakobovits, A., et al., *Nature* 362 (1993) 255-258; Bruggemann, M., et al., *Year Immunol.* 7 (1993) 3340). Human antibodies can also be produced in phage display libraries (Hoogenboom, H. R., and Winter, G., *J. Mol. Biol.* 227 (1992) 381-388; Marks, J. D., et al., *J. Mol. Biol.* 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., *J. Immunol.* 147 (1991) 86-95). Preferably, human monoclonal antibodies are prepared by using improved EBV-B cell immortalization as described in Traggiai E, Becker S, Subbarao K, Kolesnikova L, Uematsu Y, Gismondo M R, Murphy B R, Rappuoli R, Lanzavecchia A. (2004): An efficient method to make human monoclonal antibodies from memory B cells: potent neutralization of SARS coronavirus. *Nat Med.* 10(8):871-5. The term "human antibody" as used herein also comprises such antibodies which are modified, e.g. in the variable region, to generate the properties according to the invention as described herein. As used herein, the term "variable region" (variable region of a light chain ($V_L$), variable region of a heavy chain ($V_H$)) denotes each of the pair of light and heavy chains which is involved directly in binding the antibody to the antigen.

Antibodies of the invention can be of any isotype (e.g., IgA, IgG, IgM i.e. an α, γ or μ heavy chain), but will preferably be IgG. Within the IgG isotype, antibodies may be IgG1, IgG2, IgG3 or IgG4 subclass, whereby IgG1 is preferred. Antibodies of the invention may have a κ or a λ light chain. Preferably, the antibody according to the present invention, or the antigen binding fragment thereof, is a purified antibody, a single chain antibody, Fab, Fab', F(ab')2, Fv or scFv.

The antibodies of the invention may thus preferably be human antibodies, monoclonal antibodies, human monoclonal antibodies, recombinant antibodies or purified antibodies. The invention also provides fragments of the antibodies of the invention, particularly fragments that retain the antigen-binding activity of the antibodies. Such fragments include, but are not limited to, single chain antibodies, Fab, Fab', F(ab')2, Fv or scFv. Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Antibodies according to the present invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies according to the present invention may be immunogenic in human and/or in non-human (or heterologous) hosts e.g., in mice. For example, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The term "specifically binding" and similar reference does not encompass non-specific sticking.

The term "vaccine" as used herein is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response. In particular, an "antigen" or an "immunogen" refers typically to a substance which may be recognized by the immune system, preferably by the adaptive immune system, and which is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

As used herein, "sequence variant" (also referred to as "variant") refers to any alteration in a reference sequence, whereby a reference sequence is any of the sequences listed in the "Tables of Sequences and SEQ ID Numbers" (sequence listing), i.e. SEQ ID NO: 1 to SEQ ID NO: 407. Thus, the term "sequence variant" includes nucleotide sequence variants and amino acid sequence variants. Of note, the sequence variants referred to herein are in particular functional sequence variants, i.e. sequence variants maintaining the biological function of, for example, the antibody. In the context of the present invention such a maintained biological function is preferably the neutralization of ZIKV infection, the binding of the antibody to the ZIKV E protein and/or the binding of the antibody to the ZIKV NS1 protein. Preferred sequence variants are thus functional sequence variants having at least 70%, at least 75%, at least 80%, at least 85%, at least 88%, at least 90%, at least 92%, at least 95%, at least 96%, at least 97%, at least 98% or at least 99% sequence identity to a reference sequence. The phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", as used herein, means (i) that the sequence variant is functional as described herein and (ii) the higher the % sequence identity, the more preferred the sequence variant. In other words, the phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", means in particular that the functional sequence variant has at least 70% sequence identity, preferably at least 75% sequence identity, preferably at least 80% sequence identity, more preferably at least 85% sequence identity, more preferably at least 88% sequence identity, even more preferably at least 90% sequence identity, even more preferably at least 92% sequence identity, still more preferably at least 95% sequence identity, still more preferably at least 96% sequence identity, particularly preferably at least 97% sequence identity, particularly preferably at least 98% sequence identity and most preferably at least 99% sequence identity to the respective reference sequence.

The term "sequence variant" includes in particular such variants that comprise mutations and/or substitutions in comparison to the reference sequence. Exemplary variants of an Fc moiety sequence include, but are not limited to, those that have an L to A substitution at position CH2 4, CH2 5, or both.

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; http://www.ncbi.nlm.nih.gov/) [Blosum 62 matrix; gap open penalty=11 and gap extension penalty=1].

As used herein, a "nucleotide sequence variant" has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "nucleotide sequence variant" can either result in a change in the respective reference amino acid sequence, i.e. in an "amino acid sequence variant" or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 80%, preferably at least 90%, more preferably at least 95% sequence identical to the reference sequence.

An "amino acid sequence variant" has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 80% identical to the reference sequence, preferably, at least 90% identical, more preferably at least 95% identical, most preferably at least 99% identical to the reference sequence. Variant sequences which are at least 90% identical have no more than 10 alterations, i.e. any combination of deletions, insertions or substitutions, per 100 amino acids of the reference sequence.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the alterations in the sequence variants do not abolish the functionality of the respective reference sequence, in the present case, e.g., the functionality of a sequence of an antibody, or antigen binding fragment thereof, to bind to the same epitope and/or to sufficiently neutralize infection of ZIKV. Guidance in determining which nucleotides and amino acid residues, respectively, may be substituted, inserted or deleted without abolishing such functionality are found by using computer programs well known in the art.

As used herein, a nucleic acid sequence or an amino acid sequence "derived from" a designated nucleic acid, peptide, polypeptide or protein refers to the origin of the nucleic acid, peptide, polypeptide or protein. Preferably, the nucleic acid sequence or amino acid sequence which is derived from a particular sequence has an amino acid sequence that is essentially identical to that sequence or a portion thereof, from which it is derived, whereby "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art. Likewise, sequences "derived from" other sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residue insertions or deletions may occur.

As used herein, the term "mutation" relates to a change in the nucleic acid sequence and/or in the amino acid sequence in comparison to a reference sequence, e.g. a corresponding genomic sequence.

A mutation, e.g. in comparison to a genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g. in a nucleic acid sequence or in an amino acid sequence. A mutation includes substitution, deletion and insertion of one or more nucleotides or amino acids as well as inversion of several successive nucleotides or amino acids. To achieve a mutation in an amino acid sequence, preferably a mutation may be introduced into the nucleotide sequence encoding said amino acid sequence in order to express a (recombinant) mutated polypeptide. A mutation may be achieved e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Antibodies Potently Neutralizing Zika Virus Infection

The present invention is based, amongst other findings, on the discovery and isolation of antibodies that bind specifically to Zika virus epitopes. Such antibodies are either (i) highly potent in neutralizing Zika virus, if directed to an antigenic site of Zika virus envelope (E) protein or to a ZIKV quaternary epitope or (ii) useful in diagnosis of Zika virus infection, if directed to Zika virus NS1 protein. Such antibodies are desirable, as only small quantities of the antibodies are required in order to neutralize Zika virus. In particular, there is currently no prevention/treatment available for Zika virus infection. The antibodies according to the present invention are highly effective in preventing as well as treating or attenuating Zika virus infection. Moreover, due to the specificity of the antibodies for Zika virus, they do not elicit ADE, but rather block ADE. In diagnosis, Zika-specific antibodies provide an important tool for distinguishing Zika virus infection from infection with other flaviviruses, such as Dengue virus.

In a first aspect the present invention provides an isolated antibody, or an antigen binding fragment thereof, that specifically binds to a Zika virus epitope and neutralizes Zika virus infection.

In other words, the antibody, or the antigen binding fragment thereof, according to the present invention, reduces viral infectivity of Zika virus.

To study and quantitate virus infectivity (or "neutralization") in the laboratory the person skilled in the art knows various standard "neutralization assays". For a neutralization assay animal viruses are typically propagated in cells and/or cell lines. In the context of the present invention a neutralization assay is preferred, wherein cultured cells are incubated with a fixed amount of Zika virus (ZIKV) in the presence (or absence) of the antibody to be tested. As a readout for example flow cytometry may be used. Alternatively, also other readouts are conceivable, such as determining the amount of ZIKV non-structural proteins (such as ZIKV NS1) secreted into culture supernatant. For example, a ZIKV nonstructural protein 1 (NS1) antigen capture enzyme-linked immunosorbent assay (ELISA)-based tissue culture infectious dose-50 (TCID50) test (TCID50-ELISA)

may be used as an alternative to the standard plaque assay for titrating Zika virus—in a similar manner as described for dengue virus (DENV) by Li J, Hu D-M, Ding X-X, Chen Y, Pan Y-X, Qiu L-W, Che X-Y: Enzyme-linked immunosorbent assay-format tissue culture infectious dose-50 test for titrating dengue virus. PLoS ONE 2011, 6:e22553. In such an assay for example the ZIKV NS1-binding antibodies as described in the present application may be advantageously used.

In a preferred embodiment of a ZIKV neutralization assay, cultured cells, for example Vero cells, are incubated with a fixed amount of ZIKV in the presence or absence of the antibody to be tested, for example for about four days. After incubation, cells may be washed and further cultivated. To measure virus infectivity, flow cytometry may be used. To this end, cells may be fixed, e.g. with 2% formaldehyde, permeabilizes, e.g. in PBS (phosphate buffered saline) 1% FCS (fetal calf serum) 0.5% saponin, and stained, e.g. with mouse antibody 4G2. Cells may then be incubated with a goat anti-mouse IgG conjugated to a dye, such as Alexa Fluor488 and analyzed by flow cytometry.

Alternatively, viable cells may be detected by flow cytometry using for example the WST-1 reagent (Roche). A preferred ZIKV strain to be used in such a neutralization assay is ZIKV H/PF/2013.

The antibody and antigen binding fragment of the invention have high neutralizing potency. The concentration of the antibody required for 50% neutralization of Zika virus ($IC_{50}$) as compared to no-antibody controls, is, for example, up to about 3 µg/ml or up to about 1 µg/ml. Preferably, the concentration of the antibody of the invention required for 50% neutralization of ZIKV ($IC_{50}$) is up to about 500 ng/ml, more preferably the concentration of the antibody of the invention required for 50% neutralization of ZIKV ($IC_{50}$) is up to about 250 ng/ml, even more preferably the concentration of the antibody of the invention required for 50% neutralization of ZIKV ($IC_{50}$) is up to about 150 ng/ml. Most preferably, the concentration of the antibody of the invention required for 50% neutralization of ZIKV ($IC_{50}$) is about 100 ng/ml or less, e.g. about 90 ng/ml or less, about 80 ng/ml or less, about 70 ng/ml or less, about 60 ng/ml or less, about 50 ng/ml or less, about 45 ng/ml or less, about 40 ng/ml or less, about 35 ng/ml or less, about 30 ng/ml or less, about 25 ng/ml or less, about 20 ng/ml or less or, particularly preferably, about 15 ng/ml or less. In particular, the concentration of the antibody of the invention required for 50% neutralization of ZIKV ($IC_{50}$) is preferably about 50 ng/ml or less. This means that only low concentrations of the antibody are required for 50% neutralization of ZIKV. The concentration of the antibody of the invention required for 50% neutralization of ZIKV ($IC_{50}$) can be measured using standard neutralization assays as known to one of skill in the art or, in particular, as described above.

In general, binding of an antibody may be assessed by use of a standard ELISA (enzyme-linked immunosorbent assay), which is well-known to the skilled person. An exemplary standard ELISA may be performed as follows: ELISA plates may be coated (e.g., overnight at 4° C.) with a sufficient amount (e.g., 1 µg/ml) of the protein/complex/particle to which binding of the antibody is to be tested (for example, for DENV binding as outlined below, DENV E proteins and/or DENV VLPs are used), e.g. in PBS. Plates may then be blocked, e.g. with a 1% w/v solution of Bovine Serum Albumin (BSA) in PBS, and incubated with the antibody to be tested, e.g. for about 1.5 hours at room temperature). After washing, antibody binding can be revealed, e.g. using goat anti-human IgG coupled to alkaline phosphatase. Plates may then be washed, the required substrate (e.g., p-NPP) may be added and plates may be read, e.g. at 405 nm. The relative affinities of antibody binding may be determined by measuring the concentration of mAb ($EC_{50}$) required to achieve 50% maximal binding at saturation. The $EC_{50}$ values may be calculated by interpolation of binding curves fitted with a four-parameter nonlinear regression with a variable slope.

Preferably, the antibody, or an antigen binding fragment thereof, according to the present invention does essentially not bind to Dengue virus-like particles and/or to Dengue envelope protein. More preferably, the antibody, or an antigen binding fragment thereof, according to the present invention does essentially not bind to Dengue virus-like particles and/or to Dengue envelope protein of any of the four DENV serotypes DENV1, DENV2, DENV3 and DENV4. Thereby "essentially not binding" means that for the antibody, or an antigen binding fragment thereof, no $EC_{50}$-value up to $10^2$ ng/ml, preferably up to $10^3$ ng/ml, more preferably up to $5*10^3$ ng/ml, even more preferably up to $8*10^3$ ng/ml, and most preferably up to $10^4$ ng/ml can be determined in a standard ELISA to Dengue virus-like particles (DENV VLP) and/or to Dengue envelope protein (DENV E protein). In other words, the concentration of the antibody, or an antigen binding fragment thereof, required to achieve 50% maximal binding at saturation ($EC_{50}$) to Dengue virus-like particles (DENV VLP) and/or to Dengue envelope protein (DENV E protein) in a standard ELISA is typically more than $10^2$ ng/ml, preferably more than $10^3$ ng/ml, more preferably more than $5*10^3$ ng/ml, even more preferably more than $8*10^3$ ng/ml, and most preferably more than $10^4$ ng/ml.

Preferably, the antibody, or an antigen binding fragment thereof, according to the present invention does not contribute to antibody-dependent enhancement (ADE) of Zika virus infection. More preferably, the antibody, or an antigen binding fragment thereof, according to the present invention blocks antibody-dependent enhancement (ADE) of Zika virus infection.

ADE may be assessed by a flow-cytometry based assay using, for example cultured cells or cell lines, such as K562 cells. For example, the antibodies to be tested and ZIKV may be mixed for 1 hour at 37° C. and added to 5000 K562 cells/well. After four days, cells may be fixed, permeabilized, and stained with m4G2, e.g. as described above for neutralization assays. The number of infected cells was determined by flow cytometry, as described above for neutralization assays.

Preferably, the antibody, or an antigen binding fragment thereof, according to the present invention is a human antibody. It is also preferred that the antibody, or an antigen binding fragment thereof, according to the present invention is a monoclonal antibody, preferably a human monoclonal antibody. Furthermore, it is also preferred that the antibody, or an antigen binding fragment thereof, according to the present invention is a recombinant antibody.

Preferably, the antibody according to the present invention, or an antigen binding fragment thereof, comprises an Fc moiety. More preferably, the Fc moiety is derived from human origin, e.g. from human IgG1, IgG2, IgG3, and/or IgG4, whereby human IgG1 is particularly preferred.

As used herein, the term "Fc moiety" refers to a sequence derived from the portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain.

Accordingly, an Fc moiety may be a complete Fc moiety or a portion (e.g., a domain) thereof. A complete Fc moiety comprises at least a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Each of the amino acid positions within an Fc moiety have been numbered according to the art-recognized EU numbering system of Kabat, see e.g., by Kabat et al., in "Sequences of Proteins of Immunological Interest", U.S. Dept. Health and Human Services, 1983 and 1987.

Preferably, in the context of the present invention an Fc moiety comprises at least one of: a hinge (e.g., upper, middle, and/or lower hinge region) domain, a CH2 domain, a CH3 domain, or a variant, portion, or fragment thereof. In preferred embodiments, an Fc moiety comprises at least a hinge domain, a CH2 domain or a CH3 domain. More preferably, the Fc moiety is a complete Fc moiety. The Fc moiety may also comprises one or more amino acid insertions, deletions, or substitutions relative to a naturally-occurring Fc moiety. For example, at least one of a hinge domain, CH2 domain or CH3 domain (or portion thereof) may be deleted. For example, an Fc moiety may comprise or consist of: (i) hinge domain (or portion thereof) fused to a CH2 domain (or portion thereof), (ii) a hinge domain (or portion thereof) fused to a CH3 domain (or portion thereof), (iii) a CH2 domain (or portion thereof) fused to a CH3 domain (or portion thereof), (iv) a hinge domain (or portion thereof), (v) a CH2 domain (or portion thereof), or (vi) a CH3 domain or portion thereof.

It will be understood by one of ordinary skill in the art that the Fc moiety may be modified such that it varies in amino acid sequence from the complete Fc moiety of a naturally occurring immunoglobulin molecule, while retaining at least one desirable function conferred by the naturally-occurring Fc moiety. Such functions include Fc receptor (FcR) binding, antibody half-life modulation, ADCC function, protein A binding, protein G binding, and complement binding. The portions of naturally occurring Fc moieties, which are responsible and/or essential for such functions are well known by those skilled in the art.

For example, to activate the complement cascade C q binds to at least two molecules of IgG1 or one molecule of IgM, attached to the antigenic target (Ward, E. S., and Ghetie, V., *Ther. Immunol.* 2 (1995) 77-94). Burton, D. R., described (*Mol. Immunol.* 22 (1985) 161-206) that the heavy chain region comprising amino acid residues 318 to 337 is involved in complement fixation. Duncan, A. R., and Winter, G. (*Nature* 332 (1988) 738-740), using site directed mutagenesis, reported that Glu318, Lys320 and Lys322 form the binding site to C1q. The role of Glu318, Lys320 and Lys 322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on hematopoietic cells. Fc receptors belong to the immunoglobulin superfamily, and were shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., *J. Leukoc. Biol.* 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., *Annu. Rev. Immunol.* 9 (1991) 457-492; Capel, P. J., et al., *Immunomethods* 4 (1994) 25-34; de Haas, M., et al., *J Lab. Clin. Med.* 126 (1995) 330-341; and Gessner, J. E., et al., *Ann. Hematol.* 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Therefore, Fc moieties providing cross-linking of receptors (FcγR) are preferred. In humans, three classes of FcγR have been characterized, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is known to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homolougous; and (iii) FcγRIII (CD16), which binds IgG with medium to low affinity and exists as two types: FcγRIIIA found on NK cells, macrophages, eosinophils and some monocytes and T cells and mediating ADCC and FcγRIIIB, which is highly expressed on neutrophils. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. Importantly, 75% of all FcγRIIB is found in the liver (Ganesan, L. P. et al., 2012: FcγRIIb on liver sinusoidal endothelium clears small immune complexes. Journal of Immunology 189: 4981-4988). FcγRIIB is abundantly expressed on Liver Sinusoidal Endothelium, called LSEC, and in Kupffer cells in the liver and LSEC are the major site of small immune complexes clearance (Ganesan, L. P. et al., 2012: FcγRIIb on liver sinusoidal endothelium clears small immune complexes. Journal of Immunology 189: 4981-4988).

Accordingly, in the present invention such antibodies, and antigen binding fragments thereof, are preferred, which are able to bind to FcγRIIb, for example antibodies comprising an Fc moiety for binding to FcγRIIb, in particular an Fc region, such as, for example IgG-type antibodies. Moreover, it is possible to engineer the Fc moiety to enhance FcγRIIB binding by introducing the mutations S267E and L328F as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933. Thereby, the clearance of immune complexes can be enhanced (Chu, S., et al., 2014: Accelerated Clearance of IgE In Chimpanzees Is Mediated By Xmab7195, An Fc-Engineered Antibody With Enhanced Affinity For Inhibitory Receptor FcγRIIb. Am J Respir Crit, American Thoracic Society International Conference Abstracts). Accordingly, in the context of the present invention such antibodies, or antigen binding fragments thereof, are preferred, which comprise an engineered Fc moiety with the mutations S267E and L328F, in particular as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933.

On B-cells it seems to function to suppress further immunoglobulin production and isotype switching to say for example the IgE class. On macrophages, FcγRIIB acts to inhibit phagocytosis as mediated through FcγRIIA. On eosinophils and mast cells the b form may help to suppress activation of these cells through IgE binding to its separate receptor.

Regarding FcγRI binding, modification in native IgG of at least one of E233-G236, P238, D265, N297, A327 and P329 reduces binding to FcγRI. IgG2 residues at positions 233-236, substituted into IgG1 and IgG4, reduces binding to FcγRI by $10^3$-fold and eliminated the human monocyte response to antibody-sensitized red blood cells (Armour, K. L., et al. *Eur. J. Immunol.* 29 (1999) 2613-2624). Regarding FcγRII binding, reduced binding for FcγRIIA is found e.g. for IgG mutation of at least one of E233-G236, P238, D265, N297, A327, P329, D270, Q295, A327, R292 and K414. Regarding FcγRIII binding, reduced binding to FcγRIIIA is found e.g. for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above-mentioned mutation sites and methods for measuring binding to FcγRI and FcγRIIA are described in Shields, R. L., et al., *J. Biol. Chem.* 276 (2001) 6591-6604.

Regarding binding to the crucial FcγRII, two regions of native IgG Fc appear to be critical for interactions of FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRI appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

For example, the Fc moiety may comprise or consist of at least the portion of an Fc moiety that is known in the art to be required for FcRn binding or extended half-life. Alternatively or additionally, the Fc moiety of the antibody of the invention comprises at least the portion of known in the art to be required for Protein A binding and/or the Fc moiety of the antibody of the invention comprises at least the portion of an Fc molecule known in the art to be required for protein G binding. Preferably, the retained function is the neutralization of Zika virus infection, which is assumed to be mediated by FcγR binding. Accordingly, a preferred Fc moiety comprises at least the portion known in the art to be required for FcγR binding. As outlined above, a preferred Fc moiety may thus at least comprise (i) the lower hinge site of native IgG Fc, in particular amino acid residues L, L, G, G (234-237, EU numbering), and (ii) the adjacent region of the CH2 domain of native IgG Fc, in particular a loop and strands in the upper CH2 domain adjacent to the lower hinge region, e.g. in a region of P331, for example a region of at least 3, 4, 5, 6, 7, 8, 9, or 10 consecutive amino acids in the upper CH2 domain of native IgG Fc around P331, e.g. between amino acids 320 and 340 (EU numbering) of native IgG Fc.

Preferably, the antibody, or antigen binding fragment thereof, according to the present invention comprises an Fc region. As used herein, the term "Fc region" refers to the portion of an immunoglobulin formed by two or more Fc moieties of antibody heavy chains. For example, the Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2. Preferably, the Fc region is a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties.

The Fc moieties of the Fc region may be of the same or different class and/or subclass. For example, the Fc moieties may be derived from an immunoglobulin (e.g., a human immunoglobulin) of an IgG1, IgG2, IgG3 or IgG4 subclass. Preferably, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. Additionally or alternatively, the chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2 or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2 or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

Moreover, an Fc region or moiety may (additionally or alternatively) for example comprise a chimeric hinge region. For example, the chimeric hinge may be derived, e.g. in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser228Pro) at EU position 228 in the middle hinge domain of an IgG4 hinge region. In another embodiment, the chimeric hinge can comprise amino acids at EU positions 233-236 are from an IgG2 antibody and/or the Ser228Pro mutation, wherein the remaining amino acids of the hinge are from an IgG4 antibody (e.g., a chimeric hinge of the sequence ESKY-GPPCPPCPAPPVAGP (SEQ ID NO: 408)). Further chimeric hinges, which may be used in the Fc moiety of the antibody according to the present invention are described in US 2005/0163783 A1.

In the present invention it is preferred that the Fc moiety, or the Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

Preferably, the antibody according to the present invention comprises, in particular in addition to an Fc moiety as described above, other parts derived from a constant region, in particular from a constant region of IgG, preferably from a constant region of IgG1, more preferably from a constant region of human IgG1. More preferably, the antibody according to the present invention comprises, in particular in addition to an Fc moiety as described above, all other parts of the constant regions, in particular all other parts of the constant regions of IgG, preferably all other parts of the constant regions of IgG1, more preferably all other parts of the constant regions of human IgG1.

Particularly preferred sequences of constant regions are the amino acid sequences according to SEQ ID NOs: 145-148 (nucleic acid sequences according to SEQ ID NOs: 149-152). Preferably, the amino acid sequence of IgG1 CH1-CH2-CH3 is according to SEQ ID NO: 145 or a functional sequence variant thereof, as described herein. Even more preferably, the amino acid sequence of IgG1 CH1-CH2-CH3 is according to SEQ ID NO: 146 or a functional sequence variant thereof, as described herein, wherein the "LALA" mutation is maintained.

As outlined above, a particularly preferred antibody according to the present invention comprises a (complete) Fc region derived from human IgG1. More preferably, the antibody according to the present invention comprises, in particular in addition to a (complete) Fc region derived from human IgG1 also all other parts of the constant regions of IgG, preferably all other parts of the constant regions of IgG1, more preferably all other parts of the constant regions of human IgG1.

Without being bound to any theory, it is believed that antibody-dependent enhancement (ADE) of Zika virus infection is brought about by the binding of the Fc moiety of the antibody, in particular, the Fc moiety of the heavy chain of an IgG molecule, to an Fc receptor, e.g., an Fcγ receptor on a host cell. It is thus preferred that the antibody according to the present invention, or an antigen binding fragment thereof, comprises one or more mutations in the Fc moiety. The mutation(s) may be any mutation that reduces binding of the antibody to an Fc receptor (FcR), in particular reduces binding of the antibody to an Fcγ receptor (FcγR). On the other hand, it is preferred that the antibody according to the present invention comprises a (complete) Fc moiety/Fc region, wherein the interaction/binding with FcRn is not compromised. Accordingly, it is particularly preferred that the antibody according to the present invention, or an antigen binding fragment thereof, comprises one or more mutations in the Fc moiety, which (i) reduce(s) binding of the antibody to an Fcγ receptor, but do(es) not compromise interaction with FcRn. One example of such a mutation is the "LALA" mutation described below.

In general, binding of the antibody to an Fc receptor may be assessed by various methods known to the skilled person, such as ELISA (Hessell A J, Hangartner L, Hunter M, Havenith C E G, Beurskens F J, Bakker J M, Lanigan C M S, Landucci G, Forthal D N, Parren P W H I, et al.: Fc receptor but not complement binding is important in antibody protection against HIV. Nature 2007, 449:101-104; Grevys A, Bern M, Foss S, Bratlie D B, Moen A, Gunnarsen K S, Aase A, Michaelsen T E, Sandlie I, Andersen J T: Fc Engineering of Human IgG1 for Altered Binding to the Neonatal Fc Receptor Affects Fc Effector Functions. 2015, 194:5497-5508) or flow-cytometry (Perez L G, Costa M R, Todd C A, Haynes B F, Montefiori D C: Utilization of immunoglobulin G Fc receptors by human immunodeficiency virus type 1: a specific role for antibodies against the membrane-proximal external region of gp4.1. J Virol 2009, 83:7397-7410; Piccoli L, Campo I, Fregni C S, Rodriguez B M F, Minola A, Sallusto F, Luisetti M, Corti D, Lanzavecchia A: Neutralization and clearance of GM-CSF by autoantibodies in pulmonary alveolar proteinosis. Nat Commun 2015, 6:1-9).

In general, the antibody according to the present invention may be glycosylated. N-linked glycans attached to the CH2 domain of a heavy chain, for instance, can influence C1q and FcR binding, with aglycosylated antibodies having lower affinity for these receptors. Accordingly, the CH2 domain of the Fc moiety of the antibody according to the present invention may comprise one or more mutations, in which a glycosylated residue is substituted by a non-glycosylated residue. The glycan structure can also affect activity e.g. differences in complement-mediated cell death may be seen depending on the number of galactose sugars (0, 1 or 2) at the terminus of a glycan's biantennary chain. Preferably, the antibody's glycans do not lead to a human immunogenic response after administration.

Furthermore, the antibody according to the present invention can be modified by introducing random amino acid mutations into particular region of the CH2 or CH3 domain of the heavy chain in order to alter their binding affinity for FcR and/or their serum half-life in comparison to unmodified antibodies. Examples of such modifications include, but are not limited to, substitutions of at least one amino acid from the heavy chain constant region selected from the group consisting of amino acid residues 250, 314, and 428.

Particularly preferably, the Fc moiety of an antibody of the invention comprises a substitution at positions CH2 4, CH2 5, or both. In general, the amino acid at positions 4 and 5 of CH2 of the wild-type IgG1 and IgG3 is a leucine ("L"). Preferably, the antibody according to the present invention comprises an amino acid at position CH2 4, CH2 5, or both, that is not an L. More preferably, antibody according to the present invention comprises an alanine ("A") at position CH2 4, or CH2 5, or both. Most preferably, the antibody according to the present invention comprises both, a CH2 L4A and a CH2 L5A substitution. Such antibodies are referred to herein as a "LALA" variant. Interestingly, such a "LALA" mutation in the Fc moiety does not only result in a lack of contribution of the respective antibody in antibody-dependent enhancement (ADE) of Zika virus infection, but also blocks antibody-dependent enhancement (ADE) of Zika virus infection. An exemplary amino acid sequence of IgG1 CH1-CH2-CH3 comprising the "LALA" mutation is according to SEQ ID NO: 146. Accordingly, the amino acid sequence of IgG1 CH1-CH2-CH3 is preferably according to SEQ ID NO: 146 or a functional sequence variant thereof, as described herein, wherein the "LALA" mutation is maintained.

Preferably, the antibody, or antigen binding fragment thereof, binds to domain III of Zika virus envelope protein (EDIII, also referred to as "DIII"). In other words, it is preferred that the, the antibody, or antigen binding fragment thereof, according to the present invention binds to an epitope of Zika virus envelope protein, which includes one or more amino acid residues of domain III of Zika virus envelope protein (EDIII). ZIKV includes a nucleocapsid core, which comprising single-stranded RNA wrapped by core proteins. The nucleocapsid core is encapsulated by a lipid bilayer membrane with "membrane proteins" and "envelope proteins". ZIKV envelope protein (E protein) is the dominant antigen. The ectodomain of the envelope protein comprises three distinct domains: E protein domain I (EDI), E protein domain II (EDII), and E protein domain III (EDIII). EDIII is highly conserved among different ZIKV strains (see FIG. 12 for an alignment of amino acid sequences of EDIII of different ZIKV strains.

Accordingly, the antibody, or antigen binding fragment thereof, more preferably binds to domain III of Zika virus envelope protein (EDIII) with EDIII having the following amino acid sequence (SEQ ID NO: 401):

TAAFTFTKXPAEXXHGTVTVEXQYXGXDGPCKXPXQMAVDXQTLTPVGRL

ITANPVITEXTENSKMMLELDPPFGDSYIVIGXGXKKITHHWHRS wherein X may be any (naturally occurring) amino acid. In other words, it is preferred that the, the antibody, or antigen binding fragment thereof, according to the present invention binds to an epitope of Zika virus envelope protein, which includes one or more amino acid residues of SEQ ID NO: 401.

It is also preferred that the antibody, or antigen binding fragment thereof, according to the present invention binds to domain III of Zika virus envelope protein (EDIII) with EDIII having the following amino acid sequence (SEQ ID NO: 407):

$X_1GX_2X_3YSLCTAAFTFTKX_4PAEX_5X_6HGTVTVEX_7QYX_8GX_9DGPCK$ $X_{10}PX_{11}QMAVDX_{12}QTLTPVGRLITANPVITEX_{13}TX_{14}NSKMMLELD$

PPFGDSYIVIGX$_{15}$GX$_{16}$X$_{17}$KITHHWHRSG wherein X1 may be any (naturally occurring) amino acid, preferably K, A, or E;
X2 may be any (naturally occurring) amino acid, preferably V, F, or L;
X3 may be any (naturally occurring) amino acid, preferably S or F;
X4 may be any (naturally occurring) amino acid, preferably I or V;
X5 may be any (naturally occurring) amino acid, preferably T or V;
X6 may be any (naturally occurring) amino acid, preferably L or D;
X7 may be any (naturally occurring) amino acid, preferably V or G;
X8 may be any (naturally occurring) amino acid, preferably A or G;
X9 may be any (naturally occurring) amino acid except R, preferably T or A;
X10 may be any (naturally occurring) amino acid, preferably V or I;
X11 may be any (naturally occurring) amino acid, preferably A or V;
X12 may be any (naturally occurring) amino acid, preferably M or T;
X13 may be any (naturally occurring) amino acid, preferably S or G;
X14 may be any (naturally occurring) amino acid, preferably E or K;
X15 may be any (naturally occurring) amino acid, preferably V or I;
X16 may be any (naturally occurring) amino acid, preferably E, A, K, or D; and
X17 may be any (naturally occurring) amino acid, preferably E, A, or K, more preferably K or A.

In other words, it is preferred that the, the antibody, or antigen binding fragment thereof, according to the present invention binds to an epitope of Zika virus envelope protein, which includes one or more amino acid residues of SEQ ID NO: 407.

For example, EDIII stretches from amino acid 309 to amino acid 403 of ZIKV E protein of the ZIKV H/PF/2013 strain (Genbank accession number KJ776791). Accordingly, the antibody, or antigen binding fragment thereof, most preferably binds to domain III of Zika virus envelope protein (EDIII) with EDIII having the following amino acid sequence (SEQ ID NO: 402):

TAAFTFTKIPAETLHGTVTVEVQYAGTDGPCKVPAQMAVDMQTLTPVGRL

ITANPVITESTENSKMMLELDPPFGDSYIVIGVGEKKITHHWHRS.

In other words, it is preferred that the, the antibody, or antigen binding fragment thereof, according to the present invention binds to an epitope of Zika virus envelope protein, which includes one or more amino acid residues of SEQ ID NO: 402.

Surprisingly, the present inventors have found that antibodies binding to domain III of Zika virus envelope protein (EDIII) show (i) increased neutralization of ZIKV and (ii) decreased cross-reactivity with DENV (in particular essentially no cross-reactivity with DENV) as compared to antibodies binding to domain I/II of Zika virus envelope protein (EDI/II).

More preferably, the antibody, or antigen binding fragment thereof, according to the present invention binds to an epitope of Zika virus envelope protein, which includes one or more amino acid residues of the lateral ridge (LR) of EDIII and/or one or more amino acid residues of the EDI-EDIII hinge region. The EDIII lateral ridge and EDI-EDIII hinge region are known to the skilled person and described, for example, in Zhao, H., Fernandez, E., Dowd, K. A., Speer, S. D., Platt, D. J., Gorman, M. J., Govero, J., Nelson, C. A., Pierson, T. C., Diamond, M. S., et al. (2016). Structural Basis of Zika Virus-Specific Antibody Protection. Cell 166(4):1016-27 and in Kostyuchenko V A, Lim E X, Zhang S, Fibriansah G, Ng T S, Ooi J S, Shi J, Lok S M. Structure of the thermally stable Zika virus. Nature. 2016 May 19; 533(7603):425-8. Without being bound to any theory, it is assumed that (i) binding to the LR may inhibit fusion by trapping a fusion transitional state of the virus and (ii) binding to the EDI-EDIII hinge and EDIII may hinder the movement of EDIII to form the trimeric post-fusion structure, thereby halting membrane fusion.

Accordingly, it is preferred that the antibody, or antigen binding fragment thereof, according to the present invention (is able to) inhibit(s) a post-attachment step of ZIKV. "Post-attachment" typically refers to any step of ZIKV infection after attachment of ZIKV to the cell membrane (of the cell targeted by ZIKV). For example, the antibody, or antigen binding fragment thereof, according to the present invention preferably (is able to) prevent(s) membrane fusion. Furthermore, it is also preferred that the antibody, or antigen binding fragment thereof, according to the present invention (is able to) cause(s) aggregation of ZIKV (particles). Most preferably, the antibody, or antigen binding fragment thereof, according to the present invention (is able to) (i) inhibit(s) a post-attachment step of ZIKV and (ii) cause(s) aggregation of ZIKV (particles). It is also preferred that the antibody, or antigen binding fragment thereof, binds to a quaternary epitope displayed on a ZIKV infectious virion. Despite considerable neutralizing activity, such antibodies show typically no detectable binding to recombinant ZIKV E protein or to ZIKV EDIII in a standard ELISA (as described above), i.e. if tested in vitro, in particular in purified form (i.e. ZIKV E protein "outside/without" a virion, a virus-like particle or the like). Thereby, "no detectable binding" typically means that no $EC_{50}$ up to 10000 ng/ml was detected in a standard ELISA. In other words, if the $EC_{50}$ detectable in a standard ELISA is above 10000 ng/ml, it is referred to as "no detectable binding".

Therefore, such antibodies are also referred to herein as "neutralizing-non-E-binding" (NNB) antibodies. The quaternary epitope displayed on a ZIKV infectious virion is typically a conformational epitope. For example, the quaternary epitope displayed on a ZIKV infectious virion may be formed at the interface of two envelope protein monomers making up a dimer ("envelope dimer epitope"; EDE) or it may be formed across neighbouring dimers ("herringbone epitope").

In general, the antibody according to the present invention, or the antigen binding fragment thereof, preferably comprises (at least) three complementarity determining regions (CDRs) on a heavy chain and (at least) three CDRs on a light chain. In general, complementarity determining regions (CDRs) are the hypervariable regions present in heavy chain variable domains and light chain variable domains. Typically, the CDRs of a heavy chain and the connected light chain of an antibody together form the antigen receptor. Usually, the three CDRs (CDR1, CDR2, and CDR3) are arranged non-consecutively in the variable domain. Since antigen receptors are typically composed of two variable domains (on two different polypeptide chains, i.e. heavy and light chain), there are six CDRs for each antigen receptor (heavy chain: CDRH1, CDRH2, and CDRH3; light chain: CDRL1, CDRL2, and CDRL3). A single antibody molecule usually has two antigen receptors and therefore contains twelve CDRs. The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR's.

The sequences of the heavy chains and light chains of exemplary antibodies of the invention, comprising three different CDRs on the heavy chain and three different CDRs on the light chain were determined. The position of the CDR amino acids are defined according to the IMGT numbering system (IMGT: http://www.imgt.org/; cf. Lefranc, M.-P. et al. (2009) Nucleic Acids Res. 37, D1006-D1012).

Table 1 shows the SEQ ID NO's of the amino acid sequences of the heavy chain CDR's (CDRH1, CDRH2, and CDRH3) and of the heavy chain variable region (referred to as "VH") of exemplary antibodies according to the present invention:

| Antibody name | CDRH1 | CDRH2 | CDRH3 | VH |
|---|---|---|---|---|
| ZKA190 | 1 | 2 | 3 | 8 |
| ZKA185 | 19 | 20 | 21 | 26 |
| ZKA230 | 37 | 38 | 39 | 44 |
| ZKA78 | 55 | 56 | 57 | 62 |
| ZKA64 | 73 | 74 | 75 | 80 |
| ZKA3 | 237 | 238 | 239 | 240 |
| ZKA4 | 241 | 242 | 243 | 244 |
| ZKA5 | 245 | 246 | 247 | 248 |
| ZKA6 | 249 | 250 | 251 | 252 |
| ZKA7 | 253 | 254 | 255 | 256 |
| ZKA8 | 257 | 258 | 259 | 260 |
| ZKA76 | 261 | 262 | 263 | 264 |
| ZKA117 | 265 | 266 | 267 | 268 |
| ZKB27 | 269 | 270 | 271 | 272 |
| ZKB29 | 273 | 274 | 275 | 276 |
| ZKB34 | 277 | 278 | 279 | 280 |
| ZKB39 | 281 | 282 | 283 | 284 |
| ZKB46 | 285 | 286 | 287 | 288 |
| ZKB53 | 289 | 290 | 291 | 292 |
| ZKC26 | 293 | 294 | 295 | 296 |
| ZKD5 | 297 | 298 | 299 | 300 |
| ZKD7 | 301 | 302 | 303 | 304 |
| ZKD8 | 305 | 306 | 307 | 308 |
| ZKD15 | 309 | 310 | 311 | 312 |
| ZKD16 | 313 | 314 | 315 | 316 |
| ZKD17 | 317 | 318 | 319 | 320 |
| ZKD20 | 321 | 322 | 323 | 324 |
| ZKA134 | 325 | 326 | 327 | 328 |
| ZKA246 | 329 | 330 | 331 | 332 |
| ZKA256 | 333 | 334 | 335 | 336 |
| ZKB42 | 337 | 338 | 339 | 340 |
| ZKB85 | 341 | 342 | 343 | 344 |
| ZKB47 | 345 | 346 | 347 | 348 |
| ZKC6 | 349 | 350 | 351 | 352 |
| ZKA160 | 353 | 354 | 355 | 356 |
| ZKA172 | 357 | 358 | 359 | 360 |
| ZKA174 | 361 | 362 | 363 | 364 |
| ZKA189 | 365 | 366 | 367 | 368 |
| ZKA195 | 369 | 370 | 371 | 372 |
| ZKA215 | 373 | 374 | 375 | 376 |
| ZKA218 | 377 | 378 | 379 | 380 |
| ZKB75 | 381 | 382 | 383 | 384 |
| ZKB83 | 385 | 386 | 387 | 388 |
| ZKC3 | 389 | 390 | 391 | 392 |
| ZKC18 | 393 | 394 | 395 | 396 |
| ZKD1 | 397 | 398 | 399 | 400 |

Table 2 below shows the SEQ ID NO's of the amino acid sequences of the light chain CDR's (CDRL1, CDRL2, and CDRL3) and of the light chain variable region (referred to as "VL") of exemplary antibodies according to the present invention:

| Antibody name | CDRL1 | CDRL2 | CDRL2 long | CDRL3 | VL |
|---|---|---|---|---|---|
| ZKA190 | 4 | 5 | 6 | 7 | 9 |
| ZKA185 | 22 | 23 | 24 | 25 | 27 |
| ZKA230 | 40 | 41 | 42 | 43 | 45 |
| ZKA78 | 58 | 59 | 60 | 61 | 63 |
| ZKA64 | 76 | 77 | 78 | 79 | 81 |

It is thus preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 1 and/or in Table 2.

It is preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 3, 75, 39, 21, 57, 239, 243, 247, 251, 255, 259, 263, 267, 271, 275, 279, 283, 287, 291, 295, 299, 303, 307, 311, 315, 319, 323, 327, 331, 335, 339, 343, 347, 351, 355, 359, 363, 367, 371, 375, 379, 383, 387, 391, 395, and 399, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 3, 21, 39, 57 and 75 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 3, 21, 39 and 75 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 3 or according to SEQ ID NO: 75; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 21 or according to SEQ ID NO: 39; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 3 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to any of SEQ ID NOs: 1, 19, 37, 55, 73, 237, 241, 245, 249, 253, 257, 261, 265, 269, 273, 277, 281, 285, 289, 293, 297, 301, 305, 309, 313, 317, 321, 325, 329, 333, 337, 341, 345, 349, 353, 357, 361, 365, 369, 373, 377, 381, 385, 389, 393, and 397, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to any of SEQ ID NOs: 2, 20, 38, 56, 74, 238, 242, 246, 250, 254, 258, 262, 266, 270, 274, 278, 282, 286, 290, 294, 298, 302, 306, 310, 314, 318, 322, 326, 330, 334, 338, 342, 346, 350, 354, 358, 362, 366, 370, 374, 378, 382, 386, 390, 394, and 398, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to any of SEQ ID NOs: 3, 21, 39, 57, 75, 239, 243, 247, 251, 255, 259, 263, 267, 271, 275, 279, 283, 287, 291, 295, 299, 303, 307, 311, 315, 319, 323, 327, 331, 335, 339, 343, 347, 351, 355, 359, 363, 367, 371, 375, 379, 383, 387, 391, 395, and 399, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to any of SEQ ID NOs: 1, 19, 37, 55 and 73 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;

(ii) the at least one CDRH2 comprises an amino acid sequence according to any of SEQ ID NOs: 2, 20, 38, 56 and 74 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or (iii) the at least one heavy chain CDRH3 comprises an amino acid sequence according to any of SEQ ID NOs: 3, 21, 39, 57 and 75 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one heavy chain CDRH1 comprises an amino acid sequence according to any of SEQ ID NOs: 1, 19, 37 and 73 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;

(ii) the at least one CDRH2 comprises an amino acid sequence according to any of SEQ ID NOs: 2, 20, 38 and 74 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or (iii) the at least one heavy chain CDRH3 comprises an amino acid sequence according to any of SEQ ID NOs: 3, 21, 39 and 75 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one heavy chain CDRH1 comprises an amino acid sequence according to SEQ ID NO: 1 or according to SEQ ID NO: 73; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;

(ii) the at least one CDRH2 comprises an amino acid sequence according to SEQ ID NO: 2 or according to SEQ ID NO: 74; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or (iii) the at least one heavy chain CDRH3 comprises an amino acid sequence according to SEQ ID NO: 3 or according to SEQ ID NO: 75; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one heavy chain CDRH1 comprises an amino acid sequence according to SEQ ID NO: 19 or according to SEQ ID NO: 37; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;

(ii) the at least one CDRH2 comprises an amino acid sequence according to SEQ ID NO: 20 or according to SEQ ID NO: 38; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or (iii) the at least one heavy chain CDRH3 comprises an amino acid sequence according to SEQ ID NO: 21 or according to SEQ ID NO: 39; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Particularly preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one heavy chain CDRH1 comprises an amino acid sequence according to SEQ ID NO: 1 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;

(ii) the at least one CDRH2 comprises an amino acid sequence according to SEQ ID NO: 2 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or (iii) the at least one heavy chain CDRH3 comprises an amino acid sequence according to SEQ ID NO: 3 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein (i) the at least one CDRL1 comprises an amino acid sequence according to any of SEQ ID NOs: 4, 22, 40, 58 and 76 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 5, 6, 23, 24, 41, 42, 59, 60, 77 and 78 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to any of SEQ ID NOs: 7, 25, 43, 61 and 79 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to any of SEQ ID NOs: 4, 22, 40 and 76 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 5, 6, 23, 24, 41, 42, 77 and 78 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to any of SEQ ID NOs: 7, 25, 43 and 79 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 4 or according to SEQ ID NO: 76; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 5, 6, 77 and 78 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 7 or according to SEQ ID NO: 79; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 22 or according to SEQ ID NO: 40; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 23, 24, 41 and 42 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 25 or according to SEQ ID NO: 43; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 4 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to SEQ ID NO: 5 or 6, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 7 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention comprises CDRH1, CDRH2, and CDRH3 amino acid sequences (i) according to SEQ ID NOs: 1-3; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 19-21; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 37-39; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 55-57; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 73-75; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 237-239; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 241-243; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 245-247; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 249-251; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (x) according to SEQ ID NOs: 253-255; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xi) according to SEQ ID NOs: 257-259; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xii) according to SEQ ID NOs: 261-263; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiii) according to SEQ ID NOs: 265-267; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiv) according to SEQ ID NOs: 269-271; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xv) according to SEQ ID NOs: 273-275; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xvi) according to SEQ ID NOs: 277-279; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xvii) according to SEQ ID NOs: 281-283; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xviii) according to SEQ ID NOs: 285-287; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xix) according to SEQ ID NOs: 289-291; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xx) according to SEQ ID NOs: 293-295; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxi) according to SEQ ID NOs: 297-299; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxii) according to SEQ ID NOs: 301-303; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxiii) according to SEQ ID NOs: 305-307; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxiv) according to SEQ ID NOs: 309-311; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxv) according to SEQ ID NOs: 313-315; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxvi) according to SEQ ID NOs: 317-319; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxvii) according to SEQ ID NOs: 321-323; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxviii) according to SEQ ID NOs: 325-327; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxix) according to SEQ ID NOs: 329-331; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxx) according to SEQ ID NOs: 333-335; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxi) according to SEQ ID NOs: 337-339; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxii) according to SEQ ID NOs: 341-343; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxiii) according to SEQ ID NOs: 345-347; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxiv) according to SEQ ID NOs: 349-351; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxv) according to SEQ ID NOs: 353-355; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxvi) according to SEQ ID NOs: 357-359; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxvii) according to SEQ ID NOs: 361-363; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxviii) according to SEQ ID NOs: 365-367; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxxix) according to SEQ ID NOs: 369-371; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xl) according to SEQ ID NOs: 373-375; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xli) according to SEQ ID NOs: 377-379; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xlii) according to SEQ ID NOs: 381-383; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xliii) according to SEQ ID NOs: 385-387; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xliv) according to SEQ ID NOs: 389-391; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xlv) according to SEQ ID NOs: 393-395; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xlvi) according to SEQ ID NOs: 397-399; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Accordingly, it is also preferred that the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 55-59 and 61; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 55-58 and 60-61; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 73-77 and 79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (x) according to SEQ ID NOs: 73-76 and 78-79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 73-77 and 79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (viii) according to SEQ ID NOs: 73-76 and 78-79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 73-77 and 79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (iv) according to SEQ ID NOs: 73-76 and 78-79; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

It is also preferred that preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 19-23 and 25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 19-22 and 24-25; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 37-41 and 43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (vi) according to SEQ ID NOs: 37-40 and 42-43; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 1-5 and 7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 1-4 and 6-7; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

In addition, it is also preferred that the antibody, or the antigen binding fragment thereof, according to the present invention comprises a heavy chain variable region (VH) and, optionally, a light chain variable region (VL), wherein the heavy chain variable region (VH) comprises or consists of an amino acid sequence according to any of SEQ ID NOs: 8, 26, 44, 62, 80, 240, 244, 248, 252, 256, 260, 264, 268, 272, 276, 280, 284, 288, 292, 296, 300, 304, 308, 312, 316, 320, 324, 328, 332, 336, 340, 344, 348, 352, 356, 360, 364, 368, 372, 376, 380, 384, 388, 392, 396, and 400; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Moreover, it is also preferred that the antibody, or the antigen binding fragment thereof, according to the present invention comprises (i) a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (ii) a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iii) a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iv) a heavy chain variable region (VH) amino acid sequence according to SEQ ID NO: 62 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 63 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (v) a heavy chain variable region (VH) amino acid sequence according to SEQ ID NO: 80 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 81 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises (i) a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (ii) a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (iii) a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (iv) a heavy chain variable region (VH) amino acid sequence according to SEQ ID NO: 80 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 81 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises (i) a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (ii) a heavy chain variable region (VH) amino acid sequence according to SEQ ID NO: 80 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 81 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises (i) a heavy chain variable region (VH) amino acid sequence according to SEQ ID NO: 26 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 27 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (ii) a heavy chain variable region (VH) amino acid sequence according to SEQ ID NO: 44 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 45 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain variable region (VH) amino acid sequence according to SEQ ID NO: 8 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 9 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention is gZKA190, gZKA64, gZKA230, gZKA185 or gZKA78, preferably the antibody, or the antigen binding fragment thereof, is gZKA190, gZKA64, gZKA230 or gZKA185, more preferably the antibody, or the antigen binding fragment thereof, is gZKA190 or gZKA64, and most preferably the antibody, or the antigen binding fragment thereof, is gZKA190.

The present inventors have isolated monoclonal antibody (mAb) according to the present invention, which are referred to herein as ZKA190, ZKA64, ZKA230, ZKA185 and ZKA78 (cf. Tables 1 and 2, Example 1). Based on those antibodies, in particular on the VH and VL genes of those antibodies, the terms "gZKA190", "gZKA64", "gZKA230", "gZKA185" and "gZKA78", as used herein, refer to the respective "generic" antibodies, or antigen binding fragments thereof.

Namely, "gZKA190" refers to an antibody, or antigen binding fragment thereof, having a CDRH1 amino acid sequence according to SEQ ID NO: 1, a CDRH2 amino acid sequence according to SEQ ID NO: 2, a CDRH3 amino acid sequence according to SEQ ID NO: 3, a CDRL1 amino acid sequence according to SEQ ID NO: 4, a CDRL2 amino acid sequence according to SEQ ID NO: 5 or 6, and a CDRL3 amino acid sequence according to SEQ ID NO: 7. The heavy chain variable region ($V_H$) has preferably an amino acid sequence according to SEQ ID NO: 8 and the light chain variable region ($V_L$) has preferably an amino acid sequence according to SEQ ID NO: 9.

"gZKA64" refers to an antibody, or antigen binding fragment thereof, having a CDRH1 amino acid sequence according to SEQ ID NO: 73, a CDRH2 amino acid sequence according to SEQ ID NO: 74, a CDRH3 amino acid sequence according to SEQ ID NO: 75, a CDRL1 amino acid sequence according to SEQ ID NO: 76, a CDRL2 amino acid sequence according to SEQ ID NO: 77 or 78, and a CDRL3 amino acid sequence according to SEQ ID NO: 79. The heavy chain variable region ($V_H$) has preferably an amino acid sequence according to SEQ ID NO: 80 and the light chain variable region ($V_L$) has preferably an amino acid sequence according to SEQ ID NO: 81.

"gZKA230" refers to an antibody, or antigen binding fragment thereof, having a CDRH1 amino acid sequence according to SEQ ID NO: 37, a CDRH2 amino acid sequence according to SEQ ID NO: 38, a CDRH3 amino acid sequence according to SEQ ID NO: 39, a CDRL1 amino acid sequence according to SEQ ID NO: 40, a CDRL2 amino acid sequence according to SEQ ID NO: 41 or 42, and a CDRL3 amino acid sequence according to SEQ ID NO: 43. The heavy chain variable region ($V_H$) has preferably an amino acid sequence according to SEQ ID NO: 44 and the light chain variable region ($V_L$) has preferably an amino acid sequence according to SEQ ID NO: 45.

"gZKA185" refers to an antibody, or antigen binding fragment thereof, having a CDRH1 amino acid sequence according to SEQ ID NO: 19, a CDRH2 amino acid sequence according to SEQ ID NO: 20, a CDRH3 amino acid sequence according to SEQ ID NO: 21, a CDRL1 amino acid sequence according to SEQ ID NO: 22, a CDRL2 amino acid sequence according to SEQ ID NO: 23 or 24, and a CDRL3 amino acid sequence according to SEQ ID NO: 25. The heavy chain variable region ($V_H$) has preferably an amino acid sequence according to SEQ ID NO: 26 and the light chain variable region ($V_L$) has preferably an amino acid sequence according to SEQ ID NO: 27.

"gZKA78" refers to an antibody, or antigen binding fragment thereof, having a CDRH1 amino acid sequence according to SEQ ID NO: 55, a CDRH2 amino acid sequence according to SEQ ID NO: 56, a CDRH3 amino acid sequence according to SEQ ID NO: 57, a CDRL1 amino acid sequence according to SEQ ID NO: 58, a CDRL2 amino acid sequence according to SEQ ID NO: 59 or 60, and a CDRL3 amino acid sequence according to SEQ ID NO: 61. The heavy chain variable region ($V_H$) has preferably an amino acid sequence according to SEQ ID NO: 62 and the light chain variable region ($V_L$) has preferably an amino acid sequence according to SEQ ID NO: 63.

Preferably, the antibody, or an antigen binding fragment thereof, according to the present invention is for use as a medicament. In other words, the antibody, or an antigen binding fragment thereof, according to the present invention may be used in the preparation of a medicament. More preferably, the antibody, or an antigen binding fragment thereof, according to the present invention is for use in the prevention and/or treatment of Zika virus infection. In other words, the antibody, or an antigen binding fragment thereof, according to the present invention may be used in the preparation of a medicament or use in the prevention and/or treatment of Zika virus infection. This aspect is described in more detail below.

Nucleic Acid Molecule

In another aspect, the invention also provides a nucleic acid molecule comprising a polynucleotide encoding the antibody, or the antigen binding fragment thereof, according to the present invention as described above. Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA. Nucleic acid sequences encoding part or all of the light and heavy chains and CDRs of the antibodies of the present invention are preferred. Preferably provided herein are thus nucleic acid sequences encoding part or all of the light and heavy chains, in particular VH and VL sequences and CDRs of the exemplary antibodies of the invention. Tables 1 and 2 provide the SEQ ID numbers for the amino acid sequences of the CDRs and VH and VL of exemplary antibodies according to the present invention.

Table 3 below provides the SEQ ID numbers for exemplary nucleic acid sequences encoding the CDRs and VH and VL of exemplary antibodies according to the present invention. Due to the redundancy of the genetic code, the present invention also comprises sequence variants of these nucleic acid sequences and in particular such sequence variants, which encode the same amino acid sequences.

A nucleic acid molecule is a molecule comprising, preferably consisting of nucleic acid components. The term nucleic acid molecule preferably refers to DNA or RNA molecules. In particular, it is used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Table 3 shows exemplary nucleic acid sequences of the CDR's and the heavy chain variable region (VH) and the light chain variable region (VL) of five exemplary antibodies according to the present invention ("ZKA190", "ZKA64", "ZKA230", "ZKA185", "ZKA78"):

| SEQ ID NO. | Nucleic acid sequence |
|---|---|

ZKA190

| | SEQ ID NO. | Nucleic acid sequence |
|---|---|---|
| CDRH1 | 10 | ggattcaccttcagtaaatatggc |
| CDRH2 | 11 | atatcatatgagggaagtaataaa |
| CDRH3 | 12 | gcgaaatcggggacccaatactatgatactactggttatg agtataggggtttggaatactttggctac |
| CDRL1 | 13 | cagagtgttagtagcagttac |
| CDRL2 | 14 | gatgcatcc |
| CDRL2 long | 15 | ctcatctatgatgcatccagcagggcc |
| CDRL3 | 16 | cagcagtatggtaggtcaaggtggaca |
| VH | 17 | caggtgcagctggtggagtctgggggaggcgtggtccagc ctgggaggtccctgagactctcctgtgcagcctctggatt caccttcagtaaatatggcatgcactgggtccgccaggct ccaggcaaggggctggagtgggtggcagttatatcatatg agggaagtaataaatattatgcagactccgtgaagggccg attcaccatctccagagacaattccaagaacacgctgtat ctgcaaatgaacagcctgagagctgaggacacggcagtgt attactgtgcgaaatcggggacccaatactatgatactac tggttatgagtataggggtttggaatactttggctactgg ggccagggaaccctggtcaccgtctcctcag |
| VL | 18 | gaaattgtgttgacgcagtctccaggcaccctgtctttgt ctccaggggaaagagccaccctctcctgcagggccagtca gagtgttagtagcagttacttagcctggtaccagcagaaa cgtggccaggctcccaggctcctcatctatgatgcatcca gcagggccactggcatcccagacaggttcagtggcagtgg gtctgggacagacttcactctcaccatcagcagactggag cctgaagattttgcagtgtattactgtcagcagtatggta ggtcaaggtggacattcggccaagggaccaaggtggaaat caaac |

ZKA185

| | SEQ ID NO. | Nucleic acid sequence |
|---|---|---|
| CDRH1 | 28 | ggatatagttttaccagttactgg |
| CDRH2 | 29 | tttgatcctagtgactctcaaacc |
| CDRH3 | 30 | gcgagaagatattgtagtagtagtagttgttatgtggaca at |
| CDRL1 | 31 | gcattgccaaataaattt |
| CDRL2 | 32 | gaggacaac |
| CDRL2 long | 33 | gtcatctatgaggacaacaaacgaccc |
| CDRL3 | 34 | tactcaacagacagcagttctaatcccctgggagta |
| VH | 35 | gaagtgcagctggtgcagtccggagcagaggtgaaaaagc ccggggagtctctgaggatctcctgtaagggttctggata tagttttaccagttactggatcacctgggtgcgccagatg cccgggaaaggcctggagtggatggcgaagtttgatccta gtgactctcaaaccaactacagcccgtccttccaaggcca cgtcaccatctcagttgacaagtccatcagcactgcctac ttgcagtggagcagcctgaaggcctcggacaccgccatgt attactgtgcgagaagatattgtagtagtagtagttgtta tgtggacaattggggccagggaaccctggtcaccatcttc tcag |
| VL | 36 | tcctatgagctgacacagccaccctcggtgtcagtgtccc caggacaaacggccaggatcacctgctctctggagatgcatt gccaaataaatttgcttattggtaccggcagaagtcaggc caggcccctgttctggtcatctatgaggacaacaaacgac cctccgggatccctgagagattctctggctccagctcagg gacaatgccaccttgactatcagtggggcccaggtggag gatgaagctgactaccactgttactcaacagacagcagtt ctaatcccctgggagtattcggcggagggaccaagctgac cgtcctag |

-continued

| | SEQ ID NO. | Nucleic acid sequence |
|---|---|---|
| ZKA230 | | |
| CDRH1 | 46 | ggtggctccatcagtagtgactac |
| CDRH2 | 47 | atctattacagtgggagcacc |
| CDRH3 | 48 | gcgaggaggaggaagtatgattccctttgggggagttttgcttttgatatc |
| CDRL1 | 49 | agctccaacatcggaggtaattat |
| CDRL2 | 50 | attaatgat |
| CDRL2 long | 51 | ctcatctgtattaatgatcaccggccc |
| CDRL3 | 52 | gcaacatgggatgacagcctgggtggccttgta |
| VH | 53 | caggtgcagctgcaggagtcgggcccaggcctggtgaagccttcggagaccctgtccctcacctgcgcagtctctggtggctccatcagtagtgactactggagctggatccggcagcccccagggaagggactggagtggattgggtatatctattacagtgggagcaccaactacaacccctccctcaagagtcgagtcaccatatcagtagacacgtccaagaaccacttctccctgaagctgaactctgtgaccgctgcggacacggccgtgtattactgtgcgaggaggaggaagtatgattcccttggggga-gttttgcttttgatatctggggccaagggacaatggtcaccgtctcttcag |
| VL | 54 | cagtctgtgctgactcagccaccctcagcgtctgggacccccgggcagagggtcaccatctcttgttctggaagcagctccaacatcggaggtaattatgtatactggtaccagcagctcccaggaacggccccccaaactcctcatctgtattaatgatcaccggccctcaggggtccctgaccgattctctggctccaagtctggcacctcagcctccctggccatcagtgggctccagtccgaggatgaggctgattattactgtgcaacatgggatgacagcctgggtggccttgtattcggcggagggaccaagctgaccgtcctag |
| ZKA78 | | |
| CDRH1 | 64 | ggcttcacttttagtaactatgca |
| CDRH2 | 65 | atcgggcgcaacggggactctatc |
| CDRH3 | 66 | gtgaaagatctggccatccccgagtcctacagaattgaagctgattat |
| CDRL1 | 67 | cagtccgtgctgtaccgctctaacaacaagaattac |
| CDRL2 | 68 | tgggcttca |
| CDRL2 long | 69 | ctgatctattgggcttcaacccgggaa |
| CDRL3 | 70 | cagcagtactattctagtcctcgaact |
| VH | 71 | gaggtgcagctggcagaatcaggcgggggactggtccagcctggcggcagcctgacactgtcttgcagtggatcaggcttcacttttagtaactatgcaatggtgtgggcaaggcaggctcctgggaagggactggagtatgtctctggcatcgggcgcaacggggactctatctactatactgatagtgtgaagggccggttcaccatcagcagagacaatagcaaatccatggtgtacctgcagatgagctccctgcgaaccgaagacacagcagtgtactattgcgtgaaagatctggccatccccgagtcctacagaattgaagctgattattggggacagggcaccctggtcatcgtgagcgccg |
| VL | 72 | gacatcgtgatgacacagtctccagatagtctggcagtcagtctgggggagagggccactattaactgcaagagctcccagtccgtgctgtaccgctctaacaacaagaattacctgtcttggtatcagcagaagcccggacagccccctaaactgctgatctattgggcttcaacccgggaaagcggcgtcccagacagattctcaggcagcgggtccggaacagacttcacccctgaca |

| SEQ ID NO. | Nucleic acid sequence |
|---|---|
| | attagcccctgcaggcagaggacgtggctgtctactatt<br>gtcagcagtactattctagtcctcgaactttcggccaggg<br>gaccaaggtggaaatcaaac |

ZKA64

| | | |
|---|---|---|
| CDRH1 | 82 | ggctacaccttcacagggtatcac |
| CDRH2 | 83 | attaaccctaattctggcgggacc |
| CDRH3 | 84 | gctcggatgagctcctctatttggggcttcgatcat |
| CDRL1 | 85 | cagtctgtgctgattaac |
| CDRL2 | 86 | ggagcatcc |
| CDRL2 long | 87 | ctgatctatggagcatcctccagggct |
| CDRL3 | 88 | cagcagtacaatgattggccccctatcaca |
| VH | 89 | caggtgcagctggtccagagcggagcagaggtgaagaaac<br>ccggcgcctcagtgaaggtcagctgcaaagcttccggcta<br>caccttcacagggtatcacatcgactgggtgaggcaggca<br>agaggacagggactggaatggatgggacggattaaccta<br>attctggcgggaccaactacgcccagaagtttcagggccg<br>agtgactatgaccagagacaccagcatctccacagcttat<br>atgcagctgtcccggctgagatctgacgatagtgccgtct<br>actattgtgctcggatgagctcctctatttggggcttcga<br>tcattgggggcagggaacactggtgactgtcagttcag |
| VL | 90 | gagatcgtgatgactcagtctccagccaccctgtcagtca<br>gcccaggagaacgggcaaccctgtcttgcagagcctccca<br>gtctgtgctgattaacctggcttggtaccagcagaagcca<br>ggccaggcacccgactgctgatctatggagcatcctcca<br>gggctaccggcattcctgcacgcttcagtggatcaggaag<br>cggaacagagtttaccctgacaatctctagtctgcagtcc<br>gaagacttcgctgtctactattgtcagcagtacaatgatt<br>ggccccctatcacatttggccagggactagactggagat<br>caagc |

Preferably, the sequence of the nucleic acid molecule according to the present invention comprises or consists of a nucleic acid sequence according to any one of SEQ ID NOs: 10-18, 28-36, 46-54, 64-72, and 82-90; or a functional sequence variant thereof.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a CDR, a VH sequence and/or a VL sequence used in an (exemplary) antibody according to the present invention, for example to the sequences shown in Table 3.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, a VH sequence and/or a VL sequence of an (exemplary) antibody of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

Vector

Further included within the scope of the invention are vectors, for example, expression vectors, comprising a nucleic acid molecule according to the present invention. Preferably, a vector comprises a nucleic acid molecule as described above.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Cells

In a further aspect, the present invention also provides cell expressing the antibody, or the antigen binding fragment thereof, according to the present invention; and/or comprising the vector according the present invention.

Examples of such cells include but are not limited to, eukaryotic cells, e.g., yeast cells, animal cells or plant cells. Preferably, the cells are mammalian cells, more preferably a mammalian cell line. Preferred examples include human cells, CHO cells, HEK293T cells, PER.C6 cells, NS0 cells, human liver cells, myeloma cells or hybridoma cells.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Moreover, the cells of the present invention may be transfected stably or transiently with the vector according to the present invention, e.g. for expressing the antibody, or the antigen binding fragment thereof, according to the present invention. Preferably, the cells are stably transfected with the vector according to the present invention encoding the antibody, or the antigen binding fragment thereof, according to the present invention. Alternatively, it is also preferred that the cells are transiently transfected with the vector according to the present invention encoding the antibody, or the antigen binding fragment thereof, according to the present invention.

Optional Additional Features of the Antibodies

Antibodies of the invention may be coupled, for example, to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. Labeled antibodies according to the present invention may be thus be used in such assays for example as described in U.S. Pat. Nos. 3,766,162; 3,791,932; 3,817,837; and 4,233,402.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *Pseudomonas* exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention, e.g., as described in U.S. Pat. No. 4,831,175. Antibodies or, antigen-binding fragments thereof may be directly labeled with radioactive iodine, indium, yttrium, or other radioactive particle known in the art, e.g., as described in U.S. Pat. No. 5,595,721. Treatment may consist of a combination of treatment with conjugated and non-conjugated antibodies administered simultaneously or subsequently e.g., as described in WO00/52031; WO00/52473.

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments the polymers may be selected from polyoxyethylated polyols and polyethylene glycol (PEG). PEG is soluble in water at room temperature and has the general formula: $R(O-CH_2-CH_2)_nO-R$, wherein R can be hydrogen, or a protective group such as an alkyl or alkanol group. Preferably, the protective group may have between 1 and 8 carbons. For example, the protective group is methyl. The symbol n is a positive integer. In one embodiment n is between 1 and 1,000. In another embodiment n is between 2 and 500. Preferably, the PEG has an average molecular weight between 1,000 and 40,000, more preferably the PEG has a molecular weight between 2,000 and 20,000, even more preferably the PEG has a molecular weight between 3,000 and 12,000. Furthermore, PEG may have at least one hydroxy group, for example the PEG may have a terminal hydroxy group. For example, it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. POG may have a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. In particular, antibodies of the invention for human use include those that cannot be easily isolated from hosts such as mice, goats, rabbits, rats, non-primate mammals, etc. and cannot generally be obtained by humanization or from xeno-mice.

Production of Antibodies

Antibodies according to the invention can be made by any method known in the art. For example, the general methodology for making monoclonal antibodies using hybridoma technology is well known (Kohler, G. and Milstein, C., 1975; Kozbar et al. 1983). In one embodiment, the alternative EBV immortalization method described in WO2004/076677 is used.

A preferred method is described in WO 2004/076677. In this method B cells producing the antibody of the invention are transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Another preferred method is described in WO 2010/046775. In this method plasma cells are cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by (i) expressing a nucleic acid sequence according to the invention in a host cell, e.g. by use of a vector according to the present invention, and (ii) isolating the expressed antibody product. Additionally, the method may include (iii) purifying the isolated antibody. Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of the invention can be used in various ways e.g., as a source of monoclonal antibodies, as a source of nucleic acid (DNA or mRNA) encoding a monoclonal antibody of interest, for research, etc.

The invention also provides a composition comprising immortalized B memory cells or transfected host cells that produce antibodies according to the present invention.

The immortalized B cell clone or the cultured plasma cells of the invention may also be used as a source of nucleic acid for the cloning of antibody genes for subsequent recombinant expression. Expression from recombinant sources is more common for pharmaceutical purposes than expression from B cells or hybridomas e.g., for reasons of stability, reproducibility, culture ease, etc.

Thus the invention also provides a method for preparing a recombinant cell, comprising the steps of: (i) obtaining one or more nucleic acids (e.g., heavy and/or light chain mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

Furthermore, the invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g., see Chapter 4 of Kuby Immunology, 4th edition, 2000).

The transfected host cell may be a eukaryotic cell, including yeast and animal cells, particularly mammalian cells (e.g., CHO cells, NS0 cells, human cells such as PER.C6 or HKB-11 cells, myeloma cells, or a human liver cell), as well as plant cells, whereby mammalian cells are preferred. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention also provides a method for preparing one or more nucleic acid molecules (e.g., heavy and light chain genes) that encode an antibody of interest, comprising the steps of (i) preparing an immortalized B cell clone or culturing plasma cells according to the invention; (ii) obtaining from the B cell clone or the cultured plasma cells nucleic acid that encodes the antibody of interest.

Further, the invention provides a method for obtaining a nucleic acid sequence that encodes an antibody of interest, comprising the steps of: (i) preparing an immortalized B cell clone or culturing plasma cells according to the invention; (ii) sequencing nucleic acid from the B cell clone or the cultured plasma cells that encodes the antibody of interest.

The invention further provides a method of preparing nucleic acid molecule(s) that encode an antibody of interest, comprising the step of obtaining the nucleic acid that was obtained from a transformed B cell clone or cultured plasma cells of the invention. Thus the procedures for first obtaining the B cell clone or the cultured plasma cell, and then obtaining nucleic acid(s) from the B cell clone or the cultured plasma cells can be performed at different times by different people in different places (e.g., in different countries).

The invention also comprises a method for preparing an antibody (e.g., for pharmaceutical use) according to the present invention, comprising the steps of: (i) obtaining and/or sequencing one or more nucleic acids (e.g., heavy and light chain genes) from the selected B cell clone or the cultured plasma cells expressing the antibody of interest; (ii) inserting the nucleic acid(s) into or using the nucleic acid(s) sequence(s) to prepare an expression vector; (iii) transfecting a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population, e.g. a stably transfected host cell population, under conditions where the antibody of interest is expressed and, optionally, purifying the antibody of interest, wherein said transfected host cell population has been prepared by (i) providing nucleic acid(s) encoding a selected antibody of interest that is produced by a B cell clone or cultured plasma cells prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g., indifferent countries).

Pharmaceutical Composition

The present invention also provides a pharmaceutical composition comprising one or more of:
 (i) the antibody, or the antibody fragment thereof, according to the present invention;
 (ii) the nucleic acid encoding the antibody, or antibody fragments according to the present invention;
 (iii) the vector comprising the nucleic acid according to the present invention; and/or
 (iv) the cell expressing the antibody according to the present invention or comprising the vector according to the present invention.

In other words, the present invention also provides a pharmaceutical composition comprising the antibody, or the antigen binding fragment thereof, according to the present invention, the nucleic acid according to the present invention, the vector according to the present invention and/or the cell according to the present invention.

The pharmaceutical composition may preferably also contain a pharmaceutically acceptable carrier, diluent and/or excipient. Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present invention may be active components or inactive components. Preferably, the pharmaceutically acceptable carrier in a pharmaceutical composition according to the present invention is not an active component in respect to Zika virus infection.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody may be provided in kit form with sterile water or a sterile buffer.

It is preferred that the active ingredient in the composition is an antibody molecule, an antibody fragment or variants and derivatives thereof, in particular the active ingredient in the composition is an antibody, an antibody fragment or variants and derivatives thereof, according to the present invention. As such, it may be susceptible to degradation in the gastrointestinal tract. Thus, if the composition is to be administered by a route using the gastrointestinal tract, the composition may contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid. A vehicle is typically understood to be a material that is suitable for storing, transporting, and/or administering a compound, such as a pharmaceutically active compound, in particular the antibodies according to the present invention. For example, the vehicle may be a physiologically acceptable liquid, which is suitable for storing, transporting, and/or administering a pharmaceutically active compound, in particular the antibodies according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Preferably, the pharmaceutical composition may be prepared for oral administration, e.g. as tablets, capsules and the like, for topical administration, or as injectable, e.g. as liquid solutions or suspensions, whereby it is particularly preferred that the pharmaceutical composition is an injectable. Solid forms suitable for solution in, or suspension in, liquid vehicles prior to injection are also be preferred, e.g. that the pharmaceutical composition is in lyophilized form.

For injection, e.g. intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated. For injection, the pharmaceutical composition according to the present invention may be provided for example in a pre-filled syringe.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Dosage treatment may be a single dose schedule or a multiple dose schedule. In particular, the pharmaceutical composition may be provided as single-dose product. Preferably, the amount of the antibody in the pharmaceutical composition—in particular if provided as single-dose product—does not exceed 200 mg, more preferably does not exceed 100 mg, and even more preferably does not exceed 50 mg.

For example, the pharmaceutical composition according to the present invention may be administered daily, e.g. once or several times per day, e.g. once, twice, three times or four times per day, preferably once or twice per day, more preferable once per day, for 1, 2, 3, 4, 5, 6, 7, 8, 9, 10, 11, 12, 13, 14, 15, 16, 17, 18, 19, 20 or 21 or more days, e.g. daily for 1, 2, 3, 4, 5, 6 months. Preferably, the pharmaceutical composition according to the present invention may be administered weekly, e.g. once or twice per week, for 1, 2, 3, 4, 5, 6, 7, 8, 9, 10, 11, 12, 13, 14, 15, 16, 17, 18, 19, 20 or 21 or more weeks, e.g. weekly for 1, 2, 3, 4, 5, 6, 7, 8, 9, 10, 11, or 12 months or weekly for 2, 3, 4, or 5 years. Moreover, the pharmaceutical composition according to the present invention may be preferably administered monthly, e.g. once per month or, more preferably, every second month for 1, 2, 3, 4, or 5 or more years. It is also preferred that the administration continues for the lifetime. In addition, also one single administration only is also envisaged, in particular in respect to certain indications, e.g. for prevention of Zika virus infection in case of accidental exposure, e.g. in non-immunised subjects. However, the most preferred treatment schedule is post-exposure prophylaxis (PEP), wherein one or more single doses are administered as soon as possible after Zika infection. A prophylactic setting, wherein one or more single doses are administered to prevent Zika infection (i.e. before Zika infection, in particular in non-Zika-immunised subjects) is also preferred.

In particular, it is preferred that for a single dose, e.g. a daily, weekly or monthly dose, preferably for a weekly dose, the amount of the antibody, or the antigen binding fragment thereof, in the pharmaceutical composition according to the present invention, does not exceed 1 g, preferably does not exceed 500 mg, more preferably does not exceed 200 mg, even more preferably does not exceed 100 mg, and particularly preferably does not exceed 50 mg.

Pharmaceutical compositions typically include an "effective" amount of one or more antibodies of the invention, i.e. an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.005 to about 100 mg/kg, preferably from about 0.0075 to about 50 mg/kg, more preferably from about 0.01 to about 10 mg/kg, and even more preferably from about 0.02 to about 5 mg/kg, of the antibody of the present invention (e.g. amount of the antibody in the pharmaceutical composition) in relation to the bodyweight (e.g., in kg) of the individual to which it is administered.

Moreover, the pharmaceutical composition according to the present invention may also comprise an additional active component, which may be a further antibody or a component, which is not an antibody. The additional active component is preferably a checkpoint inhibitor. It is also preferred that a ZIKV neutralizing antibody, or an antigen binding fragment thereof, as described herein is combined with a ZIKV NS1-binding antibody, or an antigen binding fragment thereof, as described herein as additional active component (co-agent). Thereby, the pathogenic role of NS1 may be blocked in addition to neutralization of ZIKV. The pharmaceutical composition according to the present invention may comprise one or more of the additional active components, e.g. as described as co-agents below in the context of a combination therapy.

The antibody, or the antigen binding fragment, according to the present invention can be present either in the same pharmaceutical composition as the additional active component or, preferably, the antibody, or the antigen binding fragment, according to the present invention is comprised by a first pharmaceutical composition and the additional active component is comprised by a second pharmaceutical composition different from the first pharmaceutical composition. Accordingly, if more than one additional active component is envisaged, each additional active component and the antibody, or the antigen binding fragment, according to the present invention is preferably comprised by a different pharmaceutical composition. Such different pharmaceutical compositions may be administered either combined/simultaneously or at separate times or at separate locations (e.g. separate parts of the body).

Preferably, antibody, or the antigen binding fragment, according to the present invention and the additional active component provide an additive therapeutic effect or, preferably, a synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

A pharmaceutical composition comprising the antibody according to gZKA190, gZKA64, gZKA230, gZKA185, gZKA78 or an antigen binding fragment thereof, and a pharmaceutically acceptable carrier is preferred.

In one embodiment, a composition of the invention may include antibodies of the invention, wherein the antibodies may make up at least 50% by weight (e.g., 60%, 70%, 75%, 80%, 85%, 90%, 95%, 96%, 97%, 98%, 99% or more) of the total protein in the composition. In such a composition, the antibodies are preferably in purified form.

The present invention also provides a method of preparing a pharmaceutical composition comprising the steps of: (i) preparing an antibody of the invention; and (ii) admixing the purified antibody with one or more pharmaceutically-acceptable carriers.

In another embodiment, a method of preparing a pharmaceutical composition comprises the step of: admixing an antibody with one or more pharmaceutically-acceptable carriers, wherein the antibody is a monoclonal antibody that was obtained from a transformed B cell or a cultured plasma cell of the invention.

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cells to a subject, such that the nucleic acid can be expressed in the subject in situ to provide a desired therapeutic effect. Suitable gene therapy and nucleic acid delivery vectors are known in the art.

Pharmaceutical compositions may include an antimicrobial particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. For example, a concentration of 10-±2 mg/ml NaCl is typical.

Further, pharmaceutical compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to between 5 and 8, or between 5.5 and 7, or around 6.1 prior to lyophilization.

The compositions of the invention may also comprise one or more immunoregulatory agents. In one embodiment, one or more of the immunoregulatory agents include(s) an adjuvant.

Medical Treatments, Kits and Uses

Medical Treatments

In a further aspect, the present invention provides the use of the antibody, or an antigen binding fragment thereof, according to the present invention, the nucleic acid according to the present invention, the vector according to the present invention, the cell according to the present invention or the pharmaceutical composition according to the present invention in (i) prevention and/or treatment of Zika virus infection; or in (ii) diagnosis of Zika virus infection. Thereby, use of the antibody, or an antigen binding fragment thereof, according to the present invention (and in particular its preferred embodiments as described above) is preferred in (i) prevention and/or treatment of Zika virus infection as described herein; or in (ii) diagnosis of Zika virus infection as described herein.

Methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably plasma or serum. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

Prevention of Zika virus infection refers in particular to prophylactic settings, wherein the subject was not diagnosed with Zika virus infection (either no diagnosis was performed or diagnosis results were negative) and/or the subject does not show symptoms of Zika virus infection. Accordingly, prevention of Zika virus infection includes "post-exposure prophylaxis" (PEP), i.e. preventive treatment after a possible Zika virus infection, for example after a mosquito bite in a Zika virus affected area. Prevention of Zika virus infection is in particular useful in high-risk subjects, such as in pregnant subjects and/or in subjects staying in Zika virus affected areas (such as subjects living in Zika virus affected areas or travelling to Zika virus affected areas).

In therapeutic settings, in contrast, the subject is typically infected by Zika virus, diagnosed with Zika virus infection and/or showing symptoms of Zika virus infection. Of note, the terms "treatment" and "therapy"/"therapeutic" of ZIKV infection include (complete) cure as well as attenuation of ZIKV infection.

Preferred methods of diagnosis of Zika virus infection are the diagnosis methods as described herein, e.g. using the neutralizing antibody, or antigen binding fragment thereof, according to the present invention and/or the ZIKV NS1-binding antibody, or antigen binding fragment thereof, according to the present invention.

Accordingly, the antibody, or an antigen binding fragment thereof, according to the present invention, the nucleic acid according to the present invention, the vector according to the present invention, the cell according to the present invention or the pharmaceutical composition according to the present invention is preferably used for treatment of Zika virus infection in subjects diagnosed with Zika virus infection or in subjects showing symptoms of Zika infection.

It is also preferred that the antibody, or an antigen binding fragment thereof, according to the present invention, the nucleic acid according to the present invention, the vector according to the present invention, the cell according to the present invention or the pharmaceutical composition according to the present invention is used for prevention and/or treatment of Zika virus infection in asymptomatic subjects. Those subjects may be diagnosed or not diagnosed with Zika virus infection.

Preferably, the antibody, or an antigen binding fragment thereof, according to the present invention, the nucleic acid according to the present invention, the vector according to the present invention, the cell according to the present invention or the pharmaceutical composition according to the present invention is used for prevention and/or treatment of Zika virus infection in pregnant subjects, in particular to prevent congenital infection. For example, this may be performed in a similar manner as for the prevention of HCMV congenital infection as described in Nigro G, Adler S P, La Torre R, Best A M, Congenital Cytomegalovirus Collaborating Group: Passive immunization during pregnancy for congenital cytomegalovirus infection; N Engl J Med 2005, 353:1350-1362.

Without being bound to any theory, it is assumed that the antibody, or the antigen-binding fragment thereof, according to the present invention can pass the placenta through the interaction with FcRn if administered to a pregnant subject, e.g. by (i.v.) injection or any other route of administration as described herein. Importantly, the interaction of "LALA" variants of antibodies as described herein with FcRn is not compromised. It is believed that FcRn is already expressed in the first trimester in the placenta.

Alternatively, the antibody, or the antigen-binding fragment thereof, according to the present invention may also be administered to the extra-amniotic space.

Preferably, the antibody, or an antigen binding fragment thereof, according to the present invention, the nucleic acid according to the present invention, the vector according to the present invention, the cell according to the present invention or the pharmaceutical composition according to the present invention is used for prevention and/or treatment of Zika virus infection, wherein the antibody, or the antigen binding fragment thereof, the nucleic acid, the vector, the cell, or the pharmaceutical composition is administered up to seven days after (a possible) Zika virus infection, preferably up to five days after (a possible) Zika virus infection, more preferably up to four days after (a possible) Zika virus infection, even more preferably up to three days after (a possible) Zika virus infection, and most preferably up to one day after (a possible) Zika virus infection. Such a treatment schedule may be useful in therapeutic settings as well as in prophylactic settings, in particular in post-exposure prophylaxis (PEP).

In PEP typically the first administration of the antibody, or an antigen binding fragment thereof, according to the present invention, the nucleic acid according to the present invention, the vector according to the present invention, the cell according to the present invention or the pharmaceutical composition according to the present invention is as soon as possible after a possible ZIKV infection, e.g. after a mosquito bite in a ZIKV affected area. Accordingly, in PEP the first administration of the antibody, or an antigen binding fragment thereof, according to the present invention, the nucleic acid according to the present invention, the vector according to the present invention, the cell according to the present invention or the pharmaceutical composition according to the present invention is typically up to one or more days after (a possible) ZIKV infection, as described above.

It is also preferred that the antibody, or an antigen binding fragment thereof, according to the present invention, the nucleic acid according to the present invention, the vector according to the present invention, the cell according to the present invention or the pharmaceutical composition according to the present invention is used for prevention and/or treatment of Zika virus infection, wherein the antibody, or the antigen binding fragment thereof, the nucleic acid, the vector, the cell, or the pharmaceutical composition is administered up to three months before (a possible) Zika virus infection, preferably up to one month before (a possible) Zika virus infection, more preferably up to two weeks before (a possible) Zika virus infection, even more preferably up to one week before (a possible) Zika virus infection, and most preferably up to one day before (a possible) Zika virus infection. Such a treatment schedule refers in particular to a prophylactic setting.

In general—and in particular in PEP—after the first administration of the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose per day or per every second day for 1, 2, 3, 4, 5, 6, 7, 8, 9, 10, 11, 12, 13, 1, 15, 16, 17, 18, 19, 20, or 21 days. It is also preferred that after the first administration of the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose once or twice per week for 1, 2, 3, 4, 5, 6, 7, 8, 9, 10, 11, 12, 13, 1, 15, 16, 17, 18, 19, 20, or 21 weeks. It is also preferred that after the first administration of the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose every 2 or 4 weeks for 1, 2, 3, 4, 5, 6, 7, 8, 9, 10, 11, 12, 13, 1, 15, 16, 17, 18, 19, 20, or 21 weeks. It is also preferred that after the first administration of the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose every two or four months for 1, 2, 3, 4, 5, 6, 7, 8, 9, 10, 11, 12, 13, 1, 15, 16, 17, 18, 19, 20, or 21 months. It is also preferred that after the first administration of the antibody, or an antigen binding fragment thereof, according to the present invention, the nucleic acid according to the present invention, the vector according to the present invention, the cell according to the present invention or the pharmaceutical composition according to the present invention, one or more subsequent administrations may follow, preferably a single dose once or twice per year for 1, 2, 3, 4, 5, 6, 7, 8, 9, or 10 years.

Preferably, the antibody, or an antigen binding fragment thereof, according to the present invention, the nucleic acid according to the present invention, the vector according to the present invention, the cell according to the present invention or the pharmaceutical composition according to the present invention is administered at a (single) dose of 0.005 to 100 mg/kg bodyweight, preferably at a (single) dose of 0.0075 to 50 mg/kg bodyweight, more preferably at a (single) dose of 0.01 to 10 mg/kg bodyweight, even more preferably at a (single) dose of 0.05 to 5 mg/kg bodyweight, and particularly preferably at a (single) dose of 0.1 to 1 mg/kg bodyweight.

The antibody, or an antigen binding fragment thereof, according to the present invention, the nucleic acid according to the present invention, the vector according to the present invention, the cell according to the present invention or the pharmaceutical composition according to the present invention may be administered by any number of routes such as oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Intravenous administration, or subcutaneous administration or intramuscular administration are preferred and intravenous administration or subcutaneous administration are more preferred.

In pregnant subjects the antibody, or an antigen binding fragment thereof, according to the present invention may also be administered intra- or extra-amniotic, e.g. by injection.

Accordingly, the present invention also provides a method of preventing and/or treating Zika virus infection in a subject, wherein the method comprises administering to a subject in need thereof the antibody, or an antigen binding fragment thereof, according to the present invention, the nucleic acid according to the present invention, the vector according to the present invention, the cell according to the present invention or the pharmaceutical composition according to the present invention. Preferred embodiments of this method correspond to preferred embodiments of the medical use as described above (and below, regarding combination therapy). For example, a preferred subject in this method is a subject diagnosed with Zika virus infection or showing symptoms of Zika virus infection. Another preferred subject in this method is a pregnant subject.

Combination Therapy

The administration of the antibody, or an antigen binding fragment thereof, according to the present invention, the nucleic acid according to the present invention, the vector according to the present invention, the cell according to the present invention or the pharmaceutical composition according to the present invention in the methods and uses according to the invention can be carried out alone or in combination with a co-agent (also referred to as "additional active component" herein), which is in particular useful for preventing and/or treating ZIKV infection.

The invention encompasses the administration of the antibody, or an antigen binding fragment thereof, according to the present invention, the nucleic acid according to the present invention, the vector according to the present invention, the cell according to the present invention or the pharmaceutical composition according to the present invention, wherein it is administered to a subject prior to, simultaneously or sequentially with other therapeutic regimens or co-agents useful for treating and/or preventing ZIKV infection. Said antibody, nucleic acid, vector, cell or pharmaceutical composition, that is administered simultaneously with said co-agents can be administered in the same or different composition(s) and by the same or different route(s) of administration.

Said other therapeutic regimens or co-agents may be, for example, a checkpoint inhibitor.

Thus, in another aspect of the present invention the antibody, or an antigen binding fragment thereof, according to the present invention, the nucleic acid according to the present invention, the vector according to the present invention, the cell according to the present invention or the pharmaceutical composition according to the present invention is administered in combination with a checkpoint inhibitor for the (medical) uses as described herein.

Preferred checkpoint inhibitors are directed to a blockade of PD-1/PD-L1 and/or of CTLA4 and, thus, include anti-PD-1 antibodies, anti-PD-L1 antibodies and anti-CTLA4 antibodies. Thus, the pharmaceutical composition according to the present invention may comprise one or more of the additional active components.

It is also preferred that a ZIKV neutralizing antibody, or an antigen binding fragment thereof, as described herein is combined with a ZIKV NS1-binding antibody, or an antigen binding fragment thereof, as described herein as additional active component (co-agent). Thereby, the pathogenic role of NS1 may be blocked in addition to neutralization of ZIKV. Accordingly, a ZIKV NS1-binding antibody, or an antigen binding fragment thereof, as described herein is a preferred additional active component (co-agent).

The antibody, or the antigen binding fragment, according to the present invention can be present either in the same pharmaceutical composition as the additional active component (co-agent) or, preferably, the antibody, or the antigen binding fragment, according to the present invention is comprised by a first pharmaceutical composition and the additional active component (co-agent) is comprised by a second pharmaceutical composition different from the first pharmaceutical composition. Accordingly, if more than one additional active component (co-agent) is envisaged, each additional active component (co-agent) and the antibody, or the antigen binding fragment, according to the present invention is preferably comprised by a different pharmaceutical composition. Such different pharmaceutical compositions may be administered either combined/simultaneously or at separate times or at separate locations (e.g. separate parts of the body).

Preferably, the antibody, or the antigen binding fragment, according to the present invention and the additional active component (co-agent) provide an additive therapeutic effect or, preferably, a synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Further Use and Kits

In a further aspect, the present invention also provides the use of the antibody, or an antigen binding fragment thereof, according to the present invention, the nucleic acid according to the present invention, the vector according to the present invention, the cell according to the present invention or the pharmaceutical composition according to the present invention for monitoring the quality of an anti-Zika vaccine by checking that the antigen of said vaccine contains the specific epitope in the correct conformation. Preferred antigens comprised by such as anti-Zika vaccine to be checked include ZIKV envelope protein or any other molecule/complex comprising or consisting of (i) domain III of ZIKV E protein (EDIII) as described above or (ii) a quaternary ZIKV epitope as described above.

Moreover, the present invention also provides the use of the antibody, or an antigen binding fragment thereof, according to the present invention, the nucleic acid according to the present invention, the vector according to the present invention, the cell according to the present invention or the pharmaceutical composition according to the present invention in diagnosis of Zika virus infection.

In addition also the use of the antibody, or an antigen binding fragment thereof, according to the present invention, the nucleic acid according to the present invention, the vector according to the present invention, the cell according to the present invention or the pharmaceutical composition according to the present invention in determining whether an isolated blood sample (e.g., whole blood, serum and/or plasma) is infected with Zika virus is provided.

As described above, methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably serum or plasma. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

In a further aspect, the present invention also provides a kit of parts comprising at least one antibody, or antigen binding fragment thereof, according to the present invention, at least one nucleic acid according to the present invention, at least one vector according to the present invention, at least one cell according to the present invention, and/or at least one pharmaceutical composition according to the present invention. In addition, the kit may comprise means for administration of the antibody, or an antigen binding fragment thereof, according to the present invention, the nucleic acid according to the present invention, the vector according to the present invention, the cell according to the present invention or the pharmaceutical composition according to the present invention, such as a syringe or a vessel, a leaflet, and/or a co-agent to be administered as described above.

Antibodies Specifically Binding to NS1 Protein of Zika Virus

In a further aspect, the present invention also provides an isolated antibody, or an antigen binding fragment thereof, that specifically binds to NS1 protein of ZIKA virus (ZIKV).

ZIKV NS1 protein (non-structural protein 1) occurs intracellular, secreted and cell-surface associated and in particular secreted ZIKV NS1 protein is typically found in body fluids, such as serum, saliva, urine etc., of subjects infected with ZIKV. Secreted and cell-surface-associated NS1 are highly immunogenic and elicit production of antibodies. NS1 is known to be an important biomarker for early diagnosis of ZIKV infection. Accordingly, the antibody, or an antigen binding fragment thereof, according to the present invention that specifically binds to NS1 protein of ZIKA virus (ZIKV), is for example useful in diagnosis of ZIKV infection.

In general, binding may be assessed by standard ELISA as known to the skilled person and as described above. Thereby, the relative affinities of antibody binding may be determined by measuring the concentration of the antibody ($EC_{50}$) required to achieve 50% maximal binding at saturation. Preferably, the $EC_{50}$ of the antibody, or an antigen binding fragment thereof, according to the present invention to ZIKV NS1 protein is no more than 50 ng/ml, preferably said $EC_{50}$ is no more than 25 ng/ml, more preferably said $EC_{50}$ is no more than 15 ng/ml, even more preferably said $EC_{50}$ is no more than 10 ng/ml, and most preferably said $EC_{50}$ is no more than 5 ng/ml, such as for example about 2 or 3 ng/ml.

Preferably, the antibody, or an antigen binding fragment thereof, according to the present invention, that specifically binds to NS1 protein of ZIKA virus (ZIKV), does essentially not bind to Dengue virus (DENV) NS1 protein. Thereby "essentially not binding" means that for the antibody, or an antigen binding fragment thereof, no $EC_{50}$-value up to $10^2$ ng/ml, preferably up to $10^3$ ng/ml, more preferably up to $5*10^3$ ng/ml, even more preferably up to $8*10^3$ ng/ml, and most preferably up to $10^4$ ng/ml can be determined in a standard ELISA to Dengue virus (DENV) NS1 protein. In other words, the concentration of the antibody, or an antigen binding fragment thereof, required to achieve 50% maximal binding at saturation ($EC_{50}$) to Dengue virus (DENV) NS protein in a standard ELISA is typically more than $10^2$ ng/ml, preferably more than $10^3$ ng/ml, more preferably more than $5*10^3$ ng/ml, even more preferably more than $8*10^3$ ng/ml, and most preferably more than $10^4$ ng/ml.

It is also preferred that the antibody, or an antigen binding fragment thereof, according to the present invention, that specifically binds to NS1 protein of ZIKA virus (ZIKV), does essentially not bind to Yellow fever virus (YFV) NS1 protein, West nile virus (WNV) NS1 protein, Japanese encephalitis virus (JEV) NS1 protein and/or to Tick-borne encephalitis virus (TBEV) NS1 protein. Thereby "essentially not binding" means that for the antibody, or an antigen binding fragment thereof, no $EC_{50}$-value up to $10^2$ ng/ml, preferably up to $10^3$ ng/ml, more preferably up to $5*10^3$ ng/ml, even more preferably up to $8*10^3$ ng/ml, and most preferably up to $10^4$ ng/ml can be determined in a standard ELISA to Yellow fever virus (YFV) NS1 protein, West nile virus (WNV) NS1 protein, Japanese encephalitis virus (JEV) NS1 protein and/or to Tick-borne encephalitis virus (TBEV) NS1 protein. In other words, the concentration of the antibody, or an antigen binding fragment thereof, required to achieve 50% maximal binding at saturation ($EC_{50}$) to Yellow fever virus (YFV) NS1 protein, West nile virus (WNV) NS1 protein, Japanese encephalitis virus (JEV) NS1 protein and/or to Tick-borne encephalitis virus (TBEV) NS1 protein in a standard ELISA is typically more than $10^2$ ng/ml, preferably more than $10^3$ ng/ml, more preferably more than $5*10^3$ ng/ml, even more preferably more than $8*10^3$ ng/ml, and most preferably more than $10^4$ ng/ml.

Preferably, the antibody, or an antigen binding fragment thereof, according to the present invention, that specifically binds to NS1 protein of ZIKA virus (ZIKV), is a human antibody. It is also preferred that the antibody, or an antigen binding fragment thereof, according to the present invention, that specifically binds to NS1 protein of ZIKA virus (ZIKV), is a monoclonal antibody, preferably a human monoclonal antibody. Furthermore, it is also preferred that the antibody, or an antigen binding fragment thereof, according to the present invention, that specifically binds to NS1 protein of ZIKA virus (ZIKV), is a recombinant antibody.

Preferably, the antibody according to the present invention, or an antigen binding fragment thereof, that specifically binds to NS1 protein of ZIKA virus (ZIKV), comprises an Fc moiety. More preferably, the antibody according to the present invention, or an antigen binding fragment thereof, that specifically binds to NS1 protein of ZIKA virus (ZIKV), comprises a CH2 L4A mutation, a CH2 L5A mutation, or both. For a detailed description of the antibody according to the present invention, or an antigen binding fragment thereof, comprising an Fc moiety and/or comprises a CH2 L4A mutation, a CH2 L5A mutation, or both, it is referred to the detailed description of the Fc moiety and of the CH2 L4A mutation, CH2 L5A mutation, or both in the context of the neutralizing antibodies according to the present invention as above. The corresponding detailed description as well as preferred embodiments apply accordingly also for the antibody according to the present invention, or an antigen binding fragment thereof, that specifically binds to NS1 protein of ZIKA virus (ZIKV).

However, it is also preferred that the antibody according to the present invention, or an antigen binding fragment thereof, that specifically binds to NS1 protein of ZIKA virus (ZIKV), does not comprise an Fc moiety. In particular it is preferred that the antibody according to the present invention, or an antigen binding fragment thereof, that specifically binds to NS1 protein of ZIKA virus (ZIKV), is a purified antibody, a single chain antibody, Fab, Fab', F(ab')2, Fv or scFv. Even more preferably, the antibody according to the present invention, or an antigen binding fragment thereof, that specifically binds to NS1 protein of ZIKA virus (ZIKV), is labelled as described herein, for example biotinylated, such as a biotinylated Fab, Fab', or F(ab')2 fragment.

Preferably, the antibody according to the present invention, or an antigen binding fragment thereof, that specifically binds to NS1 protein of ZIKA virus (ZIKV), binds to antigenic site S1 and/or to antigenic site S2 of Zika virus NS1 protein. The present inventors have surprisingly found that anti-ZIKV NS1 antibodies binding to antigenic site S1 and/or to antigenic site S2 of ZIKV NS1 protein are not cross-reactive with dengue virus NS1 protein (DENV NS1). Anti-ZIKV NS1 antibodies, which bind neither to antigenic site S1 nor to antigenic site S2 of ZIKV NS1 protein, in contrast, are typically cross-reactive with DENV NS1. This surprising finding indicates that antigenic sites S1 and S2 on ZIKV NS1 can be used to distinguish ZIKV NS1-specific antibodies from antibodies cross-reactive to DENV NS1.

Most preferably, the antibody according to the present invention, or an antigen binding fragment thereof, that specifically binds to NS1 protein of ZIKA virus (ZIKV), binds to antigenic site S2 of Zika virus NS1 protein. Antigenic site S2 is highly conserved in multiple ZIKV lineages, but it is not homologous in sequence and structure with the corresponding site on NS1 of other flaviviruses, thereby providing a unique specificity for ZIKV.

Antigenic sites S1 and S2 of ZIKV NS1 protein were identified by the present inventors as described in Example 3, FIG. 6. Whether an antibody is binding to antigenic site S1 and/or S2 may be easily identified by the skilled person by using cross-competition studies, for example as described below or in Example 3, wherein the S1-specific antibody according to gZKA15 (SEQ ID NOs: 91-99) and/or the S2-specific antibody according to gZKA35 (SEQ ID NOs:

127-135) may be used as "second antibody". In such a competition assay, presence of any competition (full or partial) with gZKA15 and/or gZKA35 indicates that the antibody to be tested binds to antigenic site S1 and/or to antigenic site S2, respectively.

In general, for a competition assay commercially available systems for characterization of protein-protein binding, such as for example "Octet® RED96 System" provided by ForteBio, may be used, in particular according to the supplier's instructions.

In an exemplary competition assay, e.g. using "Octet® RED96 System" provided by ForteBio, ZIKV-NS1 protein (e.g. diluted to 2.5 µg/ml in PBS) may be immobilized (e.g. for 7-9 minutes) on the surface of an APS coated sensor-chip. Coated biosensors may then be placed into wells containing blocking buffer (e.g., 0.1% BSA in PBS; e.g. for 6 minutes) to block free Biosensor binding sites. Coated-Biosensors may then be incubated (e.g., for 8 minutes) with the antibody/antibodies to be tested (e.g. diluted in blocking buffer for example at 10 µg/ml). After binding of the antibodies to be tested (step 1), Biosensors were moved to wells containing the "second antibodies", e.g. gZKA15 and/or gZKA35 (e.g. for 8 minutes) (step 2). Competition, partial competition or no competition can thus be determined in step 2, depending on whether no association (competition), low association (partial competition) or (strong) association (no competition) is detected.

As described above, the antibody according to the present invention, or the antigen binding fragment thereof, preferably comprises (at least) three complementarity determining regions (CDRs) on a heavy chain and (at least) three CDRs on a light chain. In general, complementarity determining regions (CDRs) are the hypervariable regions present in heavy chain variable domains and light chain variable domains. Typically, the CDRs of a heavy chain and the connected light chain of an antibody together form the antigen receptor. Usually, the three CDRs (CDR1, CDR2, and CDR3) are arranged non-consecutively in the variable domain. Since antigen receptors are typically composed of two variable domains (on two different polypeptide chains, i.e. heavy and light chain), there are six CDRs for each antigen receptor (heavy chain: CDRH1, CDRH2, and CDRH3; light chain: CDRL1, CDRL2, and CDRL3). A single antibody molecule usually has two antigen receptors and therefore contains twelve CDRs. The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR's.

The sequences of the heavy chains and light chains of five exemplary antibodies of the invention, comprising three different CDRs on the heavy chain and three different CDRs on the light chain were determined. The position of the CDR amino acids are defined according to the IMGT numbering system (IMGT: http://www.imgt.org/; cf. Lefranc, M.-P. et al. (2009) *Nucleic Acids Res.* 37, D1006-D1012).

Table 4 shows the SEQ ID NO's of the amino acid sequences of the heavy chain CDR's (CDRH1, CDRH2, and CDRH3) and of the heavy chain variable region (referred to as "VH") of exemplary antibodies according to the present invention:

| Antibody name | CDRH1 | CDRH2 | CDRH3 | VH |
|---|---|---|---|---|
| ZKA15 | 91 | 92 | 93 | 98 |
| ZKA25 | 109 | 110 | 111 | 116 |
| ZKA35 | 127 | 128 | 129 | 134 |
| ZKA10 | 153 | 154 | 155 | 156 |
| ZKA18 | 157 | 158 | 159 | 160 |
| ZKA28 | 161 | 162 | 163 | 164 |
| ZKA29 | 165 | 166 | 167 | 168 |
| ZKA33 | 169 | 170 | 171 | 172 |
| ZKA39 | 173 | 174 | 175 | 176 |
| ZKA43 | 177 | 178 | 179 | 180 |
| ZKA44 | 181 | 182 | 183 | 184 |
| ZKA46 | 185 | 186 | 187 | 188 |
| ZKA50 | 189 | 190 | 191 | 192 |
| ZKA54 | 193 | 194 | 195 | 196 |
| ZKB18 | 197 | 198 | 199 | 200 |
| ZKB20 | 201 | 202 | 203 | 204 |
| ZKB21 | 205 | 206 | 207 | 208 |
| ZKB23 | 209 | 210 | 211 | 212 |
| ZKC29 | 213 | 214 | 215 | 216 |
| ZKC31 | 217 | 218 | 219 | 220 |
| ZKC32 | 221 | 222 | 223 | 224 |
| ZKC33 | 225 | 226 | 227 | 228 |
| ZKC34 | 229 | 230 | 231 | 232 |
| ZKD25 | 233 | 234 | 235 | 236 |

Table 5 below shows the SEQ ID NO's of the amino acid sequences of the light chain CDR's (CDRL1, CDRL2, and CDRL3) and of the light chain variable region (referred to as "VL") of exemplary antibodies according to the present invention:

| Antibody name | CDRL1 | CDRL2 | CDRL2 long | CDRL3 | VL |
|---|---|---|---|---|---|
| ZKA15 | 94 | 95 | 96 | 97 | 99 |
| ZKA25 | 112 | 113 | 114 | 115 | 117 |
| ZKA35 | 130 | 131 | 132 | 133 | 135 |

It is thus preferred that the antibody, or the antigen binding fragment thereof, according to the present invention comprises amino acid sequences having at least 70%, at least 75%, at least 80%, at least 85%, at least 88%, at least 90%, at least 92%, at least 95%, at least 96%, at least 97%, at least 98% or at least 99% identity to at least one of the CDR sequences, the VH sequence and/or the VL sequence shown in Table 4 and/or in Table 5.

It is preferred that the antibody or antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 93, 111, 129, 155, 159, 163, 167, 171, 175, 179, 183, 187, 191, 195, 199, 203, 207, 211, 215, 219, 223, 227, 231, and 235; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to any of SEQ ID NOs: 93, 111 and 129, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Thereby, it is preferred that at least one CDR, preferably the at least one heavy chain CDRH3, comprises or consists of an amino acid sequence according to SEQ ID NO: 93 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. It is also preferred that at least one CDR, preferably the at least one heavy chain CDRH3, comprises or consists of an amino acid sequence according to SEQ ID NO: 111 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity. Moreover, it is also preferred that at least one CDR, preferably the at least one heavy chain CDRH3, comprises or consists of an amino acid sequence according to SEQ ID NO: 129 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein at least one CDR, preferably the at least one heavy chain CDRH3, comprises or consists of an amino acid sequence according to SEQ ID NO: 129, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also preferred, that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one heavy chain CDRH1 comprises an amino acid sequence according to any of SEQ ID NOs: 91, 109, 127, 153, 157, 161, 165, 169, 173, 177, 181, 185, 189, 193, 197, 201, 205, 209, 213, 217, 221, 225, 229, and 233; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRH2 comprises an amino acid sequence according to any of SEQ ID NOs: 92, 110, 128, 154, 158, 162, 166, 170, 174, 178, 182, 186, 190, 194, 198, 202, 206, 210, 214, 218, 222, 226, 230, and 234; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one heavy chain CDRH3 comprises an amino acid sequence according to any of SEQ ID NOs: 93, 111, 129, 155, 159, 163, 167, 171, 175, 179, 183, 187, 191, 195, 199, 203, 207, 211, 215, 219, 223, 227, 231, and 235; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Still more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one heavy chain CDRH1 comprises an amino acid sequence according to any of SEQ ID NOs: 91, 109 and 127, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRH2 comprises an amino acid sequence according to any of SEQ ID NOs: 92, 110 and 128, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one heavy chain CDRH3 comprises an amino acid sequence according to any of SEQ ID NOs: 93, 111 and 129, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one heavy chain CDRH1 comprises an amino acid sequence according to SEQ ID NO: 91 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
  (ii) the at least one CDRH2 comprises an amino acid sequence according to SEQ ID NO: 92 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
  (iii) the at least one heavy chain CDRH3 comprises an amino acid sequence according to SEQ ID NOs: 93 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also even more preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
  (i) the at least one heavy chain CDRH1 comprises an amino acid sequence according to SEQ ID NO: 109 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 110 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NOs: 111 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is particularly preferred, that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one heavy chain CDRH1 comprises an amino acid sequence according to SEQ ID NO: 127 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRH2 comprises an amino acid sequence according to SEQ ID NO: 128 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one heavy chain CDRH3 comprises an amino acid sequence according to SEQ ID NOs: 129 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

More preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to any of SEQ ID NOs: 94, 112 and 130, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to any of SEQ ID NOs: 95, 96, 113, 114, 131 and 132, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to any of SEQ ID NOs: 97, 115 and 133, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Even more preferably, the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 94 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to SEQ ID NO: 95 or 96, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 97 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is also even more preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 112 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to SEQ ID NO: 113 or 114, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 115 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

It is particularly preferred that the antibody, or the antigen binding fragment thereof, according to the present invention comprises a heavy chain comprising at least one CDRH1, at least one CDRH2 and at least one CDRH3 and a light chain comprising at least one CDRL1, at least one CDRL2 and at least one CDRL3, wherein
(i) the at least one CDRL1 comprises an amino acid sequence according to SEQ ID NO: 130 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity;
(ii) the at least one CDRL2 comprises an amino acid sequence according to SEQ ID NO: 131 or 132, or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; and/or
(iii) the at least one CDRL3 amino comprises an amino acid sequence according to SEQ ID NO: 133 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises CDRH1, CDRH2, and CDRH3 amino acid sequences (i) according to SEQ ID NOs: 91-93; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 109-111; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 127-129; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 153-155; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 157-159; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vi) according to SEQ ID NOs: 161-163; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (vii) according to SEQ ID NOs: 165-167; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (viii) according to SEQ ID NOs: 169-171; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ix) according to SEQ ID NOs: 173-175; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (x) according to SEQ ID NOs: 177-179; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xi) according to SEQ ID NOs: 181-183; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xii) according to SEQ ID NOs: 185-187; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiii) according to SEQ ID NOs: 189-191; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xiv) according to SEQ ID NOs: 193-195; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xv) according to SEQ ID NOs: 197-199; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xvi) according to SEQ ID NOs: 201-203; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xvii) according to SEQ ID NOs: 205-207; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xviii) according to SEQ ID NOs: 209-211; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xix) according to SEQ ID NOs: 213-215; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xx) according to SEQ ID NOs: 217-219; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxi) according to SEQ ID NOs: 221-223; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxii) according to SEQ ID NOs: 225-227; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (xxiii) according to SEQ ID NOs: 229-231; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (xxiv) according to SEQ ID NOs: 233-235; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

It is particularly preferred that the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 91-95 and 97; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (ii) according to SEQ ID NOs: 91-94 and 96-97; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iii) according to SEQ ID NOs: 109-113 and 115; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (iv) according to SEQ ID NOs: 109-112 and 114-115; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; (v) according to SEQ ID NOs: 127-131 and 133; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (vi) according to SEQ ID NOs: 127-130 and 132-133; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises CDRH1, CDRH2, and CDRH3 amino acid sequences and CDRL1, CDRL2, and CDRL3 amino acid sequences (i) according to SEQ ID NOs: 127-131 and 133; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 127-130 and 132-133; or functional sequence variants thereof having at least 70%, at least 75%, at least 80%, at least 85%, at least 88%, at least 90%, at least 92%, at least 95%, at least 96%, at least 97%, at least 98% or at least 99% sequence identity.

It is also preferred that the antibody, or the antigen binding fragment thereof, according to the present invention comprises a heavy chain variable region (VH) and, optionally, a light chain variable region (VL), wherein the heavy chain variable region (VH) comprises or consists of an amino acid sequence according to any of SEQ ID NOs: 98, 116, 134, 156, 160, 164, 168, 172, 176, 180, 184, 188, 192, 196, 200, 204, 208, 212, 216, 220, 224, 228, 232, and 236; or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises (i) a heavy chain variable region (VH) amino acid sequence according to SEQ ID NO: 98 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 99 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; (ii) a heavy chain variable region (VH) amino acid sequence according to SEQ ID NO: 116 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 117 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity; or (iii) a heavy chain variable region (VH) amino acid sequence according to SEQ ID NO: 134 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 135 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Most preferably, the antibody, or the antigen binding fragment thereof, according to the present invention comprises a heavy chain variable region (VH) amino acid sequence according to SEQ ID NO: 134 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 135 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

Preferably, the antibody, or the antigen binding fragment thereof, according to the present invention is gZKA15, gZKA25, or gZKA35, more preferably the antibody, or the antigen binding fragment thereof, is gZKA25 or gZKA35, even more preferably the antibody, or the antigen binding fragment thereof, is gZKA35.

The present inventors have isolated monoclonal antibody (mAb) according to the present invention, which are referred to herein as ZKA15, ZKA25 and ZKA35 (cf. Tables 4 and 5, Example 1). Based on those antibodies, in particular on the VH and VL genes of those antibodies, the terms "gZKA15", "gZKA25" and "gZKA35", as used herein, refer to the respective "generic" antibodies, or antigen binding fragments thereof.

Namely, "gZKA15" refers to an antibody, or antigen binding fragment thereof, having a CDRH1 amino acid sequence according to SEQ ID NO: 91, a CDRH2 amino acid sequence according to SEQ ID NO: 92, a CDRH3 amino acid sequence according to SEQ ID NO: 93, a CDRL1 amino acid sequence according to SEQ ID NO: 94, a CDRL2 amino acid sequence according to SEQ ID NO: 95 or 96, and a CDRL3 amino acid sequence according to SEQ ID NO: 97. The heavy chain variable region ($V_H$) has preferably an amino acid sequence according to SEQ ID NO: 98 and the light chain variable region ($V_L$) has preferably an amino acid sequence according to SEQ ID NO: 99.

"gZKA25" refers to an antibody, or antigen binding fragment thereof, having a CDRH1 amino acid sequence according to SEQ ID NO: 109, a CDRH2 amino acid sequence according to SEQ ID NO: 110, a CDRH3 amino acid sequence according to SEQ ID NO: 111, a CDRL1 amino acid sequence according to SEQ ID NO: 112, a CDRL2 amino acid sequence according to SEQ ID NO: 113 or 114, and a CDRL3 amino acid sequence according to SEQ ID NO: 115. The heavy chain variable region ($V_H$) has preferably an amino acid sequence according to SEQ ID NO: 116 and the light chain variable region ($V_L$) has preferably an amino acid sequence according to SEQ ID NO: 117.

"gZKA35" refers to an antibody, or antigen binding fragment thereof, having a CDRH1 amino acid sequence according to SEQ ID NO: 127, a CDRH2 amino acid sequence according to SEQ ID NO: 128, a CDRH3 amino acid sequence according to SEQ ID NO: 129, a CDRL1 amino acid sequence according to SEQ ID NO: 130, a CDRL2 amino acid sequence according to SEQ ID NO: 131 or 132, and a CDRL3 amino acid sequence according to SEQ ID NO: 133. The heavy chain variable region ($V_H$) has preferably an amino acid sequence according to SEQ ID NO: 134 and the light chain variable region ($V_L$) has preferably an amino acid sequence according to SEQ ID NO: 135.

The detailed description above referring to "production of antibodies" (above section "production of antibodies") and "optional additional features of antibodies" (above section "optional additional features of antibodies") apply to all antibodies, and antigen binding fragments thereof, as described in the present application—i.e. those sections apply not only to the neutralizing antibodies, and antigen-binding fragments thereof, according to the present invention, but also to the NS1-protein binding antibodies, and antigen-binding fragments thereof, according to the present invention.

In particular, it is preferred that the antibody, or the antigen binding fragment thereof, according to the present invention is labelled, for example biotinylated.

Preferably, the antibody, or the antigen binding fragment thereof, according to the present invention is biotinylated.

It is also preferred that the antibody, or the antigen binding fragment thereof, according to the present invention is conjugated to an enzyme, such as horseradish peroxidase (HRP). Conjugation of antibodies to HRP are, for example, described in Wisdom G B. Conjugation of antibodies to horseradish peroxidase. Methods Mol Biol. 2005; 295:127-30 or in Antibodies—a laboratory manual. Edited by Edward A. Greenfield, Second edition 2012, Cold Spring Harbor Laboratory Press, ISBN: 9781936113811.

For example, antibodies of the invention, or the antigen binding fragments thereof, may be coupled to a detectable label, for example to provide measurability, e.g. for quantification or to facilitate imaging. Labeled antibodies may be employed in a wide variety of assays, in particular in immunoassays, employing a wide variety of labels. Preferred labels include radionuclides, enzymes, coenzymes, fluorescers, chemiluminescers, chromogens, enzyme substrates or co-factors, enzyme inhibitors, prosthetic group complexes, free radicals, particles, dyes (e.g., fluorescent dyes, tandem dyes), and the like. Examples of suitable enzymes include horseradish peroxidase (HRP), alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like, preferably in ELISA. Labeled antibodies according to the present invention may be thus be used in such assays for example as described in U.S. Pat. Nos. 3,766,162; 3,791,932; 3,817,837; and 4,233,402.

Preferred labels include (i) enzymes as described above, e.g. horseradish peroxidase (HRP) or alkaline phosphatase, in particular in Blockade-of-binding assay, Western Blotting, ELISA and immunohistochemistry; (ii) prosthetic group complexes as described above, e.g. streptavidin/biotin and avidin/biotin, in particular in ELISA and immunohistochemistry; (iii) fluorescers as described above, such as fluorescent dyes and fluorescent proteins (e.g., (enhanced) green fluorescent protein (EGFP); TagBFP, Turquoise, Venus, KO2, Cherry, Apple, Kate2), in particular in immunofluorescence and flow cytometry; and (iv) tandem dyes in flow cytometry.

Preferably, the antibody, or the antigen binding fragment thereof, is biotinylated. Biotinylation is rapid, specific and is unlikely to perturb the natural function of the molecule due to the small size of biotin (MW=244.31 g/mol). Biotin binds to streptavidin and avidin with an extremely high affinity, fast on-rate, and high specificity. Biotin-binding to streptavidin and avidin is resistant to extremes of heat, pH and proteolysis, making capture of biotinylated molecules possible in a wide variety of environments. The antibody, or the antigen binding fragment thereof, according to the present invention may be biotinylated chemically or enzymatically. Chemical biotinylation utilizes various conjugation chemistries to yield nonspecific biotinylation of amines (e.g., NHS-coupling gives biotinylation of any primary amines in the antibody, see below). Enzymatic biotinylation results in biotinylation of a specific lysine within a certain sequence by use of a bacterial biotin ligase.

Moreover, a second antibody, or antibody fragment thereof, may also be used as label. In this case, the antibody, or the antigen binding fragment thereof, according to the present invention is conjugated to a second antibody, or antibody fragment thereof, to form an antibody heteroconjugate as described for example in U.S. Pat. No. 4,676,980. In this case, the second antibody may optionally be labelled as described herein.

Methods for coupling antibodies to labels are well known in the art. For example, in the antibody or in the antigen binding fragment thereof the side chain of lysine, which terminates in a primary amine (—NH$_2$), may be used to link labels covalently to the antibody or in the antigen binding fragment thereof. Many variant labeling procedures are described in the literature. For example, the labelling approach may be selected from the group consisting of NHS esters, heterobifunctional reagents, carbodiimides and sodium periodate.

NHS esters may be used in particular in the case of fluorescent dye labels. A fluorescent dye label may be purchased in an activated form of the label with an inbuilt NHS ester (also called a 'succinimidyl ester'). The activated dye can be reacted under appropriate conditions with the antibody or with the antigen binding fragment thereof (e.g. via a lysine group). Excess reactive dye can be removed (e.g. by column chromatography) before the labeled antibody or antigen binding fragment thereof can be used in an immunoassay.

Heterobifunctional reagents may be used in particular if the label is a protein molecule (e.g. HRP, alkaline phosphatase, or phycoerythrin). In this case, the antibody or the antigen binding fragment thereof and the label may have multiple amines. In this situation some of the lysines on one molecule (e.g. on the antibody or on the antigen binding fragment thereof) may be modified to create a new reactive group (X) and lysines on the label to create another reactive group (Y) (or vice versa). A 'heterobifunctional reagent' is then used to introduce the Y groups, which subsequently react with X groups when antibody and label are mixed, thus creating heterodimeric conjugates.

Carbodiimides, such as EDC, may be used in particular to create covalent links between amine- and carboxyl-containing molecules. Carbodiimides activate carboxyl groups, and the activated intermediate is then attacked by an amine (e.g. provided by a lysine residue on the antibody or the antigen binding fragment thereof). Carbodiimides may be used in particular to conjugate antibodies to carboxylated particles (e.g. latex particles, magnetic beads), and to other carboxylated surfaces, such as microwell plates or chip surfaces. Carbodiimides may also be used to attach dyes or protein labels to antibodies or antigen binding fragments thereof.

Sodium periodate may be used in particular for labelling with horseradish peroxidase (HRP). Periodate activates carbohydrate chains on the HRP molecule to create aldehyde groups, which are capable of reacting with lysines on the antibody or antigen binding fragment thereof. Since HRP itself has very few lysines, it is relatively easy to create antibody-HRP conjugates without significant HRP polymerization.

Optionally, linkers may be used between the labels and the antibodies of the invention, e.g., as described in U.S. Pat. No. 4,831,175. Antibodies or, antigen-binding fragments thereof may be directly labeled with radioactive iodine, indium, yttrium, or other radioactive particle known in the art, e.g., as described in U.S. Pat. No. 5,595,721.

Accordingly, the present invention also provides a complex comprising
(i) the antibody, or the antigen binding fragment thereof, according to the present invention; and
(ii) a label as described above.

Accordingly, such a complex is preferably a label conjugated to the antibody, or the antigen binding fragment thereof, according to the present invention. Preferably, the label and the antibody, or the antigen binding fragment thereof, according to the present invention are covalently linked.

For example, the complex according to the present invention may be a fusion protein comprising (i) the antibody according to the present invention and (ii) a label, which is a peptide or a protein, such as a fluorescent peptide or protein, e.g. EGFP.

In another aspect, the present invention also provides a nucleic acid molecule comprising a polynucleotide encoding the antibody, or the antigen binding fragment thereof, according to the present invention as described above or the complex according to the present invention as described above, in particular if the complex according to the present invention is a fusion protein as described above.

Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA.

Nucleic acid sequences encoding part or all of the light and heavy chains and CDRs of the antibodies of the present invention are preferred. Preferably provided herein are thus nucleic acid sequences encoding part or all of the light and heavy chains, in particular VH and VL sequences and CDRs of the exemplary antibodies of the invention. Tables 4 and 5 provide the SEQ ID numbers for the amino acid sequences of the CDRs and VH and VL of exemplary antibodies according to the present invention.

Table 6 below provides the SEQ ID numbers for exemplary nucleic acid sequences encoding the CDRs and VH and VL of exemplary antibodies according to the present invention. Due to the redundancy of the genetic code, the present invention also comprises sequence variants of these nucleic acid sequences and in particular such sequence variants, which encode the same amino acid sequences.

A nucleic acid molecule is a molecule comprising, preferably consisting of nucleic acid components. The term nucleic acid molecule preferably refers to DNA or RNA molecules. In particular, it is used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Table 6 shows exemplary nucleic acid sequences of the CDR's and the heavy chain variable region (VH) and the light chain variable region (VL) of three exemplary antibodies according to the present invention ("ZKA15", "ZKA25", "ZKA35"):

| | SEQ ID NO. | Nucleic acid sequence |
|---|---|---|
| ZKA15 | | |
| CDRH1 | 100 | ggtggcttcatcaatagttactac |
| CDRH2 | 101 | atctataaaagtgggagcacc |
| CDRH3 | 102 | gcgagagatccctacggtgactacgttaaggctttgatat t |
| CDRL1 | 103 | cagagcctcctgcatagtaatggatacaactat |
| CDRL2 | 104 | ttgggttct |
| CDRL2 long | 105 | ctgatctatttgggttctaatcgggcc |
| CDRL3 | 106 | atgcaagctctacaaactgtcact |

| SEQ ID NO. | Nucleic acid sequence |
|---|---|
| VH 107 | caggtgcagctgcaggagtcggggccaggactggtgaagcc ttcggagaccctgtccctcacctgcactgtctccggtggct tcatcaatagttactactggagctggatccggcagcccgcc gggaagggactggagtggattgggcgtatctataaaagtgg gagcaccaactacaacccctccctcaagagtcgagtcacca tgtcactagacacgtccaagtaccagttctccctgaagctg aggtctgtgaccgccgctgacacggccgtgtattactgtgc gagagatccctacggtgactacgttaaggcttttgatattt ggggccaagggacaatggtcaccgtctcttcag |
| VL 108 | gatattgtgatgactcagtctccactctccctgcccgtcac ccctggagagccggcctccatctcctgcaggtctagtcaga gcctcctgcatagtaatggatacaactatttgaattggtac ctgcagaagccagggcagtctccacagctcctgatctattt gggttctaatcgggcctccggggtccctgacaggttcagtg gcagtggatcaggcacagattttacactgaaaatcagcaga gtggaggctgaggatgttgggg tttattactgcatgcaagc tctacaaactgtcactttcggccctgggaccaaagtggata tcaaac |
| ZKA25 | |
| CDRH1 118 | ggattcacctttagaagtcattgg |
| CDRH2 119 | ataaaggaagatggatatgagaaa |
| CDRH3 120 | gcgagagatttgagggtatatagtgggagaggtttcgaccc c |
| CDRL1 121 | aaattgggggataaatat |
| CDRL2 122 | caagatagc |
| CDRL2 long 123 | gtcatctatcaagatagcaagcggccc |
| CDRL3 124 | caggcgtgggacagcagcactgtggta |
| VH 125 | gaggtgcagttggtggagtctgggggaggcttggtccggcc tggggggtccctgagactctcctgtgcagcctctggattca cctttagaagtcattggatgagttgggtccgccaggctcca gggaaggggctggagtgggtggccaacataaaggaagatgg atatgagaaatactatgtggactctgtgaagggccgattca ccatctccagagacaacgccaagaactcactgtatctgcaa atgaagagcctgagagccgaggacacggccgtgtattactg tgcgagagatttgagggtatatagtgggagaggtttcgacc cctggggccagggaaccctggtcaccgtctcctcag |
| VL 126 | tcctatgagctgactcagccaccctcactgtccgtgtcccc aggacagacagccagcatcacctgctctgagataaattgg gggataaatatgcttgctggtatcagcagaagccaggccag tcccctgtgttggtcatctatcaagatagcaagcggccctc agggatccctgcgcgattctctggctccaactctgggaaca cagccactctgaccatcagcgggacccaggctatggatgag gctgactattactgtcaggcgtgggacagcagcactgtggt attcggtggagggaccaagctgaccgtcctag |
| ZKA35 | |
| CDRH1 136 | ggtggctccatcagcactggtggttactac |
| CDRH2 137 | atctattacagtgggaacacc |
| CDRH3 138 | gcgaaggaggagggaggagcgacccttt gactac |
| CDRL1 139 | agctccaacatcggaagaaattat |
| CDRL2 140 | aggaataat |
| CDRL2 long 141 | ctcatctataggaataatcagcggccc |
| CDRL3 142 | gtagcatgggatgacagccggagtggttttgtggta |
| VH 143 | caggtgcagctgcaggagtcgggcccaggactggtgaagcc ttcacagaccctgtccctcacctgcactgtctctggtggct ccatcagcactggtggttactactggagctggatccgccag |

| SEQ ID NO. | Nucleic acid sequence |
|---|---|
| | cacccagggaagggcctggagtggattggttacatctatta |
| | cagtgggaacacctactacaacccgtccctcaagagtcgag |
| | ttaccatatcagttgacacctctaagaagcagttctccctg |
| | aagctgagctctgtgactgccgcggacacggccgtgtatta |
| | ctgtgcgaaaggaggagggagggagcgaccctttgactact |
| | ggggccagggaaccctggtcaccgtctcctcag |
| VL 144 | cagtctgtgctgactcagccaccctcagcgtctgggacccc |
| | cgggcagagggtcaccatctcttgttctggaagcagctcca |
| | acatcggaagaaattatgtagactggtaccagcaactccca |
| | ggaacggcccccaaactcctcatctataggaataatcagcg |
| | gccctcaggggtccctgagcgattctctggctccaagtctg |
| | gcacctcagcctccctggccatcagtgggctccggtccgag |
| | gatgaggctgattattactgtgtagcatgggatgacagccg |
| | gagtggttttgtggtattcggcggagggaccaaggtgaccg |
| | tcctag |

Preferably, the sequence of the nucleic acid molecule according to the present invention comprises or consists of a nucleic acid sequence according to any one of SEQ ID NOs: 100-108, 118-126, and 136-144.

It is also preferred that nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a CDR, a VH sequence and/or a VL sequence used in an (exemplary) antibody according to the present invention, for example to the sequences shown in Table 6.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, a VH sequence and/or a VL sequence of an (exemplary) antibody of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

Further included within the scope of the invention are vectors, for example, expression vectors, comprising a nucleic acid molecule according to the present invention. Preferably, a vector comprises a nucleic acid molecule as described above.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors.

A vector in the context of the present invention may be, e.g., an RNA vector or a DNA vector.

Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

In a further aspect, the present invention also provides cell expressing the antibody, or the antigen binding fragment thereof, according to the present invention; and/or comprising the vector according the present invention.

Examples of such cells include but are not limited to, eukaryotic cells, e.g., yeast cells, animal cells or plant cells. Preferably, the cells are mammalian cells, more preferably a mammalian cell line. Preferred examples include human cells, CHO cells, HEK293T cells, PER.C6 cells, NS0 cells, human liver cells, myeloma cells or hybridoma cells.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Moreover, the cells of the present invention may be transfected stably or transiently with the vector according to the present invention, e.g. for expressing the antibody, or the antigen binding fragment thereof, according to the present invention. Preferably, the cells are stably transfected with the vector according to the present invention encoding the antibody, or the antigen binding fragment thereof, according to the present invention. Alternatively, it is also preferred that the cells are transiently transfected with the vector according to the present invention encoding the antibody, or the antigen binding fragment thereof, according to the present invention.

In a further aspect, the present invention also provides a composition comprising the antibody, or the antigen binding fragment thereof, according to the present invention; the complex according to the present invention as described above; the nucleic acid molecule according to the present invention as described above; the vector according to the present invention as described above; or the cell according to the present invention as described above. A composition comprising the antibody, or the antigen binding fragment thereof, according to the present invention or the complex according to the present invention as described above is preferred.

Such a composition may be a pharmaceutical composition as described above in the context of the neutralizing antibodies, whereby the detailed description and preferred embodiments of such a pharmaceutical composition as described above apply accordingly to the antibody, or the antigen binding fragment thereof, according to the present invention, that binds to ZIKV NS1 protein. However, the composition may also be used for non-pharmaceutical purposes, such as in diagnosis (of ZIKV infection) or for analytical purposes.

Preferably, the composition is in liquid form, e.g. to provide the antibody or the antigen binding fragment thereof in a liquid for direct use, e.g. in a diagnosis assay. The liquid (vehicle) may be chosen according to the purpose, e.g. depending on the assay. Preferably, the composition according to the present invention comprises PBS (phosphate-buffered saline) or another buffer. Such buffers are preferably biological buffers, and the composition may thus comprise any of MES, BIS-TRIS, ADA, PIPES, ACES, MOPSO, BIS-TRIS propane, BES, MOPS, TES, HEPES, DIPSO, TAPSO, Trizma, POPSO, HEPPS, TRICINE, Gly-Gly, BICINE, HEPBS, TAPS, AMPD, AMPSO, CHES, CAPSO, AMP, CAPS and CABS. It is also preferred that the composition comprises Ringer's solution. In addition, the composition may also comprise Tris, e.g., Tris-HCl.

The composition according to the present invention may also comprise a detergent e.g., a Tween (polysorbate), such as Tween 20 or Tween 80. Detergents are preferably present at low levels e.g., less than 0.01%. Compositions may also include sodium salts (e.g., sodium chloride) to give tonicity. For example, a concentration of 10±2 mg/ml NaCl is typical.

In addition, the composition according to the present invention may optionally comprise a protein stabilizer, such as BSA (bovine serum albumin) or HSA (human serum albumin). Further examples of protein stabilizers, which may optionally be included in the composition according to the present invention, include buffers, e.g. as described above; salts, such as sodium chloride; amino acids, such as histidine, glycine, and arginine; polyols/disaccharides/polysaccharides, such as trehalose and sucrose (disaccharides), mannitol and sorbitol (sugar alcohols); surfactants, such as polysorbate 20, polysorbate 80, and proteins like HSA or BSA; polymers, such as dextran and polyethylene glycol; and antioxidants.

Furthermore, the composition according to the present invention may optionally comprise a preservative, such as sodium azide. Preservatives are typically used to prevent microbial contamination.

In a further aspect, the present invention also provides a kit of parts comprising the antibody, or the antigen binding fragment thereof, according to the present invention, the complex according to the present invention or the composition according to the present invention.

Such a kit of parts may optionally further comprise one or more of the following:
(i) one or more solutions, e.g. to be used in a diagnosis assay, e.g. to dilute the antibody or the antigen binding fragment thereof;
(ii) a leaflet, e.g. with instructions to use;
(iii) a label as described above and, optionally, solutions and/or further components required for labeling; and/or
(iv) vessels or devices, e.g. useful in a diagnosis assay, for example one or more ELISA plates.

Preferably, the kit according to the present invention as described above also comprises a substrate for the development of the color. Examples of such a substrate include p-NPP, in particular in case of detection through alkaline phosphatase; or an enzyme like ABTS, TMB or OPD, in particular in case of use of horse-radish peroxidase (HRP). Optionally, the substrate may be diluted in an appropriate buffer, e.g. a buffer as described above in the context of the composition according to the present invention. Alternatively, the substrate and the buffer may be provided as separate entities in the kit.

With regard to the label, the kit according to the present invention may also comprise an enzyme conjugated streptavidin, or another system to detect the binding of the probe antibody. For example, the probe antibody may be made in murinized form and in this case the binding may be detected with an anti-mouse secondary antibody—without the need for biotinylation. The anti-mouse secondary antibody is typically polyclonal and/or cross-adsorbed for not reacting with human antibodies.

Moreover, the kit according to the present invention preferably comprises one or more ELISA plates. More preferably, those ELISA plates are pre-coated with ZIKV-NS1 protein. Optionally, such pre-coated ELISA-plates may be pre-blocked.

Diagnosis of Zika Virus Infection

In a further aspect, the present invention also provides the use of the antibody, or the antigen binding fragment thereof, according to the present invention, that binds to ZIKV NS1 protein, the complex according to the present invention, the composition according to the present invention or the kit of parts according to the present invention in diagnosis of Zika virus (ZIKV) infection.

Diagnosis of Zika virus (ZIKV) infection is typically performed in vitro, e.g. in an isolated sample of the subject to be diagnosed. Preferred isolated samples of the subject include samples of a body fluid and tissue samples. A sample of a body fluid is more preferred. Preferred body fluids for diagnosis of ZIKV infection include blood (e.g. whole blood, plasma, serum), saliva and urine. Blood, in particular plasma or serum, is most preferred.

Accordingly, the present invention also provides the use of the antibody, or the antigen binding fragment thereof, according to the present invention, that binds to ZIKV NS1 protein, the complex according to the present invention, the composition according to the present invention or the kit of parts according to the present invention in determining whether an isolated sample (of a body fluid), such as an isolated blood sample, is infected with Zika virus. As described above, preferred body fluids for diagnosis of ZIKV infection include blood (e.g. whole blood, plasma, serum), saliva and urine. Blood, in particular plasma or serum, is more preferred.

For diagnosis of Zika virus infection, different diagnosis assays may be used. Preferred diagnosis assays are immunoassays. Preferred examples of immunoassays include ELISA, immunofluorescence, immunohistochemistry and flow cytometry. Preferably, diagnosis includes ELISA. For example, a standard ELISA, a sandwich ELISA or a blockade of binding assay may be used.

Preferably, the diagnosis assay detects
(i) (the presence of) ZIKV NS1 protein itself; and/or
(ii) (the presence of) anti-ZIKV NS1 antibodies
in an (isolated) sample of a subject to be diagnosed.

Preferably, a blockade-of-binding assay is used. In this assay, an isolated sample from a subject to be diagnosed (e.g., a sample of a body fluid, such as blood (e.g. whole blood, plasma, serum), saliva and urine) is added to an ELISA plate coated with ZIKV NS1 protein and incubated (for example, for at least about 30 min or at least about one hour) to allow for binding. Thereafter, the antibody, or the antigen binding fragment thereof, according to the present invention is added (as "probe antibody"), wherein the antibody or the antigen binding fragment thereof according to the present invention is preferably labelled, e.g. biotinylated or conjugated to horseradish peroxidase (HRP). After another incubation time (e.g., at least about 1 min, preferably at least about 3 min, more preferably at least about 5 min, even more preferably at least about 10 min, most preferably at least about 15 min), inhibition of binding of the antibody or the antigen binding fragment thereof according to the present invention can be determined.

In general, inhibition of binding shows the presence of anti-ZIKV NS1 antibodies in the sample of the subject, thus indicating ZIKV infection of the subject. In samples of non-infected subjects, in contrast, typically no inhibition of binding is expected. Importantly, such an assay using the ZIKV NS1-binding antibodies of the present invention does not score positive in subjects that were already infected with other flaviviruses. Flaviviruses typically induce a large number of antibodies that are cross-reactive with ZIKV. In other words this assay is highly specific and not affected by cross-reactive Abs.

Accordingly, the present invention also provides a Blockade-of-binding assay for in-vitro diagnosis of Zika virus infection comprising the following steps:
(i) adding an isolated sample from a subject to be diagnosed to a plate coated with ZIKV NS1 protein and incubating said sample on said plate,
(ii) adding an antibody, or an antigen binding fragment thereof, that specifically binds to NS1 protein of ZIKA virus or a complex including the antibody,
(iii) determining inhibition of binding of said antibody or antigen-binding fragment thereof.

Preferably, the isolated sample from a subject to be diagnosed is selected from blood, saliva and urine; preferably the sample is a blood sample, such as whole blood, plasma or serum.

It is also preferred that the antibody, or the antigen-binding fragment thereof, added in step (ii), is labelled, preferably biotinylated or conjugated to horseradish peroxidase (HRP).

Moreover, the isolated sample from a subject to be diagnosed is preferably diluted, for example 1:5-1:50, preferably 1:5-1:25, such as 1:10.

Preferably, the incubation time in step (i) is at least 5 min, preferably at least 15 min, more preferably at least 30 min, even more preferably at least 45 min and most preferably at least 60 min.

It is furthermore preferred that in step (ii) after adding the antibody, or the antigen binding fragment thereof, the antibody, or the antigen binding fragment thereof, is incubated for at least 1 min, preferably, at least 3 min, more preferably at least 5 min, even more preferably at least 10 min and most preferably at least 15 min.

Preferably, the antibody, or the antigen binding fragment thereof, according to the present invention, which is used as probe antibody in the blockade of binding assay is a preferred antibody, or antigen binding fragment thereof, according to the present invention. For example, the antibody, or the antigen binding fragment thereof, according to the present invention may preferably be an antibody, or antigen binding fragment thereof, according to the present invention binding to antigenic site S2 of Zika virus NS1 protein. Most preferably, the antibody, or the antigen binding fragment thereof, according to the present invention, which is used as probe antibody in the blockade of binding assay is an antibody, or the antigen binding fragment thereof, comprising CDRH1, CDRH2, and CDRH3 amino acid sequences and CDRL1, CDRL2, and CDRL3 amino acid sequences (i) according to SEQ ID NOs: 127-131 and 133; or functional sequence variants thereof having at least 70%, at least 75%, at least 80%, at least 85%, at least 88%, at least 90%, at least 92%, at least 95%, at least 96%, at least 97%, at least 98% or at least 99% sequence identity; or (ii) according to SEQ ID NOs: 127-130 and 132-133; or functional sequence variants thereof having at least 70%, at least 75%, at least 80%, at least 85%, at least 88%, at least 90%, at least 92%, at least 95%, at least 96%, at least 97%, at least 98% or at least 99% sequence identity. Particularly preferably, the antibody, or the antigen binding fragment thereof, according to the present invention, which is used as probe antibody in the blockade of binding assay is an antibody, or the antigen binding fragment thereof, comprising a heavy chain variable region (VH) amino acid sequence according to SEQ ID NO: 134 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity and/or a light chain variable region (VL) amino acid sequence according to SEQ ID NO: 135 or a functional sequence variant thereof having at least 70%, at least 75%, at least 80%, at least 85%, at least 88%, at least 90%, at least 92%, at least 95%, at least 96%, at least 97%, at least 98% or at least 99% sequence identity.

For example, inhibition of binding of exemplary biotinylated antibodies or antigen binding fragments thereof according to the present invention may be assessed by determining the optimal concentration of the antibody or the antigen binding fragment thereof according to the present invention to achieve 70% maximal binding to ZIKV NS1 protein. For example, the optimal concentrations of the exemplary antibodies gZKA15, gZKA25 and gZKA35 to achieve 70% maximal binding to ZIKV NS1 protein may be 38, 17 and 7 ng/ml, respectively. After performing the above described blockade-of-binding assay, substrate, such as p-NPP may be added and the ELISA plate may be read at 405 nm and the percentage of inhibition of binding may be calculated by the following equation (I):

$$\% \text{ inhib} = (1 - [(\text{OD sample} - \text{OD neg ctr})/(\text{OD pos ctr} - \text{OD neg ctr})]) \times 100 \quad (I)$$

wherein "% inhib" refers to the percentage of inhibition of binding of the antibody or the antigen binding fragment thereof according to the present invention to ZIKV NS1 protein; "OD sample" refers to the optical density of the sample; "OD neg ctr" refers to the optical density of a negative control; and "OD pos ctr" refers to the optical density of a positive control.

This assay provides several advantages, such as the ability to detect clinical, sub-clinical and asymptomatic ZIKV infections at the population level, being able to distinguish them from other flavivirus infections, such as DENV. In particular, the diagnosis assay according to the present invention provides higher precision than direct ELISA binding assays.

Moreover, the present invention also provides a method for (in vitro) diagnosis of Zika infection (in an isolated sample), wherein the antibody, or the antigen binding fragment thereof, according to the present invention, that binds to ZIKV NS1 protein, the complex according to the present invention, the composition according to the present invention or the kit of parts according to the present invention is used for determining whether an isolated sample (of a body fluid), such as an isolated blood sample, is infected with Zika virus.

Preferred embodiments of the above use in diagnosis apply also for the diagnosis method. For example, preferred isolated samples (of the subject) include samples of a body fluid and tissue samples. A sample of a body fluid is more preferred. Preferred body fluids for diagnosis of ZIKV infection include blood (e.g. whole blood, plasma, serum), saliva and urine. Blood, in particular plasma or serum, is most preferred. Moreover, preferred diagnosis assays are immunoassays. Preferred examples of immunoassays include ELISA, immunofluorescence, immunohistochemistry and flow cytometry. Preferably, diagnosis includes ELISA. Most preferably, a blockade-of-binding assay as described above is used.

Preferably, the method for (in vitro) diagnosis of Zika infection (in an isolated sample) comprises a step of
(i) contacting the isolated sample with the antibody, or the antigen binding fragment thereof, according to the present invention, that binds to ZIKV NS1 protein, the complex according to the present invention, or the composition according to the present invention.

More preferably, the method for (in vitro) diagnosis of Zika infection (in an isolated sample) comprises the following steps:
(0) adding an isolated sample from a subject to be diagnosed (e.g., a sample of a body fluid, such as blood (e.g. whole blood, plasma, serum), saliva and urine) to an ELISA plate coated with ZIKV NS1 protein;
(i') further adding the antibody or the antigen binding fragment thereof according to the present invention to the ELISA plate, wherein the antibody or the antigen binding fragment thereof according to the present invention is preferably labelled, e.g. biotinylated;
(ii) optionally, washing the ELISA plate; and
(iii) determining the inhibition of binding of the antibody or the antigen binding fragment thereof according to the present invention.

In a further aspect, the present invention also provides the neutralizing antibody, or the antigen binding fragment thereof, according to the present invention, the nucleic acid according to the present invention, the vector according to the present invention, the cell according to the present invention, or the pharmaceutical composition according to the present invention for use according in treatment or prevention of ZIKV infection in subjects diagnosed with Zika virus infection by using the antibody, or the antigen binding fragment thereof, according to the present invention, that binds to ZIKV NS1 protein, the complex according to the present invention, the composition according to the present invention, the kit of parts according to the present invention or the method for ZIKV diagnosis according to the present invention.

In a further aspect, the present invention also provides a method of preventing and/or treating Zika virus infection, the method comprising the following steps:
(i) diagnosing Zika virus infection in a subject by using the antibody, or the antigen binding fragment thereof, according to the present invention, that binds to ZIKV NS1 protein, the complex according to the present invention, the composition according to the present invention, the kit of parts according to the present invention or the method for ZIKV diagnosis according to the present invention; and
(ii) administering to said subject the neutralizing antibody, or the antigen binding fragment thereof, according to the present invention, the nucleic acid according to the present invention, the vector according to the present invention, the cell according to the present invention, or the pharmaceutical composition according to the present invention.

Preferably, in this method of preventing and/or treating Zika virus infection, step (i) of diagnosing Zika virus infection is performed as in-vitro diagnosis on an isolated sample (of a body fluid), such as an isolated blood sample.

In a further aspect, the present invention also provides a kit of parts comprising
(i) the antibody, or the antigen binding fragment thereof, according to the present invention, that binds to ZIKV NS1 protein, the complex according to the present invention, the composition according to the present invention, or the kit of parts according to the present invention; and
(ii) the neutralizing antibody, or the antigen binding fragment thereof, according to the present invention, the nucleic acid according to the present invention, the vector according to the present invention, the cell according to the present invention, or the pharmaceutical composition according to the present invention.

Such a kit of parts is particularly useful in a method as described above. By use of such a method and/or such a kit, ZIKV infection can be specifically diagnosed as well as prevented and/or treated.

DESCRIPTION OF FIGURES

FIG. 1 shows the reactivity (ELISA) and ZIKV and DENV1 neutralizing activity of antibodies derived from four ZIKV immune donors (ZKA, ZKB, ZKC and ZKD) to E protein of ZIKV and DENV1-4 and to EDIII-domain of ZIKV E protein; NNB-neutralizing, non-E-protein binding antibodies.

FIG. 2 shows the reactivity (ELISA) of antibodies derived from four ZIKV immune donors (ZKA, ZKB, ZKC and ZKD) to NS1 protein of ZIKV, DENV1-4 and other flaviviruses. YFV—yellow-fever virus; WVN—West-Nile virus; JEV—Japanese Encephalitis virus; and TBEV—Tick-borne Encephalitis virus (nd, not determined).

FIG. 17 shows for Example 10 the identification of ZKA190 epitope and analysis of its conservation in ZIKV strains. (A) Overlay of [$^{15}$N, $^{1}$H]-HSQC spectra of $^{15}$N-labeled ZIKV EDIII in absence (black) or presence (red) of unlabelled ZKA190 Fab. Differences identify EDIII residues affected by antibody binding. (B) NMR epitope mapping of ZKA190 Fab in complex with ZKV EDIII. The chemical shift perturbation (CSP, y-axis) is plotted against the EDIII residue number. Residues affected by antibody binding are in red. (C) Residues in FG loop identified by NMR epitope mapping is partially hidden in E protein mol A but largely exposed in mols B and C. EDIII of E protein was coloured in blue. Residues identified by NMR epitope mapping are coloured in magenta except those in the FG loop are coloured in green. Adjacent E proteins are shown as grey surface. (D) Level of amino acid residue conservation in ZKA190 epitope as calculated by the analysis of sequences from 217 ZIKV strains found in ZIKV Resources (NCBI) databases as of Nov. 24, 2016. (E) Open-book representation showing charge complementarity between the epitope and paratope of the docking result. Boundaries of the epitope and paratope are circled in green. The borders between heavy and light chains of Fab and its corresponding footprint on EDIII are shown as yellow dashed lines.

FIG. 2). Positive cultures were collected and expanded. From positive cultures the VH and VL sequences were retrieved by RT-PCR. Antibodies were cloned into human IgG1 and Ig kappa or Ig lambda expression vectors (kindly provided by Michel Nussenzweig, Rockefeller University, New York, US) essentially as described (Tiller T, Meffre E, Yurasov S, Tsuiji M, Nussenzweig M C, Wardemann H (2008) Efficient generation of monoclonal antibodies from single human B cells by single cell RT-PCR and expression vector cloning. J Immunol Methods 329: 112-124). Monoclonal antibodies were produced from EBV-immortalized B cells or by transient transfection of 293 Freestyle cells (Invitrogen). Supernatants from B cells or transfected cells were collected and IgG were affinity purified by Protein A or Protein G chromatography (GE Healthcare) and desalted against PBS.

FIG. 2 provides an overview over selected ZIKV NS1-protein binding antibodies (cf. Tables 4 and 5 for the amino acid sequences of their CDRs and heavy/light chain variable regions). Namely, FIG. 2 provides binding activities ($EC_{50}$) of the antibodies to ZIKV NS1 protein (ZIKV NS1), DENV1 NS1 protein (DENV1 NS1), DENV2 NS1 protein (DENV2 NS1), DENV3 NS1 protein (DENV3 NS1), DENV4 NS1 protein (DENV4 NS1), yellow-fever virus NS1 protein (YFV NS1), West-Nile virus NS1 protein (WNV NS1), Japanese-Encephalitis virus NS1 protein (JEV NS1), and to Tick-borne Encephalitis virus NS1 protein (TBEV NS1).

Example 2: Characterization of Antibodies ZKA190, ZKA185, ZKA230, ZKA64 and ZKA78

In Example 1, a large number of ZIKV-neutralizing antibodies were identified and characterized for their specificity to ZIKV, in particular ZIKV E protein and ZIKV EDIII as well as for their cross-reactivity towards DENV. Antibodies ZKA190 (SEQ ID NOs: 1-18), ZKA185 (SEQ ID NOs: 19-36), ZKA230 (SEQ ID NOs: 37-54), ZKA64 (SEQ ID NOs: 73-90) and ZKA 78 (SEQ ID NOs: 55-72) described in Example 1 were then selected and further tested against ZIKV E protein ("ZIKV"), ZIKV EDIII ("DIIIZI"), and also tested against the E protein of dengue virus (DENV, serotype number 1) by ELISA. To this end, a standard ELISA was used. Briefly, ELISA plates were coated with ZIKV E protein at 1 or 3 μg/ml, blocked with 10% FCS in PBS, incubated with sera or human antibodies and washed. Bound antibodies were detected by incubation with AP-conjugated goat anti-human IgG (Southern Biotech). Plates were then washed, substrate (p-NPP, Sigma) was added and plates were read at 405 nm. The relative affinities of monoclonal antibody binding were determined by measuring the concentration of antibody (EC50) required to achieve 50% maximal binding at saturation.

Figure 3:
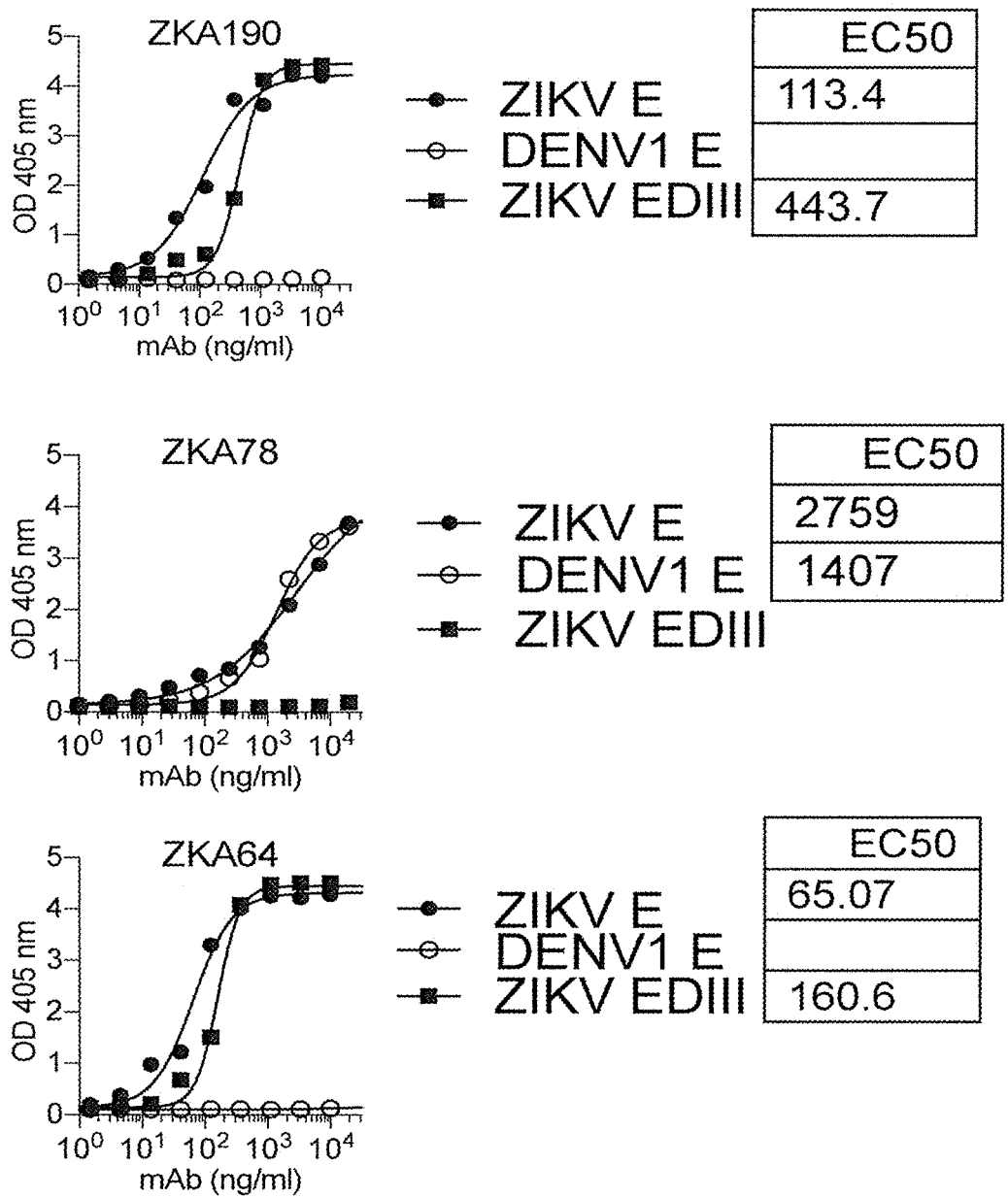
FIG. 3 shows the binding of ZKA190, ZKA78 and ZKA64 antibodies to ZIKV and DENV1 E and to ZIKV EDIII proteins as measured by ELISA.
Figure 4:
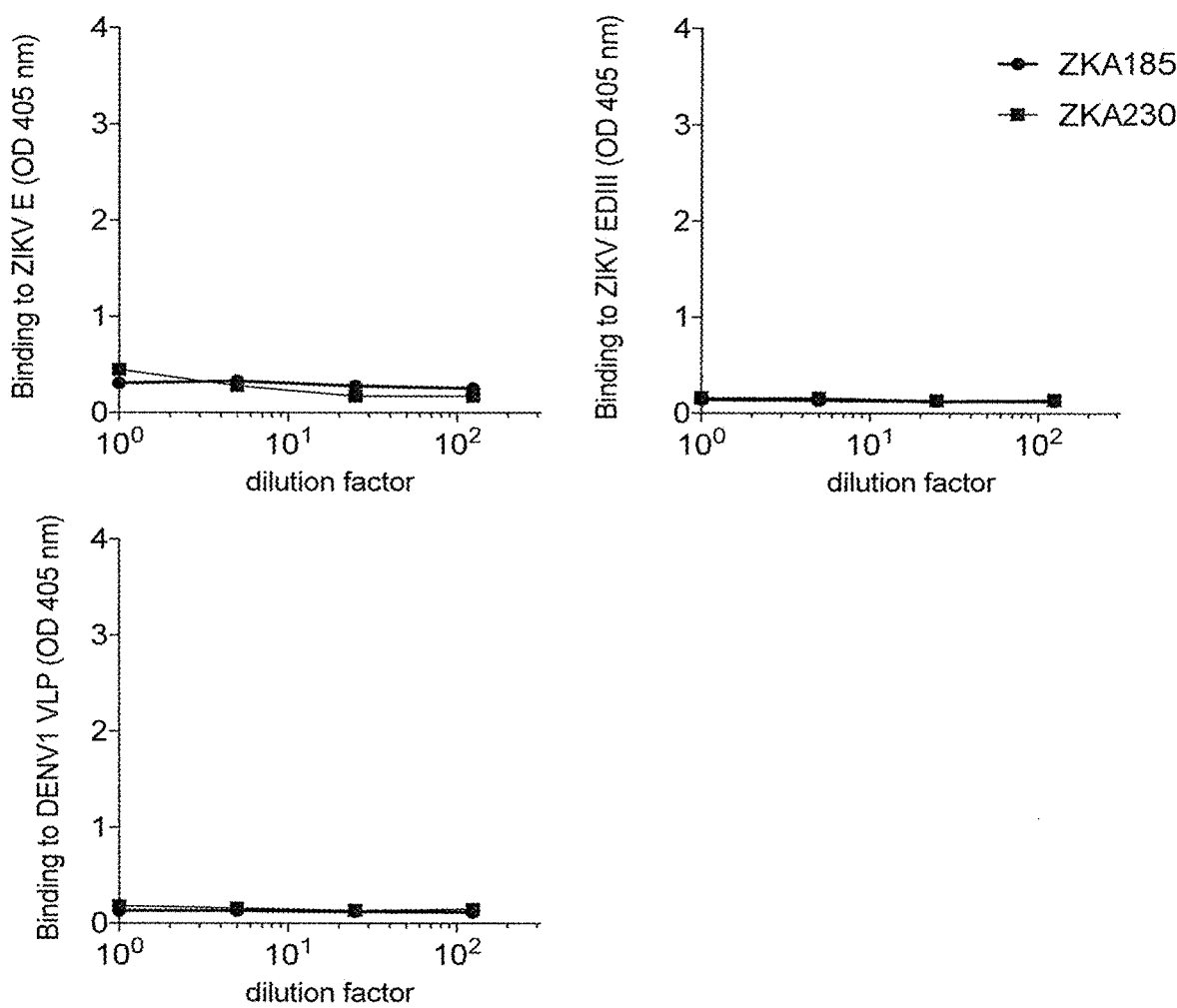
FIG. 4 shows the binding of ZKA185 and ZKA190 antibodies to ZIKV E, DENV1 VLP and to ZIKV EDIII proteins as measured by ELISA.

Results are shown in FIGS. 3 and 4. Of note, ZKA64 and ZKA190 bound to ZIKV E and ZIKV EDIII ("DIII ZI") with low EC50 values, thereby indicating that ZKA64 and ZKA190 are binding to domain III of ZIKV E protein (EDIII). ZKA78 bound to ZIKV E, but not to ZIKV EDIII, indicating that ZKA78 is binding to ZIKV E, but not targeting the EDIII region. Despite their considerable ZIKV neutralizing activity (cf. FIG. 1), antibodies ZKA185 and ZKA230 did not show any detectable binding to ZIKV E and ZIKV EDIII (FIG. 4). Accordingly, ZKA185 and ZKA230 were referred to as "neutralizing-non-E-binding" (NNB) antibodies. Those NNB antibodies are assumed to recognize quaternary epitopes that are displayed on the ZIKV infectious virions but not on soluble proteins.

Moreover, none of ZKA190, ZKA185, ZKA230, and ZKA64 showed any detectable binding to DENV E proteins (FIG. 1, DENV1-4 serotypes, and FIGS. 3 and 4), indicating that ZKA190, ZKA185, ZKA230, and ZKA64 are specific for ZIKV and not cross-reactive to dengue virus. ZKA78, in contrast, which is assumed to bind to ZIKV EDI/II, but not to ZIKV EDIII (cf. FIG. 3), bound to DENV E proteins (FIGS. 1 and 3), indicating that ZKA78 is a cross-reactive antibody binding to both, ZIKV and DENV.

To further confirm those results, the ZIKV E protein binding antibodies ZKA190, ZKA64 and ZKA78 were additionally tested against E protein of dengue virus (DENV, serotypes number 1-4). ZKA64 and ZKA190 did not bind to DENV1-4 E protein, thereby confirming that ZKA64 and ZKA190 are specific for ZIKV. ZKA78, in contrast, bound to DENV1-4 E, confirming that ZKA78 is a cross-reactive antibody binding to the E protein of both ZIKV and DENV (cf. FIG. 1).

Example 3: Characterization of ZIKV NS1-Specific Antibodies for Serological Diagnosis In Example 1, a large number of NS1-reactive antibodies were identified and then characterized for their specificity to ZIKV NS1 and cross-reactivity towards other flavivirus NS1 proteins (FIG. 2). Antibodies ZKA15 (SEQ ID NOs: 91-108), ZKA25 (SEQ ID NOs: 109-126) and ZKA35 (SEQ ID NOs: 127-144) were then further characterized for binding to ZIKV NS1 and DENV1 NS1, DENV2 NS1, DENV3 NS1 and DENV4 NS1. To this end, a standard ELISA was used. Briefly, ELISA plates were coated with ZIKV NS1 protein at 1 μg/ml, blocked with 10% FCS in PBS, incubated with sera or human antibodies and washed. Bound antibodies were detected by incubation with AP-conjugated goat anti-human IgG (Southern Biotech). Plates were then washed, substrate (p-NPP, Sigma) was added and plates were read at 405 nm. The relative affinities of monoclonal antibody binding were determined by measuring the concentration of antibody (EC50) required to achieve 50% maximal binding at saturation.

Figure 5:
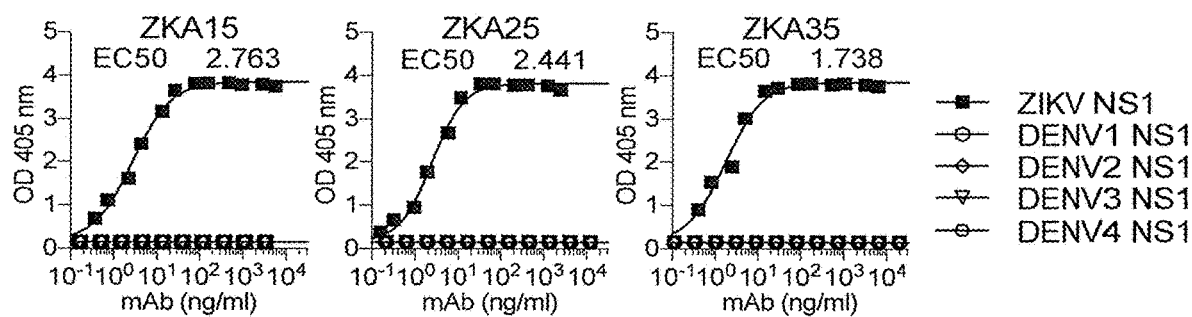
FIG. 5 shows the binding of ZKA15, ZKA25 and ZKA35 antibodies to ZIKV and DENV1-4 NS1 proteins as measured by ELISA.

Results are shown in FIG. 5. All three antibodies (ZKA15, ZKA25 and ZKA35) bound with high affinity to ZIKV NS1 but not to the DENV1-4 NS1 antigens (FIG. 5).

To investigate the binding of the antibodies to ZIKV NS1 further, bio-layer interferometry competition assays were used. A cross-competition matrix was generated using bio-layer interferometry (BLI; Octet) on 13 antibodies specific for ZIKV NS1 (i.e. not cross-reactive with DENV NS1), namely antibodies ZKA24, ZKA15, ZKA32, ZKA19, ZKA50, ZKA37, ZKA46, ZKA10, ZKA48, ZKA35, ZKA25, ZKA44, and ZKA30 (cf. FIG. 6A). As can be retrieved from FIG. 2 none of those 13 antibodies showed detectable binding to DENV NS1.

Competition assays and antigenic sites determination were determined at 37° C. with a Octet RED96 system, ForteBio. The ZIKV-NS1 protein diluted to 2.5 μg/ml in PBS was immobilized for 7-9 minutes on the surface of an APS coated sensor-chip. Coated biosensors were placed in wells containing blocking buffer (0.1% BSA in PBS) for 6 minutes to block free Biosensor binding sites. Coated-Biosensors were then incubated for 8 minutes with a set of single purified mAbs specific for ZIKV-NS1 diluted in blocking buffer at 10 μg/ml. After binding of the first set of mAbs (step 1), Biosensors were moved to wells containing different mAbs for 8 minutes (step 2). Association of the second mAb resulted in recognition of a different antigenic site compared to the first mAb (e.g. non-competition). Competition or partial competition were determined in step 2 when no association or low association was detected, respectively. A cross-competition matrix was created by multiple runs of competitions in order to predict antigenic site mapping on ZIKV NS1.

Figure 6:
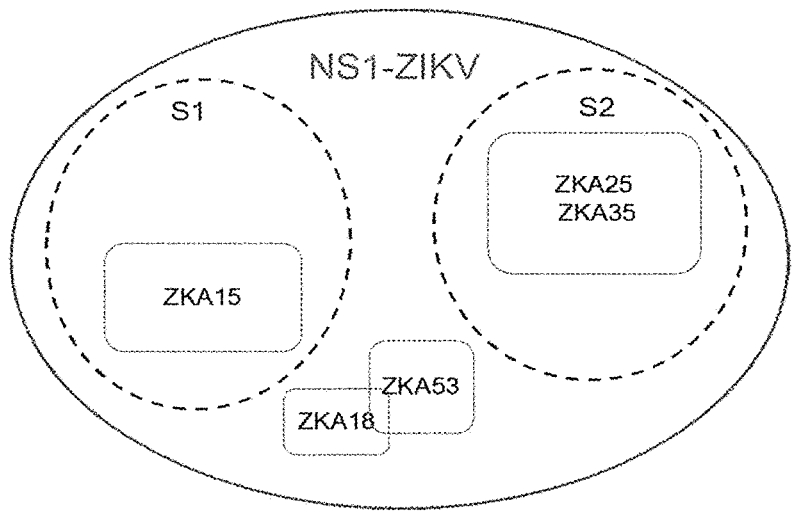
FIG. 6 shows for Example 3 ZIKV NS1 protein antigenic site mapping using cross-competition Octet-binding studies. (A-B) Cross-competition matrix performed by Octet on 24 mAbs specific for ZIKV NS1 (A) or cross-reactive to DENV NS1 (B). +, lack of binding of the secondary Ab; +/−, partial loss of binding of the secondary mAb; binding of the secondary mAb. Strikethrough cells, not tested. (C) Map of the antigenic sites targeted by ZIKV NS1-specific mAbs as defined using BLI (Octet) cross-competition.

Results are shown in FIGS. 6A and 6C. Firstly, all of the ZIKV NS1-specific antibodies tested were binding to antigenic site(s) S1 and/or S2 (FIG. 6A). However, some of the antibodies did not compete with others. For example, ZKA15 did not compete for binding with ZKA25 and ZKA35 and vice versa (FIG. 6A). Accordingly, antibody ZKA15 was assigned to the antigenic site S1, while antibodies ZKA25 and ZKA35 were assigned to the antigenic site S2 (FIG. 6C). In summary, based on the antibodies used, antigenic sites (S1 and S2) on ZIKV NS1 were identified (FIG. 6C).

Additionally, binding of 10 antibodies cross-reacting to ZIKV NS1 protein and to DENV NS protein (namely, ZKA18, ZKA29, ZKA39, ZKA53, ZKA54, ZKB19, ZKB23, ZKC29, ZKC33, and ZKC34; FIG. 6B) to antigenic sites S1 and/or S2 on ZIKV NS1 was investigated. As can be retrieved from FIG. 2 all of those 10 antibodies showed binding to DENV NS1. Those 10 cross-reactive antibodies were tested in a cross-competition assay as described above (for the ZIKV NS1-specific antibodies) against ZIKV NS1 S1-specific antibody ZKA15 and against ZIKV NS1 S2-specific antibody ZKA35.

Results are shown in FIG. 6B. Interestingly, none of the ten cross-reactive antibodies tested competed with ZKA 15 and/or ZKA35 for binding to antigenic site(s) S1 and/or S2 on ZIKV NS (FIG. 6B). These results show that ZKA15 and ZKA35 antigenic site is not targeted by NS cross-reactive antibodies. Thus, NS1 antigenic sites S1 and S2 were targeted by ZIKV-specific, but not by cross-reactive antibodies.

Example 4: Use of ZIKV NS1-Specific Antibodies in Diagnosis of ZIKV Infection

In the present Example, the usefulness of the ZIKV NS1-specific antibodies of the present invention in diagnosis of ZIKV infection was investigated. More specifically, the use of ZIKV NS1-specific antibodies of the present invention to specifically detect the presence or absence of antibodies elicited against ZIKV NS1 in plasma samples of ZIKV- or DENV-infected donors was determined.

To this end, a "blockade of binding" assay was used. In particular, the ability of ZIKV NS1-reactive plasma antibodies to inhibit the binding of the biotinylated antibody ZKA35 to ZIKV NS1 was measured. To this end, ZIKV NS1-specific antibody ZKA35 was biotinylated using the EZ-Link NHS-PEO solid phase biotinylation kit (Pierce). Labelled ZKA35 was tested for binding to ZIKV NS1 to determine the optimal concentration of ZKA35 to achieve 70% maximal binding. Plasma samples from ZIKV- (n=4), DENV-immune (n=5) donors and control (n=48) plasma (1/10 dilution) were added to ELISA plates coated with ZIKV NS1. After 1 h, biotinylated anti-ZIKV NS1 antibody ZKA35 was added at the concentration achieving 70% maximal binding and the mixture was incubated at room temperature for 15 minutes. Plates were washed, substrate (p-NPP, Sigma) was added and plates were read at 405 nm. The percentage of inhibition was calculated as follow: (1−[(OD sample−OD neg ctr)/(OD pos ctr−OD neg ctr)])×100.

Figure 7:
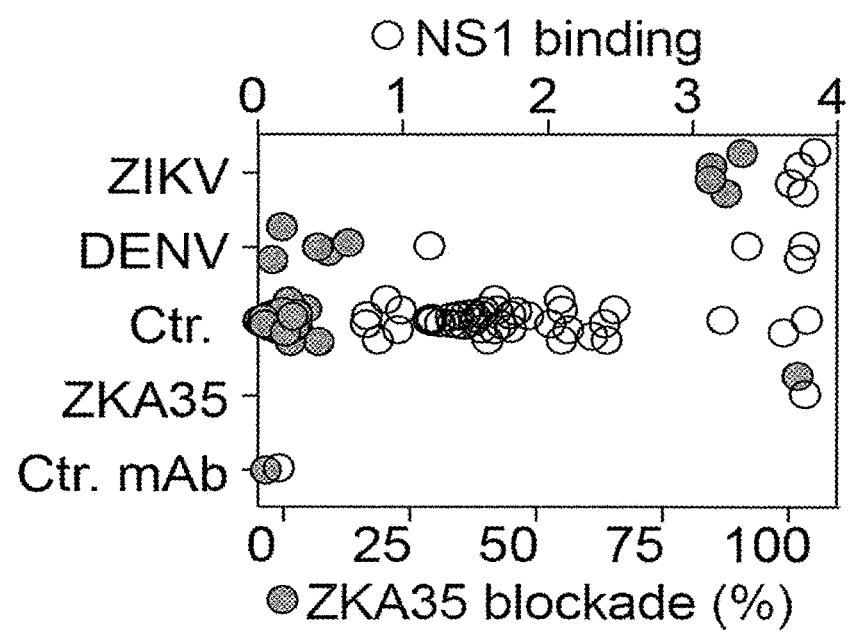
FIG. 7 shows for Example 4 blockade of binding assay using mAb ZKA35 as a probe to detect ZIKV NS1 in plasma from ZIKV-immune (n=4), DENV-immune (n=5) and control donors (n=48) (1/10 dilution). Plasma samples were tested for their capacity to bind NS1 (empty dots) and to inhibit the binding of the biotinylated mAB ZKA35 to NS1 (filled dots).

Results are shown in FIG. 7. Of note, antibody ZKA35 binding to the antigenic site S2 on NS was inhibited only by plasma samples from ZIKV-immune donors, but not DENV-immune donors, and its binding was also not inhibited by 48 control plasma samples (FIG. 7). Accordingly, this assay may be used as to specifically detect clinical and sub-clinical ZIKV infections at the population level.

Example 5: The Antibodies According to the Present Invention Potently Neutralize ZIKV Infection The isolated antibodies ZKA190, ZKA185, ZKA230, ZKA64 and ZKA78 were tested for their ability to neutralize ZIKV and DENV1 infection in vitro.

Neutralization of DENV and ZIKV infection by antibodies was measured using a micro-neutralization flow cytometry-based assay. Different dilutions of antibodies were mixed with ZIKV (MOI of 0.35) or attenuated DENV1 (all at MOI of 0.04) for 1 hour at 37° C. and added to 5000 Vero cells/well in 96-well flat-bottom plates. After four days for ZIKV and five days for DENV, the cells were fixed with 2% formaldehyde, permeabilized in PBS 1% FCS 0.5% saponin, and stained with the mouse mAb 4G2. The cells were incubated with a goat anti-mouse IgG conjugated to Alexa Fluor488 (Jackson Immuno-Research, 115485164) and analyzed by flow cytometry. In other cases the ZIKV neutralization data are also determined measuring cell viability using the WST-1 reagent (Roche). The neutralization titer (50% inhibitory concentration [IC50]) was expressed as the antibody concentration that reduced the infection by 50% compared to cell-only control wells.

Figure 8:
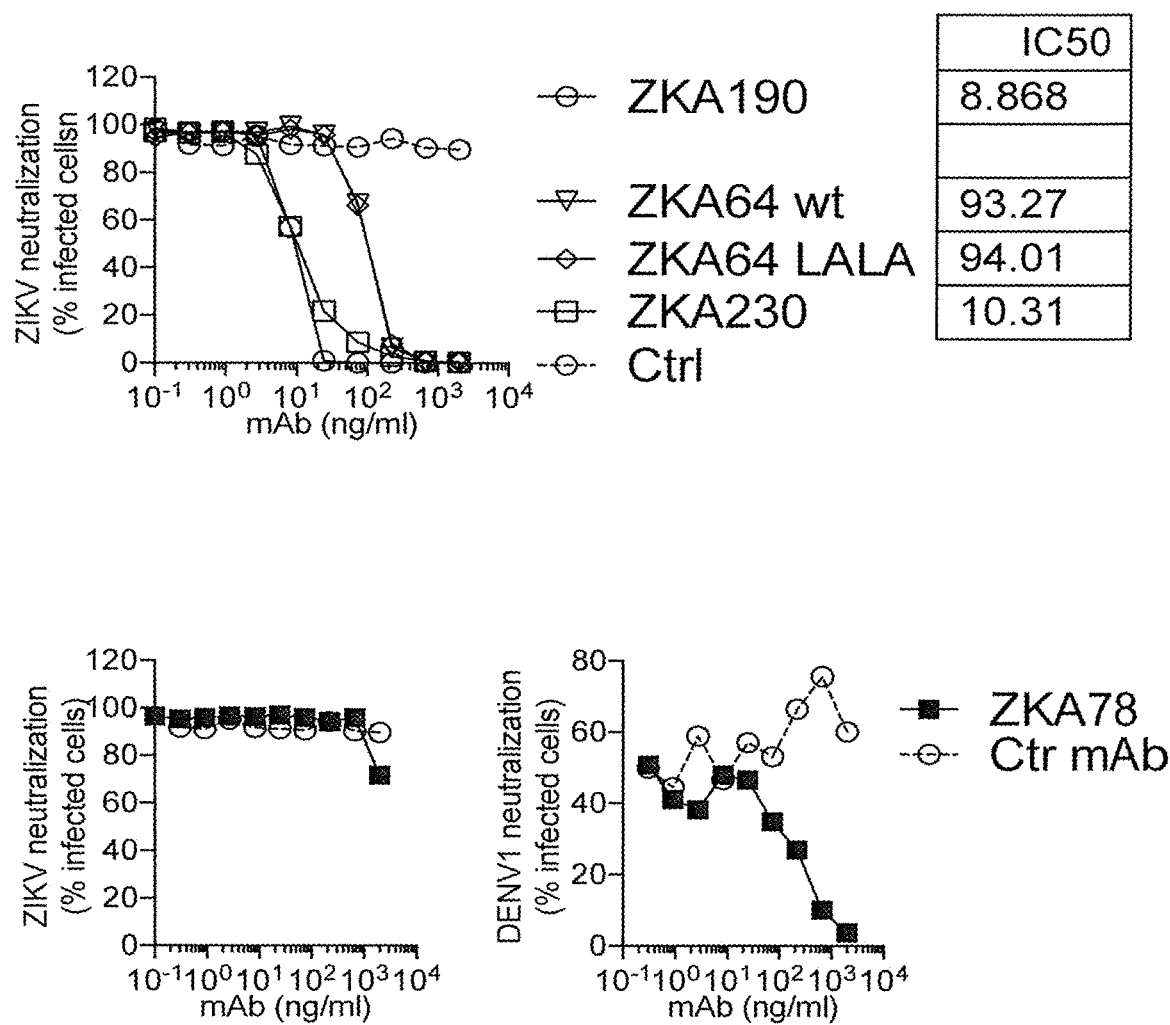
FIG. 8 shows for Example 5 the neutralizing activity of ZKA190, ZKA64, ZKA64-LALA, ZKA230 and ZKA78 antibodies against ZIKV (H/PF/2013 strain) and DENV1 on Vero cells as measured by flow-cytometry (% of infected cells).
Figure 9:
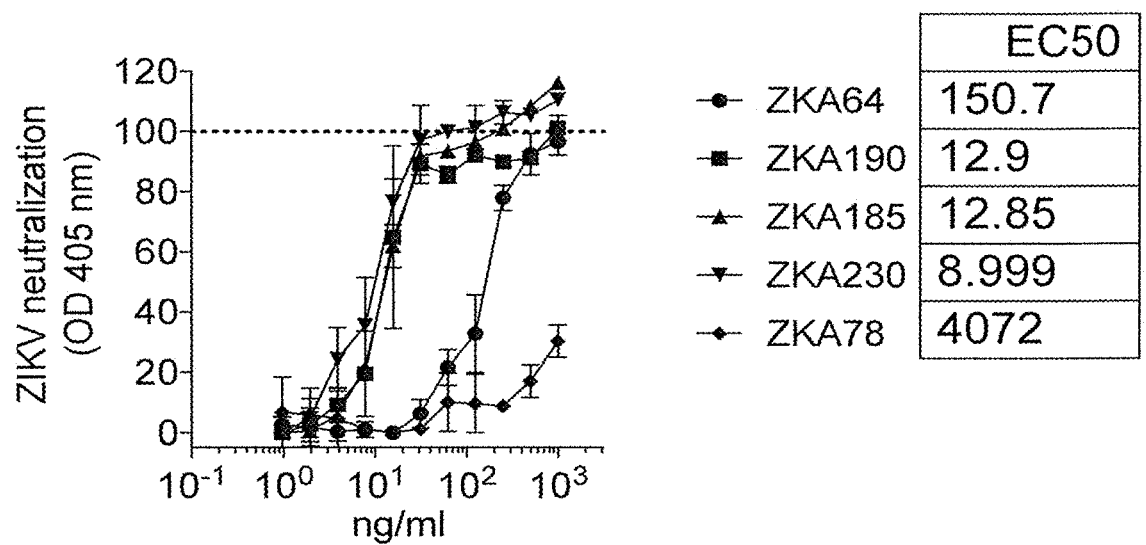
FIG. 9 shows for Example 5 the neutralizing activity of ZKA190, ZKA64, ZKA185, ZKA230 and ZKA78 antibodies against ZIKV (H/PF/2013 strain) on Vero cells as measured with a cell viability readout (wst-1, Roche).
Figure 13:
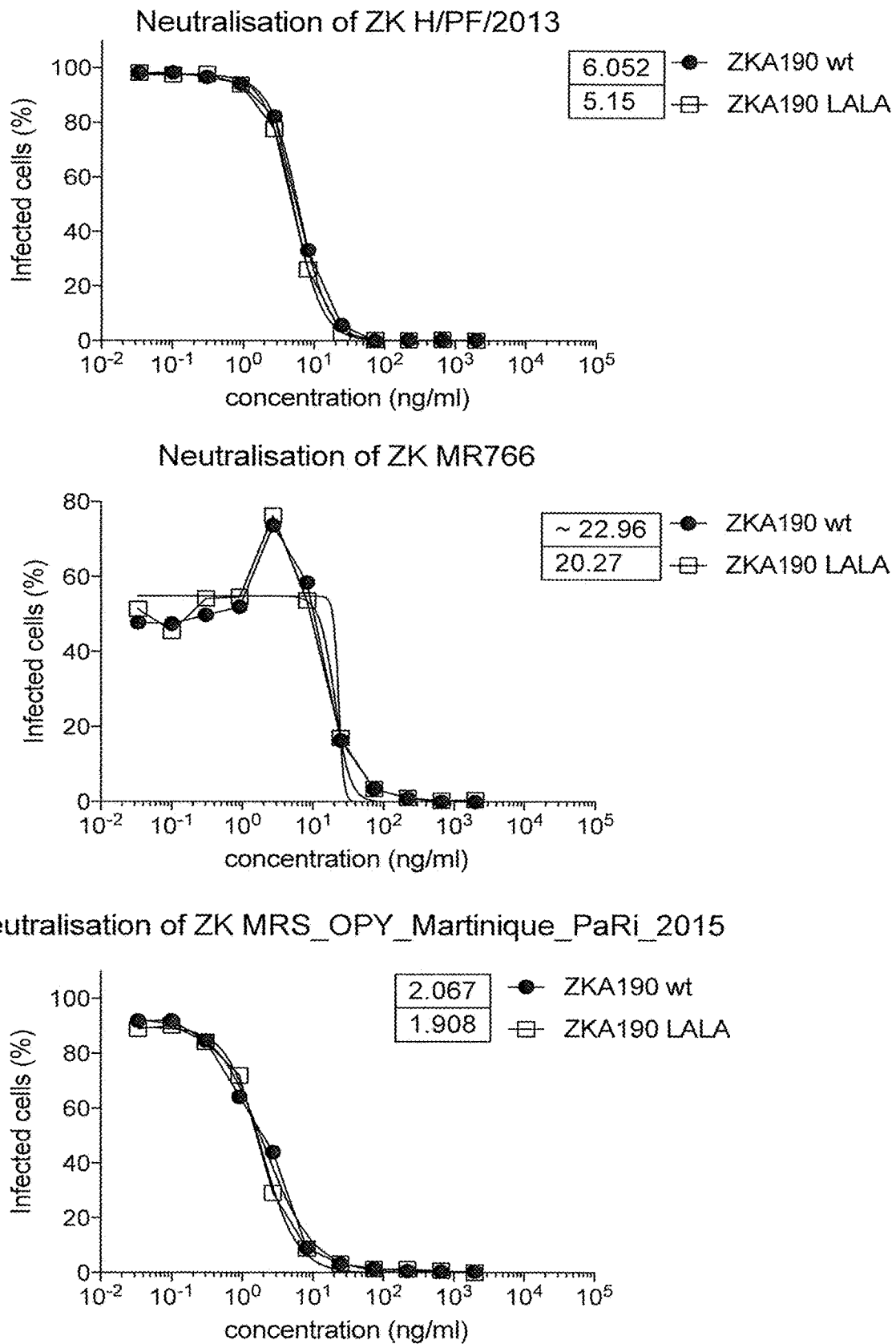
FIG. 13 shows for Example 5 the neutralizing activity of ZKA190 and ZKA190-LALA antibody against three strains of ZIKV (H/PF/2013, MR766 and MRS_OPY_Martinique_PaRi_2015) on Vero cells as measured by flow-cytometry (% of infected cells).

Results are shown in FIGS. 8, 9 and 13. The EDIII-specific mAbs ZKA64 and ZKA190 and the NNB mAb ZKA230 were highly potent in ZIKV neutralization (strain H/PF/2013), with IC50 values of 93, 9 and 10 ng/ml, respectively (FIG. 8, upper panel). In contrast, the cross-reactive antibody ZKA78 only partially neutralized ZIKV infectivity and cross-neutralized DENV1 infectivity (FIG. 8, lower panels). Similar data were obtained by measuring the ZIKV-induced cytopathic effect as measured with the WST-1 reagent (FIG. 9). In this second assay, NNB antibody ZKA185 was also included in the panel of tested antibodies and showed an IC50 similar to the most potent antibodies ZKA190 (EDIII-specific) and ZKA230 (NNB).

It is important to note that the ultra-potent ZKA64 and ZKA190 antibodies in addition to their ability to neutralize the ZIKV H/PH/2013 strain (present example), also bound to the E protein and EDIII derived from the ZIKV strains MR766 and SPH2015, respectively (FIG. 1 and FIG. 3). ZKA190 and ZKA190-LALA was also confirmed to effectively neutralize two additional ZIKV strains (MR766 and MRS_OPY_Martinique_PaRi_2015) (FIG. 13). Taken together the results indicate that the ultra-potent ZKA64 and ZKA190 antibodies cross-react with multiple strains of ZIKV belonging to different genotypes and origins (East African and Asian from Uganda, French Polynesia, Martinique and Brazil).

Example 6: The "LALA" Mutation Inhibits Antibody-Dependent Enhancement of ZIKV Infection by Serum Antibodies Neutralizing antibodies were also tested for their ability to enhance the infection of ZIKV in the non-permissive K562 cells (antibody-dependent enhancement assay, ADE assay). ADE was measured by a flow based assay using K562 cells.

Antibodies and ZIKV H/PF/2013 (MOI 0.175) were mixed for 1 hour at 37° C. and added to 5000 K562 cells/well. After four days, cells were fixed, permeabilized, and stained with m4G2. The number of infected cells was determined by flow cytometry.

Figure 10:
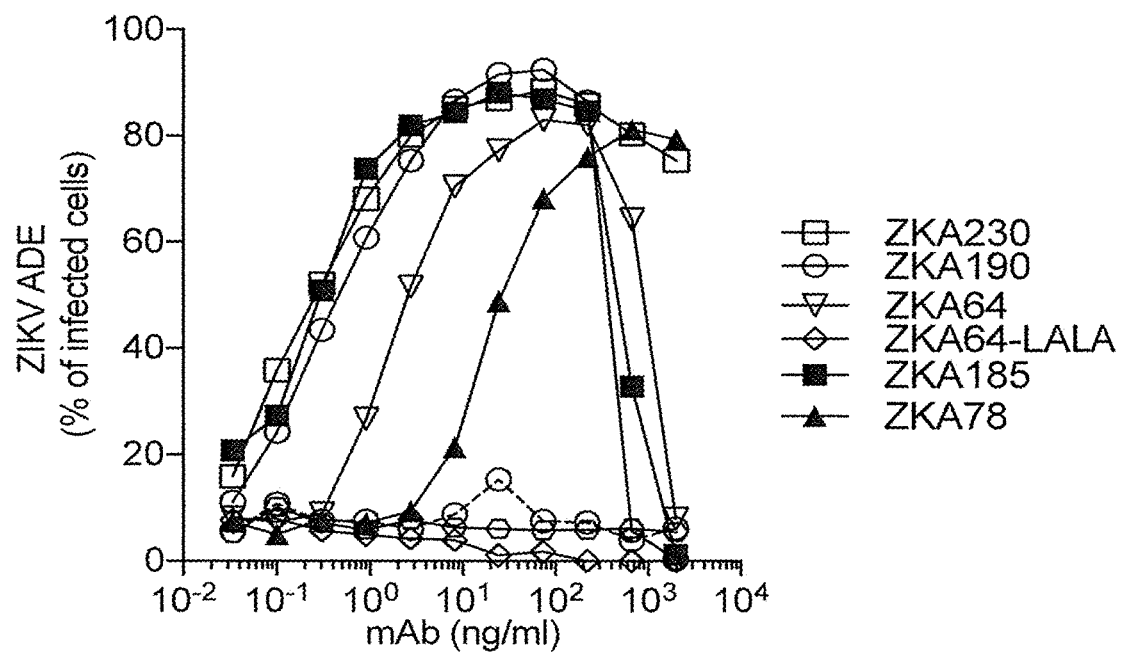
FIG. 10 shows for Example 6 the infection enhancing activity (ADE, antibody-dependent enhancement) of ZKA190, ZKA64, ZKA64-LALA, ZKA185, ZKA230 and ZKA78 antibodies for ZIKV (H/PF/2013 strain) on non-permissive K562 cells as measured by flow-cytometry (% of infected cells).

Results are shown in FIG. 10. All antibodies enhanced infection of ZIKV in the non-permissive K562 cells at a broad range of concentrations, including those that fully neutralized ZIKV infection on Vero cells (FIG. 10). Of note, while EDIII-specific antibodies ZKA64 and ZKA190 fully neutralized ZIKV infections of K562 cells above 1 µg/ml, the NNB antibody ZKA230 failed to do so, a result that might be due to the different mechanisms of neutralization of free viruses versus Fc-gamma-receptor-internalized viruses. In contrast, the cross-reactive ZKA78 that only partially neutralized ZIKV infectivity, effectively enhanced ZIKV infection of K562 cells. These results show that cross-reactive antibodies elicited by either ZIKV or DENV infection can mediate heterologous ADE.

In view thereof it was investigated whether ADE could be also induced by immune sera and whether this could be blocked by neutralizing antibodies delivered as a "LALA variant". To obtain the LALA variant, each of the heavy chains was mutated at amino acids 4 and 5 of CH2 domain by substituting an alanine in place of the natural leucine using site-directed mutagenesis. As described above, LALA variants (of human IgG1 antibodies) do not bind to Fc-gamma-receptors and complement.

To investigate the effect of ZKA64-LALA antibody in ZIKV ADE, an inhibition of ADE assay was used. Since ADE of ZIKV is observed using ZIKV- or DENV-immune plasma, ZIKV (MOI 0.175) was mixed with plasma from primary ZIKV- or DENV-infected donors for 30 minutes at 37° C. ZKA64-LALA antibody was added at 50 µg/ml, mixed with 5000 K562 cells/well and incubated for three days. Cells were then stained with 4G2 and analyzed by flow cytometry.

Figure 11:
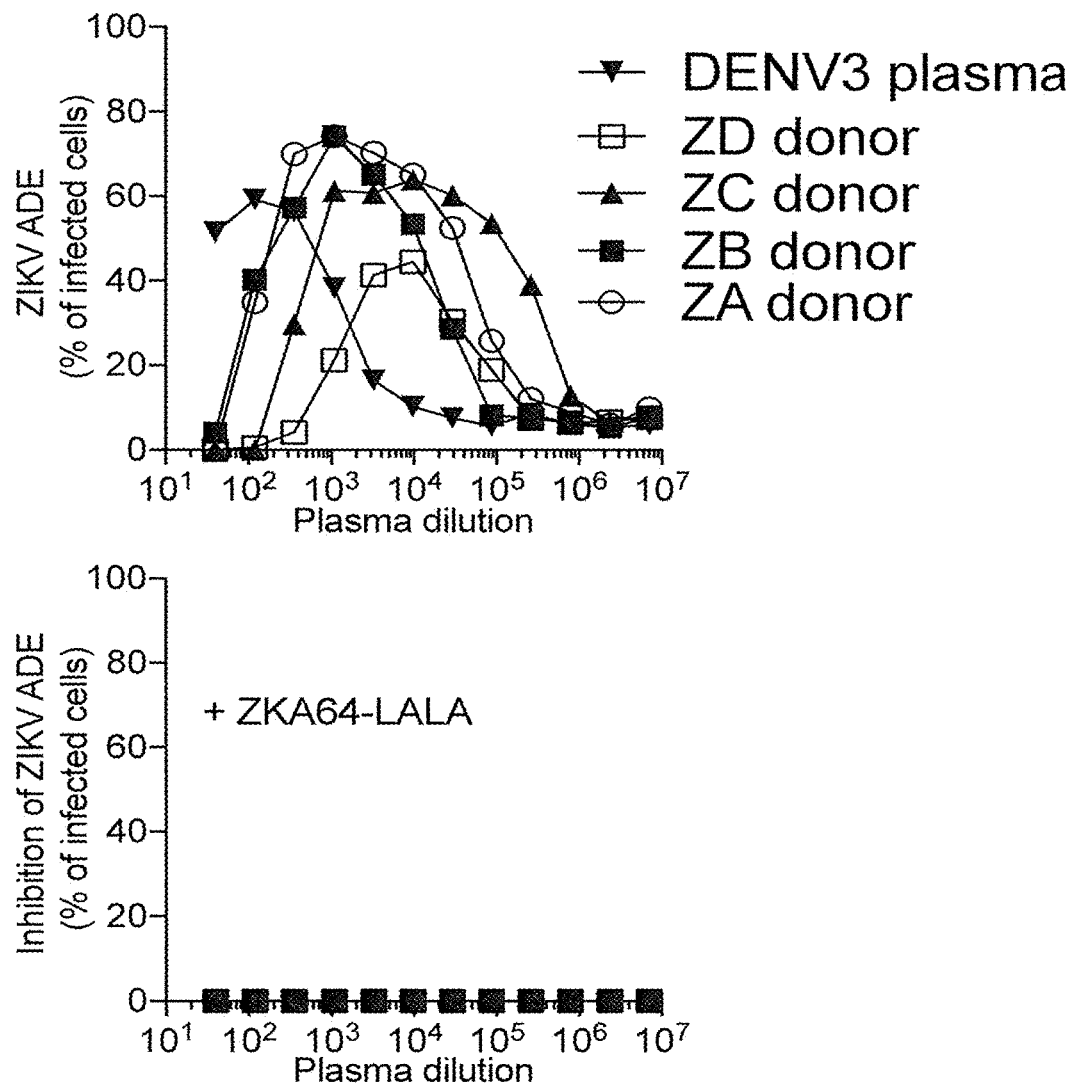
FIG. 11 shows for Example 6 that four ZIKV-immune plasma and one DENV-immune plasma showed similar capacity to enhance ZIKV infection of K562 cells (upper panel). This ADE effect was completely blocked in all five immune plasma by the EDIII-specific ZKA64-LALA antibody (lower panel).
Figure 12:
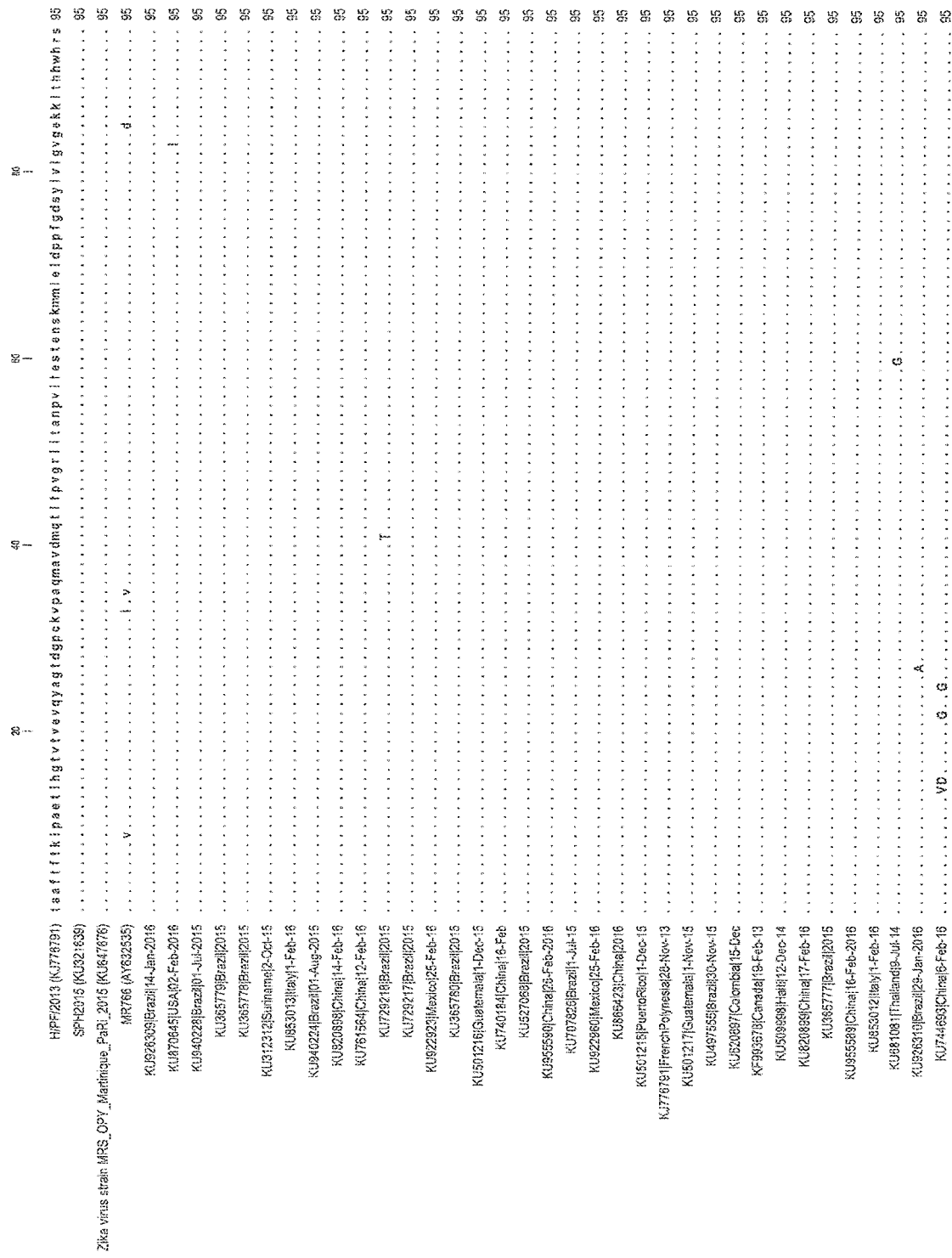
FIG. 12 shows the amino acid alignment of the EDIII region of 39 ZIKV strains from the Asian lineage since 2013 (including the prototypic strain MR766 of the African lineage isolated in 1947). The EDIII region amino acid sequence of ZIK V H/PF/2013 (SEQ ID NO: 402) is shown at the top of the alignment. Depicted EDIII sequences differing from ZIKV H/PF/2013 are those of strains MR766 (SEQ ID NO: 409), KU870645|USA|2 Feb. 2016 (SEQ ID NO: 410), KU729218|Brazil|2015 (SEQ ID NO: 411), KU681081|Thailand|9 Jul. 2014 (SEQ ID NO: 412), KU926310|Brazil|29 Jan. 2016 (SEQ ID NO: 413), and KU744693|China|6 Feb. 2016 (SEQ ID NO: 414).

Results are shown in FIG. 11. In a homologous setting, four ZIKV-immune plasma collected from convalescent patients and one DENV-immune plasma showed similar capacity to enhance ZIKV infection of K562 cells (FIG. 11, upper panel), and this ADE effect was completely blocked by the EDIII-specific ZKA64-LALA antibody (FIG. 11, lower panel).

Of note, the ADE effect of ZIKV- and DENV-immune plasma was completely blocked by the EDIII-specific ZKA64-LALA antibody. The ADE blocking ability of a single EDIII-specific LALA antibody could be related not only to its capacity to out-compete serum enhancing antibodies but also to neutralize virus once internalized into endosomes.

These results indicate that a potently neutralizing antibody, such as ZKA190, ZKA230, ZKA185 or ZKA64, developed in the "LALA" form, have a strong potential to be used in prophylactic or therapeutic settings to prevent congenital ZIKV infection, e.g. in pregnant women and/or in people living in high risk areas. The use of the LALA form avoids the risk of ZIKV ADE and, as shown above, could also block ADE of pre-existing cross-reactive antibodies, such as in the case of patients already immune to DENV.

Example 7: Analysis of Samples from European Residents Using ZIKV NS1-Specific Antibodies for Diagnosis of ZIKV Infection The present Example is based on the blockade of binding assay described in Example 4. To further assess the specificity of the ZIKV NS1 BOB assay, a large set of samples obtained from patients infected with DENV, WNV or Chikungunya virus (CHIKV) was tested.

To this end, a "blockade of binding" assay was used. Polystyrene plates were coated overnight with 1 µg/ml of ZIKV NS1 and blocked for 1 hour with PBS containing 1% BSA. Plasma or serum (1:10 dilution) were added to NS1-coated ELISA plates. Thereafter, e.g. after 1 hour, an equal volume of biotinylated anti-NS1 ZKA35 was added, and the mixture was incubated, e.g. at room temperature for 15 minutes. Plates were washed and alkaline-phosphatase-conjugated streptavidin was added, e.g. for 30 minutes. Plates were washed again and the substrate was added. The percentage of inhibition was calculated as follow: (1−[(OD sample−OD neg ctr)/(OD pos ctr−OD neg ctr)])×100.

Figure 14:
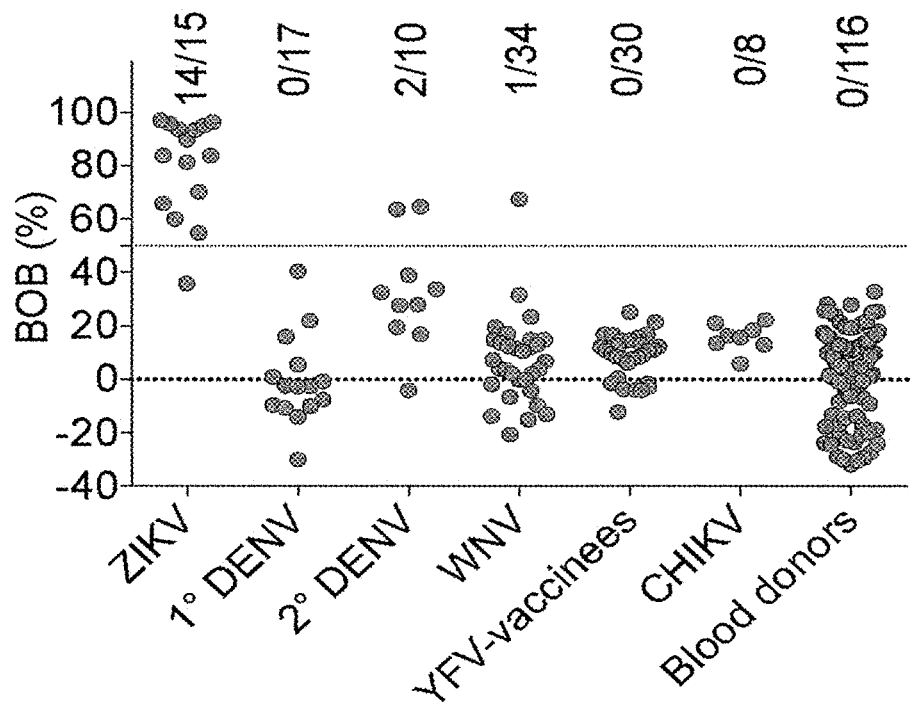
FIG. 14 shows for Example 7 NS1 blockade-of-binding analysis of European residents. Shown are the BOB values for samples collected in Italy and Switzerland. Plotted are the BOB values in samples from ZIKV, primary and secondary DENV-, WNV-, and CHIKV-infected individuals and a panel of samples from healthy blood donors from Switzerland.

Results are shown in FIG. 14. Thirty-one of 32 samples (96.9%) from WNV patients collected more than 10 days after symptom onset scored negative. Of note, the only positive was obtained from a sample collected in 2016. Two of 27 samples from DENV patients collected more than 10 days after symptom onset scored positive, and the two positive samples were derived from secondary DENV infections. In addition, none of the samples derived from chikungunya patients or YFV-vaccines scored positive. A large number of plasma samples from Swiss blood donors (n=116) collected between 2010 and 2016 was also tested. None of those samples scored positive. The results obtained confirmed and strengthened the high sensitivity and specificity of the NS1 BOB ELISA assay.

Example 8: An Antibody According to the Present Invention Neutralizes ZIKV More Potently than Prior Art Antibody EDE1 mAb C8

To compare the neutralizing antibodies according to the present invention with highly neutralizing anti-ZIKV antibodies of the prior art, neutralization performance of ZKA190 was compared to that of prior art highly neutralizing mAb EDE1 C8 (Barba-Spaeth G, Dejnirattisai W, Rouvinski A, Vaney M C, Medits I, Sharma A, Simon-Lorière E, Sakuntabhai A, Cao-Lormeau V M, Haouz A, England P, Stiasny K, Mongkolsapaya J, Heinz F X, Screaton G R, Rey F A. Structural basis of potent Zika-dengue virus antibody cross-neutralization. Nature. 2016 Aug. 4; 536(7614):48-53). Neutralization of both antibodies was tested against a panel of four distinct ZIKV strains (H/PF/2013; MR766, MRS-OPY and PV10552).

Briefly, neutralization of ZIKV infection by mAbs was measured using a micro-neutralization flow cytometry-based assay. Different dilutions of mAbs were mixed with ZIKV (MOI of 0.35) for 1 hour at 37° C. and added to 5000 Vero cells/well in 96-well flat-bottom plates. After four days for ZIKV, the cells were fixed with 2% formaldehyde, permeabilized in PBS containing 1% fetal calf serum (Hyclone) and 0.5% saponin, and stained with the mouse mAb 4G2. The cells were incubated with a goat anti-mouse IgG conjugated to Alexa Fluor488 (Jackson Immuno-Research, 115485164) and analyzed by flow cytometry. The neutralization titer (50% inhibitory concentration [IC50]) is expressed as the antibody concentration that reduced the infection by 50% compared to virus-only control wells.

Figure 15:
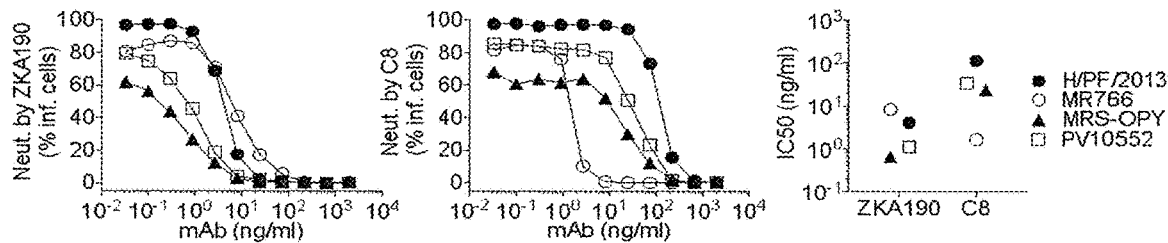
FIG. 15 shows for Example 8 neutralization of ZKA190 and C8 mAbs tested against a panel of four strains of ZIKV, as determined by the percentage of infected Vero cells in the presence of increasing amounts of the mAbs (A). Shown are also the IC50 values (B) and statistics (C). Data are representative of at least two independent experiments.

Results are shown in FIG. 15. ZKA190 mAb potently neutralized African, Asian and American strains with an IC50 ranging from 0.6 to 8 ng/ml. In comparison, prior art antibody C8 was about 24-fold less potent.

Example 9: Further Characterization of Antibody ZKA190

The potency of antibody ZKA190 was further investigated in vitro and in vivo. To this end, the mAb was synthesized in IgG1 wild-type (wt) format and in an IgG1 Fc-LALA format. Briefly, the VH and VL sequences were cloned into human Igγ1, Igκ and Igλ expression vectors (kindly provided by Michel Nussenzweig, Rockefeller University, New York, NY, USA), essentially as described (Tiller T, Meffre E, Yurasov S, Tsuiji M, Nussenzweig M C, Wardemann H: Efficient generation of monoclonal antibodies from single human B cells by single cell RT-PCR and expression vector cloning. *J Immunol Methods* 2008, 329: 112-124). Recombinant mAbs were produced by transient transfection of EXPI293 cells (Invitrogen), purified by Protein A chromatography (GE Healthcare) and desalted against PBS. To obtain the LALA variant, each of the heavy chains was mutated at amino acids 4 and 5 of CH2 domain by substituting an alanine in place of the natural leucine using site-directed mutagenesis. As described above, LALA variants (of human IgG1 antibodies) do not bind to Fc-gamma-receptors and complement.

As shown in FIG. 15A and described in Example 8, ZKA190 was tested against a panel of four ZIKV strains. ZKA190 mAb potently neutralized African, Asian and American strains with an IC50 ranging from 0.004 to 0.05 nM (FIG. 15A; 0.6 to 8 ng/ml).

Figure 16:
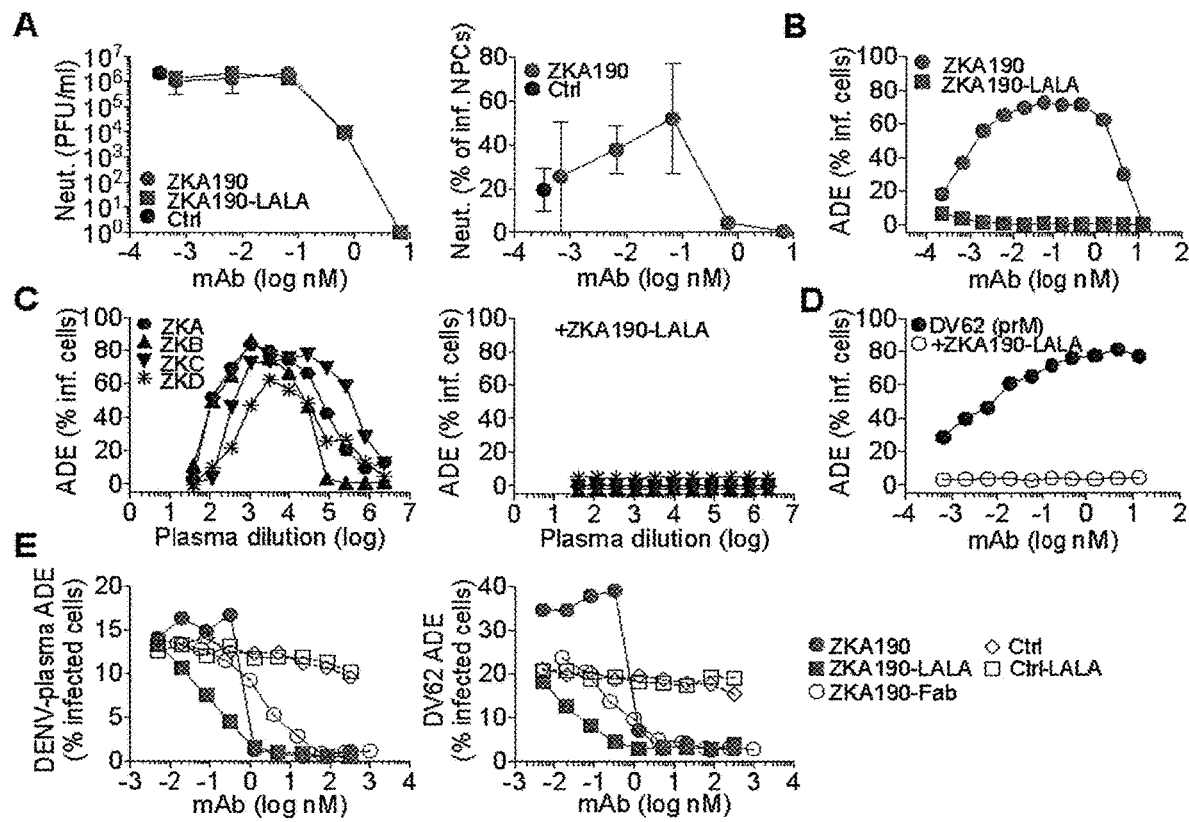
FIG. 16 shows for Example 9 the neutralization and enhancement of ZIKV infection by antibody ZKA190. (A) Neutralization of ZIKV PRVABC59 strain infection of hNPCs by ZKA190, ZKA190-LALA and a control mAb as determined by plaque assay on Vero cells (left panel) and indirect immunofluorescence of infected hNPCs using fluorophore-labelled anti-E antibody (right panel). (B) ADE of ZIKV infection of non-permissive K562 cells by ZKA190 and ZKA190-LALA. (C) ADE induced in K562 cells when ZIKV is pre-incubated with serial dilutions of plasma serum from different ZIKV-positive patients (left panel). When ZKA190 LALA is added to the ZIKV-serum complexes, ADE is inhibited (right panel). (D) ADE induced in K562 cells when ZIKV is pre-incubated with serial dilutions of a prM cross-reactive mAb (DV62) derived from a DENV-immune donor. ZKA190-LALA inhibits ADE of ZIKV when complexed with prM-reactive antibody DV62. (E) Effect on ADE induced by peak enhancing dilution of a DENV2 plasma (left panel) or anti-prM DV62 mAb (right panel) by serial dilutions of indicated mAbs.

Since ZIKV has been shown to infect human neural progenitor cells (hNPC) leading to heightened cell toxicity, dysregulation of cell-cycle and reduced cell growth, ZKA190 and ZKA190-LALA were tested in hNPCs. To this end, adult male fibroblasts obtained from the Movement Disorders Bio-Bank (Neurogenetics Unit of the Neurological Institute 'Carlo Besta', Milan) were reprogrammed using the CytoTune-iPS 2.0 Sendai kit (Life Technologies). hiPSCs were maintained in feeder-free conditions in mTeSR1 (Stem Cell Technologies). To generate embryoid bodies (EBs), dissociated hiPSCs were plated into low adhesion plates in mTeSR1 supplemented with N2 (0.5×) (ThermoFisher Scientific), human Noggin (0.5 mg/ml, R&D System), SB431542 (5 M, Sigma), Y27632 (10 μM, Miltenyi Biotec) and penicillin/streptomycin (1%, Sigma) (as described in Marchetto M C N, Carromeu C, Acab A, Yu D, Yeo G W, Mu Y, Chen G, Gage F H, Muotri A R: A model for neural development and treatment of Rett syndrome using human induced pluripotent stem cells. *Cell* 2010, 143:527-539). To obtain rosettes, EBs were plated after 10 days onto matrigel-coated plates (1:100, matrigel growth factor reduced, Corning) in DMEM/F12 (Sigma) with N2 (1:100), non-essential amino acids (1%, ThermoFisher Scientific) and penicillin/streptomycin. After 10 days, cells were passaged with Accutase (Sigma) and seeded onto matrigel coated-flasks in NPC media containing DMEM/F12, N2 (0.25%), B27 (0.5%, ThermoFisher Scientific), penicillin/streptomycin and FGF2 (20 ng/ml, ThermoFisher Scientific). hNPCs (3×104) were plated on coverslips in 24-well plates 3 days prior to infection with PRVABC59 strain. Virus stock was incubated with the mAbs 1 h prior to addition to hNPCs to obtain an MOI of 0.5. After 4 h of virus adsorption, culture supernatant was removed and fresh medium containing the mAbs was re-added. Supernatant was collected 96 h post-infection to measure virus titers by plaque assay on Vero cells. Cells were fixed in 4% paraformaldehyde (PFA, Sigma) solution in phosphate-buffered saline (PBS, Euroclone) for 30 min for indirect immunofluorescence. Fixed cells were permeabilized for 30 minutes (min) in blocking solution, containing 0.2% Triton X-100 (Sigma) and 10% donkey serum (Sigma), and incubated overnight at 4° C. with the primary antibodies in blocking solution. The following antibody was used for detection: anti-envelope (1:200, Millipore, MAB10216). Then, cells were washed with PBS and incubated for 1 h with Hoechst and anti-mouse Alexa Fluor-488 secondary antibodies (1:1, 000 in blocking solution, ThermoFisher Scientific). After PBS washes, cells were washed again and mounted. Results are shown in FIG. 16A. Both, ZKA190 and ZKA190-LALA, fully abolished infection and replication of ZIKV in hNPCs.

Next, the ability of ZKA190 and ZKA190-LALA to cause ADE was tested in the K562 cell line as described in Example 6. Briefly, ADE was measured by a flow based assay using K562 cells. Briefly, for ZKA190, ZKA190 and ZIKV H/PF/2013 (MOI 0.175) were mixed for 1 hour at 37° C. and added to 5000 K562 cells/well. After four days, cells were fixed, permeabilized, and stained with mAb m4G2. The number of infected cells was determined by flow cytometry. For ZKA190-LALA, ZIKV (MOI 0.175) was mixed with plasma from primary ZIKV-infected donors for 30 minutes at 37° C. ZKA190-LALA was added at 50 μg/ml, mixed with 5000 K562 cells/well and incubated for three days. Cells were then stained with 4G2 and analyzed by flow cytometry. Results are shown in FIG. 16B. ZKA190 supports ADE from 0.0001 to 1 nM; as expected, ZKA190-LALA did not show any ADE activity. The ability of ZKA190-LALA to inhibit ADE induced by plasma from four ZIKV-immune donors in K562 cells was also tested. Results are shown in FIG. 16C. It was found that ZKA190-LALA completely inhibited the ADE induced by plasma antibodies (FIG. 16C).

Anti-prM antibodies form part of the predominant antibodies elicited during the human immune response against flaviviruses and have been shown to enhance virus infection in vitro (Dejnirattisai, W., Jumnainsong, A., Onsirisakul, N., Fitton, P., Vasanawathana, S., Limpitikul, W., Puttikhunt, C., Edwards, C., Duangchinda, T., Supasa, S., et al. (2010). Cross-reacting antibodies enhance dengue virus infection in humans. Science 328, 745-748). K562 cells were pre-incubated with serial dilutions of prM cross-reactive antibody DV62 (Beltramello, M., Williams, K. L., Simmons, C. P., Macagno, A., Simonelli, L., Quyen, N. T. H., Sukupolvi-Petty, S., Navarro-Sanchez, E., Young, P. R., de Silva, A. M., et al. (2010). The human immune response to Dengue virus is dominated by highly cross-reactive antibodies endowed with neutralizing and enhancing activity. *Cell Host Microbe* 8, 271-283) derived from a DENV immune donor. Results are shown in FIG. 16D. DV62 cross-reacted with ZIKV prM protein and caused ADE at a broad range of concentrations (FIG. 16D). ZKA190-LALA can fully block anti-prM DV62 mAb-induced ADE of immature or partially immature ZIKV particles (FIG. 16D).

Finally, the ability of different concentrations of ZKA190, ZKA190-LALA and ZKA190 Fab to cause or block ADE of ZIKV in the presence of enhancing concentrations of human anti-DENV2 plasma or DV62 was tested. Results are shown in FIG. 16E. ZKA190 at low concentrations increased the prM DV62-mediated ADE of ZIKV infection, consistent with its ability to promote the entry of both immature and mature virions, while at concentrations above 1.3 nM (i.e., 200 ng/ml) ZKA190 blocked ADE induced by both DENV plasma and mAb DV62. ZKA190-LALA, as well as its Fab fragment, reduced ADE at concentrations above 0.06 nM, indicating that both inhibited virus infection at a post-attachment step, such as fusion.

Example 10: ZKA190 Binds to a Conserved and Highly Accessible Region of EDIII To determine the ZKA190 epitope at the residue level, solution NMR spectroscopy was used as described in Bardelli, M., Livoti, E., Simonelli, L., Pedotti, M., Moraes, A., Valente, A. P., and Varani, L. (2015). Epitope mapping by solution NMR spectroscopy. J. Mol. Recognit. 28, 393-400; Simonelli, L., Beltramello, M., Yudina, Z., Macagno, A., Calzolai, L., and Varani, L. (2010). Rapid structural characterization of human antibody-antigen complexes through experimentally validated computational docking. J Mol Biol 396, 1491-1507; and Simonelli, L., Pedotti, M., Beltramello, M., Livoti, E., Calzolai, L., Sallusto, F., Lanzavecchia, A., and Varani, L. (2013). Rational Engineering of a Human Anti-Dengue Antibody through Experimentally Validated Computational Docking. PLoS ONE 8, e55561.

Briefly, spectra were recorded on a Bruker Avance 700 MHz NMR spectrometer at 300 K. For assignments of backbone resonances standard triple resonance experiments (HNCO, HN(CA)CO, HN(CO)CACB, HNCACB were used, while sidechains were annotated using HCCH-TOCSY and HBHA(CO)NH experiments. All NMR experiments were processed using Topspin 2.1 (Bruker Biospin) and analysed with CARA. NOESY cross peaks were automatically assigned using the CYANA "noeassign" macro based on the manually assigned chemical shifts. Upper-distance restraints used for the structure calculations in CYANA using the standard simulated annealing protocol were derived from 70 ms $^{15}$N- and $^{13}$C-resolved NOESY spectra. Backbone dynamics of ZIKV EDIII were derived from $^{15}$N relaxation measurements recorded on 600 and 700 MHz spectrometers. Proton-detected versions of the CPMG (R2), inversion-recovery (R1) and $^{15}$N {$^{1}$H}-steady-state NOE were utilized. Delay settings for the T2 series were in the range of 0 to 0.25 sec and for the T1 series between 0.02 to 2 sec. The $^{15}$N {$^{1}$H}-NOE experiment used a relaxation delay of 5 s. The R1 and R2 relaxation rates were derived from least-squares fits of corresponding exponential functions to the measured data using home-written scripts. The relaxation data were analyzed in a model-free approach using the software package DYNAMICS. The program ROTDIF was used to calculate the overall correlation time from the relaxation data (8.5 ns). NMR epitope mapping was performed as previously described (Bardelli et al., 2015; Simonelli et al., 2010; 2013). Briefly, overlay of $^{15}$NHSQC spectra of labelled EDIII free or bound to ZKA190 Fab allowed identification of EDIII residues whose NMR signal changed upon complex formation, indicating that they were affected by ZKA190 binding. Changes were identified by manual inspection and by the Chemical Shift Perturbation (CSP), $CSP=((\Delta\delta_H)^2 \pm (\Delta\delta_N/10)^2)^{1/2}$. NMR samples were typically 800 μM of [$^{15}$N, $^{13}$C]-labeled EDIII in 20 mM sodium phosphate, 50 mM NaCl, pH 6.0. Perdeuterated (nominally 70%) $^2$H, $^{15}$N EDIII samples were used for NMR epitope mapping with a EDIII:ZKA190 Fab ratio of 1:1.1; EDIII concentration was typically 0.4 mM.

Figure 17:
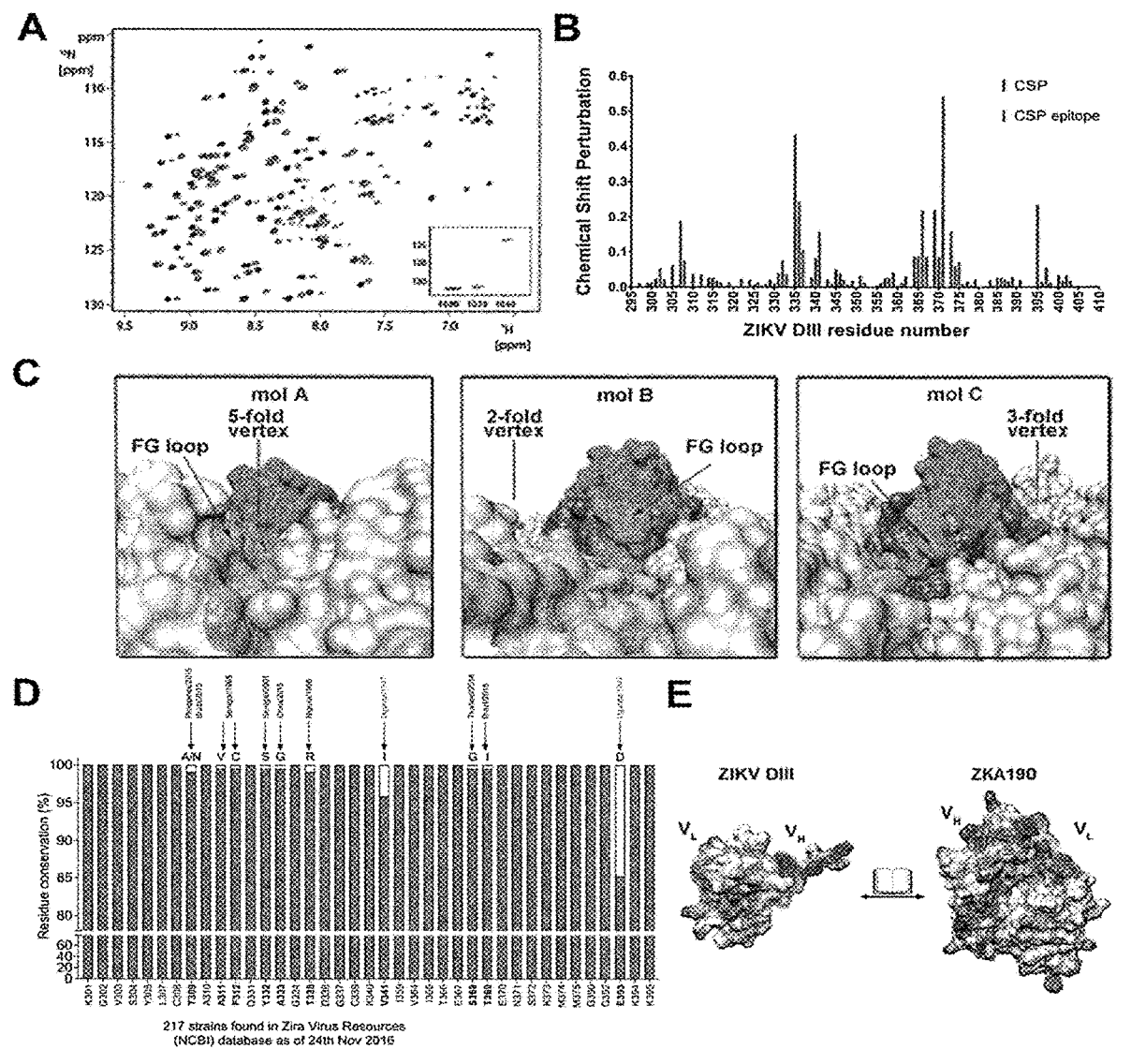
Figure 18:
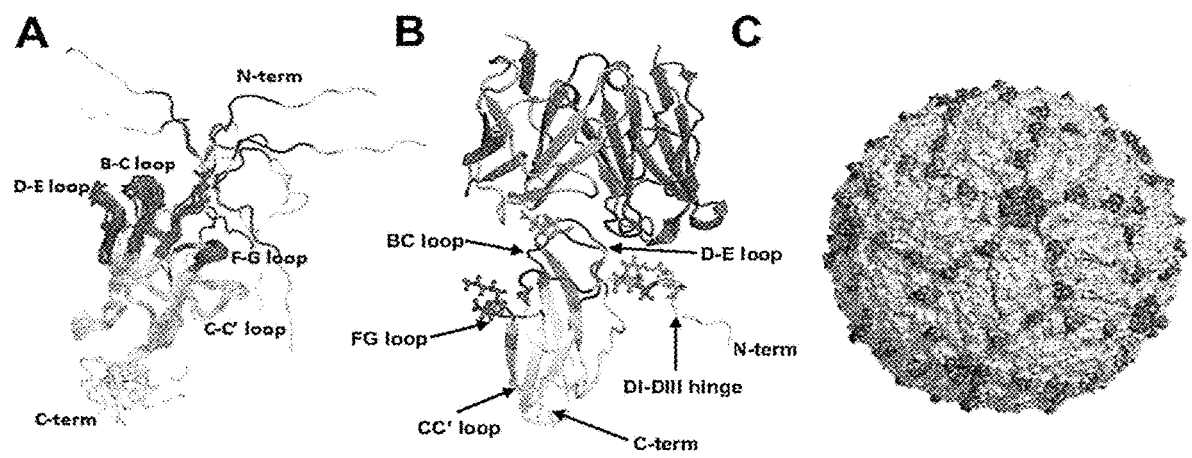
FIG. 18 shows for Example 10 the ZKA190 epitope identified by NMR and Docking. (A) Cartoon representation of the 12 lowest energy NMR structures of ZIKV EDIII, with residues affected by ZKA190 binding in red. Flexibility in the N-terminus of the construct is apparent. (B) Model of the ZKA190:EDIII complex derived by computational docking and molecular simulation validated by NMR results. The NMR identified epitope on EDIII (grey) is in red. The ZKA190 heavy and light chain are colored in dark and light green, respectively. EDIII residues that affect or not antibody binding when mutated are shown as orange and blue sticks, respectively. (C) NMR identified ZKA190 epitope (red) is accessible on the virus surface (white).

Since the NMR signal is strongly dependent on the local chemical environment, changes upon complex formation identify antigen residues that are affected by antibody binding, either directly or through allosteric effects. By comparing the NMR spectra of free and bound EDIII (FIG. 17A), residues affected by ZKA190 were mapped to the LR of EDIII, in particular to the BC, DE and FG loops, as well as to part of the EDI-EDIII hinge (FIG. 18A). These residues are nearly identical among 217 known ZIKV strains, with the exception of substitutions at V341I and E393D in the Uganda 1947 isolate (FIG. 17D). These mutations are also present in the MR766 strain that was efficiently neutralized by ZKA190 (FIG. 15A). Analysis of the ZKA190 epitope on the uncomplexed ZIKV structure showed that the epitope is highly accessible, except for the FG loop in the 5-fold vertex (FIGS. 18B and 17C, molecule A).

Figure 19:
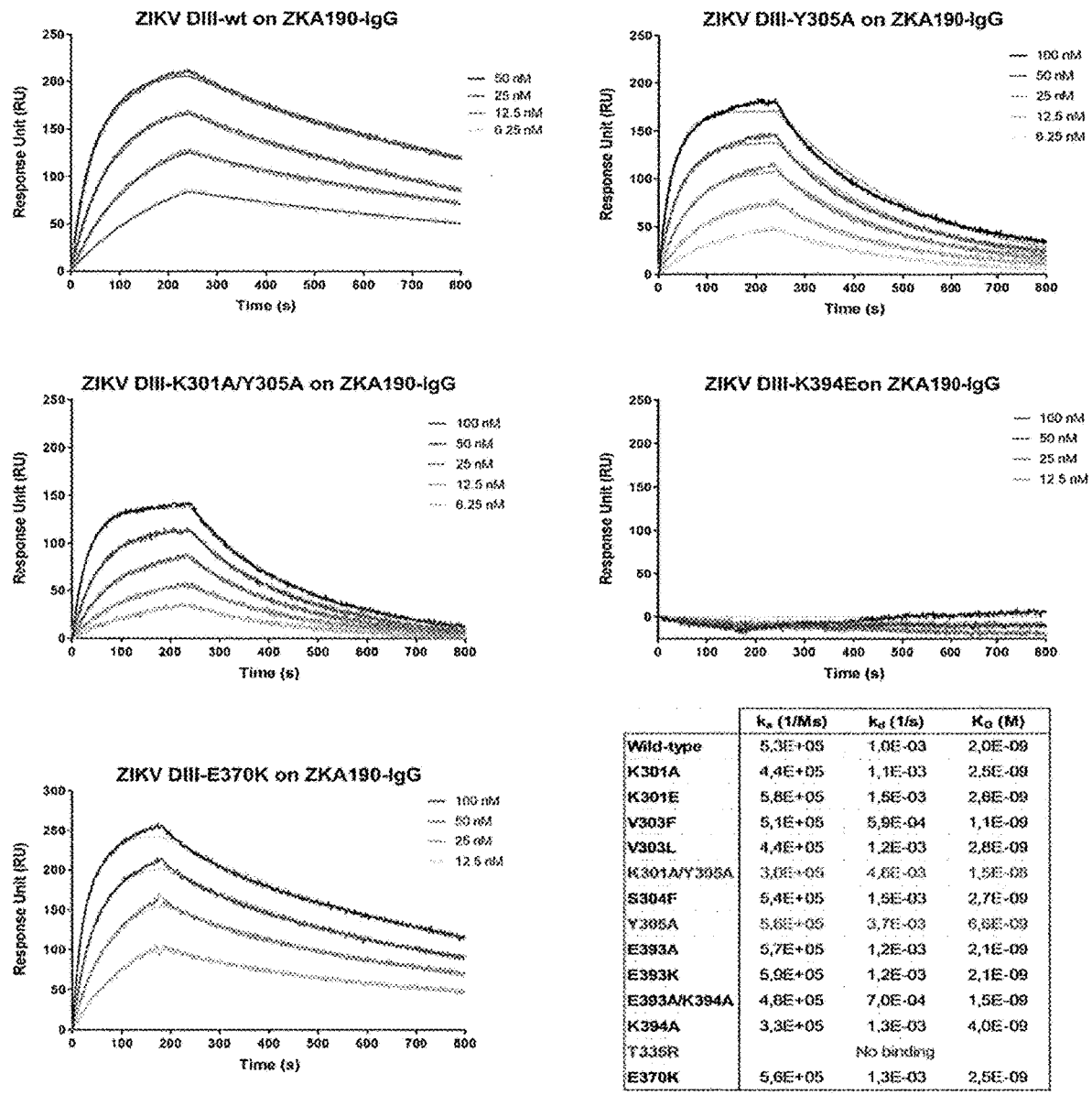
FIG. 19 shows for Example 10 the binding of wt or mutated EDIII to ZKA190 IgG. SPR data and binding kinetics are sh Additional antibodies were isolated for their ability to bind to ZIKV NS1 protein (cf.

Computational docking followed by molecular dynamics simulation, guided and validated by NMR-derived epitope information as well as EDIII mutagenesis, showed that ZKA190 binds through an interface characterized by shape and charge complementarity (FIGS. 18B and 17E). Docking indicates that there are no direct contacts between ZKA190 and the FG loop on EDIII, suggesting that changes in its NMR signals upon antibody binding derive from allosteric effects. This notion is supported by the fact that mutations of FG loop residues in recombinant EDIII, but not in other epitope regions, did not affect the binding affinity of ZKA190 for EDIII (FIGS. 18B and 19).

Example 11: Mechanisms of ZKA190 Neutralization

The ability of ZKA190 to efficiently neutralize the virus may involve inhibition of either cell attachment or membrane fusion. A further mechanism might involve virus inactivation through cross-linking of viral particles.

ZKA190 Fab can neutralize ZIKV, albeit less efficiently than the corresponding IgG. By binding to the EDI-EDIII linker, ZKA190 (both Fab and IgG) might inhibit the ~70 degree rotation of DIII required for viral fusion to the host cell membrane (Bressanelli, S., Stiasny, K., Allison, S. L., Stura, E. A., Duquerroy, S., Lescar, J., Heinz, F. X., and Rey, F. A. (2004). Structure of a flavivirus envelope glycoprotein in its low-pH-induced membrane fusion conformation. Embo J 23, 728-738; Modis, Y., Ogata, S., Clements, D., and Harrison, S. C. (2004). Structure of the dengue virus envelope protein after membrane fusion. Nature 427, 313-319). Alternatively, ZKA190 might prevent the attachment of ZIKV to target cells.

The ability of ZKA190 to inhibit membrane fusion is supported by confocal microscopy analysis. To this end, Vero cells were plated at 7,500 cells/well on 12 mm-diameter coverslips in 24-well plates and incubated overnight. Cells were infected with ZIKV H/PF/2013 (MOI of 100) in the presence or absence of neutralizing concentrations of Alexa-488 conjugated mAbs (0.7 μM) at 37° C. for 3 h, washed with PBS, and fixed with 2% paraformaldehyde in PBS for 30 min at room temperature. Acidified endosome were identified with Lysotracker red (Invitrogen) by adding the dye (50 nM) to the cells for the last 30 min of the incubation prior to fixation. Fixation was followed by extensive washes in PBS and 50 mM glycine and finally the coverslips were prepared for microscopy analysis using Vectashield mounting medium for fluorescence with DAPI (Vector Laboratories). Samples were analyzed by confocal microscopy using a Leica TCS SP5 microscope with a 63×/1.4 N.A. objective. Image analysis and processing was performed with FIJI software.

Figure 20:
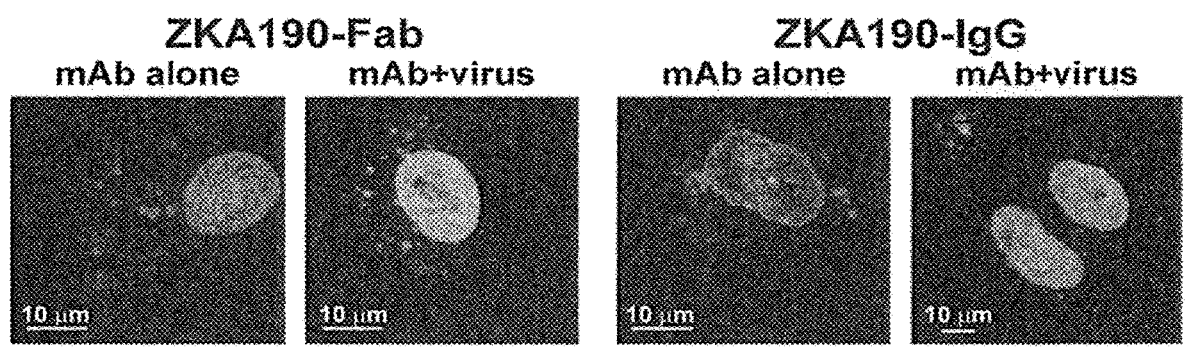

Results are shown in FIG. 20. Confocal microscopy analysis shows that ZKA190 (Fab or IgG) can enter Vero cells only when complexed with ZIKV, at neutralizing concentrations exceeding the IC50 by 10,000-fold (FIG. 20).

Example 12: In Vivo Characterization of the EDIII-Specific mAb ZKA190

To evaluate their prophylactic and therapeutic properties, ZKA190 and ZKA190-LALA were tested in A129 mice challenged with a lethal dose of ZIKV strain MP1751 (African lineage). To test their prophylactic potencies, ZKA190 and ZKA190-LALA were administered one day before virus challenge.

Female A129 mice (IFN-alpha/beta receptor −/−) and wild-type 129Sv/Ev mice aged 5-8 weeks were administered mAbs (ZKA190, ZKA190-LALA and control antibody MPE8 (Corti, D., et al. Cross-neutralization of four paramyxoviruses by a human monoclonal antibody. Nature 501, 439-443 (2013)) diluted in PBS at different doses via the intraperitoneal (i.p.) route in a volume of 500 µl. MAbs were administered either 1 day before or 1, 2, 3 or 4 days after virus challenge. Animals were challenged subcutaneously with 102 pfu ZIKV (strain MP1751) and followed for 14 days. Weights and temperatures were monitored daily and clinical observations were recorded at least twice per day. On day 5 post-challenge, 50 µl of blood was collected from each animal into a RNA protect tube (Qiagen, UK) and frozen at −80° C. At the end of the study (14 days post-challenge) or when animals met human endpoints, necropsies were undertaken, and blood and sections of brain, spleen, liver, kidney and ovary were collected for virological analysis.

Tissue samples from A129 mice were weighed and homogenized into PBS using ceramic beads and an automated homogenizer (Precellys, UK) using six 5 second cycles of 6500 rpm with a 30 second gap. Two hundred µl of tissue homogenate or blood solution was transferred into 600 µL RLT buffer (Qiagen, UK) for RNA extraction using the RNeasy Mini extraction kit (Qiagen, UK); samples were passed through a QIAshredder (Qiagen, UK) as an initial step. A ZIKV specific realtime RT-PCR assay was utilized for the detection of viral RNA from subject animals. The primer and probe sequences were adopted from Quick et al., 2017 (Quick, J, Grubaugh N D, Pullan S T, Claro I M, Smith A D, Gangavarapu K, Oliveira G, Robles-Sikisaka R, Rogers T F, Beutler N A, et al.: Multiplex PCR method for MinION and Illumina sequencing of Zika and other virus genomes directly from clinical samples. Nat Protoc 2017, 12:1261-1276) with in-house optimization and validation performed to provide optimal mastermix and cycling conditions. Realtime RT-PCR was performed using the SuperScript III Platinum One-step qRT-PCR kit (Life Technologies, UK). The fmal mastermix (15 µl) was comprised of 10 µl of 2× Reaction Mix, 1.2 µl of PCR-grade water, 0.2 µl of 50 mM MgSO4, 1 µl of each primer (ZIKV 1086 and ZIKV 1162c both at 18 µM working concentration), 0.8 µl of probe (ZIKV 1107-FAM at 25 µM working concentration) and 0.8 µl of SSIII enzyme mix. Five µl of template RNA was added to the mastermix, yielding a final reaction volume of 20 µl. The cycling conditions used were 50° C. for 10 minutes, 95° C. for 2 minutes, followed by 45 cycles of 95° C. for 10 seconds and 60° C. for 40 seconds, plus a final cooling step of 40° C. for 30 seconds. Quantification analysis using fluorescence was performed at the end of each 60° C. step. Reactions were run and analyzed on the 7500 Fast platform (Life Technologies, UK) using 7500 software version 2.0.6. Quantification of viral load in samples was performed using a dilution series of quantified RNA oligonucleotide (Integrated DNA Technologies). The oligonucleotide comprised the 77 bases of ZIKV RNA targeted by the assay, based on GenBank accession AY632535.2 and was synthesized to a scale of 250 nmole with HPLC purification.

Figure 21:
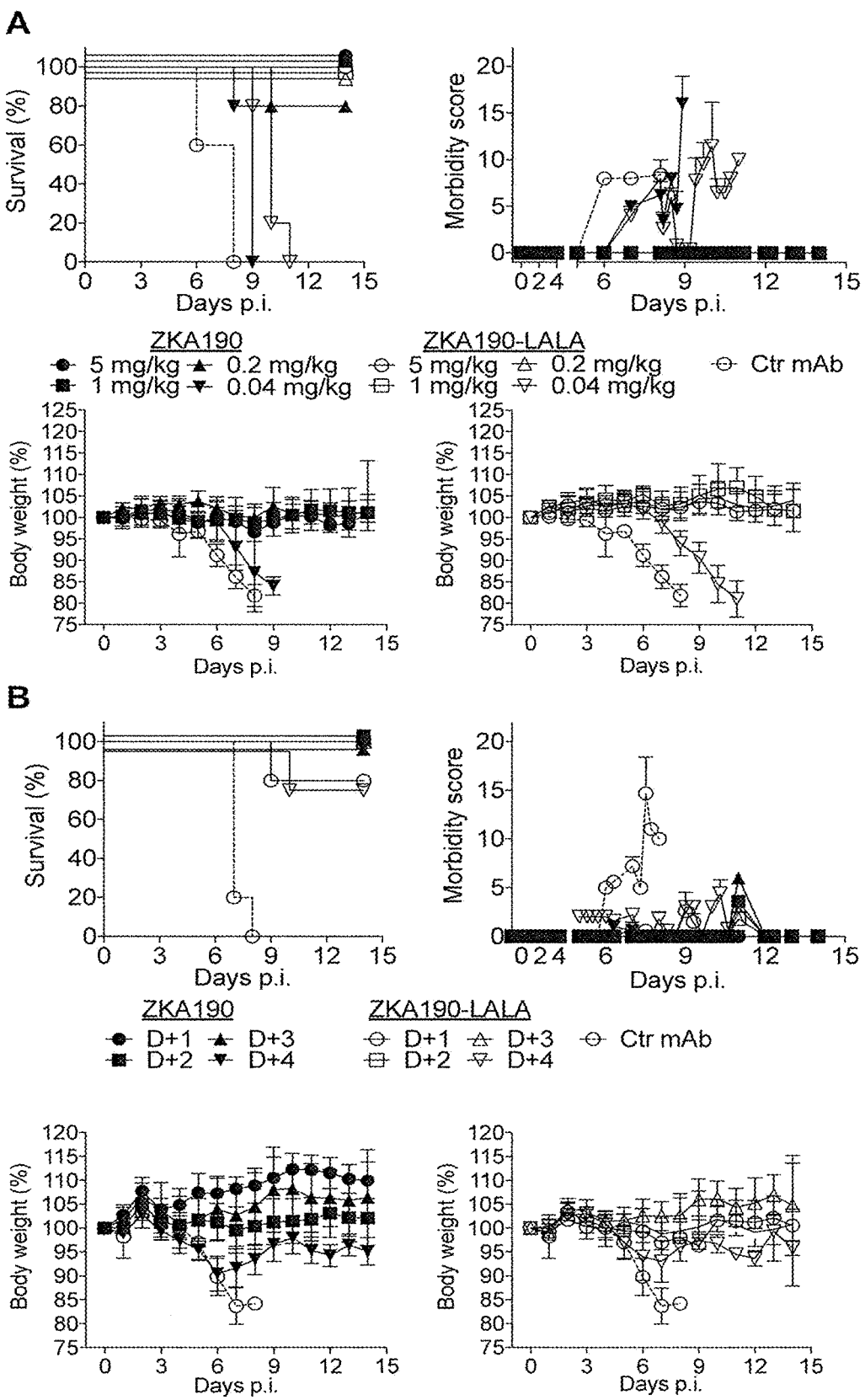
Figure 22:
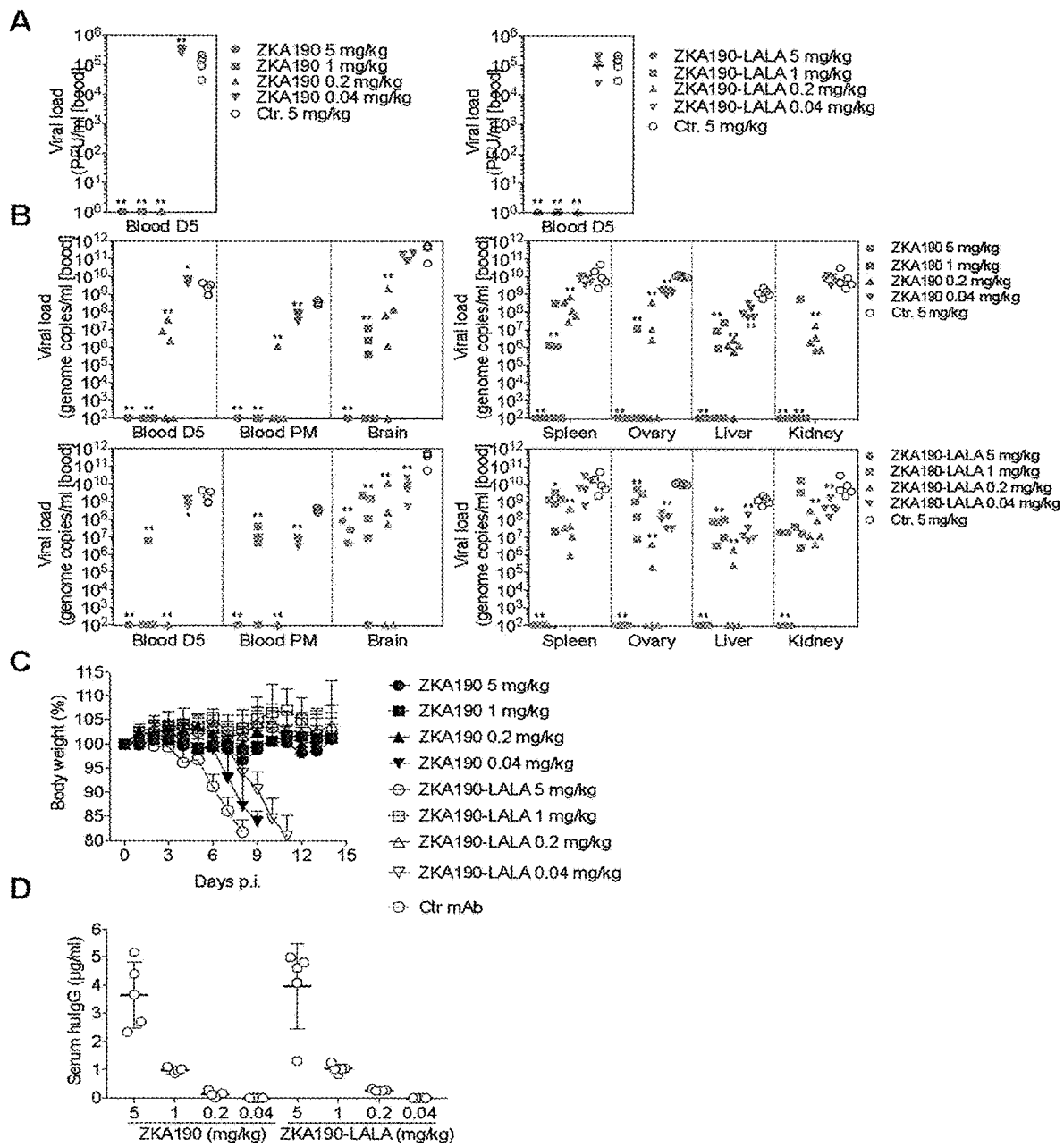
Figure 23:
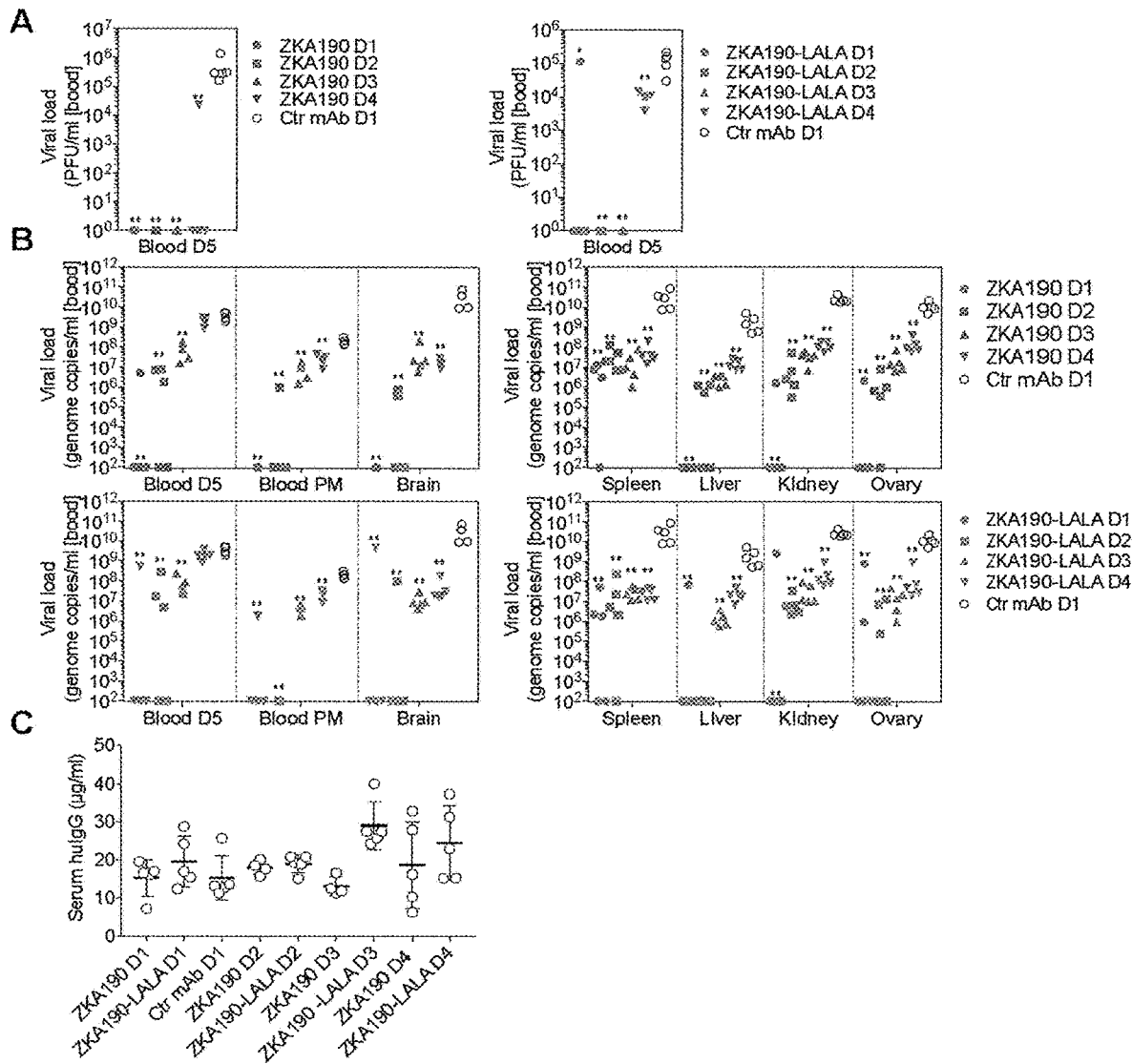

Results are shown in FIGS. 21, 22 and 23. ZKA190 and ZKA190-LALA were shown to protect mice from mortality and morbidity at concentrations of 5, 1 or 0.2 mg/kg (FIG. 21A-B). ZKA190-LALA, and to a lesser extent ZKA190, delayed morbidity and mortality as compared to the control group at 0.04 mg/kg. Viral titers in blood and organs were reduced significantly compared to control antibody-treated animals, even in the presence of serum antibody levels below 1 µg/ml (FIG. 22A-D).

To evaluate the therapeutic potential of ZKA190, we administered ZKA190 and ZKA190-LALA at different time-points following ZIKV infection. At a dose of 15 mg/kg, survival rates of 80%-100% were achieved, and the morbidity was greatly reduced even when treatment was given four days post-infection (FIG. 21E-G). ZKA190 and ZKA190-LALA treatment at all post-infection time-points resulted in significantly reduced viral titers, compared to animals treated with control antibody, with a clear trend for greater reduction with earlier treatment (FIG. 23A-21C). Of note, ZKA190-LALA showed a significantly reduced antiviral activity in the blood day 5 sample as compared to ZKA190 when mAbs were given four days post-infection, a result that might be related to the impaired ability of the LALA variant to facilitate rapid clearance of coated virions.

Tables of Sequences and SEQ ID Numbers

| ZKA190 | SEQ ID NO. | Amino acid sequence |
|---|---|---|
| CDRH1 | 1 | GFTFSKYG |
| CDRH2 | 2 | ISYEGSNK |
| CDRH3 | 3 | AKSGTQYYDTTGYEYRGLEYFGY |
| CDRL1 | 4 | QSVSSSY |
| CDRL2 | 5 | DAS |
| CDRL2 long | 6 | LIYDASSRA |
| CDRL3 | 7 | QQYGRSRWT |
| VH | 8 | QVQLVESGGGVVQPGRSLRLSCAASGFTFSKYGMHWVRQA PGKGLEWVAVISYEGSNKYYADSVKGRFTISRDNSKNTLY LQMNSLRAEDTAVYYCAKSGTQYYDTTGYEYRGLEYFGYW GQGTLVTVSS |

-continued

| | | |
|---|---|---|
| VL | 9 | EIVLTQSPGTLSLSPGERATLSCRASQSVSSSYLAWYQQKRGQAPRLLIYDASSRATGIPDRFSGSGSGTDFTLTISRLEPEDFAVYYCQQYGRSRWTFGQGTKVEIK |
| ZKA190 | SEQ ID NO. | Nucleic acid sequence |
| CDRH1 | 10 | ggattcaccttcagtaaatatggc |
| CDRH2 | 11 | atatcatatgagggaagtaataaa |
| CDRH3 | 12 | gcgaaatcggggacccaatactatgatactactggttatgagtataggggtttggaatactttggctac |
| CDRL1 | 13 | cagagtgttagtagcagttac |
| CDRL2 | 14 | gatgcatcc |
| CDRL2 long | 15 | ctcatctatgatgcatccagcagggcc |
| CDRL3 | 16 | cagcagtatggtaggtcaaggtggaca |
| VH | 17 | caggtgcagctggtggagtctggggggaggcgtggtccagcctggggaggtccctgagactctcctgtgcagcctctggattcaccttcagtaaatatggcatgcactgggtccgccaggctccaggcaaggggctggagtgggtggcagttatatcatatgagggaagtaataaaattatgcagactccgtgaagggccgattcaccatctccagagacaattccaagaacacgctgtatctgcaaatgaacagcctgagagctgaggacacggcagtgtattactgtgcgaaatcggggacccaatactatgatactactggttatgagtataggggtttggaatactttggctactggggccagggaaccctggtcaccgtctcctcag |
| VL | 18 | gaaattgtgttgacgcagtctccaggcaccctgtctttgtctccaggggaaagagccaccctctcctgcagggccagtcagagtgttagtagcagttacttagcctggtaccagcagaaacgtggccaggctcccaggctcctcatctatgatgcatccagcagggccactggcatcccagacaggttcagtggcagtgggtctgggacagacttcactctcaccatcagcagactggagcctgaagattttgcagtgtattactgtcagcagtatggtaggtcaaggtggacattcggccaagggaccaaggtggaaatcaaac |
| ZKA185 | SEQ ID NO. | Amino acid sequence |
| CDRH1 | 19 | GYSFTSYW |
| CDRH2 | 20 | FDPSDSQT |
| CDRH3 | 21 | ARRYCSSSSCYVDN |
| CDRL1 | 22 | ALPNKF |
| CDRL2 | 23 | EDN |
| CDRL2 long | 24 | VIYEDNKRP |
| CDRL3 | 25 | YSTDSSSNPLGV |
| VH | 26 | EVQLVQSGAEVKKPGESLRISCKGSGYSFTSYWITWVRQMPGKGLEWMAKFDPSDSQTNYSPSFQGHVTISVDKSISTAYLQWSSLKASDTAMYYCARRYCSSSSCYVDNWGQGTLVTIFS |
| VL | 27 | SYELTQPPSVSVSPGQTARITCSGDALPNKFAYWYRQKSGQAPVLVIYEDNKRPSGIPERFSGSSSGTMATLTISGAQVEDEADYHCYSTDSSSNPLGVFGGGTKLTVL |
| ZKA185 | SEQ ID NO. | Nucleic acid sequence |
| CDRH1 | 28 | ggatatagttttaccagttactgg |
| CDRH2 | 29 | tttgatcctagtgactctcaaacc |
| CDRH3 | 30 | gcgagaagatattgtagtagtagtagttgttatgtggacaat |

| | | |
|---|---|---|
| CDRL1 | 31 | gcattgccaaataaattt |
| CDRL2 | 32 | gaggacaac |
| CDRL2 long | 33 | gtcatctatgaggacaacaaacgaccc |
| CDRL3 | 34 | tactcaacagacagcagttctaatcccctgggagta |
| VH | 35 | gaagtgcagctggtgcagtccggagcagaggtgaaaaagc ccgggggagtctctgaggatctcctgtaagggttctggata tagttttaccagttactggatcacctgggtgcgccagatg cccgggaaaggcctggagtggatggcgaagtttgatccta gtgactctcaaaccaactacagcccgtccttccaaggcca cgtcaccatctcagttgacaagtccatcagcactgcctac ttgcagtggagcagcctgaaggcctcggacaccgccatgt attactgtgcgagaagatattgtagtagtagtagttgtta tgtggacaattggggccagggaaccctggtcaccatcttc tcag |
| VL | 36 | tcctatgagctgacacagccaccctcggtgtcagtgtccc caggacaaacggccaggatcacctgctctctggagatgcatt gccaaataaatttgcttattggtaccggcagaagtcaggc caggcccctgttctggtcatctatgaggacaacaaacgac cctcggatccctgagagattctctggctccagctcagg gacaatggccaccttgactatcagtggggcccaggtggag gatgaagctgactaccactgttactcaacagacagcagtt ctaatcccctgggagtattcggcggagggaccaagctgac cgtcctag |

| ZKA230 | SEQ ID NO. | Amino acid sequence |
|---|---|---|
| CDRH1 | 37 | GGSISSDY |
| CDRH2 | 38 | IYYSGST |
| CDRH3 | 39 | ARRRKYDSLWGSFAFDI |
| CDRL1 | 40 | SSNIGGNY |
| CDRL2 | 41 | IND |
| CDRL2 long | 42 | LICINDHRP |
| CDRL3 | 43 | ATWDDSLGGLV |
| VH | 44 | QVQLQESGPGLVKPSETLSLTCAVSGGSISSDYWSWIRQP PGKGLEWIGYIYYSGSTNYNPSLKSRVTISVDTSKNHFSL KLNSVTAADTAVYYCARRRKYDSLWGSFAFDIWGQGTMVT VSS |
| VL | 45 | QSVLTQPPSASGTPGQRVTISCSGSSSNIGGNYVYWYQQL PGTAPKLLICINDHRPSGVPDRFSGSKSGTSASLAISGLQ SEDEADYYCATWDDSLGGLVFGGGTKLTVL |

| ZKA230 | SEQ ID NO. | Nucleic acid sequence |
|---|---|---|
| CDRH1 | 46 | ggtggctccatcagtagtgactac |
| CDRH2 | 47 | atctattacagtgggagcacc |
| CDRH3 | 48 | gcgaggaggaggaagtatgattcccttggggggagttttg cttttgatatc |
| CDRL1 | 49 | agctccaacatcggaggtaattat |
| CDRL2 | 50 | attaatgat |
| CDRL2 long | 51 | ctcatctgtattaatgatcaccggccc |
| CDRL3 | 52 | gcaacatgggatgacagcctgggtggccttgta |
| VH | 53 | caggtgcagctgcaggagtcgggcccaggcctggtgaagc cttcggagaccctgtccctcacctgcgcagtctctggtgg ctccatcagtagtgactactggagctggatccggcagccc ccagggaagggactggagtggattgggtatatctattaca gtgggagcaccaactacaacccctcactcaagagtcgagt |

|   |   | caccatatcagtagacacgtccaagaaccacttctccctg |
|---|---|---|
|   |   | aagctgaactctgtgaccgctgcggacacggccgtgtatt |
|   |   | actgtgcgaggaggaggaagtatgattcccttgggggag |
|   |   | ttttgcttttgatatctggggccaagggacaatggtcacc |
|   |   | gtctcttcag |
| VL | 54 | cagtctgtgctgactcagccaccctcagcgtctgggaccc |
|   |   | ccgggcagagggtcaccatctcttgttctggaagcagctc |
|   |   | caacatcggaggtaattatgtatactggtaccagcagctc |
|   |   | ccaggaacggccccccaaactcctcatctgtattaatgatc |
|   |   | accggccctcaggggtccctgaccgattctctggctccaa |
|   |   | gtctggcacctcagcctccctggccatcagtgggctccag |
|   |   | tccgaggatgaggctgattattactgtgcaacatgggatg |
|   |   | acagcctgggtggccttgtattcggcggagggaccaagct |
|   |   | gaccgtcctag |

| ZKA78 | SEQ ID NO. | Amino acid sequence |
|---|---|---|
| CDRH1 | 55 | GFTFSNYA |
| CDRH2 | 56 | IGRNGDSI |
| CDRH3 | 57 | VKDLAIPESYRIEADY |
| CDRL1 | 58 | QSVLYRSNNKNY |
| CDRL2 | 59 | WAS |
| CDRL2 long | 60 | LIYWASTRE |
| CDRL3 | 61 | QQYYSSPRT |
| VH | 62 | EVQLAESGGGLVQPGGSLTLSCSGSGFTFSNYAMVWARQA PGKGLEYVSGIGRNGDSIYYTDSVKGRFTISRDNSKSMVY LQMSSLRTEDTAVYYCVKDLAIPESYRIEADYWGQGTLVI VSA |
| VL | 63 | DIVMTQSPDSLAVSLGERATINCKSSQSVLYRSNNKNYLS WYQQKPGQPPKLLIYWASTRESGVPDRFSGSGSGTDFTLT ISPLQAEDVAVYYCQQYYSSPRTFGQGTKVEIK |

| ZKA78 | SEQ ID NO. | Nucleic acid sequence |
|---|---|---|
| CDRH1 | 64 | ggcttcacttttagtaactatgca |
| CDRH2 | 65 | atcgggcgcaacggggactctatc |
| CDRH3 | 66 | gtgaaagatctggccatccccgagtcctacagaattgaag ctgattat |
| CDRL1 | 67 | cagtccgtgctgtaccgctctaacaacaagaattac |
| CDRL2 | 68 | tgggcttca |
| CDRL2 long | 69 | ctgatctattgggcttcaacccgggaa |
| CDRL3 | 70 | cagcagtactattctagtcctcgaact |
| VH | 71 | gaggtgcagctggcagaatcaggcgggggactggtccagc ctggcggcagcctgacactgtcttgcagtggatcaggctt cacttttagtaactatgcaatggtgtgggcaaggcaggct cctgggaagggactggagtatgtctctggcatcgggcgca acggggactctatctactatactgatagtgtgaagggccg gttcaccatcagcagagacaatagcaaatccatggtgtac ctgcagatgagctccctgcgaaccgaagacacagcagtgt actattgcgtgaaagatctggccatccccgagtcctacag aattgaagctgattattggggacagggcaccctggtcatc gtgagcgccg |
| VL | 72 | gacatcgtgatgacacagtctccagatagtctggcagtca gtctgggggagagggccactattaactgcaagagctccca gtccgtgctgtaccgctctaacaacaagaattacctgtct tggtatcagcagaagcccggacagccccctaaactgctga tctattgggcttcaacccgggaaagcggcgtcccagacag attctcaggcagcgggtccggaacagacttcaccctgaca attagccccctgcaggcagaggacgtggctgtctactatt gtcagcagtactattctagtcctcgaacttttcggccaggg |

| | | |
|---|---|---|
| | | gaccaaggtggaaatcaaac |
| ZKA64 | SEQ ID NO. | Amino acid sequence |
| CDRH1 | 73 | GYTFTGYH |
| CDRH2 | 74 | INPNSGGT |
| CDRH3 | 75 | ARMSSSIWGFDH |
| CDRL1 | 76 | QSVLIN |
| CDRL2 | 77 | GAS |
| CDRL2 long | 78 | LIYGASSRA |
| CDRL3 | 79 | QQYNDWPPIT |
| VH | 80 | QVQLVQSGAEVKKPGASVKVSCKASGYTFTGYHIDWVRQA RGQGLEWMGRINPNSGGTNYAQKFQGRVTMTRDTSISTAY MQLSRLRSDDSAVYYCARMSSSIWGFDHWGQGTLVTVSS |
| VL | 81 | EIVMTQSPATLSVSPGERATLSCRASQSVLINLAWYQQKP GQAPRLLIYGASSRATGIPARFSGSGSGTEFTLTISSLQS EDFAVYYCQQYNDWPPITFGQGTRLEIK |
| ZKA64 | SEQ ID NO. | Nucleic acid sequence |
| CDRH1 | 82 | ggctacaccttcacagggtatcac |
| CDRH2 | 83 | attaaccctaattctggcgggacc |
| CDRH3 | 84 | gctcggatgagctcctctatttggggcttcgatcat |
| CDRL1 | 85 | cagtctgtgctgattaac |
| CDRL2 | 86 | ggagcatcc |
| CDRL2 long | 87 | ctgatctatggagcatcctccagggct |
| CDRL3 | 88 | cagcagtacaatgattggccccctatcaca |
| VH | 89 | caggtgcagctggtccagagcggagcagaggtgaagaaac ccggcgcctcagtgaaggtcagctgcaaagcttccggcta caccttcacagggtatcacatcgactgggtgaggcaggca agaggacagggactggaatggatgggacgattaaccctaa ttctggcgggaccaactacgcccagaagtttcagggccg agtgactatgaccagagacaccagcatctccacagcttat atgcagctgtcccggctgagatctgacgatagtgccgtct actattgtgctcggatgagctcctctatttggggcttcga tcattgggggcagggaacactggtgactgtcagttcag |
| VL | 90 | gagatcgtgatgactcagtctccagccaccctgtcagtca gcccaggagaacgggcaaccctgtcttgcagagcctccca gtctgtgctgattaacctggcttggtaccagcagaagcca ggccaggcaccccgactgctgatctatggagcatcctcca gggctaccggcattcctgcacgcttcagtggatcaggaag cggaacagagtttaccctgacaatctctagtctgcagtcc gaagacttcgctgtctactattgtcagcagtacaatgatt ggccccctatcacatttggccaggggactagactggagat caagc |
| ZKA15 | SEQ ID NO. | Amino acid sequence |
| CDRH1 | 91 | GGFINSYY |
| CDRH2 | 92 | IYKSGST |
| CDRH3 | 93 | ARDPYGDYVKAFDI |
| CDRL1 | 94 | QSLLHSNGYNY |
| CDRL2 | 95 | LGS |
| CDRL2 long | 96 | LIYLGSNRA |

| | | -continued |
|---|---|---|
| CDRL3 | 97 | MQALQTVT |
| VH | 98 | QVQLQESGPGLVKPSETLSLTCTVSGGFINSYYWSIRQPAGKGLEWIGRIYKSGSTNYNPSLKSRVTMSLDTSKYQFSLKLRSVTAADTAVYYCARDPYGDYVKAFDIWGQGTMVTVSS |
| VL | 99 | DIVMTQSPLSLPVTPGEPASISCRSSQSLLHSNGYNYLNWYLQKPGQSPQLLIYLGSNRASGVPDRFSGSGSGTDFTLKISRVEAEDVGVYYCMQALQTVTFGPGTKVDIK |

| ZKA15 | SEQ ID NO. | Nucleic acid sequence |
|---|---|---|
| CDRH1 | 100 | ggtggcttcatcaatagttactac |
| CDRH2 | 101 | atctataaaagtgggagcacc |
| CDRH3 | 102 | gcgagagatccctacggtgactacgttaaggcttttgatatt |
| CDRL1 | 103 | cagagcctcctgcatagtaatggatacaactat |
| CDRL2 | 104 | ttgggttct |
| CDRL2 long | 105 | ctgatctatttgggttctaatcgggcc |
| CDRL3 | 106 | atgcaagctctacaaactgtcact |
| VH | 107 | caggtgcagctgcaggagtcggggccaggactggtgaagccttcggagaccctgtccctcacctgcactgtctccggtggcttcatcaatagttactactggagctggatccggcagcccgccgggaagggactggagtggattgggcgtatctataaaagtgggagcaccaactacaacccctccctcaagagtcgagtcaccatgtcactagacacgtccaagtaccagttctccctgaagctgaggtctgtgaccgccgctgacacggccgtgtattactgtgcgagagatccctacggtgactacgttaaggctttt gatatttggggccaagggacaatggtcaccgtctcttcag |
| VL | 108 | gatattgtgatgactcagtctccactctccctgcccgtcacccctggagagccggcctccatctcctgcaggtctagtcagagcctcctgcatagtaatggatacaactatttgaattggtacctgcagaagccagggcagtctccacagctcctgatctatttgggttctaatcgggcctccggggtccctgacaggttcagtggcagtggatcaggcacagattttacactgaaaatcagcagagtggaggctgaggatgttggggtttattactgcatgcaagctctacaaactgtcactttcggccctgggaccaaagtggatatcaaac |

| ZKA25 | SEQ ID NO. | Amino acid sequence |
|---|---|---|
| CDRH1 | 109 | GFTFRSHW |
| CDRH2 | 110 | IKEDGYEK |
| CDRH3 | 111 | ARDLRVYSGRGFDP |
| CDRL1 | 112 | KLGDKY |
| CDRL2 | 113 | QDS |
| CDRL2 long | 114 | VIYQDSKRP |
| CDRL3 | 115 | QAWDSSTVV |
| VH | 116 | EVQLVESGGGLVRPGGSLRLSCAASGFTFRSHWMSWVRQAPGKGLEWVANIKEDGYEKYYVDSVKGRFTISRDNAKNSLYLQMKSLRAEDTAVYYCARDLRVYSGRGFDPWGQGTLVTVSS |
| VL | 117 | SYELTQPPSLSVSPGQTASITCSGDKLGDKYACWYQQKPGQSPVLVIYQDSKRPSGIPARFSGSNSGNTATLTISGTQAMDEADYYCQAWDSSTVVFGGGTKLTVL |

-continued

| ZKA25 | SEQ ID NO. | Nucleic acid sequence |
|---|---|---|
| CDRH1 | 118 | ggattcacctttagaagtcattgg |
| CDRH2 | 119 | ataaaggaagatggatatgagaaa |
| CDRH3 | 120 | gcgagagatttgagggtatatagtgggagaggtttcgacccc |
| CDRL1 | 121 | aaattgggggataaatat |
| CDRL2 | 122 | caagatagc |
| CDRL2 long | 123 | gtcatctatcaagatagcaagcggccc |
| CDRL3 | 124 | caggcgtgggacagcagcactgtggta |
| VH | 125 | gaggtgcagttggtggagtctggggggaggcttggtccggcctggggggtccctgagactctcctgtgcagcctctggattcacctttagaagtcattggatgagttgggtccgccaggctccagggaaggggctggagtgggtggccaacataaaggaagatggatatgagaaatactatgtggactctgtgaagggccgattcaccatctccagagacaacgccaagaactcactgtatctgcaaatgaagagcctgagagccgaggacacggccgtgtattactgtgcgagagatttgagggtatatagtgggagaggtttcgaccccctggggccagggaaccctggtcaccgtctcctcag |
| VL | 126 | tcctatgagctgactcagccaccctcactgtccgtgtcccaggacagacagccagcatcacctgctctggagataaattgggggataaatatgcttgctggtatcagcagaagccaggccagtcccctgtgttggtcatctatcaagatagcaagcggccctcagggatccctgcgcgattctctggctccaactctggggaacacagccactctgaccatcagcgggacccaggctatgatgaggctgactattactgtcaggcgtgggacagcagcactgtggtattcggtggagggaccaagctgaccgtcctag |

| ZKA35 | SEQ ID NO. | Amino acid sequence |
|---|---|---|
| CDRH1 | 127 | GGSISTGGYY |
| CDRH2 | 128 | IYYSGNT |
| CDRH3 | 129 | AKGGGRERPFDY |
| CDRL1 | 130 | SSNIGRNY |
| CDRL2 | 131 | RNN |
| CDRL2 long | 132 | LIYRNNQRP |
| CDRL3 | 133 | VAWDDSRSGFVV |
| VH | 134 | QVQLQESGPGLVKPSQTLSLTCTVSGGSISTGGYYWSWIRQHPGKGLEWIGYIYYSGNTYYNPSLKSRVTISVDTSKKQFSLKLSSVTAADTAVYYCAKGGGRERPFDYWGQGTLVTVSS |
| VL | 135 | QSVLTQPPSASGTPGQRVTISCSGSSSNIGRNYVDWYQQLPGTAPKLLIYRNNQRPSGVPERFSGSKSGTSASLAISGLRSEDEADYYCVAWDDSRSGFVVFGGGTKVTVL |

| ZKA35 | SEQ ID NO. | Nucleic acid sequence |
|---|---|---|
| CDRH1 | 136 | ggtggctccatcagcactggtggttactac |
| CDRH2 | 137 | atctattacagtgggaacacc |
| CDRH3 | 138 | gcgaaaggaggagggagggagcgaccctttgactac |
| CDRL1 | 139 | agctccaacatcggaagaaattat |
| CDRL2 | 140 | aggaataat |
| CDRL2 long | 141 | ctcatctataggaataatcagcggccc |

| | SEQ ID NO. | Sequence |
|---|---|---|
| CDRL3 | 142 | gtagcatgggatgacagccggagtggttttgtggta |
| VH | 143 | caggtgcagctgcaggagtcgggcccaggactggtgaagc cttcacagaccctgtccctcacctgcactgtctctggtgg ctccatcagcactggtggttactactggagctggatccgc cagcacccagggaagggcctggagtggattggttacatct attacagtgggaacacctactacaacccgtccctcaagag tcgagttaccatatcagttgacacctctaagaagcagttc tccctgaagctgagctctgtgactgccgcggacacggccg tgtattactgtgcgaaaggaggagggagggagcgacccc tgactactggggccagggaaccctggtcaccgtctcctca g |
| VL | 144 | cagtctgtgctgactcagccaccctcagcgtctgggaccc ccgggcagagggtcaccatctcttgttctggaagcagctc caacatcggaagaaattatgtagactggtaccagcaactc ccaggaacggcccccaaactcctcatctataggaataatc agcggccctcaggggtccctgagcgattctctggctccaa gtctggcacctcagcctccctggccatcagtgggctccgg tccgaggatgaggctgattattactgtgtagcatgggatg acagccggagtggttttgtggtattcggcggagggaccaa ggtgaccgtcctag |

| Constant regions | SEQ ID NO. | Sequence |
|---|---|---|
| IgG1 CH1-CH2-CH3 aa | 145 | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK |
| IgG1 CH1-CH2-CH3 LALA aa | 146 | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPE<u>AA</u>GG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGK |
| IgG CK aa | 147 | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC |
| IgG CL aa | 148 | GQPKAAPSVTLFPPSSEELQANKATLVCLISDFYPGAV TVAWKADSSPVKAGVETTTPSKQSNNKYAASSYLSLT PEQWKSHRSYSCQVTHEGSTVEKTVAPTECS |
| IgG1 CH1-CH2-CH3 nucl | 149 | gcgtcgaccaagggcccatcggtcttccccctggcaccct cctccaagagcacctctggggggcacagcggccctgggctg cctggtcaaggactacttccccgaacctgtgacggtgtcg tggaactcaggcgccctgaccagcggcgtgcacaccttcc cggctgtcctacagtcctcaggactctactccctcagcag cgtggtgaccgtgccctccagcagcttgggcacccagacc tacatctgcaacgtgaatcacaagcccagcaacaccaagg tggacaagagagttgagcccaaatcttgtgacaaaactca cacatgcccaccgtgcccagcacctgaactcctgggggga ccgtcagtcttcctcttccccccaaaacccaaggacaccc tcatgatctcccggacccctgaggtcacatgcgtggtggt ggacgtgagccacgaAgaCcctgaggtcaagttcaactgg tacgtggacggcgtggaggtgcataatgccaagacaaagc cgcgggaggagcagtacaacagcacgtaccgtgtggtcag cgtcctcaccgtcctgcaccaggactggctgaatggcaag gagtacaagtgcaaggtctccaacaaagcccttccagccc ccatcgagaaaaccatctccaaagccaaagggcagccccg agaaccacaggtgtacaccctgcccccatcccgggaggag atgaccaagaaccaggtcagcctgacctgcctggtcaaag gcttctatcccagcgacatcgccgtggagtgggagagcaa tgggcagccggagaacaactacaagaccacgcctcccgtg |

-continued

| | | |
|---|---|---|
| | | ctggactccgacggctccttcttcctctatagcaagctca<br>ccgtggacaagagcaggtggcagcaggggaacgtcttctc<br>atgctccgtgatgcatgaggctctgcacaaccactacacg<br>cagaagagcctctccctgtccccgggtaaa |
| IgG1<br>CH1-CH2-CH3<br>LALA<br>nucl | 150 | gcgtcgaccaagggcccatcggtcttccccctggcaccct<br>cctccaagagcacctctggggggcacagcggccctgggctg<br>cctggtcaaggactacttccccgaacctgtgacggtctcg<br>tggaactcaggcgccctgaccagcggcgtgcacaccttcc<br>cggctgtcctacagtcctcaggactctactccctcagcag<br>cgtggtgaccgtgccctccagcagcttgggcacccagacc<br>tacatctgcaacgtgaatcacaagcccagcaacaccaagg<br>tggacaagagagttgagcccaaatcttgtgacaaaactca<br>cacatgcccaccgtgcccagcacctgaaGCCGCGggggga<br>ccgtcagtcttcctcttccccccaaaacccaaggacaccc<br>tcatgatctcccggaccctgaggtcacatgcgtggtggt<br>ggacgtgagccacgaagaccctgaggtcaagttcaactgg<br>tacgtggacggcgtggaggtgcataatgccaagacaaagc<br>cgcgggaggagcagtacaacagcacgtaccgtgtggtcag<br>cgtcctcaccgtcctgcaccaggactggctgaatggcaag<br>gagtacaagtgcaaggtctccaacaaagcccctcccagccc<br>ccatcgagaaaaccatctccaaagccaaagggcagccccg<br>agaaccacaggtgtacaccctgcccccatcccgggaggag<br>atgaccaagaaccaggtcagcctgacctgcctggtcaaag<br>gcttctatcccagcgacatcgccgtggagtgggagagcaa<br>tgggcagccggagaacaactacaagaccacgcctcccgtg<br>ctggactccgacggctccttcttcctctatagcaagctca<br>ccgtggacaagagcaggtggcagcaggggaacgtcttctc<br>atgctccgtgatgcatgaggctctgcacaaccactacacg<br>cagaagagcctctccctgtccccgggtaaa |
| IgG CK<br>nucl | 151 | cgTacGgtggctgcaccatctgtcttcatcttcccgccat<br>ctgatgagcagttgaaatctggaactgcctctgttgtgtg<br>cctgctgaataacttctatcccagagaggccaaagtacag<br>tggaaggtggataacgccctccaatcgggtaactcccagg<br>agagtgtcacagagcaggacagcaaggacagcacctacag<br>cctcagcagcaccctgacgctgagcaaagcagactacgag<br>aaacacaaagtctacgcctgcgaagtcacccatcagggcc<br>tgagctcgcccgtcacaaagagcttcaacaggggagagtg<br>t |
| IgG CL<br>nucl | 152 | ggtcagcccaaggctgccccctcggtcactctgttcccgc<br>cctcctctgaggagcttcaagccaacaaggccacactggt<br>gtgtctcataagtgacttctacccgggagccgtgacagtg<br>gcttggaaagcagatagcagccccgtcaaggcgggagtgg<br>agaccaccacaccctccaaacaaagcaacaacaagtacgc<br>ggccagcagctatctgagcctgacgcctgagcagtggaag<br>tcccacagaagctacgctgccaggtcacgcatgaaggga<br>gcaccgtggagaagacagtggcccctacagaatgttca |

| | SEQ ID NO. | Amino acid sequence |
|---|---|---|
| ZKA10 | | |
| CDRH1 | 153 | GFTFSDSY |
| CDRH2 | 154 | ISSSSPFT |
| CDRH3 | 155 | ARGLVRDGYKWLYFFDY |
| VH | 156 | QVQLVESGGGLVEPRGSLRLSCAASGFTFSDSYMSWIRQA<br>PGKGLEWISYISSSSPFTNYADSVKGRFTISRDNAKNSLY<br>LQMNSLRAEDTAVYYCARGLVRDGYKWLYFFDYWGQGTLV<br>TVSS |
| ZKA18 | | |
| CDRH1 | 157 | GFTFSSYG |
| CDRH2 | 158 | IWYDGSNK |
| CDRH3 | 159 | ARDDSGYSEPFDY |
| VH | 160 | QVQLVESGGGVVQPGRSLRLSCAASGFTFSSYGMHWVRQA<br>PGKGLEWVAVIWYDGSNKYYADSVKGRFTITRDNSKNTLY<br>LQMNSLRPEDTAVYYCARDDSGYSEPFDYWGQGTLVTVSS |

-continued

ZKA28

| | | |
|---|---|---|
| CDRH1 | 161 | GFTVSRNY |
| CDRH2 | 162 | IYSGGST |
| CDRH3 | 163 | ARWINDAFDI |
| VH | 164 | EVQLVESGGGLIQPGGSLRLSCAASGFTVSRNYMSWVRQA PGKGLEWVSIYSGGSTYYADSVKGRFTISRDNSKNTLYL QMNSLRAEDTAVYYCARWINDAFDIWGQGTMVTVSS |

ZKA29

| | | |
|---|---|---|
| CDRH1 | 165 | GFTFSRYS |
| CDRH2 | 166 | ISPRSTTI |
| CDRH3 | 167 | AREDCTNGVCYRVDY |
| VH | 168 | EVQLVESGGGLVQPGGSLRLSCVVSGFTFSRYSMNWVRQA PGKGLEWVSYISPRSTTIYYADSVEGRFTVSRDNAKNSLY LQLNSLRAEDTAVYYCAREDCTNGVCYRVDYWGQGTLVTV SS |

ZKA33

| | | |
|---|---|---|
| CDRH1 | 169 | GFTFSRNW |
| CDRH2 | 170 | IKEDGNEK |
| CDRH3 | 171 | ARPFHQGGYAYGLAY |
| VH | 172 | EVQLVESGGGLVQPGGSLRLSCAASGFTFSRNWMTWVRQA PGKGLEWVANIKEDGNEKYYVDSVKGRFTISRDNAKNSLY LQMNSLRAEDTAVYYCARPFHQGGYAYGLAYWGQGTLVTV SS |

ZKA39

| | | |
|---|---|---|
| CDRH1 | 173 | GFTFSTYS |
| CDRH2 | 174 | ISPSSSTI |
| CDRH3 | 175 | AREYCSGGSCYLLDY |
| VH | 176 | EVQLVESGGGLVQPGGSLRLSCAASGFTFSTYSMNWVRQA PGKGLEWVSYISPSSSTIYYPDSLKGRFTISRDNAKNSLY LQMDSLRAEDTAQYYCAREYCSGGSCYLLDYWGQGTLVTV SS |

ZKA43

| | | |
|---|---|---|
| CDRH1 | 177 | GGSITSYY |
| CDRH2 | 178 | SHYSGST |
| CDRH3 | 179 | ARGIYSGKNWFDP |
| VH | 180 | QVQLQESGPGLVKPSETLSLTCTVYGGSITSYYWTWIRQP PGKGLEWIGYSHYSGSTNYNPSLKSRVTISIDTSKSQFSL NLNSVTAADTAVYYCARGIYSGKNWFDPWGQGTLVTVSS |

ZKA44

| | | |
|---|---|---|
| CDRH1 | 181 | GFTVSTSY |
| CDRH2 | 182 | IYSSGST |
| CDRH3 | 183 | ARVSLGGLDP |
| VH | 184 | EVQLVESGGGLIQPGGSLRLSCVASGFTVSTSYMNWVRQA PGKGLEWVSIYSSGSTYYADSVKGRFTISRNTSKNTLYL QMNSLRAEDTAVYYCARVSLGGLDPWGQGTPVTVSS |

ZKA46

| | | |
|---|---|---|
| CDRH1 | 185 | GFSLSNGRMG |
| CDRH2 | 186 | IFSNDEK |
| CDRH3 | 187 | ARVEFRAGNYLDS |
| VH | 188 | QVTLKESGPVLVKPTETLTLTCTVSGFSLSNGRMGVSWIRQPPGKALEWLAHIFSNDEKYYSTSLKNRLTISKDTSKSQVVLTMTNMDPVDTATYYCARVEFRAGNYLDSWGQGTLVTVSS |

ZKA50

| | | |
|---|---|---|
| CDRH1 | 189 | GYTFTNSW |
| CDRH2 | 190 | IYPGDSDT |
| CDRH3 | 191 | ARQPFFDY |
| VH | 192 | EVQLVQSGAQVKKPGESLKISCKASGYTFTNSWIGWVRQMPGKGLEWMGIIYPGDSDTRYSPSFQGQVTISADKSISTAYLQWSSLKASDTAMYYCARQPFFDYWGQGTLVTVSS |

ZKA54

| | | |
|---|---|---|
| CDRH1 | 193 | GYTFTGYY |
| CDRH2 | 194 | INANSGGT |
| CDRH3 | 195 | AHSDIVVVPSDDYYALDV |
| VH | 196 | QVQLVQSGAEVKKPGASVKVSCKTSGYTFTGYYMHWVRQAPGQGLEWMGWINANSGGTNFAQRFQGRVTMTWDTSISTAYMELSRLRSDDTAVYYCAHSDIVVVPSDDYYALDVWGQGTTVTVSS |

ZKB18

| | | |
|---|---|---|
| CDRH1 | 197 | GYSFTSYW |
| CDRH2 | 198 | IYPGDSDT |
| CDRH3 | 199 | ARQTPGDY |
| VH | 200 | EVQLVQSGAEVKKPGESLKISCKTFGYSFTSYWIGWVRQMPGKGLEWMGMIYPGDSDTRYSPSFQGQVTISADMSISTAYLQWSSLKASDTAMYYCARQTPGDYWGQGTLVTVSS |

ZKB20

| | | |
|---|---|---|
| CDRH1 | 201 | GYFFTRYV |
| CDRH2 | 202 | INTDNGST |
| CDRH3 | 203 | ARGTGRDGYNSFFAN |
| VH | 204 | QVQLVQSGAEVKKPGASVRVSCKASGYFFTRYVILWVRQAPGQRPEWMGWINTDNGSTRYSQKFQGRVTITKDTSATTAYMDLSSLKSDDTAVYYCARGTGRDGYNSFFANWGQGTLVTVSP |

ZKB21

| | | |
|---|---|---|
| CDRH1 | 205 | GYTFTGYS |
| CDRH2 | 206 | IDTNSGDT |
| CDRH3 | 207 | ARDRERHPFSY |
| VH | 208 | QVQLVQSGAEVKKPGASVKVSCKASGYTFTGYSIHWVRQAPGQGLAWMGRIDTNSGDTNYAERFQGRVTMTRDTSISTAYMEVRRLRSDDTAVYYCARDRERHPFSYWGQGTLVTVSS |

ZKB23

| | | |
|---|---|---|
| CDRH1 | 209 | GGSISSGDYS |
| CDRH2 | 210 | ITHSGTT |
| CDRH3 | 211 | ARHFGWFDP |
| VH | 212 | QLQLQESGSGLVKPSQTLSLTCAVSGGSISSGDYSWSWIRQPPGKGLEWIGYITHSGTTYFNPSLKSRVTISVDRSRNQFSLKVTSVTAADTAVYYCARHFGWFDPWGQGTLVTVSS |

ZKC29

| | | |
|---|---|---|
| CDRH1 | 213 | GGSISSGEYF |
| CDRH2 | 214 | IHNRGNT |
| CDRH3 | 215 | ARGGGDLVVVPDSIWDYYGMDV |
| VH | 216 | QVQLQESGPGLVRPSQTLSLTCTVSGGSISSGEYFWTWIRQHPKKGLEWIGYIHNRGNTYYNPSLKSRLSISLDTSKNHLSLRLSSVTAADTAVYYCARGGGDLVVVPDSIWDYYGMDVWGQGTTVTVSS |

ZKC31

| | | |
|---|---|---|
| CDRH1 | 217 | GGSISSGGYH |
| CDRH2 | 218 | IYYSGST |
| CDRH3 | 219 | ARDRSEPGEYHYYYYAMDV |
| VH | 220 | QVQLQESGPGLVKPSQTLSLTCTVSGGSISSGGYHWSWIRQHPGKGLEWIGYIYYSGSTYYNPSLKRRVTISVDTSKNQFSLKLSSVSAADTAVYYCARDRSEPGEYHYYYYAMDVWGQGTTVTVSS |

ZKC32

| | | |
|---|---|---|
| CDRH1 | 221 | GFTVSSNY |
| CDRH2 | 222 | IYSSGST |
| CDRH3 | 223 | ARGKKGNAFDI |
| VH | 224 | EVQLVESGGDLIQPGGSLRLSCAASGFTVSSNYMSWVRQAPGKGLEWVSVIYSSGSTYYADSVKGRFTISRDNSKNTLYLQMNSLRAGDTAVYYCARGKKGNAFDIWGQGTVVTVSS |

ZKC33

| | | |
|---|---|---|
| CDRH1 | 225 | GDSISSRTFS |
| CDRH2 | 226 | IYYSGST |
| CDRH3 | 227 | ARRNAEFFSFWSYYGMDV |
| VH | 228 | QVQLQESGPGLVKPSQTLSLTCTVSGDSISSRTFSWSWIRQPPGKGLEWVGHIYYSGSTDYNPSLKSRISISIDTSKNQFSLKLSSVTAADTAVYYCARRNAEFFSFWSYYGMDVWGHGTAVIVSS |

ZKC34

| | | |
|---|---|---|
| CDRH1 | 229 | GGSINSGGYY |
| CDRH2 | 230 | ILHSGNT |
| CDRH3 | 231 | ARAGDYYSGYVPPEY |
| VH | 232 | QVQLQESGPGLVKPSQTLSLTCAVSGGSINSGGYYWSWVRQHPGKGLEWIGYILHSGNTNYNPSLKSRVNIFVDTSENQFSLKLRSVTAADTAIYFCARAGDYYSGYVPPEYWGPGTLVTVSS |

-continued

ZKD25

| | | |
|---|---|---|
| CDRH1 | 233 | GFTVSSNY |
| CDRH2 | 234 | IYSGGST |
| CDRH3 | 235 | ARFGGNPSFDY |
| VH | 236 | EVQLVESGGGLVQPGGSLRLSCAASGFTVSSNYMSWVRQA PGKGLEWVSVIYSGGSTYYANSVKGRFTISRDKSNTLYL QMNNLRAEDTAVYFCARFGGNPSFDYWGQGTLVTVSS |

ZKA3

| | | |
|---|---|---|
| CDRH1 | 237 | GFIFSNYA |
| CDRH2 | 238 | IGGKGDSI |
| CDRH3 | 239 | VKDLAVLESDRLEVDQ |
| VH | 240 | EVQLAESGGGLVQPGGSLRLSCSGSGFIFSNYAMWARQA PGKGLEYVSGIGGKGDSIYHIDSVKGRFTISRDNSKRTVY LQMSRLRTEDTAVYYCVKDLAVLESDRLEVDQWGQGTLVI VSA |

ZKA4

| | | |
|---|---|---|
| CDRH1 | 241 | GFTFSSYV |
| CDRH2 | 242 | TSYDGSNK |
| CDRH3 | 243 | ARGPVPYWSGESYSGAYFDF |
| VH | 244 | QVQLVESGGGVVQPGRSLRLSCAASGFTFSSYVMHWVRQA PGKGLEWVTVTSYDGSNKYYADSVKGRFTISRDNAKNTLY LQMNSLRGEDTAIYYCARGPVPYWSGESYSGAYFDFWGQG ILVTVSS |

ZKA5

| | | |
|---|---|---|
| CDRH1 | 245 | GFTFSNYY |
| CDRH2 | 246 | MSSSETIK |
| CDRH3 | 247 | ARSGIETVAGSIDYYGMDV |
| VH | 248 | QVQLVESGGGLVKPGGSLRLSCAGSGFTFSNYYMTWIRQA PGKGLELVSYMSSSETIKYYADSVKGRFTISRDNAKNSLY LQMNSLRADDTARYYCARSGIETVAGSIDYYGMDVWGHGT PVTVSS |

ZKA6

| | | |
|---|---|---|
| CDRH1 | 249 | DFTVSNYA |
| CDRH2 | 250 | VSYDGSNK |
| CDRH3 | 251 | ATGVTMFQGAQTNAEYLHY |
| VH | 252 | QVHLVESGGGVVQPGRSLRLSCEASDFTVSNYAMHWVRQA PGKGLEWVAVVSYDGSNKYYADSVKGRFTISRDNSKNTLY LQMNSLRAEDTALYYCATGVTMFQGAQTNAEYLHYWGQGS LVTISS |

ZKA7

| | | |
|---|---|---|
| CDRH1 | 253 | GFTFSRYG |
| CDRH2 | 254 | VSGDGSST |
| CDRH3 | 255 | VKDFWSGDQSLESDF |
| VH | 256 | EVQLVESGGGLVQPGGSLRLSCSASGFTFSRYGMVWARQA PGKGLEYLSGVSGDGSSTYYANSVKGRFTISRDNSKNTLY LHMSRLRDEDTAMYYCVKDFWSGDQSLESDFWGQGALVTV SS |

| ZKA8 | | |
|---|---|---|
| CDRH1 | 257 | GFTFSAHA |
| CDRH2 | 258 | ISRNEDYT |
| CDRH3 | 259 | VKDFGTSPQTDF |
| VH | 260 | DERLVESGGGLVQPGGSLRLVCSASGFTFSAHAMHWVRQP PGKGLEYVSTISRNEDYTYYADSVKGRFTISRDNSKNSLY LQMRRLRPEDTAIYYCVKDFGTSPQTDFWGQGTLVAVSS |
| ZKA76 | | |
| CDRH1 | 261 | GFTFSTYF |
| CDRH2 | 262 | ISSTGSYK |
| CDRH3 | 263 | ARPFHSEYTYGLDAFDI |
| VH | 264 | EVQLVESGGGLVKPGGSLRLSCAASGFTFSTYFMHWVRQA PGKGLEWVASISSTGSYKFYADSVKGRFTISRDNTKNSLF LQMNSLRAEDTAVFYCARPFHSEYTYGLDAFDIWGQGTML TVSS |
| ZKA117 | | |
| CDRH1 | 265 | GGSIRRTNSY |
| CDRH2 | 266 | ISYSGST |
| CDRH3 | 267 | ARLNDGSTVTTSSYFDY |
| VH | 268 | QLQLQESGPGLVKPSETLSLTCTVSGGSIRRTNSYWGWIR QTTGKGLQWIGSISYSGSTFYNPSLKSRVTISLDTSKDHF SLELSSVTAADTAIYYCARLNDGSTVTTSSYFDYWGQGTL VTVSS |
| ZKB27 | | |
| CDRH1 | 269 | GYSFTSSW |
| CDRH2 | 270 | IDPSDSYT |
| CDRH3 | 271 | ARHDYSVSENGMDV |
| VH | 272 | EVQLVQSGAEVKKPGESLRISCKASGYSFTSSWINWVRQM PGKGLEWMGRIDPSDSYTTYNPSFQGHVTISVDKSIGTAY LQWNSLRASDTAMYYCARHDYSVSENGMDVWGQGTTVTVS S |
| ZKB29 | | |
| CDRH1 | 273 | GFTFSSYT |
| CDRH2 | 274 | ISYDGSHK |
| CDRH3 | 275 | ARRSYSISCFDY |
| VH | 276 | QVQLVESGGGVVQPGRSLRLSCAASGFTFSSYTMHWVRQA PGKGLEWVAVISYDGSHKFYADSVKGRFTISRDNSKDTLY LQMNSLRAEDTALYYCARRSYSISCFDYWGQGTLVTISS |
| ZKB34 | | |
| CDRH1 | 277 | GFTFSRSG |
| CDRH2 | 278 | VSYDGSNK |
| CDRH3 | 279 | AKDLTMVRGVHYYYYVMDV |
| VH | 280 | QVQLVESGGGVVQPGRSLRLSCAASGFTFSRSGMHWVRQA PGKGLEWVAVVSYDGSNKYYSDSVKGRFTISRDNSKNTLY LQMNSLRVEDTAVYYCAKDLTMVRGVHYYYYVMDVWGQGT TVTVSS |

ZKB39

| | | |
|---|---|---|
| CDRH1 | 281 | GYTFDDYY |
| CDRH2 | 282 | INPHRGGT |
| CDRH3 | 283 | VRDQYCDGGNCYGIHQPHYGMDV |
| VH | 284 | QVQLVQSGAEVKKPGASLKVSCKASGYTFDDYYIHWVRQAPGQGLEWLGRINPHRGGTNYAQKFQGRVIMTLDMSISTTYMELRRITSDDAAVYYCVRDQYCDGGNCYGIHQPHYGMDVWGQGTTVTVSS |

ZKB46

| | | |
|---|---|---|
| CDRH1 | 285 | GYSFTSYW |
| CDRH2 | 286 | IDPSDSYT |
| CDRH3 | 287 | ARREYSSSSGQEDWFDP |
| VH | 288 | EVQLVQSGAEVKKPGESLRISCKGSGYSFTSYWISWVRQMPGKGLEWMGRIDPSDSYTNYSPSFQGHVTISADKSISTAYLQWSSLKASDTAMYYCARREYSSSSGQEDWFDPWGQGTLVTVSS |

ZKB53

| | | |
|---|---|---|
| CDRH1 | 289 | GFTFSSYA |
| CDRH2 | 290 | ISYDGSNR |
| CDRH3 | 291 | ARHVEQLPSSGYFQH |
| VH | 292 | QVQLVESGGGVVQPGRSLRLSCAASGFTFSSYAMHWVRQTPGKGLEWVTISYDGSNRYYADSVKGRFTISRDNSKNTLYLQMNSLRSEDTAVYYCARHVEQLPSSGYFQHWGQGTLVTVSS |

ZKC26

| | | |
|---|---|---|
| CDRH1 | 293 | GFIFSDFY |
| CDRH2 | 294 | IGHDGSYI |
| CDRH3 | 295 | ARAHGGFRH |
| VH | 296 | QVQVVESGGGLVKPGGSLRLSCAASGFIFSDFYMSWMRQAPGKGLEWVAYIGHDGSYILYADSVKGRFTISRDNAKNSLFLRMNSLRVEDTAVYYCARAHGGFRHWGQGTVVAVSP |

ZKD5

| | | |
|---|---|---|
| CDRH1 | 297 | GFTFTSYG |
| CDRH2 | 298 | ISYDGSNK |
| CDRH3 | 299 | ARDRDHYDLWNAYTFDY |
| VH | 300 | QVQLVESGGGVVQPGRSLRLSCAASGFTFTSYGMHWVRQTPGKGLDWVAVISYDGSNKYYADSVKGRFTISRDNSKDTLYLQMNSLRAADTALYYCARDRDHYDLWNAYTFDYWGQGTLVTVSS |

ZKD7

| | | |
|---|---|---|
| CDRH1 | 301 | GFTFSNYA |
| CDRH2 | 302 | ISYDVSDK |
| CDRH3 | 303 | AGGPLGVVVIKPSNAEHFHH |
| VH | 304 | QVQLVESGGGVVQPGRSLRLSCAASGFTFSNYAMHWVRQAPGKGLEWVAVISYDVSDKYYADSVKGRFTISRDNSKNTLFLQMNSLRAEDTAAYYCAGGPLGVVVIKPSNAEHFHHWGQGTLVTVSS |

ZKD8

| | | |
|---|---|---|
| CDRH1 | 305 | GFTFINYA |
| CDRH2 | 306 | ISYDGSNK |
| CDRH3 | 307 | ATDADAYGDSGANFHY |
| VH | 308 | QVQLVESGGGVVQPGKSLRLSCAASGFTFINYAIHWVRQAPGKGLEWVAVISYDGSNKFYTDSVKGRFTISRDNSKNTLYLQMNSLRADDTAVYYCATDADAYGDSGANFHYWGQGTLVTVSS |

ZKD15

| | | |
|---|---|---|
| CDRH1 | 309 | DASISSGGFS |
| CDRH2 | 310 | IYSSGDT |
| CDRH3 | 311 | ARAHTPTSKFYYYYAMDV |
| VH | 312 | QLQLQESGSGLVKPSQTLSLTCTVSDASISSGGFSWSWIRQPLGKGLEWLGYIYSSGDTFYNPSLQGRVTMSVDIFRSQFSLKLTSVTAADTAMYYCARAHTPTSKFYYYYAMDVWGQGTTVTVSS |

ZKD16

| | | |
|---|---|---|
| CDRH1 | 313 | GFTFSDHF |
| CDRH2 | 314 | SRNKPNSYTT |
| CDRH3 | 315 | AKVGGCYGGDCHVENDY |
| VH | 316 | EVQLVESGGDLVQPGGSLRLSCVASGFTFSDHFMDWVRQAPGKGLEWVGRSRNKPNSYTTEYAASVKGRFSISRDDSKKALYLQMNSLQTEDTAVYYCAKVGGCYGGDCHVENDYWGQGTLVTVSS |

ZKD17

| | | |
|---|---|---|
| CDRH1 | 317 | GFIFSDYA |
| CDRH2 | 318 | ISYDGSSR |
| CDRH3 | 319 | ARGYCSSGTCFSTNAEYFHP |
| VH | 320 | QVQMVESGGGVVQPGTSLRLSCATSGFIFSDYAMHWVRQAPGKGLEWVAVISYDGSSRLYADSVKGRFTVSRDNSKNTLYLQMHSLRAGDTAVYYCARGYCSSGTCFSTNAEYFHPWGQGTLATISS |

ZKD20

| | | |
|---|---|---|
| CDRH1 | 321 | GFTFSDHF |
| CDRH2 | 322 | SRNKPNSYTT |
| CDRH3 | 323 | ARVGGCNGGDCHVENDY |
| VH | 324 | EVQLVESGGGLVQPGGSLRLSCVASGFTFSDHFMDWVRQAPGKGLEWVGRSRNKPNSYTTEYAASVKGRFTISRDDSKNSLYLQMNSLQTEDTAVYYCARVGGCNGGDCHVENDYWGQGTLVTVSS |

ZKA134

| | | |
|---|---|---|
| CDRH1 | 325 | GGTFSAYA |
| CDRH2 | 326 | IIPFFGTA |
| CDRH3 | 327 | ARSDIVSTTRGYHHYGMDV |
| VH | 328 | QVHLVQSGAEVKKPGSSVNVSCKASGGTFSAYAISWVRQAPGQGLEWMGGIIPFFGTAYYAQKFKGRVTVTADKSTSTVYMEMTSLRSEDTAVYYCARSDIVSTTRGYHHYGMDVWGQGTTVTVSS |

| ZKA246 | | |
|---|---|---|
| CDRH1 | 329 | GYTFSDYY |
| CDRH2 | 330 | INPYSGGT |
| CDRH3 | 331 | ARGFTMISDREFDP |
| VH | 332 | QVQLVQSGAEVKRPGASVKVSCKASGYTFSDYYMHWVRQA PGQGLEWMGRINPYSGGTNYAQKFHGRVTVTRDTSISTVY MELRGLRSDDTAVYYCARGFTMISDREFDPWGQGTLVTVS S |

| ZKA256 | | |
|---|---|---|
| CDRH1 | 333 | GFTFSTYW |
| CDRH2 | 334 | IKQDGSEK |
| CDRH3 | 335 | ARDPGYDDFWSGSYSGSFDI |
| VH | 336 | EVQLVESGGGLVQPGGSLRLSCAASGFTFSTYWMTWVRQA PGKGLEWVANIKQDGSEKYYVDSVKGRFTISRDNTKNSLY LQVNSLRAEDTAIYYCARDPGYDDFWSGSYSGSFDIWGQG TMVTVSS |

| ZKB42 | | |
|---|---|---|
| CDRH1 | 337 | GFTFNNYG |
| CDRH2 | 338 | ISYDGNKK |
| CDRH3 | 339 | VKYGERINGYSDPFDH |
| VH | 340 | QVQVVESGGGVVQPGRSLRLFCAASGFTFNNYGMHWVRQA PGKGLEWVALISYDGNKKYYADSVKGRFSISRDNSKNTLY LQMNRLRSDTAVYHCVKYGERINGYSDPFDHWGQGTLVT VSS |

| ZKB85 | | |
|---|---|---|
| CDRH1 | 341 | GYTFTTYA |
| CDRH2 | 342 | INTNTGNP |
| CDRH3 | 343 | ARVIVPYAFDI |
| VH | 344 | QVQLVQSGSELKKPGASVKVSCKASGYTFTTYAMNWVRQA PGQGPEWVGWINTNTGNPTYAQGFTGRFVLSLDTSVSTAF LQISSLKAEDTAVYYCARVIVPYAFDIWGQGTMVTVSS |

| ZKB47 | | |
|---|---|---|
| CDRH1 | 345 | GYTFTNYY |
| CDRH2 | 346 | INPSGGPT |
| CDRH3 | 347 | ARDQYGGYARYGMDV |
| VH | 348 | QVQLVQSGAEVKKPGASVKVSCQASGYTFTNYYMHWVRQA PGQGLEWMGIINPSGGPTSYAQKFQGRVTMTDTSTSTVY MELSSLRSEDTAVYYCARDQYGGYARYGMDVWGQGTTVTV SS |

| ZKC6 | | |
|---|---|---|
| CDRH1 | 349 | GYTFTGYY |
| CDRH2 | 350 | INPNSGGT |
| CDRH3 | 351 | ARVSDWGFAFDI |
| VH | 352 | QVQLVQSGTEVKKPGASVKVSCKASGYTFTGYYMHWVRQA PGQGLEWMGRINPNSGGTNYAQKFQGRVTMTRDTSISTAY MELSGLRSDDTAVYYCARVSDWGFAFDIWGQGTMVTVSQ |

ZKA160

| | | |
|---|---|---|
| CDRH1 | 353 | GGSITSYS |
| CDRH2 | 354 | IFYSGST |
| CDRH3 | 355 | ARDQTMPVWVGGMDV |
| VH | 356 | QVQLQESGPGLVKPSETLSLTCTVSGGSITSYSWSWIRQP PGKGLEWIGYIFYSGSTDYNPSLKSRVTISVDTSKDQFSL RLRSVTAADTAVYYCARDQTMPVWVGGMDVWGQGTTVTVS S |

ZKA172

| | | |
|---|---|---|
| CDRH1 | 357 | GYIFTRYW |
| CDRH2 | 358 | IDPSDSYT |
| CDRH3 | 359 | ARQETAREDGMAV |
| VH | 360 | EVQLVQSGAEVKKPGKSLRISCKGSGYIFTRYWISWVRQM PGKGLEWMGRIDPSDSYTNYSPSFQGHVTISADKSISTAY LQWSSLKASDTAMYYCARQETAREDGMAVWGQGTTVIVSS |

ZKA174

| | | |
|---|---|---|
| CDRH1 | 361 | GGSMSNSYYH |
| CDRH2 | 362 | IYYSGST |
| CDRH3 | 363 | ARNPVFNPLTLTHDAFDI |
| VH | 364 | QLQLQESGPGLVKPSETLSLTCTVSGGSMSNSYYHWGWIR QPPGKGLEWIGSIYYSGSTYYNPSLKSRVTISVDTSKNQF SLKLNSVTAADTAVYYCARNPVFNPLTLTHDAFDIWGQGT MVTVSS |

ZKA189

| | | |
|---|---|---|
| CDRH1 | 365 | GFTFSSYA |
| CDRH2 | 366 | ISGSGDNT |
| CDRH3 | 367 | AKWPYYDFWSGSESYFDP |
| VH | 368 | GVQLLESGGALVQPGKSLRLSCAASGFTFSSYALTWVRQA PGKGLQWVSAISGSGDNTYYADSVKGRFTISRDNSKNTLY LQMNSLRAEDTAVYYCAKWPYYDFWSGSESYFDPWGQGTL VTVSS |

ZKA195

| | | |
|---|---|---|
| CDRH1 | 369 | GYNFPSYW |
| CDRH2 | 370 | IDPSDSYT |
| CDRH3 | 371 | ARADCRSTSCYLVFE |
| VH | 372 | EVQLVQSGAEVKKPGESLRISCKDSGYNFPSYWIHWVRQM PGKGLEWMGTIDPSDSYTNYSPSFQGHVTISADKSISTAY LQWSSLKASDTAMYYCARADCRSTSCYLVFEGQGTLVTVS S |

ZKA215

| | | |
|---|---|---|
| CDRH1 | 373 | GYTFTSYW |
| CDRH2 | 374 | IDPSDSHT |
| CDRH3 | 375 | ARHALPNYFDS |
| VH | 376 | EVQLVQSGAEVKKPGESLRISCKGSGYTFTSYWISWVRQM PGKGLEWMGRIDPSDSHTDYSPSFQGHVTISADKSISAAY LQWSSLKASDTAMYYCARHALPNYFDSWGQGTLVTVSS |

ZKA218

| | | |
|---|---|---|
| CDRH1 | 377 | GFPFSSYW |
| CDRH2 | 378 | INSDGRNT |
| CDRH3 | 379 | ARGGYDYDSSGCFDY |
| VH | 380 | EVQLVESGGGLVQPGGSLRLSCAASGFPFSSYWMHWVRQAPGKGLVWVSRINSDGRNTNYADSVKGRFTISRDNAENTVYLQMNSLRAEDTAVYYCARGGYDYDSSGCFDYWGQGTLVTVSS |

ZKB75

| | | |
|---|---|---|
| CDRH1 | 381 | GFTFSNYA |
| CDRH2 | 382 | ISGTGGST |
| CDRH3 | 383 | AKDSASRGGYCSGGVCYLNPGHHDY |
| VH | 384 | EVQVLESGGGLLQPGGSLRLSCAASGFTFSNYAMSWVRQAPGKGLEWVSTISGTGGSTYYADSVKGRFTISRDNSKNTLYLQMNSLRAEDTAVYYCAKDSASRGGYCSGGVCYLNPGHHDYWGQGTLVTVSS |

ZKB83

| | | |
|---|---|---|
| CDRH1 | 385 | GYSFTNYW |
| CDRH2 | 386 | IDPSDSYT |
| CDRH3 | 387 | ARLRGSLYCSGGRCYSVPGETPNWFDP |
| VH | 388 | EVQLVQSGAEVKKPGESLRISCKGSGYSFTNYWITWVRQMPGKGLEWMGSIDPSDSYTNYSPSFQGHVTISADWSINTAYLQWSSLKASDTAKYYCARLRGSLYCSGGRCYSVPGETPNWFDPWGQGTLVTVSS |

ZKC3

| | | |
|---|---|---|
| CDRH1 | 389 | GGSITSYY |
| CDRH2 | 390 | IYYSGST |
| CDRH3 | 391 | ARVGGAPYYYYGMDV |
| VH | 392 | QVQLQESGPGLVKPSETLSLTCTVSGGSITSYYWSWIRQPPGKGLEWIGYIYYSGSTNYNPSLKSRVTISVDTSKNQFSLKLSSVTAADTAVYYCARVGGAPYYYYGMDVWGQGTTVTVSS |

ZKC18

| | | |
|---|---|---|
| CDRH1 | 393 | GFTFGDYA |
| CDRH2 | 394 | IRSKAYGGTT |
| CDRH3 | 395 | SRDHTGTTYAFDI |
| VH | 396 | EVQLVESGGGLVQPGRSLRLSCTASGFTFGDYAMSWFRQAPGKGLEWVGFIRSKAYGGTTEYAASVKGRFTISRDDSKSIAYLQMNSLKTEDTAVYYCSRDHTGTTYAFDIWGQGTMVTVSQ |

ZKD1

| | | |
|---|---|---|
| CDRH1 | 397 | GFTFSSYG |
| CDRH2 | 398 | IWYDGSNK |
| CDRH3 | 399 | ARDRRGYGDYVGYYYGMDV |
| VH | 400 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARDRRGYGDYVGYYYGMDVWGQGTTVTVSS |

-continued

| Name | SEQ ID NO. | Amino acid sequence |
|---|---|---|
| ZIKV EDIII generic | 401 | TAAFTFTKXPAEXXHGTVTVEXQYXGXDGPCKXPXQMAVD XQTLTPVGRLITANPVITEXTENSKMMLELDPPFGDSYIV IGXGXKKITHHWHRS |
| ZIKV H/PF/ 2013 EDIII | 402 | TAAFTFTKIPAETLHGTVTVEVQYAGTDGPCKVPAQMAVD MQTLTPVGRLITANPVITESTENSKMMLELDPPFGDSYIV IGVGEKKITHHWHRS |
| ZIKV-NS1 forward primer | 403 | TGGAGTTCAACTGACGGTCG |
| ZIKV-NS1-reverse primer | 404 | TACCCCGAACCCATGATCCT |
| Gapdh-forward primer | 405 | GGCAAGTTCAAAGGCACAGTC |
| Gapdh-reverse primer | 406 | CACCAGCATCACCCCATTT |
| ZIKV EDIII generic | 407 | $X_1GX_2X_3$YSLCTAAFTFTK$X_4$PAEX$_5X_6$HGTVTVEX$_7$QY $X_8GX_9$DGPCKX$_{10}$PX$_{11}$QMAVDX$_{12}$QTLTPVGRLITANP VITEX$_{13}$TX$_{14}$NSKMMLELDPPFGDSYIVIGX$_{15}$GX$_{16}$ X$_{17}$KITHHWHRSG<br>wherein<br>$X_1$ may be any (naturally occurring) amino acid, preferably K, A, or E;<br>$X_2$ may be any (naturally occurring) amino acid, preferably V, F, or L;<br>$X_3$ may be any (naturally occurring) amino acid, preferably S or F;<br>$X_4$ may be any (naturally occurring) amino acid, preferably I or V;<br>$X_5$ may be any (naturally occurring) amino acid, preferably T or V;<br>$X_6$ may be any (naturally occurring) amino acid, preferably L or D;<br>$X_7$ may be any (naturally occurring) amino acid, preferably V or G;<br>$X_8$ may be any (naturally occurring) amino acid, preferably A or G;<br>$X_9$ may be any (naturally occurring) amino acid except R, preferably T or A;<br>$X_{10}$ may be any (naturally occurring) amino acid, preferably V or I;<br>$X_{11}$ may be any (naturally occurring) amino acid, preferably A or V;<br>$X_{12}$ may be any (naturally occurring) amino acid, preferably M or T;<br>$X_{13}$ may be any (naturally occurring) amino acid, preferably S or G;<br>$X_{14}$ may be any (naturally occurring) amino acid, preferably E or K;<br>$X_{15}$ may be any (naturally occurring) amino acid, preferably V or I;<br>$X_{16}$ may be any (naturally occurring) amino acid, preferably E, A, K, or D; and<br>$X_{17}$ may be any (naturally occurring) amino acid, preferably E, A, or K, more preferably K or A |

\* the sequences highlighted in bold are CDR regions (nucleotide or aa) and the underlined residues are mutated residues as compared to the "germline" sequence.

The invention claimed is:

1. Method of inhibiting a Zika virus infection in a subject, the method comprising administering to the subject an antibody, or an antigen binding fragment thereof, that specifically binds to a Zika virus EDIII epitope, wherein the antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

2. The method of claim 1, wherein the antibody or antigen binding fragment thereof comprises a heavy chain variable region (VH) amino acid sequence having at least 70% sequence identity to the amino acid sequence of SEQ ID NO: 26, and a light chain variable region (VL) amino acid sequence having at least 70% sequence identity to the amino acid sequence of SEQ ID NO: 27, provided that the antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

3. The method of claim 2, wherein the antibody or antigen binding fragment thereof comprises a heavy chain variable region (VH) amino acid sequence having at least 75% sequence identity to the amino acid sequence of SEQ ID NO: 26, and a light chain variable region (VL) amino acid sequence having at least 75% sequence identity to the amino acid sequence of SEQ ID NO: 27, provided that the antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

4. The method of claim 2, wherein the antibody or antigen binding fragment thereof comprises a heavy chain variable region (VH) amino acid sequence having at least 80% sequence identity to the amino acid sequence of SEQ ID NO: 26, and a light chain variable region (VL) amino acid sequence having at least 80% sequence identity to the amino acid sequence of SEQ ID NO: 27, provided that the antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

5. The method of claim 2, wherein the antibody or antigen binding fragment thereof comprises a heavy chain variable region (VH) amino acid sequence having at least 85% sequence identity to the amino acid sequence of SEQ ID NO: 26, and a light chain variable region (VL) amino acid sequence having at least 85% sequence identity to the amino acid sequence of SEQ ID NO: 27, provided that the antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

6. The method of claim 2, wherein the antibody or antigen binding fragment thereof comprises a heavy chain variable region (VH) amino acid sequence having at least 90% sequence identity to the amino acid sequence of SEQ ID NO: 26, and a light chain variable region (VL) amino acid sequence having at least 90% sequence identity to the amino acid sequence of SEQ ID NO: 27, provided that the antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

7. The method of claim 2, wherein the antibody or antigen binding fragment thereof comprises a heavy chain variable region (VH) amino acid sequence having at least 92% sequence identity to the amino acid sequence of SEQ ID NO: 26, and a light chain variable region (VL) amino acid sequence having at least 92% sequence identity to the amino acid sequence of SEQ ID NO: 27, provided that the antibody or antigen binding fragment thereof comprises CDRH1, CDRH2, CDRH3, CDRL1, CDRL2, and CDRL3 amino acid sequences of:

(i) SEQ ID NO: 19, SEQ ID NO: 20, SEQ ID NO: 21, SEQ ID NO: 22, EDN, and SEQ ID NO: 25, respectively; or (ii) SEQ ID NO: 19, SEQ ID NO: 20, SEQ ID NO: 21, SEQ ID NO: 22, SEQ ID NO: 24, and SEQ ID NO: 25, respectively.

8. The method of claim 2, wherein the antibody or antigen binding fragment thereof comprises a heavy chain variable region (VH) amino acid sequence having at least 95% sequence identity to the amino acid sequence of SEQ ID NO: 26, and a light chain variable region (VL) amino acid sequence having at least 95% sequence identity to the amino acid sequence of SEQ ID NO: 27, provided that the antibody or antigen binding fragment thereof comprises CDRH1, CDRH2, CDRH3, CDRL1, CDRL2, and CDRL3 amino acid sequences of:

(i) SEQ ID NO: 19, SEQ ID NO: 20, SEQ ID NO: 21, SEQ ID NO: 22, EDN, and SEQ ID NO: 25, respectively; or (ii) SEQ ID NO: 19, SEQ ID NO: 20, SEQ ID NO: 21, SEQ ID NO: 22, SEQ ID NO: 24, and SEQ ID NO: 25, respectively.

9. The method of claim 2, wherein the antibody or antigen binding fragment thereof comprises the heavy chain variable region (VH) amino acid sequence of SEQ ID NO: 26 and the light chain variable region (VL) amino acid sequence of SEQ ID NO: 27.

10. The method of claim 1, wherein the antibody or antigen binding fragment thereof comprises an Fc moiety.

11. The method of claim 10, wherein the antibody or antigen binding fragment thereof comprises a mutation in the Fc moiety that reduces binding of the antibody or antigen binding fragment to an Fc receptor.

12. The method of claim 11, wherein the antibody or antigen binding fragment thereof comprises a CH2 L4A mutation, a CH2 L5A mutation, or both.

13. The method of claim 1, wherein the antibody or antigen binding fragment thereof is comprised in a composition that further comprises a pharmaceutically acceptable excipient, diluent, or carrier.

14. The method of claim 1, wherein the antibody or antigen binding fragment thereof is a human antibody.

15. The method of claim 1, wherein the subject was diagnosed with Zika virus infection or shows symptoms of Zika virus infection.

16. The method of claim 1, wherein the subject is pregnant.

17. The method of claim 1, wherein the antibody or antigen binding fragment thereof is an IgG1 isotype.

18. A method of inhibiting a Zika virus infection in a subject, the method comprising administering to the subject an antibody, or an antigen binding fragment thereof, that specifically binds to a Zika virus EDIII epitope, wherein the antibody or antigen binding fragment thereof comprises CDRH1, CDRH2, CDRH3, CDRL1, CDRL2, and CDRL3 amino acid sequences of:

(i) SEQ ID NO: 19, SEQ ID NO: 20, SEQ ID NO: 21, SEQ ID NO: 22, EDN, and SEQ ID NO: 25, respectively; or (ii) SEQ ID NO: 19, SEQ ID NO: 20, SEQ ID NO: 21, SEQ ID NO: 22, SEQ ID NO: 24, and SEQ ID NO: 25, respectively, and wherein the antibody or antigen binding fragment thereof comprises a Fc moiety that comprises a CH2 L4A mutation, a CH2 L5A mutation, or both.

19. A method of inhibiting a Zika virus infection in a subject, the method comprising administering to the subject an antibody, or an antigen binding fragment thereof, that specifically binds to a Zika virus EDIII epitope, wherein the antibody or antigen binding fragment thereof comprises the heavy chain variable region (VH) amino acid sequence of SEQ ID NO.: 26 and the light chain variable region (VL) amino acid sequence of SEQ ID NO.: 27, and wherein the antibody or antigen binding fragment thereof comprises a Fc moiety that comprises a CH2 L4A mutation, a CH2 L5A mutation, or both.

20. An antibody, or an antigen binding fragment thereof, that specifically binds to a Zika virus EDIII epitope, wherein the antibody or antigen binding fragment thereof comprises:

(a) CDRH1, CDRH2, CDRH3, CDRL1, CDRL2, and CDRL3 amino acid sequences of:

(a)(i) SEQ ID NO: 19, SEQ ID NO: 20, SEQ ID NO: 21, SEQ ID NO: 22, EDN, and SEQ ID NO: 25, respectively; or (a)(ii) SEQ ID NO: 19, SEQ ID NO: 20, SEQ ID NO: 21, SEQ ID NO: 22, SEQ ID NO: 24, and SEQ ID NO: 25, respectively, and (b) an Fc moiety comprising a mutation at at least one of E233-G236, P238, D265, N297, A327, P329, D270, Q295, A327, R292, S239, E269, E293, Y296, V303, A327, P331, K338 and D376, and K414, wherein the mutation reduces binding of the antibody or antigen binding fragment to an FcγRI, an FcγRIIa, an FcγRIIIa, or any combination thereof.

21. The antibody or antigen binding fragment of claim 20, wherein the Fc moiety comprises a CH2 L4A mutation, a CH2 L5A mutation, or both.

22. The antibody or antigen binding fragment of claim 20, wherein the Fc moiety comprises a CH2 L4A mutation and a CH2 L5A mutation.

23. The antibody or antigen binding fragment of claim 20, wherein the antibody further comprises a mutation in the CH2 and/or CH3 domain of the heavy chain that increases the serum half-life of the antibody as compared to an unmutated antibody.

24. The antibody or antigen binding fragment of claim 20, comprising a heavy chain variable region (VH) amino acid sequence having at least 70% sequence identity to the amino acid sequence of SEQ ID NO.:26, and a light chain variable region (VL) amino acid sequence having at least 70% sequence identity to the amino acid sequence of SEQ ID NO.:27, provided that antibody or antigen binding fragment thereof comprises CDRH1, CDRH2, CDRH3, CDRL1, CDRL2, and CDRL3 amino acid sequences of:

(i) SEQ ID NO: 19, SEQ ID NO: 20, SEQ ID NO: 21, SEQ ID NO: 22, EDN, and SEQ ID NO: 25, respectively; or (ii) SEQ ID NO: 19, SEQ ID NO: 20, SEQ ID NO: 21, SEQ ID NO: 22, SEQ ID NO: 24, and SEQ ID NO: 25, respectively.

25. The antibody or antigen binding fragment of claim 20, comprising a heavy chain variable region (VH) amino acid sequence having at least 75% sequence identity to the amino acid sequence of SEQ ID NO.:26, and a light chain variable region (VL) amino acid sequence having at least 75% sequence identity to the amino acid sequence of SEQ ID NO.:27, provided that antibody or antigen binding fragment thereof comprises CDRH1, CDRH2, CDRH3, CDRL1, CDRL2, and CDRL3 amino acid sequences of:

(i) SEQ ID NO: 19, SEQ ID NO: 20, SEQ ID NO: 21, SEQ ID NO: 22, EDN, and SEQ ID NO: 25, respectively; or (ii) SEQ ID NO: 19, SEQ ID NO: 20, SEQ ID NO: 21, SEQ ID NO: 22, SEQ ID NO: 24, and SEQ ID NO: 25, respectively.

26. The antibody or antigen binding fragment of claim 20, comprising a heavy chain variable region (VH) amino acid sequence having at least 80% sequence identity to the amino acid sequence of SEQ ID NO.:26, and a light chain variable region (VL) amino acid sequence having at least 80% sequence identity to the amino acid sequence of SEQ ID NO.:27, provided that antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

27. The antibody or antigen binding fragment of claim 20, comprising a heavy chain variable region (VH) amino acid sequence having at least 85% sequence identity to the amino acid sequence of SEQ ID NO.:26, and a light chain variable region (VL) amino acid sequence having at least 85% sequence identity to the amino acid sequence of SEQ ID NO.:27, provided that antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

28. The antibody or antigen binding fragment of claim 20, comprising a heavy chain variable region (VH) amino acid sequence having at least 90% sequence identity to the amino acid sequence of SEQ ID NO.:26, and a light chain variable region (VL) amino acid sequence having at least 90% sequence identity to the amino acid sequence of SEQ ID NO.:27, provided that antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

29. The antibody or antigen binding fragment of claim 20, comprising a heavy chain variable region (VH) amino acid sequence having at least 92% sequence identity to the amino acid sequence of SEQ ID NO.:26, and a light chain variable region (VL) amino acid sequence having at least 92% sequence identity to the amino acid sequence of SEQ ID NO.:27, provided that antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

30. The antibody or antigen binding fragment of claim 20, comprising a heavy chain variable region (VH) amino acid sequence having at least 95% sequence identity to the amino acid sequence of SEQ ID NO.:26, and a light chain variable region (VL) amino acid sequence having at least 95% sequence identity to the amino acid sequence of SEQ ID NO.:27, provided that antibody or antigen binding fragment thereof comprises CDRH1, CDRH2, CDRH3, CDRL1, CDRL2, and CDRL3 amino acid sequences of:
   (i) SEQ ID NO: 19, SEQ ID NO: 20, SEQ ID NO: 21, SEQ ID NO: 22, EDN, and SEQ ID NO: 25, respectively; or
   (ii) SEQ ID NO: 19, SEQ ID NO: 20, SEQ ID NO: 21, SEQ ID NO: 22, SEQ ID NO: 24, and SEQ ID NO: 25, respectively.

31. An antibody, or an antigen binding fragment thereof, that specifically binds to a Zika virus EDIII epitope, wherein the antibody or antigen binding fragment thereof comprises:
   (a) a heavy chain variable region (VH) amino acid sequence SEQ ID NO: 26;
   (b) a light chain variable region (VL) amino acid sequence SEQ ID NO: 27; and
   (c) an Fc moiety comprising a mutation at at least one of E233-G236, P238, D265, N297, A327, P329, D270, Q295, A327, R292, S239, E269, E293, Y296, V303, A327, P331, K338 and D376, and K414, wherein the mutation reduces binding of the antibody or antigen binding fragment to an FcγRI, an FcγRIIa, an FcγRIIIa, or any combination thereof.

32. The antibody or antigen binding fragment of claim 31, wherein the Fc moiety comprises a CH2 L4A mutation, a CH2 L5A mutation, or both.

\* \* \* \* \*

UNITED STATES PATENT AND TRADEMARK OFFICE
CERTIFICATE OF CORRECTION

| | |
|---|---|
| PATENT NO. | : 11,912,757 B2 |
| APPLICATION NO. | : 17/335792 |
| DATED | : February 27, 2024 |
| INVENTOR(S) | : Davide Corti |

It is certified that error appears in the above-identified patent and that said Letters Patent is hereby corrected as shown below:

On the Title Page

<u>Item (30):</u>
"(30) Foreign Application Priority Data
July 13, 2016 (WO) ........PCT/EP2016/066684"

Should read:
--(30) Foreign Application Priority Data
July 13, 2016 (EP) ........PCT/EP2016/066684--

Signed and Sealed this
Thirtieth Day of April, 2024

Katherine Kelly Vidal
*Director of the United States Patent and Trademark Office*